US010941424B2

(12) United States Patent
Koch et al.

(10) Patent No.: US 10,941,424 B2
(45) Date of Patent: *Mar. 9, 2021

(54) MICROORGANISMS AND METHODS FOR THE CO-PRODUCTION OF ETHYLENE GLYCOL AND THREE CARBON COMPOUNDS

(71) Applicant: Braskem S.A., Camaçari (BR)

(72) Inventors: Daniel Johannes Koch, Camaçari (BR); Mateus Schreiner Lopes, Camaçari (BR); Ane Fernanda Beraldi Zeidler, Camaçari (BR); Lucas Pedersen Parizzi, Camaçari (BR)

(73) Assignee: BRASKEM S.A., Camacari (BR)

( * ) Notice: Subject to any disclaimer, the term of this patent is extended or adjusted under 35 U.S.C. 154(b) by 5 days.

This patent is subject to a terminal disclaimer.

(21) Appl. No.: 15/726,978

(22) Filed: Oct. 6, 2017

(65) Prior Publication Data

US 2018/0179558 A1 Jun. 28, 2018

Related U.S. Application Data

(63) Continuation of application No. 15/453,094, filed on Mar. 8, 2017.

(60) Provisional application No. 62/430,742, filed on Dec. 6, 2016, provisional application No. 62/305,814, filed on Mar. 9, 2016.

(51) Int. Cl.

| | | |
|---|---|---|
| *C12N 9/10* | (2006.01) | |
| *C12N 1/20* | (2006.01) | |
| *C12P 7/18* | (2006.01) | |
| *C12P 7/28* | (2006.01) | |
| *C12N 9/02* | (2006.01) | |
| *C12N 9/12* | (2006.01) | |
| *C12N 9/88* | (2006.01) | |
| *C12N 9/90* | (2006.01) | |
| *C12N 15/52* | (2006.01) | |
| *C12P 5/02* | (2006.01) | |
| *C12P 7/04* | (2006.01) | |
| *C12P 7/26* | (2006.01) | |

(52) U.S. Cl.
CPC .............. *C12P 7/28* (2013.01); *C12N 9/0008* (2013.01); *C12N 9/1029* (2013.01); *C12N 9/1205* (2013.01); *C12N 9/13* (2013.01); *C12N 9/88* (2013.01); *C12N 9/90* (2013.01); *C12N 15/52* (2013.01); *C12P 5/026* (2013.01); *C12P 7/04* (2013.01); *C12P 7/18* (2013.01); *C12P 7/26* (2013.01); *C12Y 102/01021* (2013.01); *C12Y 203/01009* (2013.01); *C12Y 207/01047* (2013.01); *C12Y 208/03008* (2013.01); *C12Y 401/01004* (2013.01); *C12Y 401/02013* (2013.01); *C12Y 501/03* (2013.01); *C12P 2203/00* (2013.01)

(58) Field of Classification Search
CPC .......... C12N 9/90; C12N 9/1205; C12N 9/88; C12N 9/0008; C12N 15/52; C12Y 207/01047; C12P 7/28; C12P 7/04

USPC ....... 435/132, 158, 189, 193, 252.2, 254.33, 435/320.1
See application file for complete search history.

(56) References Cited

U.S. PATENT DOCUMENTS

| | | |
|---|---|---|
| 7,977,083 B1 | 7/2011 | Sakakibara et al. |
| 2007/0259411 A1 | 11/2007 | Bramucci et al. |
| 2008/0293125 A1 | 11/2008 | Subbian et al. |
| 2010/0047878 A1 | 2/2010 | Nagai et al. |
| 2010/0311135 A1 | 12/2010 | Takebayashi et al. |
| 2013/0280775 A1 | 10/2013 | Grotkjaer et al. |
| 2013/0316416 A1 | 11/2013 | Stephanopoulos et al. |
| 2014/0065686 A1 | 3/2014 | Marliere |
| 2014/0141482 A1 | 5/2014 | Pearlman et al. |
| 2015/0147794 A1 | 5/2015 | Chung et al. |
| 2017/0260551 A1 | 9/2017 | Koch et al. |
| 2018/0179558 A1 | 6/2018 | Koch et al. |

FOREIGN PATENT DOCUMENTS

| | | |
|---|---|---|
| WO | WO 2006/135075 A1 | 12/2006 |
| WO | WO 2009/008377 A1 | 1/2009 |
| WO | WO 2011/012697 A2 | 2/2011 |
| WO | WO 2011/076691 A1 | 6/2011 |
| WO | WO 2011/130378 A1 | 10/2011 |
| WO | WO 2012/088467 A2 | 6/2012 |
| WO | WO 2013/126721 A1 | 8/2013 |
| WO | WO 2013/163230 A2 | 10/2013 |
| WO | WO 2014/004625 A1 | 1/2014 |
| WO | WO 2015/002977 A1 | 1/2015 |
| WO | WO 2015/032761 A1 | 3/2015 |
| WO | WO 2015/042588 A1 | 3/2015 |
| WO | WO 2016/079440 A1 | 5/2016 |
| WO | WO 2017/156166 A1 | 9/2017 |

OTHER PUBLICATIONS

Devos et al., (Proteins: Structure, Function and Genetics, 2000, vol. 41: 98-107.*

(Continued)

*Primary Examiner* — Robert B Mondesi
*Assistant Examiner* — Mohammad Y Meah
(74) *Attorney, Agent, or Firm* — Morgan, Lewis & Bockius LLP

(57) ABSTRACT

The present application relates to recombinant microorganisms useful in the biosynthesis of monoethylene glycol (MEG) and one or more three-carbon compounds such as acetone, isopropanol or propene. The MEG and one or more three-carbon compounds described herein are useful as starting material for production of other compounds or as end products for industrial and household use. The application further relates to recombinant microorganisms co-expressing a C2 branch pathway and a C3 branch pathway for the production of MEG and one or more three-carbon compounds. Also provided are methods of producing MEG and one or more three-carbon compounds using the recombinant microorganisms, as well as compositions comprising the recombinant microorganisms and/or optionally the products MEG and one or more three-carbon compounds.

7 Claims, 15 Drawing Sheets
Specification includes a Sequence Listing.

(56) References Cited

OTHER PUBLICATIONS

Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Alkim et al. (Microb cel fact 2015, pp. 1-12.*
May et al. ( Met. Eng. 15, 2013, pp. 218-225 .*
Clomburg et al ( Appl micro boil biotec 2010, 86, 419-434).*
Alkim, Ceren, et al. "Optimization of ethylene glycol production from (D)-xylose via a synthetic pathway implemented in *Escherichia coli*." Microbial Cell Factories (2015); 14.1: 127.
Boonstra, Birgitte, et al. "The udhA gene of *Escherichia coli* encodes a soluble pyridine nucleotide transhydrogenase." Journal of Bacteriology (1999); 181.3: 1030-1034.
Canonaco, Fabrizio, et al. "Metabolic flux response to phosphoglucose isomerase knock-out in *Escherichia coli* and impact of overexpression of the soluble transhydrogenase UdhA." FEMS Microbiology Letters (2001); 204.2: 247-252.
Charusanti, Pep, et al. "Genetic basis of growth adaptation of *Escherichia coli* after deletion of pgi, a major metabolic gene." PLoS Genet (2010); 6.11: e1001186.
Chen, Zhen, et al. "Metabolic engineering of Corynebacterium glutamicum for the de novo production of ethylene glycol from glucose." Metabolic Engineering (2016); 33: 12-18.
Ehrensberger, Andreas H., et al. "Structure-guided engineering of xylitol dehydrogenase cosubstrate specificity." Structure (2006); 14.3: 567-575.
Hao, Jijun, and Berry, Alan. "A thermostable variant of fructose bisphosphate aldolase constructed by directed evolution also shows increased stability in organic solvents." Protein Engineering Design and Selection (2004); 17.9: 689-697.
International Application No. PCT/US2017/021421, International Search Report and Written Opinion dated Jul. 10, 2017, 15 pages.
International Application No. PCT/US2017/041732, International Search Report and Written Opinion dated Nov. 20, 2017, 19 pages.
Jarboe, Laura R. "YqhD: a broad-substrate range aldehyde reductase with various applications in production of biorenewable fuels and chemicals." Applied Microbiology and Biotechnology (2011); 89.2: 249-257.
Li, Hongmei, et al. "Enhanced activity of yqhD oxidoreductase in synthesis of 1, 3-propanediol by error-prone PCR." Progress in Natural Science (2008); 18.12: 1519-1524.
Marmulla, R., et al., "Linalool isomerase, a membrane-anchored enzyme in the anaerobic monoterpene degradation in Thauera linaloolentis 47Lol." BMC Biochemistry (2016) 17: 6, pp. 1-11.
Patel, Darshan H., et al. "Engineering of the catalytic site of xylose isomerase to enhance bioconversion of a non-preferential substrate." Protein Engineering Design and Selection (2012); 25(7): 331-336.
Sauer, Uwe, et al. "The soluble and membrane-bound transhydrogenases UdhA and PntAB have divergent functions in NADPH metabolism of *Escherichia coli*." Journal of Biological Chemistry (2004); 279.8: 6613-6619.
Sulzenbacher, Gerlind, et al. "Crystal structure of *E. coli* alcohol dehydrogenase YqhD: evidence of a covalently modified NADP coenzyme." Journal of Molecular Biology (2004); 342.2: 489-502.
UniProtKB P0AB87 (Nov. 8, 2005) [retrieved on Jun. 18, 2017 from http://www.uniprot.org/uniprot/P0AB87, 8 pages.
Bermejo et al., "Expression of Clostridium acetobutylicum ATCC 824 Genes in *Escherichia coli* for Acetone Production and Acetate Detoxification," Applied and Enviromental Microbiology, Mar. 1998, 64(3):1079-1085.
Elsinghorst et al., "D-Arabinose Metabolism in *Escherichia coli* B: Induction and Cotransductional Mapping of the L-Fucose-D-Arabinose Pathway Enzymes," Journal of Bacteriology, Dec. 1988, 170(12):5423-5432.
Hanai et al., "Engineered Synthetic Pathway for Isogropanol Production in *Escherichia coli*," Applied and Enviromental Microbiology, Dec. 2007, 73(24):7814-7818.

Hayward et al., "Structure and alternative splicing of the ketohexokinase gene," Eur. J. Biochem. (1998), 257:85-91.
Itoh et al., "Purification and Characterization of D-Tagatose 3-Epimerase from *Pseudomonas* sp. ST-24 ," Biosci. Biotech. Biochem., 1994, 58 (12), 2168-2171.
LeBlanc et al., "Metabolism of D-Arabinose: a New Pathway in *Escherichia coli*," Journal of Bacteriology, Apr. 1971, 106(1):90-96.
Liu et al., "Biosynthesis of ethylene glycol in *Escherichia coli*," Appl Microbiol Biotechnol (2013) 97:3409-3417.
UniProtKB—B2TLN8 (ADC_CLOBB) Apr. 14, 2009, retrieved from https://www.uniprot.org/uniprot/B2TLN8, 4 pages.
UniProtKB—C1KKR1 (DT3E_RHOSH) Jan. 20, 2016, retrieved from https://www.uniprot.org/uniprot/C1KKR1, 6 pages.
UniProtKB—E3PHW0 (E3PHW0_ECOH1) Jan. 11, 2011, retrieved from https://www.uniprot.org.uniprot/E3PHW0, 4 pages.
UniProtKB—O50580 (DT3E_PSECI) Dec. 1, 2000, retrieved from https://www.uniprot.org/uniprot/O50580, 8 pages.
UniProtKB—P00884 (ALDOB_RAT) Jul. 21, 1986, retrieved from https://www.uniprot.org/uniprot/P00884, 9 pages.
UniProtKB—P05062 (ALDOB_HUMAN) Aug. 13, 1987, retrieved from https://www.uniprot.org/uniprot/P05062, 14 pages.
UniProtKB—P07097 (THIL_ZOORA) Apr. 1, 1988, retrieved from https://www.uniprot.org/uniprot/P07097, 7 pages.
UniProtKB—P11553 (FUCK_ECOLI) Oct. 1, 1989, retrieved from https://www.uniprot.org/uniprot/P11553, 5 pages.
UniProtKB—P14611 (THIL_CUPNH) Apr. 1, 1990, retrieved from https://www.uniprot.org/uniprot/P14611, 7 pages.
UniProtKB—P17764 (THIL_RAT) Aug. 1, 1990, retrieved from https://www.uniprot.org/uniprot/P17764, 9 pages.
UniProtKB—P23670 (ADC_CLOAB) Nov. 1, 1991, retrieved from https://www.uniprot.org/uniprot/P23670, 5 pages.
UniProtKB—P23673 (CTFB_CLOAB) Nov. 1, 1991, retrieved from https://www.uniprot.org.uniprot/P23673, 4 pages.
UniProtKB—P24752 (THIL_HUMAN) Mar. 1, 1992, retrieved from https://www.uniprot.org/uniprot/P24752, 14 pages.
UniProtKB—P33752 (CTFA_CLOAB) Feb. 1, 1994, retrieved from https://www.uniprot.org/uniprot/P33752, 4 pages.
UniProtKB—P41338 (THIL_YEAST) Feb. 1, 1995, retrieved from https://www.uniprot.org/uniprot/P41338, 9 pages.
UniProtKB—P50053 (KHK_HUMAN) Oct. 1, 1996, retrieved from https://www.uniprot.org/uniprot/P50053, 9 pages.
UniProtKB—P76459 (ATOA_ECOLI) Nov. 1, 1997, retrieved from https://www.uniprot.org/uniprot/P76459, 5 pages.
UniProtKB—P76461 (ATOB_ECOLI) Nov. 1, 1997, retrieved from https://www.uniprot.org/uniprot/P76461, 9 pages.
UniProtKB—P79226 (ALDOB_RABIT) Nov. 1, 1997, retrieved from https://www.uniprot.org/uniprot/P79226, 9 pages.
UniProtKB—P81336 (ADC_CLOPA) Jul. 15, 1998, retrieved from https://www.uniprot.org/uniprot/P81336, 2 pages.
UniProtKB—P97328 (KHK_MOUSE) Jul. 15, 1999, retrieved from https://www.uniprot.org/uniprot/P97328, 6 pages.
UniProtKB —Q02974 (KHK_RAT) Jul. 1, 1993, retrieved from https://www.uniprot.org/uniprot/Q02974, 6 pages.
UniProtKB—Q3A042 (Q3A042_PELCD) Nov. 22, 2005, retrieved from https://uniprot.org/uniprot/Q3A042, 4 pages.
UniProtKB—Q5RD71 (KHK_PONAB) Jan. 24, 2006, retrieved from https://www.uniprot.org/uniprot/Q5RD71, 4 pages.
UniProtKB—Q7NSA6 (ADC_CHRVO) Mar. 1, 2004, retrieved from https://www.uniprot.org/uniprot/Q7NSA6, 4 pages.
UniProtKB—Q89EP4 (ADC2_BRADU) Mar. 1, 2004, retrieved from https://www.uniprot.org/uniprot/Q89EP4, 4 pages.
UniProtKB—Q8QZT1 (THIL_MOUSE) Sep. 13, 2004, retrieved from https://www.uniprot.org/uniprot/Q8QZT1, 9 pages.
UniProtKB—Q8S4Y1 (THIC1_ARATH) Aug. 30, 2005, retrieved from https://www.uniprot.org/uniprot/Q8S4Y1, 8 pages.
UniProtKB—Q91Y97 (ALDOB_MOUSE) Apr. 23, 2003, retrieved from https://www.uniprot.org/uniprot/Q8S4Y1, 9 pages.
UniProtKB—Q98FW0 (LR3E_RHILO) Jan. 20, 2016, retrieved from https://www.uniprot.org/uniprot/Q98FW0, 6 pages.
UniProtKB—Q9BWD1 (THIC_HUMAN) Sep. 13, 2004, retrieved fromhttps://www.uniprot.org/uniprot/Q9BWD1, 11 pages.
UniProtKB—Q9RPK1 (ADC_CLOBE) Nov. 15, 2002, retrieved from https://www.uniprot.org/uniprot/Q9RPK1, 3 pages.

(56) References Cited

OTHER PUBLICATIONS

Yoshida et al., "X-ray structures of the Pseudomonas cichorii D-tagatose 3-epimerase mutant form C66S recognizing deoxy sugars as substrates," Applied Microbiology and Biotechnology, Dec. 2016, vol. 100, Issue 24, pp. 10403-10415.

Cabulong et al., "Enhanced yield of ethylene glycol production from d-xylose by pathway optimization in *Escherichia coli*," Enzyme and Microbial Technology 97 (2017) 11-20.

Cao et al., "Metabolic Engineering of *Escherichia coli* for the Production of Xylonate," Plos One, Jul. 2013, vol. 8, Issue 7, 7 pages.

Extended European Search Report for European Application No. 17764027.3 dated Dec. 10, 2019, 9 pages.

Haapalainen et al., "The thiolase superfamily: condensing enzymes with diverse reaction specificities," Trends In Biochemical Sciences, Jan. 2006, vol. 31, No. 1, pp. 64-71.

Partial Supplementary European Search Report for European Application No. 17764027.3 dated Aug. 23, 2019, 11 pages.

Wiesenborn et al., "Thiolase from Clostridium acetobutylicum ATCC 824 and Its Role in the Synthesis of Acids and Solvents," Applied and Environmental Microbiology, Nov. 1988, vol. 54, No. 11 pp. 2717-2722.

\* cited by examiner

SEQUENCE LISTING

<160> NUMBER OF SEQ ID NOS: 120

<210> SEQ ID NO 1
<211> LENGTH: 873
<212> TYPE: DNA
<213> ORGANISM: Pseudomonas cichorii

<400> SEQUENCE: 1

```
gtgaacaaag ttggcatgtt ctacacctac tggtcgactg agtggatggt cgactttccg      60
gcgactgcga agcgcattgc cgggctcggc ttcgacttaa tggaaatctc gctcggcgag     120
tttcacaatc tttccgacgc gaagaagcgt gagctaaaag ccgtggctga tgatctgggg     180
ctcacggtga tgtgctgtat cggactgaag tctgagtacg actttgcctc gccggacaag     240
agcgttcgtg atgccggcac ggaatatgtg aagcgcttgc tcgacgactg tcacctcctc     300
ggcgcgccgg tctttgctgg ccttacgttc tgcgcgtggc cccaatctcc gccgctggac     360
atgaaggata agcgccctta cgtcgaccgt gcaatcgaaa gcgttcgtcg tgttatcaag     420
gtagctgaag actacggcat tatttatgca ctggaagtgg tgaaccgatt cgagcagtgg     480
ctttgcaatg acgccaagga agcaattgcg tttgccgacg cggttgacag tccggcgtgc     540
aaggtccagc tcgacacatt ccacatgaat atcgaagaga cttccttccg cgatgcaatc     600
cttgcctgca agggcaagat gggccatttc catttgggcg aagcgaaccg tctgccgccg     660
ggcgagggtc gcctgccgtg ggatgaaata ttcggggcgc tgaaggaaat cggatatgac     720
ggcaccatcg ttatggaacc gttcatgcgc aagggcggct cggtcagccg cgcggtgggc     780
gtatggcggg atatgtcgaa cggtgcgacg gacgaagaga tggacgagcg cgctcgccgc     840
tcgttgcagt tgttcgtgaa caagctggcc tga                                 873
```

<210> SEQ ID NO 2
<211> LENGTH: 873
<212> TYPE: DNA
<213> ORGANISM: Pseudomonas cichorii

<400> SEQUENCE: 2

```
atgaacaaag tgggtatgtt ctatacgtac tggtccacgg aatggatggt tgactttccg      60
gcaaccgcga aacgtattgc gggcctgggc ttcgacctga tggaaatttc tctgggcgaa     120
tttcacaacc tgtccgatgc gaaaaagcgt gaactgaaag ccgttgccga cgatctgggt     180
ctgactgtga tgtgctgtat cggcctgaaa tctgaatacg atttcgcgag cccggataaa     240
agcgttcgcg acgccggtac tgaatatgtc aaacgtctgc tggatgactg tcacctgctg     300
ggcgcaccag tgttcgcggg tctgaccttc tgtgcgtggc cgcagtcccc accgctggac     360
atgaaggata aacgtccgta cgtggaccgt gccatcgaaa gcgtgcgccg cgtaatcaaa     420
gtcgctgaag attatggcat tatttacgct ctggaagttg ttaaccgttt cgaacagtgg     480
ctgtgcaacg acgcgaaaga ggccattgcc ttcgctgacg cggtggattc tccggcttgc     540
aaagttcagc tggacacttt ccatatgaac atcgaggaaa cctccttccg tgacgcgatc     600
ctggcttgca agggtaaaat gggccatttc catctgggcg aagcaaaccg cctgccgccg     660
ggcgaaggtc gtctgccgtg ggacgaaatt tttgcgctct gaaggaaat cggctacgat     720
ggcacgattg ttatggagcc gttcatgcgc aaaggtggct ccgtttcccg tgcagttggt     780
```

```
gtttggcgtg atatgtctaa cggtgccacc gatgaagaaa tggacgaacg tgcacgtcgc      840
tccctgcaat tcgttcgcga taaactggcg taa                                    873
```

<210> SEQ ID NO 3
<211> LENGTH: 290
<212> TYPE: PRT
<213> ORGANISM: Pseudomonas cichorii

<400> SEQUENCE: 3

```
Met Asn Lys Val Gly Met Phe Tyr Thr Tyr Trp Ser Thr Glu Trp Met
1               5                   10                  15

Val Asp Phe Pro Ala Thr Ala Lys Arg Ile Ala Gly Leu Gly Phe Asp
            20                  25                  30

Leu Met Glu Ile Ser Leu Gly Glu Phe His Asn Leu Ser Asp Ala Lys
        35                  40                  45

Lys Arg Glu Leu Lys Ala Val Ala Asp Asp Leu Gly Leu Thr Val Met
    50                  55                  60

Cys Cys Ile Gly Leu Lys Ser Glu Tyr Asp Phe Ala Ser Pro Asp Lys
65                  70                  75                  80

Ser Val Arg Asp Ala Gly Thr Glu Tyr Val Lys Arg Leu Leu Asp Asp
                85                  90                  95

Cys His Leu Leu Gly Ala Pro Val Phe Ala Gly Leu Thr Phe Cys Ala
            100                 105                 110

Trp Pro Gln Ser Pro Leu Asp Met Lys Asp Lys Arg Pro Tyr Val
        115                 120                 125

Asp Arg Ala Ile Glu Ser Val Arg Arg Val Ile Lys Val Ala Glu Asp
    130                 135                 140

Tyr Gly Ile Ile Tyr Ala Leu Glu Val Val Asn Arg Phe Glu Gln Trp
145                 150                 155                 160

Leu Cys Asn Asp Ala Lys Glu Ala Ile Ala Phe Ala Asp Ala Val Asp
                165                 170                 175

Ser Pro Ala Cys Lys Val Gln Leu Asp Thr Phe His Met Asn Ile Glu
            180                 185                 190

Glu Thr Ser Phe Arg Asp Ala Ile Leu Ala Cys Lys Gly Lys Met Gly
        195                 200                 205

His Phe His Leu Gly Glu Ala Asn Arg Leu Pro Pro Gly Glu Gly Arg
    210                 215                 220

Leu Pro Trp Asp Glu Ile Phe Gly Ala Leu Lys Glu Ile Gly Tyr Asp
225                 230                 235                 240

Gly Thr Ile Val Met Glu Pro Phe Met Arg Lys Gly Gly Ser Val Ser
                245                 250                 255

Arg Ala Val Gly Val Trp Arg Asp Met Ser Asn Gly Ala Thr Asp Glu
            260                 265                 270

Glu Met Asp Glu Arg Ala Arg Arg Ser Leu Gln Phe Val Arg Asp Lys
        275                 280                 285

Leu Ala
    290
```

<210> SEQ ID NO 4
<211> LENGTH: 888
<212> TYPE: DNA
<213> ORGANISM: Rhodobacter sphaeroides

<400> SEQUENCE: 4

```
gtgaaaaatc ctgtcggcat catctcgatg cagttcatcc ggcccttcac ctcggagtcg      60
```

-continued

```
ctgcatttcc tgaagaagtc ccgggccctg ggcttcgatt tcatcgagct tctcgtgccc    120
gagcccgaag acgggctcga cgcggccgag gtgcggcgca tctgcagggg cgaggggctg    180
ggcctcgttc tggccgcgcg cgtgaacctc cagcgctcga tcgcgagcga ggaggccgcg    240
gcgcgggccg gcgggcgcga ctatctgaaa tactgcatcg aggccgccga ggcgctcggc    300
gcgaccatcg tcggcggccc gctctatggc gagccgctgg tcttcgccgg ccgcccgccc    360 ttccctgga cggccgagca gatcgccacc cgcgccgccc gcaccgtcga ggggctggcc     420
gaagtggccc cgctcgccgc gagcgcgggc aaggtcttcg gctcgagcc gctgaaccgc     480 ttcgagaccg acatcgtgaa cacgaccgca caggccatcg aggtggtgga tgcggtgggc    540
tcgcccggtc tcggcgtcat gctcgacacg ttccacatga acatggagga acgctcgatc    600
cccgatgcga tccgcgccac aggcgcgcgc ctcgtccatt ttcaggccaa cgagaaccac    660
cgcggcttcc ccggcaccgg caccatggac tggacggcca tcgcgcgggc gctggggcag    720
gcgggctacg cgggtccggt ctcgctcgag cctttccggc gcgacgacga gcgcgtggcg    780
ctgcccatcg cccactggcg cgccccgcac gaggacgagg acgagaagct gcgcgcgggg    840
ctgggtctca tccgctccgc gatcaccctg gcggaggtga cccactga                 888
```

<210> SEQ ID NO 5
<211> LENGTH: 295
<212> TYPE: PRT
<213> ORGANISM: Rhodobacter sphaeroides

<400> SEQUENCE: 5

```
Met Lys Asn Pro Val Gly Ile Ile Ser Met Gln Phe Ile Arg Pro Phe
1               5                  10                  15

Thr Ser Glu Ser Leu His Phe Leu Lys Lys Ser Arg Ala Leu Gly Phe
            20                  25                  30

Asp Phe Ile Glu Leu Leu Val Pro Glu Pro Glu Asp Gly Leu Asp Ala
        35                  40                  45

Ala Glu Val Arg Arg Ile Cys Glu Gly Glu Gly Leu Gly Leu Val Leu
    50                  55                  60

Ala Ala Arg Val Asn Leu Gln Arg Ser Ile Ala Ser Glu Glu Ala Ala
65                  70                  75                  80

Ala Arg Ala Gly Gly Arg Asp Tyr Leu Lys Tyr Cys Ile Glu Ala Ala
                85                  90                  95

Glu Ala Leu Gly Ala Thr Ile Val Gly Gly Pro Leu Tyr Gly Glu Pro
            100                 105                 110

Leu Val Phe Ala Gly Arg Pro Pro Phe Pro Trp Thr Ala Glu Gln Ile
        115                 120                 125

Ala Thr Arg Ala Ala Arg Thr Val Glu Gly Leu Ala Glu Val Ala Pro
    130                 135                 140

Leu Ala Ala Ser Ala Gly Lys Val Phe Gly Leu Glu Pro Leu Asn Arg
145                 150                 155                 160

Phe Glu Thr Asp Ile Val Asn Thr Thr Ala Gln Ala Ile Glu Val Val
                165                 170                 175

Asp Ala Val Gly Ser Pro Gly Leu Gly Val Met Leu Asp Thr Phe His
            180                 185                 190

Met Asn Met Glu Glu Arg Ser Ile Pro Asp Ala Ile Arg Ala Thr Gly
        195                 200                 205

Ala Arg Leu Val His Phe Gln Ala Asn Glu Asn His Arg Gly Phe Pro
    210                 215                 220

Gly Thr Gly Thr Met Asp Trp Thr Ala Ile Ala Arg Ala Leu Gly Gln
```

```
                225                 230                 235                 240
Ala Gly Tyr Ala Gly Pro Val Ser Leu Glu Pro Phe Arg Arg Asp Asp
            245                 250                 255

Glu Arg Val Ala Leu Pro Ile Ala His Trp Arg Ala Pro His Glu Asp
        260                 265                 270

Glu Asp Glu Lys Leu Arg Ala Gly Leu Gly Leu Ile Arg Ser Ala Ile
    275                 280                 285

Thr Leu Ala Glu Val Thr His
    290                 295

<210> SEQ ID NO 6
<211> LENGTH: 1422
<212> TYPE: DNA
<213> ORGANISM: Escherichia coli

<400> SEQUENCE: 6
atgatgaaac aagaagttat cctggtactc gactgtggcg cgaccaatgt cagggccatc       60
gcggttaatc ggcagggcaa aattgttgcc cgcgcctcaa cgcctaatgc cagcgatatc      120
gcgatggaaa acaacacctg gcaccagtgg tctttagacg ccattttgca acgctttgct      180
gattgctgtc ggcaaatcaa tagtgaactg actgaatgcc acatccgcgg tatcgccgtc      240
accacctttg gtgtggatgg cgctctggta gataagcaag gcaatctgct ctatccgatt      300
attagctgga atgtccgcg aacagcgcg gttatggaca atattgaacg gttaatctcc      360
gcacagcggt tgcaggctat ttctggcgtc ggagccttta gtttcaatac gttatataag      420
ttggtgtggt tgaaagaaaa tcatccacaa ctgctggaac gcgcgcacgc ctggctcttt      480
atttcgtcgc tgattaacca ccgtttaacc ggcgaattca ctactgatat cacgatggcc      540
ggaaccagcc agatgctgga tatccagcaa cgcgatttca gtccgcaaat tttacaagcc      600
accggtattc cacgccgact cttccctcgt ctggtggaag cgggtgaaca gattggtacg      660
ctacagaaca gcgccgcagc aatgctcggc ttacccgttg gcataccggt gatttccgca      720
ggtcacgata cccagttcgc cctttttggc gctggtgctg aacaaaatga cccgtgctc      780 tcttccggta catgggaaat tttaatggtt cgcagcgccc aggttgatac ttcgctgtta      840
agtcagtacg ccggttccac ctgcgaactg gatagccagg cagggttgta acccaggt      900 atgcaatggc tggcatccgg cgtgctgaa tgggtgagaa actgttctg gacggctgaa      960 acaccctggc aaatgttgat tgaagaagct cgtctgatcg cgcctggcgc ggatggcgta     1020
aaaatgcagt gtcgatttat gtcgtgtcag aacgctggct ggcaaggagt gacgcttaat     1080
accacgcggg ggcatttcta tcgcgcggcg ctggaagggt taactgcgca attacagcgc     1140
aatctacaga tgctggaaaa aatcgggcac tttaaggcct ctgaattatt gttagtcggt     1200
ggaggaagtc gcaacacatt gtggaatcag attaaagcca atatgcttga tattccggta     1260
aaagttctcg acgacgccga aacgaccgtc gcaggagctg cgctgttcgg ttggtatggc     1320
gtaggggaat taacagccc ggaagaagcc cgcgcacaga ttcattatca gtaccgttat     1380
ttctacccgc aaactgaacc tgaatttata gaggaagtgt ga                        1422

<210> SEQ ID NO 7
<211> LENGTH: 1422
<212> TYPE: DNA
<213> ORGANISM: Escherichia coliv

<400> SEQUENCE: 7
atgatgaaac aagaagttat cctggtactc gactgtggcg cgaccaatgt cagggccatc       60
```

```
gcggttaatc ggcagggcaa aattgttgcc cgcgcctcaa cgcctaatgc cagcgatatc    120
gcgatggaaa acaacacctg gcaccagtgg tctttagacg ccattttgca acgctttgct    180
gattgctgtc ggcaaatcaa tagtgaactg actgaatgcc acatccgcgg tatcgccgtc    240
accacctttg gtgtggatgg cgctctggta gataagcaag gcaatctgct ctatccgatt    300
attagctgga aatgtccgcg aacagcagcg gttatggaca atattgaacg gttaatctcc    360
gcacagcggt tgcaggctat ttctggcgtc ggagccttta gtttcaatac gttatataag    420
ttggtgtggt tgaaagaaaa tcatccacaa ctgctggaac gcgcgcacgc ctggctcttt    480
atttcgtcgc tgattaacca ccgtttaacc ggcgaattca ctactgatat cacgatggcc    540
ggaaccagcc agatgctgga tatccagcaa cgcgatttca gtccgcaaat tttacaagcc    600
accggtattc cacgccgact cttccctcgt ctggtggaag cgggtgaaca gattggtacg    660
ctacagaaca gcgccgcagc aatgctcggc ttacccgttg gcataccggt gatttccgca    720
ggtcacgata cccagttcgc ccttttttggc gctggtgctg aacaaaatga acccgtgctc    780
tcttccggta catgggaaat tttaatggtt cgcagcgccc aggttgatac ttcgctgtta    840
agtcagtacg ccggttccac ctgcgaactg gatagccagg cagggttgta taacccaggt    900
atgcaatggc tggcatccgg cgtgctggaa tgggtgagaa aactgttctg gacggctgaa    960 acccctggc aaatgttgat tgaagaagct cgtctgatcg cgcctggcgc ggatggcgta   1020
aaaatgcagt gtgatttatt gtcgtgtcag aacgctggct ggcaaggagt gacgcttaat   1080
accacgcggg ggcatttcta tcgcgcggcg ctggaagggt taactgcgca attacagcgc   1140
aatctacaga tgctggaaaa aatcgggcac tttaaggcct ctgaattatt gttagtcggt   1200
ggaggaagtc gcaacacatt gtggaatcag attaaagcca atatgcttga tattccggta   1260
aaagttctcg acgacgccga aacgaccgtc gcaggagctg cgctgttcgg ttggtatggc   1320
gtaggggaat ttaacagccc ggaagaagcc cgcgcacaga ttcattatca gtaccgttat   1380
ttctacccgc aaactgaacc tgaatttata gaggaagtgt ga                      1422
```

<210> SEQ ID NO 8
<211> LENGTH: 473
<212> TYPE: PRT
<213> ORGANISM: Escherichia coli

<400> SEQUENCE: 8

```
Met Met Lys Gln Glu Val Ile Leu Val Leu Asp Cys Gly Ala Thr Asn
1               5                   10                  15

Val Arg Ala Ile Ala Val Asn Arg Gln Gly Lys Ile Val Ala Arg Ala
            20                  25                  30

Ser Thr Pro Asn Ala Ser Asp Ile Ala Met Glu Asn Asn Thr Trp His
        35                  40                  45

Gln Trp Ser Leu Asp Ala Ile Leu Gln Arg Phe Ala Asp Cys Cys Arg
    50                  55                  60

Gln Ile Asn Ser Glu Leu Thr Glu Cys His Ile Arg Gly Ile Ala Val
65                  70                  75                  80

Thr Thr Phe Gly Val Asp Gly Ala Leu Val Asp Lys Gln Gly Asn Leu
                85                  90                  95

Leu Tyr Pro Ile Ile Ser Trp Lys Cys Pro Arg Thr Ala Ala Val Met
            100                 105                 110

Asp Asn Ile Glu Arg Leu Ile Ser Ala Gln Arg Leu Gln Ala Ile Ser
        115                 120                 125
```

```
Gly Val Gly Ala Phe Ser Phe Asn Thr Leu Tyr Lys Leu Val Trp Leu
            130                 135                 140

Lys Glu Asn His Pro Gln Leu Leu Glu Arg Ala His Ala Trp Leu Phe
145                 150                 155                 160

Ile Ser Ser Leu Ile Asn His Arg Leu Thr Gly Glu Phe Thr Thr Asp
                165                 170                 175

Ile Thr Met Ala Gly Thr Ser Gln Met Leu Asp Ile Gln Gln Arg Asp
            180                 185                 190

Phe Ser Pro Gln Ile Leu Gln Ala Thr Gly Ile Pro Arg Arg Leu Phe
        195                 200                 205

Pro Arg Leu Val Glu Ala Gly Glu Gln Ile Gly Thr Leu Gln Asn Ser
210                 215                 220

Ala Ala Ala Met Leu Gly Leu Pro Val Gly Ile Pro Val Ile Ser Ala
225                 230                 235                 240

Gly His Asp Thr Gln Phe Ala Leu Phe Gly Ala Gly Ala Glu Gln Asn
                245                 250                 255

Glu Pro Val Leu Ser Ser Gly Thr Trp Glu Ile Leu Met Val Arg Ser
            260                 265                 270

Ala Gln Val Asp Thr Ser Leu Leu Ser Gln Tyr Ala Gly Ser Thr Cys
        275                 280                 285

Glu Leu Asp Ser Gln Ala Gly Leu Tyr Asn Pro Gly Met Gln Trp Leu
290                 295                 300

Ala Ser Gly Val Leu Glu Trp Val Arg Lys Leu Phe Trp Thr Ala Glu
305                 310                 315                 320

Thr Pro Trp Gln Met Leu Ile Glu Glu Ala Arg Leu Ile Ala Pro Gly
                325                 330                 335

Ala Asp Gly Val Lys Met Gln Cys Asp Leu Leu Ser Cys Gln Asn Ala
            340                 345                 350

Gly Trp Gln Gly Val Thr Leu Asn Thr Thr Arg Gly His Phe Tyr Arg
        355                 360                 365

Ala Ala Leu Glu Gly Leu Thr Ala Gln Leu Gln Arg Asn Leu Gln Met
370                 375                 380

Leu Glu Lys Ile Gly His Phe Lys Ala Ser Glu Leu Leu Val Gly
385                 390                 395                 400

Gly Gly Ser Arg Asn Thr Leu Trp Asn Gln Ile Lys Ala Asn Met Leu
                405                 410                 415

Asp Ile Pro Val Lys Val Leu Asp Asp Ala Glu Thr Thr Val Ala Gly
            420                 425                 430

Ala Ala Leu Phe Gly Trp Tyr Gly Val Gly Glu Phe Asn Ser Pro Glu
        435                 440                 445

Glu Ala Arg Ala Gln Ile His Tyr Gln Tyr Arg Tyr Phe Tyr Pro Gln
450                 455                 460

Thr Glu Pro Glu Phe Ile Glu Glu Val
465                 470

<210> SEQ ID NO 9
<211> LENGTH: 648
<212> TYPE: DNA
<213> ORGANISM: Escherichia coli

<400> SEQUENCE: 9
atggaacgaa ataaacttgc tcgtcagatt attgacactt gcctggaaat gacccgcctg      60
ggactgaacc aggggacagc ggggaacgtc agtgtacgtt atcaggatgg gatgctgatt     120
acgcctacag gcattccata tgaaaaactg acggagtcgc atattgtctt tattgatggc     180
```

```
aacggtaaac atgaggaagg aaagctcccc tcaagcgaat ggcgtttcca tatggcagcc        240
tatcaaagca gaccggatgc caacgcggtt gttcacaatc atgccgttca ttgcacggca        300
gtttccattc ttaaccgatc gatccccgct attcactaca tgattgcggc ggctggcggt        360
aattctattc cttgcgcgcc ttatgcgacc tttggaacac gcgaactttc tgaacatgtt        420
gcgctggctc tcaaaaatcg taaggcaact ttgttacaac atcatgggct tatcgcttgt        480
gaggtgaatc tggaaaaagc gttatggctg gcgcatgaag ttgaagtgct ggcgcaactt        540
tacctgacga ccctggcgat tacggacccg gtgccagtgc tgagcgatga agagattgcc        600
gtagtgctgg agaaattcaa aacctatggg ttacgaattg aagagtaa                      648
```

<210> SEQ ID NO 10
<211> LENGTH: 648
<212> TYPE: DNA
<213> ORGANISM: Escherichia coli

<400> SEQUENCE: 10

```
atggaacgaa ataaacttgc tcgtcagatt attgacactt gcctggaaat gacccgcctg         60
ggactgaacc aggggacagc ggggaacgtc agtgtacgtt atcaggatgg gatgctgatt        120
acgcctacag gcattccata tgaaaaactg acggagtcgc atattgtctt tattgatggc        180
aacggtaaac atgaggaagg aaagctcccc tcaagcgaat ggcgtttcca tatggcagcc        240
tatcaaagca gaccggatgc caacgcggtt gttcacaatc atgccgttca ttgcacggca        300
gtttccattc ttaaccgatc gatccccgct attcactaca tgattgcggc ggctggcggt        360
aattctattc cttgcgcgcc ttatgcgacc tttggaacac gcgaactttc tgaacatgtt        420
gcgctggctc tcaaaaatcg taaggcaact ttgttacaac atcatgggct tatcgcttgt        480
gaggtgaatc tggaaaaagc gttatggctg gcgcatgaag ttgaagtgct ggcgcaactt        540
tacctgacga ccctggcgat tacggacccg gtgccagtgc tgagcgatga agagattgcc        600
gtagtgctgg agaaattcaa aacctatggg ttacgaattg aagagtaa                      648
```

<210> SEQ ID NO 11
<211> LENGTH: 215
<212> TYPE: PRT
<213> ORGANISM: Escherichia coli

<400> SEQUENCE: 11

```
Met Glu Arg Asn Lys Leu Ala Arg Gln Ile Ile Asp Thr Cys Leu Glu
1               5                   10                  15

Met Thr Arg Leu Gly Leu Asn Gln Gly Thr Ala Gly Asn Val Ser Val
            20                  25                  30

Arg Tyr Gln Asp Gly Met Leu Ile Thr Pro Thr Gly Ile Pro Tyr Glu
        35                  40                  45

Lys Leu Thr Glu Ser His Ile Val Phe Ile Asp Gly Asn Gly Lys His
    50                  55                  60

Glu Glu Gly Lys Leu Pro Ser Ser Glu Trp Arg Phe His Met Ala Ala
65                  70                  75                  80

Tyr Gln Ser Arg Pro Asp Ala Asn Ala Val Val His Asn His Ala Val
                85                  90                  95

His Cys Thr Ala Val Ser Ile Leu Asn Arg Ser Ile Pro Ala Ile His
            100                 105                 110

Tyr Met Ile Ala Ala Ala Gly Gly Asn Ser Ile Pro Cys Ala Pro Tyr
        115                 120                 125
```

```
Ala Thr Phe Gly Thr Arg Glu Leu Ser Glu His Val Ala Leu Ala Leu
            130                 135                 140

Lys Asn Arg Lys Ala Thr Leu Leu Gln His His Gly Leu Ile Ala Cys
145                 150                 155                 160

Glu Val Asn Leu Glu Lys Ala Leu Trp Leu Ala His Glu Val Glu Val
                165                 170                 175

Leu Ala Gln Leu Tyr Leu Thr Thr Leu Ala Ile Thr Asp Pro Val Pro
            180                 185                 190

Val Leu Ser Asp Glu Glu Ile Ala Val Val Leu Glu Lys Phe Lys Thr
        195                 200                 205

Tyr Gly Leu Arg Ile Glu Glu
    210                 215
```

<210> SEQ ID NO 12
<211> LENGTH: 1104
<212> TYPE: DNA
<213> ORGANISM: Escherichia coli

<400> SEQUENCE: 12

```
atggaccgca ttattcaatc accgggtaaa tacatccagg gcgctgatgt gattaatcgt    60
ctgggcgaat acctgaagcc gctggcagaa cgctggttag tggtgggtga caaatttgtt   120
ttaggttttg ctcaatccac tgtcgagaaa agctttaaag atgctggact ggtagtagaa   180
attgcgccgt ttggcggtga atgttcgcaa atgagatcg accgtctgcg tggcatcgcg   240
gagactgcgc agtgtggcgc aattctcggt atcggtggcg aaaaaccct cgatactgcc   300
aaagcactgg cacatttcat gggtgttccg gtagcgatcg caccgactat cgcctctacc   360
gatgcaccgt gcagcgcatt gtctgttatc taccaccgatg agggtgagtt tgaccgctat   420
ctgctgttgc aaataacccc gaatatggtc attgtcgaca ccaaaatcgt cgctggcgca   480
cctgcacgtc tgttagcggc gggtatcggc gatgcgctgg caacctggtt tgaagcgcgt   540
gcctgctctc gtagcggcgc gaccaccatg gcgggcggca gtgcacccca ggctgcgctg   600
gcactggctg aactgtgcta acacacccctg ctggaagaag gcgaaaaagc gatgcttgct   660
gccgaacagc atgtagtgac tccggcgctg gagcgcgtga ttgaagcgaa cacctatttg   720
agcggtgttg gttttgaaag tggtggtctg gctgcggcgc acgcagtgca taacggcctg   780
accgctatcc cggacgcgca tcactattat cacggtgaaa agtggcatt cggtacgctg   840
acgcagctgg ttctggaaaa tgcgccggtg gaggaaatcg aaaccgtagc tgcccttagc   900
catgcggtag gtttgccaat aactctcgct caactggata ttaaagaaga tgtcccggcg   960
aaaatgcgaa ttgtggcaga gcggcatgt gcagaaggtg aaaccattca caacatgcct  1020
ggcggcgcga cgccagatca ggtttacgcc gctctgctgg tagccgacca gtacggtcag  1080
cgtttcctgc aagagtggga ataa                                         1104
```

<210> SEQ ID NO 13
<211> LENGTH: 367
<212> TYPE: PRT
<213> ORGANISM: Escherichia coli

<400> SEQUENCE: 13

```
Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
```

```
              35                  40                  45
Glu Lys Ser Phe Lys Asp Ala Gly Leu Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
            115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
            195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His Tyr Tyr His Gly
            260                 265                 270

Glu Lys Val Ala Phe Gly Thr Leu Thr Gln Leu Val Leu Glu Asn Ala
            275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
    355                 360                 365

<210> SEQ ID NO 14
<211> LENGTH: 1029
<212> TYPE: DNA
<213> ORGANISM: Saccharomyces cerevisiae

<400> SEQUENCE: 14
atgtcagttt tcgtttcagg tgctaacggg ttcattgccc aacacattgt cgatctcctg      60
ttgaaggaag actataaggt catcggttct gccagaagtc aagaaaaggc cgagaattta     120
acggaggcct ttggtaacaa cccaaaaatt ccatggaag ttgtcccaga catatctaag     180
ctggacgcat tgaccatgt tttccaaaag cacggcaagg atatcaagat agttctacat     240
acggcctctc cattctgctt tgatatcact gacagtgaac gcgatttatt aattcctgct     300
```

```
gtgaacggtg ttaagggaat tctccactca attaaaaaat acgccgctga ttctgtagaa      360
cgtgtagttc tcacctcttc ttatgcagct gtgttcgata tggcaaaaga aaacgataag      420
tctttaacat ttaacgaaga atcctggaac ccagctacct gggagagttg ccaaagtgac      480
ccagttaacg cctactgtgg ttctaagaag tttgctgaaa aagcagcttg ggaatttcta      540
gaggagaata gagactctgt aaaattcgaa ttaactgccg ttaacccagt ttacgttttt      600
ggtccgcaaa tgtttgacaa agatgtgaaa aaacacttga acacatcttg cgaactcgtc      660
aacagcttga tgcatttatc accagaggac aagataccgg aactatttgg tggatacatt      720
gatgttcgtg atgttgcaaa ggctcattta gttgccttcc aaaagaggga aacaattggt      780
caaagactaa tcgtatcgga ggccagattt actatgcagg atgttctcga tatccttaac      840
gaagacttcc ctgttctaaa aggcaatatt ccagtgggga aaccaggttc tggtgctacc      900
cataacaccc ttggtgctac tcttgataat aaaaagagta agaaattgtt aggtttcaag      960
ttcaggaact tgaaagagac cattgacgac actgcctccc aaattttaaa atttgagggc     1020
agaatataa                                                              1029
```

<210> SEQ ID NO 15
<211> LENGTH: 342
<212> TYPE: PRT
<213> ORGANISM: Saccharomyces cerevisiae

<400> SEQUENCE: 15

```
Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240
```

```
Asp Val Arg Asp Val Ala Lys Ala His Leu Val Ala Phe Gln Lys Arg
            245                 250                 255

Glu Thr Ile Gly Gln Arg Leu Ile Val Ser Glu Ala Arg Phe Thr Met
        260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
        290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340
```

<210> SEQ ID NO 16
<211> LENGTH: 984
<212> TYPE: DNA
<213> ORGANISM: Saccharomyces cerevisiae

<400> SEQUENCE: 16

```
atgtcttcac tggttactct taataacggt ctgaaaatgc ccctagtcgg cttagggtgc        60
tggaaaattg acaaaaaagt ctgtgcgaat caaatttatg aagctatcaa attaggctac       120
cgtttattcg atggtgcttg cgactacggc aacgaaaagg aagttggtga aggtatcagg       180
aaagccatct ccgaaggtct tgtttctaga aggagatatat tgttgtttc aaagttatgg       240
aacaattttc accatcctga tcatgtaaaa ttagctttaa agaagacctt aagcgatatg       300
ggacttgatt atttagacct gtattatatt cacttcccaa tcgccttcaa atatgttcca       360
tttgaagaga atacccctcc aggattctat acgggcgcag atgacgagaa gaaaggtcac       420
atcaccgaag cacatgtacc aatcatagat acgtaccggg ctctggaaga atgtgttgat       480
gaaggcttga ttaagtctat tggtgttttcc aactttcagg gaagcttgat tcaagattta       540
ttacgtggtt gtagaatcaa gcccgtggct ttgcaaattg aacaccatcc ttatttgact       600
caagaacacc tagttgagtt ttgtaaatta cacgatatcc aagtagttgc ttactcctcc       660
ttcggtcctc aatcattcat tgagatggac ttacagttgg caaaaaccac gccaactctg       720
ttcgagaatg atgtaatcaa gaaggtctca caaaaccatc caggcagtac cacttcccaa       780
gtattgctta gatgggcaac tcagagaggc attgccgtca ttccaaaatc ttccaagaag       840
gaaaggttac ttggcaacct agaaatcgaa aaaagttca ctttaacgga gcaagaattg       900
aaggatattt ctgcactaaa tgccaacatc agatttaatg atccatggac ctggttggat       960
ggtaaattcc ccacttttgc ctga                                             984
```

<210> SEQ ID NO 17
<211> LENGTH: 327
<212> TYPE: PRT
<213> ORGANISM: Saccharomyces cerevisiae

<400> SEQUENCE: 17

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
```

```
                35                  40                  45
Tyr Gly Asn Glu Lys Glu Val Gly Glu Gly Ile Arg Lys Ala Ile Ser
 50                  55                  60

Glu Gly Leu Val Ser Arg Lys Asp Ile Phe Val Ser Lys Leu Trp
 65                  70                  75                  80

Asn Asn Phe His His Pro Asp His Val Lys Leu Ala Leu Lys Lys Thr
                 85                  90                  95

Leu Ser Asp Met Gly Leu Asp Tyr Leu Asp Leu Tyr Tyr Ile His Phe
                100                 105                 110

Pro Ile Ala Phe Lys Tyr Val Pro Phe Glu Glu Lys Tyr Pro Pro Gly
                115                 120                 125

Phe Tyr Thr Gly Ala Asp Asp Glu Lys Lys Gly His Ile Thr Glu Ala
130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
                180                 185                 190

Ile Glu His His Pro Tyr Leu Thr Gln Glu His Leu Val Glu Phe Cys
                195                 200                 205

Lys Leu His Asp Ile Gln Val Val Ala Tyr Ser Ser Phe Gly Pro Gln
210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
                260                 265                 270

Val Ile Pro Lys Ser Ser Lys Lys Glu Arg Leu Leu Gly Asn Leu Glu
                275                 280                 285

Ile Glu Lys Lys Phe Thr Leu Thr Glu Gln Glu Leu Lys Asp Ile Ser
                290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 18
<211> LENGTH: 1164
<212> TYPE: DNA
<213> ORGANISM: Escherichia coli

<400> SEQUENCE: 18
atgaacaact taatctgca caccccaacc cgcattctgt ttggtaaagg cgcaatcgct    60
ggtttacgcg aacaaattcc tcacgatgct cgcgtattga ttacctacgg cggcggcagc   120
gtgaaaaaaa ccggcgttct cgatcaagtt ctggatgccc tgaaaggcat ggacgtgctg   180
gaatttggcg gtattgagcc aaaccccggct tatgaaacgc tgatgaacgc cgtgaaactg   240
gttcgcgaac agaaagtgac tttcctgctg gcggttggcg gcggttctgt actggacggc   300
accaaattta tcgccgcagc ggctaactat ccggaaaata tcgatccgtg gcacattctg   360
caaacgggcg gtaagagat taaagcgcc atccgatgg ctgtgtgct gacgctgcca   420 gcaaccggtt cagaatccaa cgcagaagcg gtgatctccc gtaaaaccac aggcgacaag   480
```

```
caggcgttcc attctgccca tgttcagccg gtatttgccg tgctcgatcc ggtttatacc      540
tacaccctgc cgccgcgtca ggtggctaac ggcgtagtgg acgcctttgt acacaccgtg      600
gaacagtatg ttaccaaacc ggttgatgcc aaaattcagg accgtttcgc agaaggcatt      660
ttgctgacgc taatcgaaga tggtccgaaa gccctgaaag agccagaaaa ctacgatgtg      720
cgcgccaacg tcatgtgggc ggcgactcag gcgctgaacg gtttgattgg cgctggcgta      780
ccgcaggact gggcaacgca tatgctgggc acgaactga ctgcgatgca cggtctggat       840
cacgcgcaaa cactggctat cgtcctgcct gcactgtgga atgaaaaacg cgataccaag      900
cgcgctaagc tgctgcaata tgctgaacgc gtctggaaca tcactgaagg ttccgatgat      960
gagcgtattg acgccgcgat tgccgcaacc cgcaatttct ttgagcaatt aggcgtgccg     1020
acccacctct ccgactacgg tctggacggc agctccatcc cggctttgct gaaaaaactg     1080
gaagagcacg gcatgaccca actgggcgaa atcatgaca ttacgttgga tgtcagccgc      1140
cgtatatacg aagccgcccg ctaa                                            1164
```

```
<210> SEQ ID NO 19
<211> LENGTH: 1167
<212> TYPE: DNA
<213> ORGANISM: Escherichia coli

<400> SEQUENCE: 19
```

```
atgaacaatt ttaatttgca tactccaact agaatattat ttggaaaagg tgcaattgca       60
ggtttaaggg aacaaatacc acatgatgca agggtattaa tcacatacgg tggtggttct      120
gtcaagaaaa ctggtgtatt ggatcaagta ttggatgctt taagggtat ggatgtcttg       180 gaatttggag gaatcgaacc aaaccctgct tacgagactt aatgaatgc tgtcaaattg       240 gtcagagaac aaaaggtaac attcttattg gctgttggag gtggatcagt attagatggt      300
acaaagttca ttgctgctgc agcaaattat ccagaaaaca ttgatccatg gcatatattg      360
caaactggtg gtaaggaaat aaagtcagct atcccaatgg gatgtgtttt gacattgcct      420
gcaacaggat cagaatcaaa cgctgaagca gtcatctcaa gaaagactac aggtgacaaa      480
caggcattcc attctgccca tgtccaacct gtatttgctg ttttagaccc tgtatacact      540
tacacattac caccaaggca gtcgcaaat ggagttgtcg atgcctttgt tcacactgta       600
gaacagtacg tcaccaaacc agtcgatgca aagatccagg acaggtttgc agaaggtatt      660
ttattgacat taatcgaaga tggaccaaaa gcattgaaag agccagagaa ctatgacgtt      720
agggcaaatg ttatgtgggc tgctacccag gcattgaacg gtttaattgg tgcaggagtt      780
ccacaagatt gggctacaca catgttgggt cacgagttga ccgccatgca cggtttggac      840
catgcacaga ctttagccat tgttttgcct gccttatgga acgagaaaag agatactaag      900
agggctaagt tattacaata cgctgaaagg gtttggaata tcaccgaggg atctgatgat      960
gaaaggattg atgccgctat tgcagccact agaaacttct ttgaacaatt aggtgttcca     1020
actcacttgt ctgactatgg tttagatgga tcatctattc cagctttgtt gaagaaattg     1080
gaagagcacg gtatgaccca gttgggtgag aatcatgata taaccttaga tgtatctagg     1140
agaatctacg aggctgctag ataatga                                         1167
```

```
<210> SEQ ID NO 20
<211> LENGTH: 387
<212> TYPE: PRT
<213> ORGANISM: Escherichia coli
```

<400> SEQUENCE: 20

```
Met Asn Asn Phe Asn Leu His Thr Pro Thr Arg Ile Leu Phe Gly Lys
1               5                   10                  15
Gly Ala Ile Ala Gly Leu Arg Glu Gln Ile Pro His Asp Ala Arg Val
            20                  25                  30
Leu Ile Thr Tyr Gly Gly Gly Ser Val Lys Lys Thr Gly Val Leu Asp
        35                  40                  45
Gln Val Leu Asp Ala Leu Lys Gly Met Asp Val Leu Glu Phe Gly Gly
    50                  55                  60
Ile Glu Pro Asn Pro Ala Tyr Glu Thr Leu Met Asn Ala Val Lys Leu
65                  70                  75                  80
Val Arg Glu Gln Lys Val Thr Phe Leu Leu Ala Val Gly Gly Gly Ser
                85                  90                  95
Val Leu Asp Gly Thr Lys Phe Ile Ala Ala Ala Asn Tyr Pro Glu
            100                 105                 110
Asn Ile Asp Pro Trp His Ile Leu Gln Thr Gly Gly Lys Glu Ile Lys
            115                 120                 125
Ser Ala Ile Pro Met Gly Cys Val Leu Thr Leu Pro Ala Thr Gly Ser
    130                 135                 140
Glu Ser Asn Ala Glu Ala Val Ile Ser Arg Lys Thr Thr Gly Asp Lys
145                 150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
            180                 185                 190
Val Asp Ala Phe Val His Thr Val Glu Gln Tyr Val Thr Lys Pro Val
        195                 200                 205
Asp Ala Lys Ile Gln Asp Arg Phe Ala Glu Gly Ile Leu Leu Thr Leu
    210                 215                 220
Ile Glu Asp Gly Pro Lys Ala Leu Lys Glu Pro Glu Asn Tyr Asp Val
225                 230                 235                 240
Arg Ala Asn Val Met Trp Ala Ala Thr Gln Ala Leu Asn Gly Leu Ile
                245                 250                 255
Gly Ala Gly Val Pro Gln Asp Trp Ala Thr His Met Leu Gly His Glu
            260                 265                 270
Leu Thr Ala Met His Gly Leu Asp His Ala Gln Thr Leu Ala Ile Val
        275                 280                 285
Leu Pro Ala Leu Trp Asn Glu Lys Arg Asp Thr Lys Arg Ala Lys Leu
    290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
        355                 360                 365
Gly Glu Asn His Asp Ile Thr Leu Asp Val Ser Arg Arg Ile Tyr Glu
    370                 375                 380
Ala Ala Arg
385
```

<210> SEQ ID NO 21

```
<211> LENGTH: 1164
<212> TYPE: DNA
<213> ORGANISM: Escherichia coli

<400> SEQUENCE: 21
atgaacaact taatctgca caccccaacc cgcattctgt ttggtaaagg cgcaatcgct      60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc acgaactga ctgcgatgca cggtctggat    840
cacgcgcaaa cactggctat cgtcctgcct gcactgtgga tgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa atcatgaca ttacgttgga tgtcagccgc   1140
cgtatatacg aagccgcccg ctaa                                           1164

<210> SEQ ID NO 22
<211> LENGTH: 1164
<212> TYPE: DNA
<213> ORGANISM: Escherichia coli

<400> SEQUENCE: 22
atgaacaact taatctgca caccccaacc cgcattctgt ttggtaaagg cgcaatcgct      60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
```

```
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa atcatgaca ttacgttgga tgtcagccgc   1140
cgtatatacg aagccgcccg ctaa                                          1164
```

<210> SEQ ID NO 23
<211> LENGTH: 387
<212> TYPE: PRT
<213> ORGANISM: Escherichia coli

<400> SEQUENCE: 23

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300
```

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 24
<211> LENGTH: 981
<212> TYPE: DNA
<213> ORGANISM: Escherichia coli

<400> SEQUENCE: 24
atgaaaaaga tacctttagg cacaacggat attacgcttt cgcgaatggg gttggggaca      60
tgggccattg gcggcggtcc tgcatggaat ggcgatctcg atcggcaaat atgtattgat     120
acgattcttg aagcccatcg ttgtggcatt aatctgattg atactgcgcc aggatataac     180
tttggcaata gtgaagttat cgtcggtcag gcgttaaaaa aactgccccg tgaacaggtt     240
gtagtagaaa ccaaatgcgg cattgtctgg aacgaaaag gaagtttatt caacaaagtt     300
ggcgatcggc agttgtataa aaacctttcc ccggaatcta tccgcgaaga ggtagcagcg     360
agcttgcaac gtctgggtat tgattacatc gatatctaca tgacgcactg gcagtcggtg     420
ccgccatttt ttacgccgat cgctgaaact gtcgcagtgc ttaatgagtt aaagtctgaa     480
gggaaaattc gcgctatagg cgctgctaac gtcgatgctg accatatccg cgagtatctg     540
caatatggtg aactggatat tattcaggcg aaatacagta tcctcgaccg ggcaatggaa     600
aacgaactgc tgccactatg tcgtgataat ggcattgtgg ttcaggttta ttcccccgcta    660 gagcagggat tgttgaccgg caccatcact cgtgattacg ttccgggcgg cgctcgggca     720
aataaagtct ggttccagcg tgaaaacatg ctgaaagtga ttgatatgct gaacagtgg     780 cagccacttt gtgctcgtta tcagtgcaca attcccactc tggcactggc gtggatatta     840
aaacagagtg atttaatctc cattcttagt gggctactg caccggaaca ggtacgcgaa     900
aatgtcgcgg cactgaatat caacttatcg gatgcagacg caacattgat gagggaaatg     960
gcagaggccc tggagcgtta a                                                981

<210> SEQ ID NO 25
<211> LENGTH: 326
<212> TYPE: PRT
<213> ORGANISM: Escherichia coli

<400> SEQUENCE: 25

Met Lys Lys Ile Pro Leu Gly Thr Thr Asp Ile Thr Leu Ser Arg Met
1               5                   10                  15

Gly Leu Gly Thr Trp Ala Ile Gly Gly Pro Ala Trp Asn Gly Asp
            20                  25                  30

Leu Asp Arg Gln Ile Cys Ile Asp Thr Ile Leu Glu Ala His Arg Cys
        35                  40                  45

Gly Ile Asn Leu Ile Asp Thr Ala Pro Gly Tyr Asn Phe Gly Asn Ser

```
        50                  55                  60
Glu Val Ile Val Gly Gln Ala Leu Lys Lys Leu Pro Arg Glu Gln Val
65                  70                  75                  80

Val Val Glu Thr Lys Cys Gly Ile Val Trp Glu Arg Lys Gly Ser Leu
                85                  90                  95

Phe Asn Lys Val Gly Asp Arg Gln Leu Tyr Lys Asn Leu Ser Pro Glu
            100                 105                 110

Ser Ile Arg Glu Glu Val Ala Ala Ser Leu Gln Arg Leu Gly Ile Asp
        115                 120                 125

Tyr Ile Asp Ile Tyr Met Thr His Trp Gln Ser Val Pro Pro Phe Phe
    130                 135                 140

Thr Pro Ile Ala Glu Thr Val Ala Val Leu Asn Glu Leu Lys Ser Glu
145                 150                 155                 160

Gly Lys Ile Arg Ala Ile Gly Ala Ala Asn Val Asp Ala Asp His Ile
                165                 170                 175

Arg Glu Tyr Leu Gln Tyr Gly Glu Leu Asp Ile Ile Gln Ala Lys Tyr
            180                 185                 190

Ser Ile Leu Asp Arg Ala Met Glu Asn Glu Leu Leu Pro Leu Cys Arg
        195                 200                 205

Asp Asn Gly Ile Val Val Gln Val Tyr Ser Pro Leu Glu Gln Gly Leu
    210                 215                 220

Leu Thr Gly Thr Ile Thr Arg Asp Tyr Val Pro Gly Gly Ala Arg Ala
225                 230                 235                 240

Asn Lys Val Trp Phe Gln Arg Glu Asn Met Leu Lys Val Ile Asp Met
                245                 250                 255

Leu Glu Gln Trp Gln Pro Leu Cys Ala Arg Tyr Gln Cys Thr Ile Pro
            260                 265                 270

Thr Leu Ala Leu Ala Trp Ile Leu Lys Gln Ser Asp Leu Ile Ser Ile
        275                 280                 285

Leu Ser Gly Ala Thr Ala Pro Glu Gln Val Arg Glu Asn Val Ala Ala
    290                 295                 300

Leu Asn Ile Asn Leu Ser Asp Ala Asp Ala Thr Leu Met Arg Glu Met
305                 310                 315                 320

Ala Glu Ala Leu Glu Arg
            325

<210> SEQ ID NO 26
<211> LENGTH: 1149
<212> TYPE: DNA
<213> ORGANISM: Escherichia coli

<400> SEQUENCE: 26
atggctaaca gaatgattct gaacgaaacg gcatggtttg gtcggggtgc tgttggggct      60
ttaaccgatg aggtgaaacg ccgtggttat cagaaggcgc tgatcgtcac cgataaaacg     120
ctggtgcaat gcggcgtggt ggcgaaagtg accgataaga tggatgctgc agggctggca     180
tgggcgattt acgacggcgt agtgcccaac ccaacaatta ctgtcgtcaa agaagggctc     240
ggtgtattcc agaatagcgg cgcggattac ctgatcgcta ttggtggtgg ttctccacag     300
gatacttgta aagcgattgg cattatcagc aacaacccgg agtttgccga tgtgcgtagc     360
ctggaagggc tttccccgac caataaaccc agtgtaccga ttctggcaat tcctaccaca     420
gcaggtactg cggcagaagt gaccattaac tacgtgatca ctgacgaaga gaacggcgc      480 aagtttgttt gcgttgatcc gcatgatatc ccgcaggtgg cgtttattga cgctgacatg     540
```

```
atggatggta tgcctccagc gctgaaagct gcgacgggtg tcgatgcgct cactcatgct    600 attgagpggt atattacccg tggcgcgtgg gcgctaaccg atgcactgca cattaaagcg    660
attgaaatca ttgctggggc gctgcgagga tcggttgctg gtgataagga tgccggagaa    720
gaaatggcgc tcgggcagta tgttgcgggt atgggcttct cgaatgttgg gttaggttg     780 gtgcatggta tggcgcatcc actgggcgcg ttttataaca ctccacacgg tgttgcgaac    840
gccatcctgt taccgcatgt catgcgttat aacgctgact ttaccggtga aagtaccgc     900 gatatcgcgc gcgttatggg cgtgaaagtg aaggtatga gcctggaaga ggcgcgtaat    960
gccgctgttg aagcggtgtt tgctctcaac cgtgatgtcg gtattccgcc acatttgcgt   1020
gatgttggtg tacgcaagga agacattccg gcactggcgc aggcggcact ggatgatgtt   1080
tgtaccggtg caacccgcg tgaagcaacg cttgaggata ttgtagagct ttaccatacc    1140
gcctggtaa                                                           1149
```

<210> SEQ ID NO 27
<211> LENGTH: 1149
<212> TYPE: DNA
<213> ORGANISM: Escherichia coli

<400> SEQUENCE: 27

```
atggctaaca gaatgattct gaacgaaacg gcatggtttg gtcggggtgc tgttggggct     60
ttaaccgatg aggtgaaacg ccgtggttat cagaaggcgc tgatcgtcac cgataaaacg    120
ctggtgcaat gcggcgtggt ggcgaaagtg accgataaga tggatgctgc agggctggca    180
tgggcgattt acgacggcgt agtgcccaac ccaacaatta ctgtcgtcaa agaagggctc    240
ggtgtattcc agaatagcgg cgcggattac ctgatcgcta ttggtggtgg ttctccacag    300
gatacttgta aagcgattgg cattatcagc aacaacccgg agtttgccga tgtgcgtagc    360
ctggaagggc tttccccgac caataaaccc agtgtaccga ttctggcaat tcctaccaca    420
gcaggtactg cggcagaagt gaccattaac tacgtgatca ctgacgaaga gaaacggcgc    480
aagtttgttt gcgttgatcc gcatgatatc ccgcaggtgg cgtttattga cgctgacatg    540
atggatggta tgcctccagc gctgaaagct gcgacgggtg tcgatgcgct cactcatgct    600 attgagggt atattacccg tggcgcgtgg gcgctaaccg atgcactgca cattaaagcg     660
attgaaatca ttgctggggc gctgcgagga tcggttgctg gtgataagga tgccggagaa    720
gaaatggcgc tcgggcagta tgttgcgggt atgggcttct cgaatgttgg gttaggttg     780 gtgcatggta tggcgcatcc actgggcgcg ttttataaca ctccacacgg tgttgcgaac    840
gccatcctgt taccgcatgt catgcgttat aacgctgact ttaccggtga aagtaccgc     900 gatatcgcgc gcgttatggg cgtgaaagtg aaggtatga gcctggaaga ggcgcgtaat    960
gccgctgttg aagcggtgtt tgctctcaac cgtgatgtcg gtattccgcc acatttgcgt   1020
gatgttggtg tacgcaagga agacattccg gcactggcgc aggcggcact ggatgatgtt   1080
tgtaccggtg caacccgcg tgaagcaacg cttgaggata ttgtagagct ttaccatacc    1140
gcctggtaa                                                           1149
```

<210> SEQ ID NO 28
<211> LENGTH: 382
<212> TYPE: PRT
<213> ORGANISM: Escherichia coli

<400> SEQUENCE: 28

Met Ala Asn Arg Met Ile Leu Asn Glu Thr Ala Trp Phe Gly Arg Gly

```
1               5                    10                   15
Ala Val Gly Ala Leu Thr Asp Glu Val Lys Arg Gly Tyr Gln Lys
                    20                   25                   30

Ala Leu Ile Val Thr Asp Lys Thr Leu Val Gln Cys Gly Val Val Ala
                    35                   40                   45

Lys Val Thr Asp Lys Met Asp Ala Ala Gly Leu Ala Trp Ala Ile Tyr
 50                      55                   60

Asp Gly Val Val Pro Asn Pro Thr Ile Thr Val Val Lys Glu Gly Leu
 65                      70                   75                   80

Gly Val Phe Gln Asn Ser Gly Ala Asp Tyr Leu Ile Ala Ile Gly Gly
                    85                   90                   95

Gly Ser Pro Gln Asp Thr Cys Lys Ala Ile Gly Ile Ile Ser Asn Asn
                    100                  105                  110

Pro Glu Phe Ala Asp Val Arg Ser Leu Glu Gly Leu Ser Pro Thr Asn
                    115                  120                  125

Lys Pro Ser Val Pro Ile Leu Ala Ile Pro Thr Thr Ala Gly Thr Ala
 130                     135                  140

Ala Glu Val Thr Ile Asn Tyr Val Ile Thr Asp Glu Glu Lys Arg Arg
 145                     150                  155                  160

Lys Phe Val Cys Val Asp Pro His Asp Ile Pro Gln Val Ala Phe Ile
                    165                  170                  175

Asp Ala Asp Met Met Asp Gly Met Pro Pro Ala Leu Lys Ala Ala Thr
                    180                  185                  190

Gly Val Asp Ala Leu Thr His Ala Ile Glu Gly Tyr Ile Thr Arg Gly
                    195                  200                  205

Ala Trp Ala Leu Thr Asp Ala Leu His Ile Lys Ala Ile Glu Ile Ile
 210                     215                  220

Ala Gly Ala Leu Arg Gly Ser Val Ala Gly Asp Lys Asp Ala Gly Glu
 225                     230                  235                  240

Glu Met Ala Leu Gly Gln Tyr Val Ala Gly Met Gly Phe Ser Asn Val
                    245                  250                  255

Gly Leu Gly Leu Val His Gly Met Ala His Pro Leu Gly Ala Phe Tyr
                    260                  265                  270

Asn Thr Pro His Gly Val Ala Asn Ala Ile Leu Leu Pro His Val Met
                    275                  280                  285

Arg Tyr Asn Ala Asp Phe Thr Gly Glu Lys Tyr Arg Asp Ile Ala Arg
 290                     295                  300

Val Met Gly Val Lys Val Glu Gly Met Ser Leu Glu Glu Ala Arg Asn
 305                     310                  315                  320

Ala Ala Val Glu Ala Val Phe Ala Leu Asn Arg Asp Val Gly Ile Pro
                    325                  330                  335

Pro His Leu Arg Asp Val Gly Val Arg Lys Glu Asp Ile Pro Ala Leu
                    340                  345                  350

Ala Gln Ala Ala Leu Asp Asp Val Cys Thr Gly Gly Asn Pro Arg Glu
                    355                  360                  365

Ala Thr Leu Glu Asp Ile Val Glu Leu Tyr His Thr Ala Trp
 370                     375                  380
```

<210> SEQ ID NO 29
<211> LENGTH: 804
<212> TYPE: DNA
<213> ORGANISM: Escherichia coli

<400> SEQUENCE: 29

```
atggctatcc ctgcatttgg tttaggtact ttccgtctga agacgacgt tgttatttca    60
tctgtgataa cggcgcttga acttggttat cgcgcaattg ataccgcaca atctatgat   120
aacgaagccg cagtaggtca ggcgattgca gaaagtggcg tgccacgtca tgaactctac   180
atcaccacta aaatctggat tgaaaatctc agcaaagaca aattgatccc aagtctgaaa   240
gagagcctgc aaaaattgcg taccgattat gttgatctga cgctaatcca ctggccgtca   300
ccaaacgatg aagtctctgt tgaagagttt atgcaggcgc tgctggaagc caaaaaacaa   360
gggctgacgc gtgagatcgg tatttccaac ttcacgatcc cgttgatgga aaaagcgatt   420
gctgctgttg gtgctgaaaa catcgctact aaccagattg aactctctcc ttatctgcaa   480
aaccgtaaag tggttgcctg ggctaaacag cacggcatcc atattacttc ctatatgacg   540
ctggcgtatg gtaaggccct gaaagatgag gttattgctc gtatcgcagc taaacacaat   600
gcgactccgg cacaagtgat tctggcgtgg gctatggggg aaggttactc agtaattcct   660
tcttctacta acgtaaaaaa cctggaaagt aatcttaagg cacaaaattt acagcttgat   720
gccgaagata aaaagcgat cgccgcactg gattgcaacg accgcctggt tagcccggaa   780
ggtctggctc ctgaatggga ttaa                                          804
```

<210> SEQ ID NO 30
<211> LENGTH: 267
<212> TYPE: PRT
<213> ORGANISM: Escherichia coli

<400> SEQUENCE: 30

```
Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
                20                  25                  30

Ile Asp Thr Ala Gln Ile Tyr Asp Asn Glu Ala Ala Val Gly Gln Ala
            35                  40                  45

Ile Ala Glu Ser Gly Val Pro Arg His Glu Leu Tyr Ile Thr Thr Lys
        50                  55                  60

Ile Trp Ile Glu Asn Leu Ser Lys Asp Lys Leu Ile Pro Ser Leu Lys
65                  70                  75                  80

Glu Ser Leu Gln Lys Leu Arg Thr Asp Tyr Val Asp Leu Thr Leu Ile
                85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
    130                 135                 140

Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
                165                 170                 175

Ser Tyr Met Thr Leu Ala Tyr Gly Lys Ala Leu Lys Asp Glu Val Ile
            180                 185                 190

Ala Arg Ile Ala Ala Lys His Asn Ala Thr Pro Ala Gln Val Ile Leu
        195                 200                 205

Ala Trp Ala Met Gly Glu Gly Tyr Ser Val Ile Pro Ser Ser Thr Lys
    210                 215                 220

Arg Lys Asn Leu Glu Ser Asn Leu Lys Ala Gln Asn Leu Gln Leu Asp
```

```
                    225                 230                 235                 240

Ala Glu Asp Lys Lys Ala Ile Ala Ala Leu Asp Cys Asn Asp Arg Leu
                        245                 250                 255

Val Ser Pro Glu Gly Leu Ala Pro Glu Trp Asp
                260                 265

<210> SEQ ID NO 31
<211> LENGTH: 828
<212> TYPE: DNA
<213> ORGANISM: Escherichia coli

<400> SEQUENCE: 31
atggctaatc caaccgttat taagctacag gatggcaatg tcatgcccca gctgggactg      60
ggcgtctggc aagcaagtaa tgaggaagta atcaccgcca ttcaaaaagc gttagaagtg     120
ggttatcgct cgattgatac cgccgcggcc tacaagaacg aagaaggtgt cggcaaagcc     180
ctgaaaaatg cctcagtcaa cagagaagaa ctgttcatca ccactaagct gtggaacgac     240
gaccacaagc gcccccgcga agccctgctc gacagcctga aaaaactcca gcttgattat     300
atcgacctct acttaatgca ctggcccgtt ccgctatcg accattatgt cgaagcatgg      360
aaaggcatga tcgaattgca aaaagaggga ttaatcaaaa gcatcggcgt gtgcaacttc     420
cagatccatc acctgcaacg cctgattgat gaaactggcg tgacgcctgt gataaaccag     480
atcgaacttc atccgctgat gcaacaacgc cagctcacg cctggaacgc acacacaaa      540 atccagaccg aatcctggag cccattagcg caaggaggga aggcgtttt cgatcagaaa     600 gtcattcgcg atctggcaga taaatacggc aaaaccccgg cgcagattgt tatccgctgg     660
catctggata gcggcctggt ggtgatcccg aaatcggtca caccttcacg tattgccgaa     720
aactttgatg tctgggattt ccgtctcgac aaagacgaac tcggcgaaat tgcaaaactc     780
gatcagggca agcgtctcgg tcccgatcct gaccagttcg gcggctaa                 828

<210> SEQ ID NO 32
<211> LENGTH: 275
<212> TYPE: PRT
<213> ORGANISM: Escherichia coli

<400> SEQUENCE: 32

Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
                20                  25                  30

Ala Ile Gln Lys Ala Leu Glu Val Gly Tyr Arg Ser Ile Asp Thr Ala
            35                  40                  45

Ala Ala Tyr Lys Asn Glu Glu Gly Val Gly Lys Ala Leu Lys Asn Ala
        50                  55                  60

Ser Val Asn Arg Glu Glu Leu Phe Ile Thr Thr Lys Leu Trp Asn Asp
65                  70                  75                  80

Asp His Lys Arg Pro Arg Glu Ala Leu Leu Asp Ser Leu Lys Lys Leu
                85                  90                  95

Gln Leu Asp Tyr Ile Asp Leu Tyr Leu Met His Trp Pro Val Pro Ala
                100                 105                 110

Ile Asp His Tyr Val Glu Ala Trp Lys Gly Met Ile Glu Leu Gln Lys
            115                 120                 125

Glu Gly Leu Ile Lys Ser Ile Gly Val Cys Asn Phe Gln Ile His His
        130                 135                 140
```

```
Leu Gln Arg Leu Ile Asp Glu Thr Gly Val Thr Pro Val Ile Asn Gln
145                 150                 155                 160

Ile Glu Leu His Pro Leu Met Gln Gln Arg Gln Leu His Ala Trp Asn
                165                 170                 175

Ala Thr His Lys Ile Gln Thr Glu Ser Trp Ser Pro Leu Ala Gln Gly
            180                 185                 190

Gly Lys Gly Val Phe Asp Gln Lys Val Ile Arg Asp Leu Ala Asp Lys
        195                 200                 205

Tyr Gly Lys Thr Pro Ala Gln Ile Val Ile Arg Trp His Leu Asp Ser
    210                 215                 220

Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
                260                 265                 270

Phe Gly Gly
        275

<210> SEQ ID NO 33
<211> LENGTH: 1179
<212> TYPE: DNA
<213> ORGANISM: Clostridium acetobutylicum

<400> SEQUENCE: 33
atgaaagaag ttgtaatagc tagtgcagta agaacagcga ttggatctta tggaaagtct      60
cttaaggatg taccagcagt agatttagga gctacagcta taaggaagc agttaaaaaa     120 gcaggaataa accgagga tgttaatgaa gtcattttag gaaatgttct tcaagcaggt     180
ttaggacaga atccagcaag acaggcatct tttaaagcag gattaccagt tgaaattcca     240
gctatgacta ttaataaggt ttgtggttca ggacttagaa cagttagctt agcagcacaa     300
attataaaag caggagatgc tgacgtaata atagcaggtg gtatggaaaa tatgtctaga     360
gctccttact tagcgaataa cgctagatgg ggatatagaa tgggaaacgc taaatttgtt     420
gatgaaatga tcactgacgg attgtgggat gcatttaatg attaccacat gggaataaca     480
gcagaaaaca tagctgagag atggaacatt tcaagagaag aacaagatga gtttgctctt     540
gcatcacaaa aaaagctga agaagctata aaatcaggtc aatttaaaga tgaaatagtt     600
cctgtagtaa ttaaaggcag aaagggagaa actgtagttg atacagatga gcaccctaga     660
tttggatcaa ctatagaagg acttgcaaaa ttaaaacctg ccttcaaaaa agatggaaca     720
gttacagctg gtaatgcatc aggattaaat gactgtgcag cagtacttgt aatcatgagt     780
gcagaaaaag ctaaagagct tggagtaaaa ccacttgcta gatagtttc ttatggttca     840 gcaggagttg acccagcaat aatgggatat ggaccttct atgcaacaaa agcagctatt     900
gaaaaagcag gttggacagt tgatgaatta gatttaatag aatcaaatga gcttttgca     960 gctcaaagtt tagcagtagc aaaagattta aaatttgata tgaataaagt aaatgtaaat    1020
ggaggagcta ttgcccttgg tcatccaatt ggagcatcag gtgcaagaat actcgttact    1080
cttgtacacg caatgcaaaa aagagatgca aaaaaaggct agcaactttt atgtataggt    1140
ggcggacaag gaacagcaat attgctagaa aagtgctag                         1179

<210> SEQ ID NO 34
<211> LENGTH: 1179
<212> TYPE: DNA
```

<213> ORGANISM: Clostridium acetobutylicum

<400> SEQUENCE: 34

```
atgaaagaag ttgttattgc gagcgcggtt cgtaccgcga ttggcagcta tggcaagagc      60
ctgaaggatg ttccggcggt ggacctgggt gcgaccgcga tcaaagaggc ggttaagaaa     120
gcgggcatta accggagga tgtgaacgaa gttatcctgg taacgtgct caagcgggt      180
ctgggccaaa accggcgcg tcaggcgagc ttcaaggcgg cctgccggt tgaaatcccg     240
gcgatgacca ttaacaaagt ttgcggtagc ggcctgcgta ccgtgagcct ggcggcgcaa    300
atcattaagg cgggtgacgc ggatgttatc attgcgggtg gcatggagaa catgagccgt    360
gcgccgtacc tggcgaacaa cgcgcgttgg ggttatcgta tgggcaacgc gaaattcgtg    420
gacgaaatga ttaccgacgg tctgtgggat gcgtttaacg actaccacat gggcatcacc    480
gcggagaaca ttgcggaacg ttggaacatt agccgtgagg aacaagatga gttcgcgctg    540
gcgagccaga agaaagcgga ggaagcgatc aagagcggcc agtttaaaga cgaaatcgtt    600
ccggtggtta ttaagggtcg taagggtgaa accgtggtgg acaccgatga acacccgcgt    660
ttcggtagca ccattgaggg cctggccgaag ctgaaaccgg cgtttaagaa agatggcacc    720
gtgaccgcgg gtaacgcgag cggcctgaac gactgcgcgg cggtgctggt tatcatgagc    780
gcggagaagg cgaaagaact gggtgtgaag ccgctggcga aaattgttag ctacggtagc    840
gcgggtgtgg acccggcgat catgggttac ggcccgtttt atgcgaccaa gcggcgatt    900
gagaaagcgg gttggaccgt ggacgaactg gatctgatcg agagcaacga agcgttcgcg    960
gcgcaaagcc tggcggtggc gaaggatctg aaatttgaca tgaacaaggt gaacgtgaac   1020
ggtggtgcga ttgcgctggg tcacccgatt ggtgcgagcg gcgcgcgtat cctggtgacc   1080
ctggttcacg cgatgcagaa acgtgacgcg aagaaaggtc tggcgaccct gtgcattggt   1140
ggtggtcaag gcaccgcgat tctgctggaa aagtgctaa                           1179
```

<210> SEQ ID NO 35
<211> LENGTH: 392
<212> TYPE: PRT
<213> ORGANISM: Clostridium acetobutylicum

<400> SEQUENCE: 35

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140
```

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
            165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
            245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
            325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 36
<211> LENGTH: 1185
<212> TYPE: DNA
<213> ORGANISM: Escherichia coli

<400> SEQUENCE: 36
atgaaaaatt gtgtcatcgt cagtgcggta cgtactgcta tcggtagttt taacggttca      60
ctcgcttcca ccagcgccat cgacctgggg gcgacagtaa ttaaagccgc cattgaacgt     120
gcaaaaatcg attcacaaca cgttgatgaa gtgattatgg gtaacgtgtt acaagccggg     180
ctggggcaaa tccggcgcg tcaggcactg ttaaaaagcg ggctggcaga aacggtgtgc     240
ggattcacgg tcaataaagt atgtggttcg ggtcttaaaa gtgtggcgct tgccgcccag     300
gccattcagg caggtcaggc gcagagcatt gtggcggggg gtatggaaaa tatgagttta     360 gcccctact tactcgatgc aaaagcacgc tctggttatc gtcttggaga cggacaggtt     420
tatgacgtaa tcctgcgcga tggcctgatg tgcgccaccc atggttatca tatgggatt     480 accgccgaaa acgtggctaa agagtacgga attacccgtg aaatgcagga tgaactggcg     540
ctacattcac agcgtaaagc ggcagccgca attgagtccg tgcttttac agccgaaatc     600 gtcccggtaa atgttgtcac tcgaaagaaa accttcgtct tcagtcaaga cgaattcccg     660
aaagcgaatt caacggctga agcgttaggt gcattgcgcc cggccttcga taaagcagga     720

```
acagtcaccg ctgggaacgc gtctggtatt aacgacggtg ctgccgctct ggtgattatg    780
gaagaatctg cggcgctggc agcaggcctt accccctgg ctcgcattaa aagttatgcc    840
agcggtggcg tgcccccgc attgatgggt atggggccag tacctgccac gcaaaaagcg    900
ttacaactgg cggggctgca actggcggat attgatctca ttgaggctaa tgaagcattt    960
gctgcacagt tccttgccgt tgggaaaaac ctgggctttg attctgagaa agtgaatgtc   1020
aacggcgggg ccatcgcgct cgggcatcct atcggtgcca gtggtgctcg tattctggtc   1080
acactattac atgccatgca ggcacgcgat aaaacgctgg ggctggcaac actgtgcatt   1140
ggcggcggtc agggaattgc gatggtgatt gaacggttga attaa                   1185
```

<210> SEQ ID NO 37
<211> LENGTH: 394
<212> TYPE: PRT
<213> ORGANISM: Escherichia coli

<400> SEQUENCE: 37

```
Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285
```

```
Met Gly Met Gly Pro Val Pro Ala Thr Gln Lys Ala Leu Gln Leu Ala
290                 295                 300
Gly Leu Gln Leu Ala Asp Ile Asp Leu Ile Glu Ala Asn Glu Ala Phe
305                 310                 315                 320
Ala Ala Gln Phe Leu Ala Val Gly Lys Asn Leu Gly Phe Asp Ser Glu
                325                 330                 335
Lys Val Asn Val Asn Gly Gly Ala Ile Ala Leu Gly His Pro Ile Gly
                340                 345                 350
Ala Ser Gly Ala Arg Ile Leu Val Thr Leu Leu His Ala Met Gln Ala
            355                 360                 365
Arg Asp Lys Thr Leu Gly Leu Ala Thr Leu Cys Ile Gly Gly Gly Gln
370                 375                 380
Gly Ile Ala Met Val Ile Glu Arg Leu Asn
385                 390
```

<210> SEQ ID NO 38
<211> LENGTH: 1197
<212> TYPE: DNA
<213> ORGANISM: Saccharomyces cerevisiae

<400> SEQUENCE: 38

```
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttttgg taacgttctt     180
tctgccaatt gggccaagc tccggccaga caagttgctt tggctgccgg tttgagtaat     240
catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga aagagatggg ttgaacgatg cgtacgatgg tctagccatg     480
ggtgtacacg cagaaaagtg tgcccgtgat tgggatatta ctagagaaca acaagacaat     540
tttgccatcg aatcctacca aaatctcaa aatctcaaa aggaaggtaa attcgacaat     600
gaaattgtac ctgttaccat taagggattt agaggtaagc ctgatactca agtcacgaag     660
gacgaggaac ctgctagatt acacgttgaa aaattgagat ctgcaaggac tgttttccaa     720
aaagaaaacg gtactgttac tgccgctaac gcttctccaa tcaacgatgg tgctgcagcc     780
gtcatcttgg tttccgaaaa agttttgaag gaaagaatt tgaagccttt ggctattatc     840
aaaggttggg gtgaggccgc tcatcaacca gctgatttta catgggctcc atctcttgca     900
gttccaaagg ctttgaaaca tgctggcatc gaagacatca attctgttga ttactttgaa     960
ttcaatgaag ccttttcggt tgtcggtttg gtgaacacta gattttgaa gctagaccca    1020
tctaaggtta atgtatatgg tggtgctgtt gctctaggtc acccattggg ttgttctggt    1080
gctagagtgg ttgttacact gctatccatc ttacagcaag aaggaggtaa gatcggtgtt    1140
gccgccattt gtaatggtgg tggtggtgct tcctctattg tcattgaaaa gatatga      1197
```

<210> SEQ ID NO 39
<211> LENGTH: 1197
<212> TYPE: DNA
<213> ORGANISM: Saccharomyces cerevisiae

<400> SEQUENCE: 39

```
atgtctcaga acgtttacat tgtatcgact gccagaaccc caattggttc attccagggt      60
```

```
tctctatcct ccaagacagc agtggaattg ggtgctgttg ctttaaaagg cgccttggct      120
aaggttccag aattggatgc atccaaggat tttgacgaaa ttattttttgg taacgttctt     180 tctgccaatt tgggccaagc tccggccaga caagttgctt tggctgccgg tttgagtaat     240
catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga agagatgggt tgaacgatg cgtacgatgg tctagccatg     480
ggtgtacacg cagaaaagtg tgcccgtgat tgggatatta ctagagaaca acaagacaat     540
tttgccatcg aatcctacca aaaatctcaa aaatctcaaa aggaaggtaa attcgacaat     600
gaaattgtac ctgttaccat taagggattt agaggtaagc ctgatactca agtcacgaag     660
gacgaggaac ctgctagatt acacgttgaa aaattgagat ctgcaaggac tgttttccaa     720
aaagaaaacg gtactgttac tgccgctaac gcttctccaa tcaacgatgg tgctgcagcc     780
gtcatcttgg tttccgaaaa agttttgaag gaaaagaatt tgaagccttt ggctattatc     840
aaaggttggg gtgaggccgc tcatcaacca gctgattta catgggctcc atctcttgca     900
gttccaaagg ctttgaaaca tgctggcatc gaagacatca attctgttga ttactttgaa     960
ttcaatgaag cctttttcggt tgtcggtttg gtgaacacta agattttgaa gctagaccca    1020
tctaaggtta atgtatatgg tggtgctgtt gctctaggtc acccattggg ttgttctggt    1080
gctagagtgg ttgttacact gctatccatc ttacagcaag aaggaggtaa gatcggtgtt    1140
gccgccattt gtaatggtgg tggtggtgct cctctctattg tcattgaaaa gatatga      1197
```

<210> SEQ ID NO 40
<211> LENGTH: 398
<212> TYPE: PRT
<213> ORGANISM: Saccharomyces cerevisiae
<400> SEQUENCE: 40

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175
```

```
Gln Gln Asp Asn Phe Ala Ile Glu Ser Tyr Gln Lys Ser Gln Lys Ser
                180                 185                 190

Gln Lys Glu Gly Lys Phe Asp Asn Glu Ile Val Pro Val Thr Ile Lys
            195                 200                 205

Gly Phe Arg Gly Lys Pro Asp Thr Gln Val Thr Lys Asp Glu Glu Pro
210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
            275                 280                 285

Gln Pro Ala Asp Phe Thr Trp Ala Pro Ser Leu Ala Val Pro Lys Ala
290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Thr Leu Leu
            355                 360                 365

Ser Ile Leu Gln Gln Glu Gly Gly Lys Ile Gly Val Ala Ala Ile Cys
370                 375                 380

Asn Gly Gly Gly Gly Ala Ser Ser Ile Val Ile Glu Lys Ile
385                 390                 395

<210> SEQ ID NO 41
<211> LENGTH: 651
<212> TYPE: DNA
<213> ORGANISM: Escherichia coli

<400> SEQUENCE: 41
atggatgcga acaacgtat  tgcgcgccgt gtggcgcaag agcttcgtga tggtgacatc    60
gttaacttag ggatcggttt acccacaatg gtcgccaatt atttaccgga gggtattcat   120
atcactctgc aatcggaaaa cggcttcctc ggtttaggcc cggtcacgac agcgcatcca   180
gatctggtga acgctggcgg gcaaccgtgc ggtgttttac ccggtgcagc catgtttgat   240
agcgccatgt catttgcgct aatccgtggc ggtcatattg atgcctgcgt gctcggcggt   300
ttgcaagtag acgaagaagc aaacctcgcg aactgggtag tgcctgggaa atggtgccc    360
ggtatgggtg gcgcgatgga tctggtgacc gggtcgcgca aagtgatcat cgccatggaa   420
cattgcgcca agatggttc  agcaaaaatt ttgcgccgct gcaccatgcc actcactgcg   480
caacatgcgg tgcatatgct ggttactgaa ctggctgtct tcgttttat  tgacggcaaa   540
atgtggctca ccgaaattgc cgacgggtgt gatttagcca ccgtgcgtgc caaaacagaa   600
gctcggtttg aagtcgccgc cgatctgaat acgcaacggg gtgatttatg a           651

<210> SEQ ID NO 42
<211> LENGTH: 651
<212> TYPE: DNA
<213> ORGANISM: Escherichia coli

<400> SEQUENCE: 42
```

```
atggatgcga acaacgtat tgcgcgccgt gtggcgcaag agcttcgtga tggtgacatc      60
gttaacttag ggatcggttt acccacaatg gtcgccaatt atttaccgga gggtattcat    120
atcactctgc aatcggaaaa cggcttcctc ggtttaggcc cggtcacgac agcgcatcca    180
gatctggtga acgctggcgg gcaaccgtgc ggtgttttac ccggtgcagc catgtttgat    240
agcgccatgt catttgcgct aatccgtggc ggtcatattg atgcctgcgt gctcggcggt    300
ttgcaagtag acgaagaagc aaacctcgcg aactgggtag tgcctgggaa aatggtgccc    360
ggtatgggtg gcgcgatgga tctggtgacc gggtcgcgca agtgatcat cgccatggaa     420
cattgcgcca agatggttc agcaaaaatt ttgcgccgct gcaccatgcc actcactgcg    480
caacatgcgg tgcatatgct ggttactgaa ctggctgtct ttcgttttat tgacggcaaa    540
atgtggctca ccgaaattgc cgacgggtgt gatttagcca ccgtgcgtgc caaaacagaa    600
gctcggtttg aagtcgccgc cgatctgaat acgcaacggg gtgatttatg a             651
```

<210> SEQ ID NO 43
<211> LENGTH: 216
<212> TYPE: PRT
<213> ORGANISM: Escherichia coli

<400> SEQUENCE: 43

```
Met Asp Ala Lys Gln Arg Ile Ala Arg Val Ala Gln Glu Leu Arg
1               5                   10                  15
Asp Gly Asp Ile Val Asn Leu Gly Ile Gly Leu Pro Thr Met Val Ala
                20                  25                  30
Asn Tyr Leu Pro Glu Gly Ile His Ile Thr Leu Gln Ser Glu Asn Gly
            35                  40                  45
Phe Leu Gly Leu Gly Pro Val Thr Thr Ala His Pro Asp Leu Val Asn
        50                  55                  60
Ala Gly Gly Gln Pro Cys Gly Val Leu Pro Gly Ala Ala Met Phe Asp
65                  70                  75                  80
Ser Ala Met Ser Phe Ala Leu Ile Arg Gly Gly His Ile Asp Ala Cys
                85                  90                  95
Val Leu Gly Gly Leu Gln Val Asp Glu Glu Ala Asn Leu Ala Asn Trp
            100                 105                 110
Val Val Pro Gly Lys Met Val Pro Gly Met Gly Gly Ala Met Asp Leu
        115                 120                 125
Val Thr Gly Ser Arg Lys Val Ile Ala Met Glu His Cys Ala Lys
    130                 135                 140
Asp Gly Ser Ala Lys Ile Leu Arg Arg Cys Thr Met Pro Leu Thr Ala
145                 150                 155                 160
Gln His Ala Val His Met Leu Val Thr Glu Leu Ala Val Phe Arg Phe
                165                 170                 175
Ile Asp Gly Lys Met Trp Leu Thr Glu Ile Ala Asp Gly Cys Asp Leu
            180                 185                 190
Ala Thr Val Arg Ala Lys Thr Glu Ala Arg Phe Glu Val Ala Ala Asp
        195                 200                 205
Leu Asn Thr Gln Arg Gly Asp Leu
    210                 215
```

<210> SEQ ID NO 44
<211> LENGTH: 663
<212> TYPE: DNA
<213> ORGANISM: Escherichia coli

<400> SEQUENCE: 44

```
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat tcgctgtggt ggagctggac ttggtggttt tctcacccca   360
acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaaccccct gatagccctt   540
gcggctgata tcacgctggt agagccagat gaactggtcg aaaccggcga gctgcaacct   600
gaccatattg tcacccctgg tgccgttatc gaccacatca tcgtttcaca ggagagcaaa   660
taa                                                                 663
```

<210> SEQ ID NO 45
<211> LENGTH: 663
<212> TYPE: DNA
<213> ORGANISM: Escherichia coli

<400> SEQUENCE: 45

```
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat tcgctgtggt ggagctggac ttggtggttt tctcacccca   360
acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaaccccct gatagccctt   540
gcggctgata tcacgctggt agagccagat gaactggtcg aaaccggcga gctgcaacct   600
gaccatattg tcacccctgg tgccgttatc gaccacatca tcgtttcaca ggagagcaaa   660
taa                                                                 663
```

<210> SEQ ID NO 46
<211> LENGTH: 220
<212> TYPE: PRT
<213> ORGANISM: Escherichia coli

<400> SEQUENCE: 46

```
Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
                20                  25                  30

Ser Arg Leu Val Glu Ala Leu Leu Glu Ser Gly Val Arg Asp Leu Thr
            35                  40                  45

Leu Ile Ala Asn Asp Thr Ala Phe Val Asp Thr Gly Ile Gly Pro Leu
        50                  55                  60

Ile Val Asn Gly Arg Val Arg Lys Val Ile Ala Ser His Ile Gly Thr
```

```
            65                  70                  75                  80
Asn Pro Glu Thr Gly Arg Arg Met Ile Ser Gly Glu Met Asp Val Val
                    85                  90                  95

Leu Val Pro Gln Gly Thr Leu Ile Glu Gln Ile Arg Cys Gly Gly Ala
                100                 105                 110

Gly Leu Gly Gly Phe Leu Thr Pro Thr Gly Val Gly Thr Val Val Glu
                115                 120                 125

Glu Gly Lys Gln Thr Leu Thr Leu Asp Gly Lys Thr Trp Leu Leu Glu
            130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
                180                 185                 190

Val Glu Thr Gly Glu Leu Gln Pro Asp His Ile Val Thr Pro Gly Ala
                195                 200                 205

Val Ile Asp His Ile Ile Val Ser Gln Glu Ser Lys
            210                 215                 220

<210> SEQ ID NO 47
<211> LENGTH: 735
<212> TYPE: DNA
<213> ORGANISM: Clostridium acetobutylicum

<400> SEQUENCE: 47
atgttaaagg atgaagtaat taaacaaatt agcacgccat taacttcgcc tgcatttcct        60
agaggaccct ataaatttca taatcgtgag tattttaaca ttgtatatcg tacagatatg       120
gatgcacttc gtaaagttgt gccagagcct ttagaaattg atgagccctt agtcaggttt       180
gaaattatgg caatgcatga tacgagtgga cttggttgtt atacagaaag cggacaggct       240
attcccgtaa gctttaatgg agttaaggga gattatcttc atatgatgta tttagataat       300
gagcctgcaa ttgcagtagg aagggaatta agtgcatatc ctaaaaagct cgggtatcca       360 aagcttttg tggattcaga tactttagta ggaactttag actatggaaa acttagagtt        420
gcgacagcta caatggggta caaacataaa gccttagatg ctaatgaagc aaaggatcaa       480
atttgtcgcc ctaattatat gttgaaaata tacccaattt atgatggaag ccctagaata       540
tgtgagctta taaatgcgaa aatcacagat gttaccgtac atgaagcttg acaggacca        600 actcgactgc agttatttga tcacgctatg gcgccactta atgatttgcc agtaaaagag       660
attgtttcta gctctcacat tcttgcagat ataatattgc ctagagctga agttatatat       720
gattatctta agtaa                                                        735

<210> SEQ ID NO 48
<211> LENGTH: 735
<212> TYPE: DNA
<213> ORGANISM: Clostridium acetobutylicum

<400> SEQUENCE: 48
atgctgaagg acgaggttat taagcagatt agcaccccgc tgaccagccc ggcgttcccg        60
cgtggtccgt acaagttcca taatcgcgaa tacttcaaca ttgtgtatcg taccgacatg       120
gatgcgctgc gtaaggtggt tccggagccg ctggaaattg acgagccgct ggttcgtttc       180
gaaatcatgg cgatgcacga taccagcggt ctgggctgct acaccgagag cggtcaggcg       240
```

-continued

```
attccggtga gctttaacgg tgttaaaggc gactacctgc acatgatgta tctggataac    300
gaaccggcga ttgcggtggg tcgtgagctg agcgcgtacc cgaagaaact gggctatccg    360
aagctgttcg tggacagcga taccctggtg gcaccctgg actacggcaa actgcgtgtt    420
gcgaccgcga ccatgggcta taagcacaaa gcgctggacg cgaacgaagc gaaggatcag    480
atttgccgtc cgaactacat gctgaaaatc attccgaact atgacggtag cccgcgtatc    540
tgcgaactga ttaacgcgaa gatcaccgat gttaccgttc atgaggcgtg gaccggcccg    600
acccgtctgc aactgtttga ccacgcgatg gcgccgctga cgatctgcc ggtgaaagag    660 atcgttagca gcagccacat cctggcggac atcatcctgc cgcgtgcgga agttatctac    720
gattacctga agtaa                                                     735
```

<210> SEQ ID NO 49
<211> LENGTH: 244
<212> TYPE: PRT
<213> ORGANISM: Clostridium acetobutylicum

<400> SEQUENCE: 49

```
Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys
```

<210> SEQ ID NO 50
<211> LENGTH: 741
<212> TYPE: DNA
<213> ORGANISM: Clostridium beijerinckii -continued

<400> SEQUENCE: 50
atgttagaaa gtgaagtatc taaacaaatt acaactccac ttgctgctcc agcgtttcct 60
agaggaccat ataggtttca caatagagaa tatctaaaca ttatttatcg aactgattta 120
gatgctcttc gaaaaatagt accagagcca cttgaattag atagagcata tgttagattt 180
gaaatgatgg ctatgcctga tacaaccgga ctaggctcat atacagaatg tggtcaagct 240
attccagtaa aatataatgg tgttaagggt gactacttgc atatgatgta tctagataat 300
gaacctgcta ttgctgttgg aagagaaagt agcgcttatc caaaaaagct tggctatcca 360
aagctatttg ttgattcaga tactttagtt gggacactta aatatggtac attaccagta 420
gctactgcaa caatgggata taagcacgag cctctagatc ttaaagaagc ctatgctcaa 480
attgcaagac ccaattttat gctaaaaatc attcaaggtt acgatggtaa gccaagaatt 540
tgtgaactaa tatgtgcaga aaatactgat ataactattc acggtgcttg gactggaagt 600
gcacgtctac aattatttag ccatgcacta gctcctcttg ctgatttacc tgtattagag 660
attgtatcag catctcatat cctcacagat ttaactcttg gaacacctaa ggttgtacat 720
gattatcttt cagtaaaata a 741

<210> SEQ ID NO 51
<211> LENGTH: 741
<212> TYPE: DNA
<213> ORGANISM: Clostridium beijerinckii

<400> SEQUENCE: 51
atgctggaga gcgaagttag caaacaaatc accaccccgc tggcggcgcc ggcgttcccg 60
cgtggcccgt accgttttca taaccgtgag tacctgaaca tcatttatcg taccgacctg 120
gatgcgctgc gtaagattgt gccggagccg ctggaactgg accgtgcgta cgttcgtttc 180
gagatgatgg cgatgccgga taccaccggt ctgggcagct acaccgaatg cggtcaggcg 240
atcccggtga agtataacgg tgttaaaggc gactacctgc acatgatgta tctggataac 300
gagccggcga ttgcggtggg tcgtgaaagc agcgcgtacc cgaagaaact gggctatccg 360
aagctgtttg tggacagcga taccctggtg ggcaccctga aatatggcac cctgccggtt 420
gcgaccgcga ccatgggcta caagcacgag ccgctggacc tgaaagaagc gtatgcgcag 480
attgcgcgtc cgaacttcat gctgaagatc attcaaggtt atgacggcaa accgcgtatc 540
tgcgagctga tttgcgcgga aaacaccgat atcaccatcc atggtgcgtg gaccggcagc 600
gcgcgtctgc aactgtttag ccatgcgctg gcgccgctgg cggatctgcc ggtgctggaa 660
atcgttagcg cgagccacat tctgaccgat ctgaccctgg gcaccccgaa ggttgtgcat 720
gactatctga gcgtgaagta a 741

<210> SEQ ID NO 52
<211> LENGTH: 246
<212> TYPE: PRT
<213> ORGANISM: Clostridium beijerinckii

<400> SEQUENCE: 52

Met Leu Glu Ser Glu Val Ser Lys Gln Ile Thr Thr Pro Leu Ala Ala
1               5                   10                  15

Pro Ala Phe Pro Arg Gly Pro Tyr Arg Phe His Asn Arg Glu Tyr Leu
            20                  25                  30

Asn Ile Ile Tyr Arg Thr Asp Leu Asp Ala Leu Arg Lys Ile Val Pro
        35                  40                  45

```
Glu Pro Leu Glu Leu Asp Arg Ala Tyr Val Arg Phe Glu Met Met Ala
    50                  55                  60
Met Pro Asp Thr Thr Gly Leu Gly Ser Tyr Thr Glu Cys Gly Gln Ala
65                  70                  75                  80
Ile Pro Val Lys Tyr Asn Gly Val Lys Gly Asp Tyr Leu His Met Met
                85                  90                  95
Tyr Leu Asp Asn Glu Pro Ala Ile Ala Val Gly Arg Glu Ser Ser Ala
            100                 105                 110
Tyr Pro Lys Lys Leu Gly Tyr Pro Lys Leu Phe Val Asp Ser Asp Thr
            115                 120                 125
Leu Val Gly Thr Leu Lys Tyr Gly Thr Leu Pro Val Ala Thr Ala Thr
        130                 135                 140
Met Gly Tyr Lys His Glu Pro Leu Asp Leu Lys Glu Ala Tyr Ala Gln
145                 150                 155                 160
Ile Ala Arg Pro Asn Phe Met Leu Lys Ile Ile Gln Gly Tyr Asp Gly
                165                 170                 175
Lys Pro Arg Ile Cys Glu Leu Ile Cys Ala Glu Asn Thr Asp Ile Thr
            180                 185                 190
Ile His Gly Ala Trp Thr Gly Ser Ala Arg Leu Gln Leu Phe Ser His
        195                 200                 205
Ala Leu Ala Pro Leu Ala Asp Leu Pro Val Leu Glu Ile Val Ser Ala
        210                 215                 220
Ser His Ile Leu Thr Asp Leu Thr Leu Gly Thr Pro Lys Val Val His
225                 230                 235                 240

Asp Tyr Leu Ser Val Lys
            245

<210> SEQ ID NO 53
<211> LENGTH: 897
<212> TYPE: DNA
<213> ORGANISM: Homo sapiens

<400> SEQUENCE: 53
atggaagaga agcagatcct gtgcgtgggg ctagtggtgc tggacgtcat cagcctggtg      60
gacaagtacc ctaaggagga ctcggagata aggtgtttgt cccagagatg gcagcgcgga     120
ggcaacgcgt ccaactcctg caccgttctc tccctgctcg agccccctg tgccttcatg      180
ggctcaatgg ctcctggcca tgttgctgat tttgtcctgg atgacctccg ccgctattct     240
gtggacctac gctacacagt ctttcagacc acaggctccg tccccatcgc acggtcatc      300
atcaacgagg ccagtggtag ccgcaccatc ctatactatg acaggagcct gccagatgtg     360
tctgctacag actttgagaa ggttgatctg acccagttca gtggatcca cattgagggc      420
cggaacgcat cggagcaggt gaagatgctg cagcggatag acgcacacaa caccaggcag     480
cctccagagc agaagatccg ggtgtccgtg gaggtggaga gccacgaga ggagctcttc      540
cagctgtttg ctacggaga cgtggtgttt gtcagcaaag atgtggccaa gcacttgggg     600
ttccagtcag cagaggaagc cttgaggggc ttgtatggtc gtgtgaggaa aggggctgtg     660
cttgtctgtg cctgggctga ggagggcgcc gacgccctgg ccctgatgg caaattgctc      720
cactcggatg ctttcccgcc accccgcgtg gtggatacac tggagctgg agacaccttc     780
aatgcctccg tcatcttcag cctctcccag gggaggagcg tgcaggaagc actgagattc     840
gggtgccagg tggccggcaa gaagtgtggc ctgcagggct tgatggcat cgtttaa         897

<210> SEQ ID NO 54
```

<211> LENGTH: 897
<212> TYPE: DNA
<213> ORGANISM: Homo sapiens

<400> SEQUENCE: 54

```
atggaggaaa agcaaattct gtgcgttggt ctggtggttc tggacgtgat tagcctggtt      60
gataagtacc cgaaagagga tagcgaaatc cgttgcctga gccagcgttg gcaacgtggt     120
ggcaacgcga gcaatagctg caccgttctg agcctgctgg gtgcgccgtg cgcgttcatg     180
ggtagcatgg cgccgggtca tgttgcggac ttcctggtgg cggatttccg tcgtcgtggt     240
gtggacgtta gccaggttgc gtggcaaagc aagggcgata ccccgagctc ctgctgcatc     300
attaacaaca gcaacggtaa ccgtaccatt gtgctgcacg acaccagcct gccggatgtt     360
agcgcgaccg acttcgagaa ggtggatctg acccagttta atggattca cattgagggc      420
cgtaacgcga gcgaacaggt taaaatgctg caacgtattg atgcgcacaa cacccgtcag     480
ccgccggaac aaaagattcg tgtgagcgtt gaggtggaaa accgcgtga ggaactgttc      540
caactgtttg gttacggcga cgtggttttc gttagcaagg atgtggcgaa acacctgggt     600
tttcaaagcg cggaggaagc gctgcgtggt ctgtatggcc gtgtgcgtaa aggcgcggtt     660
ctggtgtgcg cgtgggcgga ggaaggcgcg gatgcgctgg gtccggatgg caaactgctg     720
cacagcgatg cgttcccgcc gccgcgtgtg gttgacaccc tgggtgcggg cgataccttc     780
aacgcgagcg ttatctttag cctgagccag ggccgtagcg tgcaagaggc gctgcgtttc     840
ggctgccaag ttgcgggtaa aaaatgcggt ctgcaaggct tgacggtat cgtgtaa        897
```

<210> SEQ ID NO 55
<211> LENGTH: 298
<212> TYPE: PRT
<213> ORGANISM: Homo sapiens

<400> SEQUENCE: 55

```
Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30

Leu Ser Gln Arg Trp Gln Arg Gly Gly Asn Ala Ser Asn Ser Cys Thr
        35                  40                  45

Val Leu Ser Leu Leu Gly Ala Pro Cys Ala Phe Met Gly Ser Met Ala
    50                  55                  60

Pro Gly His Val Ala Asp Phe Leu Val Ala Asp Phe Arg Arg Arg Gly
65                  70                  75                  80

Val Asp Val Ser Gln Val Ala Trp Gln Ser Lys Gly Asp Thr Pro Ser
                85                  90                  95

Ser Cys Cys Ile Ile Asn Asn Ser Asn Gly Asn Arg Thr Ile Val Leu
            100                 105                 110

His Asp Thr Ser Leu Pro Asp Val Ser Ala Thr Asp Phe Glu Lys Val
        115                 120                 125

Asp Leu Thr Gln Phe Lys Trp Ile His Ile Glu Gly Arg Asn Ala Ser
    130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190
```

Lys Asp Val Ala Lys His Leu Gly Phe Gln Ser Ala Glu Glu Ala Leu
        195                 200                 205

Arg Gly Leu Tyr Gly Arg Val Arg Lys Gly Ala Val Leu Val Cys Ala
    210                 215                 220

Trp Ala Glu Gly Ala Asp Ala Leu Gly Pro Asp Gly Lys Leu Leu
225                 230                 235                 240

His Ser Asp Ala Phe Pro Pro Arg Val Val Asp Thr Leu Gly Ala
                245                 250                 255

Gly Asp Thr Phe Asn Ala Ser Val Ile Phe Ser Leu Ser Gln Gly Arg
            260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
    290                 295

<210> SEQ ID NO 56
<211> LENGTH: 1095
<212> TYPE: DNA
<213> ORGANISM: Homo sapiens

<400> SEQUENCE: 56
atggcccacc gatttccagc cctcacccag gagcagaaga aggagctctc agaaattgcc      60
cagagcattg ttgccaatgg aaaggggatc ctggctgcag atgaatctgt aggtaccatg     120
gggaaccgcc tgcagaggat caaggtggaa acactgaag agaaccgccg gcagttccga     180
gaaatcctct tctctgtgga cagttccatc aaccagagca tcgggggtgt gatccttttc     240
cacgagaccc tctaccagaa ggacagccag ggaaagctgt tcagaaacat cctcaaggaa     300
aaggggatcg tggtgggaat caagttagac caaggaggtg ctcctcttgc aggaacaaac     360
aaagaaacca ccattcaagg gcttgatggc ctctcagagc gctgtgctca gtacaagaaa     420
gatggtgttg actttgggaa gtggcgtgct gtgctgagga ttgccgacca gtgtccatcc     480
agcctcgcta tccaggaaaa cgccaacgcc ctggctcgct acgccagcat ctgtcagcag     540
aatggactgg tacctattgt tgaaccagag gtaattcctg atggagacca tgacctggaa     600
cactgccagt atgttactga aggtcctg gctgctgtct acaaggccct gaatgaccat     660
catgtttacc tggagggcac cctgctaaag cccaacatgg tgactgctgg acatgcctgc     720
accaagaagt atactccaga acaagtagct atggccaccg taacagctct ccaccgtact     780
gttcctgcag ctgttcctgg catctgcttt ttgtctggtg gcatgagtga agaggatgcc     840
actctcaacc tcaatgctat caacctttgc cctctaccaa agccctggaa actaagtttc     900
tcttatggac gggccctgca ggccagtgca ctggctgcct ggggtggcaa ggctgcaaac     960
aaggaggcaa cccaggaggc ttttatgaag cgggccatgg ctaactgcca ggcggccaaa    1020
ggacagtatg ttcacacggg ttcttctggg gctgcttcca cccagtcgct cttcacagcc    1080
tgctatacct actag                                                    1095

<210> SEQ ID NO 57
<211> LENGTH: 1095
<212> TYPE: DNA
<213> ORGANISM: Homo sapiens

<400> SEQUENCE: 57
atggcgcacc gttttccggc gctgacccaa gagcagaaga aggagctgag cgagattgcg      60
cagagcatcg tggcgaatgg taaaggtatt ctggcggcgg atgagagcgt tggtaccatg     120

```
ggcaaccgtc tgcagcgtat taaggtggag aacaccgagg aaaaccgtcg tcaattccgt      180
gaaatcctgt ttagcgttga tagcagcatc aaccagagca ttggtggcgt gatcctgttc      240
cacgaaaccc tgtaccagaa ggacagccaa ggtaaactgt ttcgtaacat tctgaaggaa      300
aaaggtattg tggttggcat caagctggat caaggtggcg cgccgctggc gggcaccaac      360
aaggaaacca ccatccaggg tctggacggc ctgagcgaac gttgcgcgca atataagaaa      420
gatggtgttg acttcggcaa gtggcgtgcg gtgctgcgta ttgcggacca gtgcccgagc      480
agcctggcga tccaagaaaa cgcgaacgcg ctggcgcgtt acgcgagcat ctgccagcaa      540
aacggtctgg tgccgattgt tgagccggaa gttatcccgg acggcgatca cgacctggag      600
cactgccagt atgtgaccga aaaggttctg gcggcggtgt acaaagcgct gaacgatcac      660
cacgtttatc tggagggtac cctgctgaaa ccgaacatgg tgaccgcggg ccatgcgtgc      720
accaagaaat acaccccgga acaggtggcg atggcgaccg tgaccgcgct gcaccgtacc      780
gttccggcgg cggtgccggg tatttgcttt ctgagcggtg gcatgagcga agaggacgcg      840
accctgaacc tgaacgcgat caacctgtgc ccgctgccga agccgtggaa actgagcttc      900
agctacggcc gtgcgctgca ggcgagcgcg ctggcggcgt ggggtggcaa ggcggcgaac      960
aaagaggcga cccaagaagc gtttatgaag cgtgcgatgg cgaactgcca ggcggcgaaa     1020
ggtcaatatg tgcataccgg cagcagcggt gcggcgagca cccagagcct gtttaccgcg     1080
tgctatacct attaa                                                      1095
```

<210> SEQ ID NO 58
<211> LENGTH: 364
<212> TYPE: PRT
<213> ORGANISM: Homo sapiens

<400> SEQUENCE: 58

Met Ala His Arg Phe Pro Ala Leu Thr Gln Glu Gln Lys Lys Glu Leu
1               5                   10                  15

Ser Glu Ile Ala Gln Ser Ile Val Ala Asn Gly Lys Gly Ile Leu Ala
                20                  25                  30

Ala Asp Glu Ser Val Gly Thr Met Gly Asn Arg Leu Gln Arg Ile Lys
            35                  40                  45

Val Glu Asn Thr Glu Glu Asn Arg Arg Gln Phe Arg Glu Ile Leu Phe
        50                  55                  60

Ser Val Asp Ser Ser Ile Asn Gln Ser Ile Gly Gly Val Ile Leu Phe
65                  70                  75                  80

His Glu Thr Leu Tyr Gln Lys Asp Ser Gln Gly Lys Leu Phe Arg Asn
                85                  90                  95

Ile Leu Lys Glu Lys Gly Ile Val Val Gly Ile Lys Leu Asp Gln Gly
            100                 105                 110

Gly Ala Pro Leu Ala Gly Thr Asn Lys Glu Thr Thr Ile Gln Gly Leu
        115                 120                 125

Asp Gly Leu Ser Glu Arg Cys Ala Gln Tyr Lys Lys Asp Gly Val Asp
    130                 135                 140

Phe Gly Lys Trp Arg Ala Val Leu Arg Ile Ala Asp Gln Cys Pro Ser
145                 150                 155                 160

Ser Leu Ala Ile Gln Glu Asn Ala Asn Ala Leu Ala Arg Tyr Ala Ser
                165                 170                 175

Ile Cys Gln Gln Asn Gly Leu Val Pro Ile Val Glu Pro Glu Val Ile
            180                 185                 190

Pro Asp Gly Asp His Asp Leu Glu His Cys Gln Tyr Val Thr Glu Lys
            195                 200                 205

Val Leu Ala Ala Val Tyr Lys Ala Leu Asn Asp His His Val Tyr Leu
    210                 215                 220

Glu Gly Thr Leu Leu Lys Pro Asn Met Val Thr Ala Gly His Ala Cys
225                 230                 235                 240

Thr Lys Lys Tyr Thr Pro Glu Gln Val Ala Met Ala Thr Val Thr Ala
                245                 250                 255

Leu His Arg Thr Val Pro Ala Ala Val Pro Gly Ile Cys Phe Leu Ser
            260                 265                 270

Gly Gly Met Ser Glu Glu Asp Ala Thr Leu Asn Leu Asn Ala Ile Asn
        275                 280                 285

Leu Cys Pro Leu Pro Lys Pro Trp Lys Leu Ser Phe Ser Tyr Gly Arg
290                 295                 300

Ala Leu Gln Ala Ser Ala Leu Ala Ala Trp Gly Gly Lys Ala Ala Asn
305                 310                 315                 320

Lys Glu Ala Thr Gln Glu Ala Phe Met Lys Arg Ala Met Ala Asn Cys
                325                 330                 335

Gln Ala Ala Lys Gly Gln Tyr Val His Thr Gly Ser Ser Gly Ala Ala
            340                 345                 350

Ser Thr Gln Ser Leu Phe Thr Ala Cys Tyr Thr Tyr
            355                 360

<210> SEQ ID NO 59
<211> LENGTH: 747
<212> TYPE: DNA
<213> ORGANISM: Caulobacter crescentus

<400> SEQUENCE: 59
atgtcctcag ccatctatcc cagcctgaag gcaagcgcg tcgtcatcac cggcggcggc      60
tcgggcatcg gggccggcct caccgccggc ttcgcccgtc agggcgcgga ggtgatcttc     120
ctcgacatcg ccgacgagga ctccagggct cttgaggcca gctggccgg ctcgccgatc     180 ccgccggtct acaagcgctg cgacctgatg aacctcgagg cgatcaaggc ggtcttcgcc     240
gagatcggcg acgtcgacgt gctggtcaac aacgccggca tgacgaccg ccacaagctg     300 gccgacgtga ccggcgccta tgggacgag cggatcaacg tcaacctgcg ccacatgctg     360
ttctgcaccc aggccgtcgc gccgggcatg aagaagcgtg cggcggggc ggtgatcaac     420 ttcggttcga tcagctggca cctggggctt gaggacctcg tcctctacga accgccaag      480 gccggcatca aggcatgac ccgcgcgctg gcccgggagc tgggtcccga cgacatccgc     540
gtcacctgcg tggtgccggg caacgtcaag accaagcgcc aggagaagtg gtacacgccc     600
gaaggcgagg cccagatcgt ggcggcccaa tgcctgaagg ccgcatcgt cccggagaac     660 gtcgccgcgc tggtgctgtt cctggcctcg gatgacgcgt cgctctgcac cggccacgaa     720
tactggatcg acgccggctg gcgttga                                         747

<210> SEQ ID NO 60
<211> LENGTH: 747
<212> TYPE: DNA
<213> ORGANISM: Caulobacter crescentus

<400> SEQUENCE: 60
atgagcagcg cgatctaccc gagcctgaaa ggtaaacgtg tggtgattac cggcggcggc      60
agcggcattg gtgcgggcct gaccgcgggc ttcgcgcgtc agggtgcgga agtgatcttt     120

-continued

```
ctggacattg cggacgaaga tagccgtgcg ctggaggcgg aactggcggg cagcccgatc      180
ccgccggtgt acaagcgttg cgatctgatg aacctggagg cgatcaaagc ggttttcgcg      240
gaaattggcg acgtggatgt tctggtgaac aacgcgggta cgacgaccg tcacaagctg       300 gcggatgtga ccgtgcgta ttgggatgag cgtattaacg ttaacctgcg tcacatgctg       360
ttctgcaccc aggcggtggc gccgggtatg aagaaacgtg gtggcggtgc ggttatcaac      420
tttggcagca ttagctggca cctgggtctg gaggacctgg tgctgtacga aaccgcgaaa      480
gcgggcatcg agggtatgac ccgtgcgctg gcgcgtgaac tgggtccgga cgatattcgt      540
gtgacctgcg tggttccggg taacgttaag accaaacgtc aagagaagtg gtatacccg      600 gagggtgaag cgcagattgt tgcggcgcaa tgcctgaaag gtcgtattgt tccggaaaac      660
gtggcggcgc tggttctgtt tctggcgagc gatgatgcga gcctgtgcac cggccatgag      720
tattggattg atgcgggctg gcgttaa                                           747
```

<210> SEQ ID NO 61
<211> LENGTH: 248
<212> TYPE: PRT
<213> ORGANISM: Caulobacter crescentus

<400> SEQUENCE: 61

```
Met Ser Ser Ala Ile Tyr Pro Ser Leu Lys Gly Lys Arg Val Val Ile
 1               5                  10                  15

Thr Gly Gly Gly Ser Gly Ile Gly Ala Gly Leu Thr Ala Gly Phe Ala
             20                  25                  30

Arg Gln Gly Ala Glu Val Ile Phe Leu Asp Ile Ala Asp Glu Asp Ser
         35                  40                  45

Arg Ala Leu Glu Ala Glu Leu Ala Gly Ser Pro Ile Pro Pro Val Tyr
     50                  55                  60

Lys Arg Cys Asp Leu Met Asn Leu Glu Ala Ile Lys Ala Val Phe Ala
 65                  70                  75                  80

Glu Ile Gly Asp Val Asp Val Leu Val Asn Asn Ala Gly Asn Asp Asp
                 85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
        115                 120                 125

Gly Met Lys Lys Arg Gly Gly Gly Ala Val Ile Asn Phe Gly Ser Ile
    130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Ala Gln Ile Val Ala
        195                 200                 205

Ala Gln Cys Leu Lys Gly Arg Ile Val Pro Glu Asn Val Ala Ala Leu
    210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245
```

<210> SEQ ID NO 62
<211> LENGTH: 1173
<212> TYPE: DNA
<213> ORGANISM: Haloferax volcanii

<400> SEQUENCE: 62

```
atgagcccccg ccccccaccga catcgtcgag gagttcacgc gccgcgactg gcagggagac      60
gacgtgacgg gcaccgtgcg ggtcgccatg atcggcctcg gctggtggac ccgcgacgag      120
gcgattcccg cggtcgaggc gtccgagttc tgcgagacga cggtcgtcgt cagcagttcg      180
aaggagaaag ccgagggcgc gacggcgttg accgagtcga taacccacgg cctcacctac      240
gacgagttcc acgaggggt cgccgccgac gcctacgacg cggtgtacgt cgtcacgccg      300
aacggtctgc atctcccgta cgtcgagacc gccgccgagt tggggaaggc ggtcctctgc      360
gagaaaccgc tggaagcgtc ggtcgagcgg gccgaaaagc tcgtcgccgc tgcgaccgc      420
gccgacgtgc ccctgatggt cgcctatcgg atgcagaccg agccggccgt ccggcgcgcc      480
cgcgaactcg tcgaggccgg cgtcatcggc gagccggtgt cgtccacgg ccacatgtcc       540
cagcgcctgc tcgacgaggt cgtccccgac cccgaccagt ggcggctcga ccccgaactc      600
tccggcggcg cgaccgtcat ggacatcggg ctctacccgc tgaacaccgc ccggttcgtc      660
ctcgacgccg accccgtccg cgtcagggcg accgcccgcg tcgacgacga ggcgttcgag      720
gccgtcggcg acgagcacgt cagtttcggc gtcgacttcg acgacggcac gctcgcggtc      780
tgcaccgcca gccagtcggc ttaccagttg agccacctcc gggtgaccgg caccgagggc      840
gaactcgaaa tcgagcccgc gttctacaac cgccaaaagc gggggattccg actgtcgtgg      900
ggggaccagt ccgccgacta cgacttcgag caggtaaacc agatgacgga ggagttcgac      960
tacttcgcgt cccggctcct gtcggattcc gaccccgcgc ccgacggcga ccacgcgctc     1020
gtggacatgc gcgcgatgga cgcgatttac gccgcggcg agcgcgggac cgatgtcgcc     1080
gtcgacgccg ccgactccga ttccgccgac tccgattccg ccgacgctgc cgccgccaac     1140
cacgacgccg accccgattc cgacgggacg tag                                  1173
```

<210> SEQ ID NO 63
<211> LENGTH: 390
<212> TYPE: PRT
<213> ORGANISM: Haloferax volcanii

<400> SEQUENCE: 63

```
Met Ser Pro Ala Pro Thr Asp Ile Val Glu Glu Phe Thr Arg Arg Asp
1               5                   10                  15

Trp Gln Gly Asp Asp Val Thr Gly Thr Val Arg Val Ala Met Ile Gly
            20                  25                  30

Leu Gly Trp Trp Thr Arg Asp Glu Ala Ile Pro Ala Val Glu Ala Ser
        35                  40                  45

Glu Phe Cys Glu Thr Thr Val Val Ser Ser Ser Lys Glu Lys Ala
    50                  55                  60

Glu Gly Ala Thr Ala Leu Thr Glu Ser Ile Thr His Gly Leu Thr Tyr
65                  70                  75                  80

Asp Glu Phe His Glu Gly Val Ala Ala Asp Ala Tyr Asp Ala Val Tyr
                85                  90                  95

Val Val Thr Pro Asn Gly Leu His Leu Pro Tyr Val Glu Thr Ala Ala
            100                 105                 110

Glu Leu Gly Lys Ala Val Leu Cys Glu Lys Pro Leu Glu Ala Ser Val
        115                 120                 125
```

```
Glu Arg Ala Glu Lys Leu Val Ala Ala Cys Asp Arg Ala Asp Val Pro
130                 135                 140

Leu Met Val Ala Tyr Arg Met Gln Thr Glu Pro Ala Val Arg Arg Ala
145                 150                 155                 160

Arg Glu Leu Val Glu Ala Gly Val Ile Gly Glu Pro Val Phe Val His
                165                 170                 175

Gly His Met Ser Gln Arg Leu Leu Asp Glu Val Val Pro Asp Pro Asp
            180                 185                 190

Gln Trp Arg Leu Asp Pro Glu Leu Ser Gly Gly Ala Thr Val Met Asp
        195                 200                 205

Ile Gly Leu Tyr Pro Leu Asn Thr Ala Arg Phe Val Leu Asp Ala Asp
210                 215                 220

Pro Val Arg Val Arg Ala Thr Ala Arg Val Asp Asp Glu Ala Phe Glu
225                 230                 235                 240

Ala Val Gly Asp Glu His Val Ser Phe Gly Val Asp Phe Asp Asp Gly
                245                 250                 255

Thr Leu Ala Val Cys Thr Ala Ser Gln Ser Ala Tyr Gln Leu Ser His
            260                 265                 270

Leu Arg Val Thr Gly Thr Glu Gly Glu Leu Glu Ile Glu Pro Ala Phe
        275                 280                 285

Tyr Asn Arg Gln Lys Arg Gly Phe Arg Leu Ser Trp Gly Asp Gln Ser
290                 295                 300

Ala Asp Tyr Asp Phe Glu Gln Val Asn Gln Met Thr Glu Glu Phe Asp
305                 310                 315                 320

Tyr Phe Ala Ser Arg Leu Leu Ser Asp Ser Asp Pro Ala Pro Asp Gly
                325                 330                 335

Asp His Ala Leu Val Asp Met Arg Ala Met Asp Ala Ile Tyr Ala Ala
            340                 345                 350

Ala Glu Arg Gly Thr Asp Val Ala Val Asp Ala Ala Asp Ser Asp Ser
        355                 360                 365

Ala Asp Ser Asp Ser Ala Asp Ala Ala Ala Asn His Asp Ala Asp
    370                 375                 380

Pro Asp Ser Asp Gly Thr
385                 390

<210> SEQ ID NO 64
<211> LENGTH: 1176
<212> TYPE: DNA
<213> ORGANISM: Trichoderma reesei

<400> SEQUENCE: 64
atggcgtctg gaaacccta caccctgaaa tggggcatca tggccaccgg cggaatcgca      60
gagaccttct gcaaggatct cctgtgcaac ccgcgattc gaggcgccga tgatgtgcgc     120
cacgagattg tggccgtggc ctcttccagc agcagcaaga gagcagagga gttcctccag     180
agaatcgacg gtgcctttga cgccaagacg tacggatcat cccggaact tgtggcagac     240 cccaacgtcg acatcgtcta tgtggcaact ccccacagcc accacttcca gaacaccatg     300
ctggcgctgg aagccggcaa gaacgtcttg tgcgaaaagg ctttcaccgt gacggccgcg     360
caggcccgaa agctggttga cggccaag gccaagaagc tcttcctgat ggaagctgtg     420
tggacacggt actttccgct gagtatcaag attcgagagc tcattgccgc cggcgagatt     480
ggcactgtct ttcgaacaat cgccgacttg tccatcaacg caaactcaga gcagggtcaa     540
gccctgaaat tcgcagactc acatcgaatg gtcaacccgg acctcgcagg cggtgccacc     600
```

-continued

```
ttggatctcg gagtctatcc cttgacctgg gtgttccaga ccctgtatca tttgcaaccg    660
gaggaagaca aggaggctcc caccgtggtt gcttccagca acaagtacac cactggcgca    720
gacgagaata ccgccatcat ctgcagcttc cctcgccaca acagcattgg aattgcttcg    780
acgacgatga gggcggacac cgaccccgag aaggacacca ttccggcggt ccgaattcaa    840
ggatccaagg gagaaatcca agtcttcttc ccgacctacc gaccgctcaa gtacaaggtg    900
gtgaagacga acggcgaggc gcagacggtt gactgcccca tccccggaga ccccgcgcgc    960
aagggctcgg gccacggaat gttctgggag gcggacgagt gtgctcgatg ccttcgcgat   1020
ggcaagttgg agagtgccac gttgccatgg aaggagagca ttgtcattat ggaaacgatg   1080
gaggaggcgc tgaggcaggg tggcgtcacg tatccggagc tgattaccac ggatgtctat   1140
gatcccaaga gccctctcaa cacggggaat cagtag                             1176
```

<210> SEQ ID NO 65
<211> LENGTH: 391
<212> TYPE: PRT
<213> ORGANISM: Trichoderma reesei

<400> SEQUENCE: 65

```
Met Ala Ser Gly Asn Pro Tyr Thr Leu Lys Trp Gly Ile Met Ala Thr
1               5                   10                  15

Gly Gly Ile Ala Glu Thr Phe Cys Lys Asp Leu Leu Cys Asn Pro Ala
            20                  25                  30

Ile Arg Gly Ala Asp Asp Val Arg His Glu Ile Val Ala Val Ala Ser
        35                  40                  45

Ser Ser Ser Lys Arg Ala Glu Glu Phe Leu Gln Arg Ile Asp Gly
    50                  55                  60

Ala Phe Asp Ala Lys Thr Tyr Gly Ser Tyr Pro Glu Leu Val Ala Asp
65                  70                  75                  80

Pro Asn Val Asp Ile Val Tyr Val Ala Thr Pro His Ser His Phe
                85                  90                  95

Gln Asn Thr Met Leu Ala Leu Glu Ala Gly Lys Asn Val Leu Cys Glu
            100                 105                 110

Lys Ala Phe Thr Val Thr Ala Ala Gln Ala Arg Lys Leu Val Glu Thr
        115                 120                 125

Ala Lys Ala Lys Lys Leu Phe Leu Met Glu Ala Val Trp Thr Arg Tyr
    130                 135                 140

Phe Pro Leu Ser Ile Lys Ile Arg Glu Leu Ile Ala Ala Gly Glu Ile
145                 150                 155                 160

Gly Thr Val Phe Arg Thr Ile Ala Asp Leu Ser Ile Asn Ala Asn Ser
                165                 170                 175

Glu Gln Gly Gln Ala Leu Lys Phe Ala Asp Ser His Arg Met Val Asn
            180                 185                 190

Pro Asp Leu Ala Gly Gly Ala Thr Leu Asp Leu Gly Val Tyr Pro Leu
        195                 200                 205

Thr Trp Val Phe Gln Thr Leu Tyr His Leu Gln Pro Glu Glu Asp Lys
    210                 215                 220

Glu Ala Pro Thr Val Val Ala Ser Ser Asn Lys Tyr Thr Thr Gly Ala
225                 230                 235                 240

Asp Glu Asn Thr Ala Ile Ile Cys Ser Phe Pro Arg His Asn Ser Ile
                245                 250                 255

Gly Ile Ala Ser Thr Thr Met Arg Ala Asp Thr Asp Pro Glu Lys Asp
            260                 265                 270
```

-continued

Thr Ile Pro Ala Val Arg Ile Gln Gly Ser Lys Gly Glu Ile Gln Val
                275                 280                 285

Phe Phe Pro Thr Tyr Arg Pro Leu Lys Tyr Lys Val Val Lys Thr Asn
        290                 295                 300

Gly Glu Ala Gln Thr Val Asp Cys Pro Ile Pro Gly Asp Pro Ala Arg
305                 310                 315                 320

Lys Gly Ser Gly His Gly Met Phe Trp Glu Ala Asp Glu Cys Ala Arg
                325                 330                 335

Cys Leu Arg Asp Gly Lys Leu Glu Ser Ala Thr Leu Pro Trp Lys Glu
                340                 345                 350

Ser Ile Val Ile Met Glu Thr Met Glu Glu Ala Leu Arg Gln Gly Gly
                355                 360                 365

Val Thr Tyr Pro Glu Leu Ile Thr Thr Asp Val Tyr Asp Pro Lys Ser
        370                 375                 380

Pro Leu Asn Thr Gly Asn Gln
385                 390

<210> SEQ ID NO 66
<211> LENGTH: 870
<212> TYPE: DNA
<213> ORGANISM: Caulobacter crescentus

<400> SEQUENCE: 66

```
atgaccgctc aagtcacttg cgtatgggat ctgaaggcca cgttgggcga aggcccgatc      60
tggcatggcg acaccctgtg gttcgtcgac atcaagcagc gtaaaatcca caactaccac     120
cccgccaccg cgagcgcttc agcttcgac gcgccggatc aggtgacctt cctcgcgccg     180
atcgtcggcg cgaccggctt tgtcgtcggt ctgaagaccg ggattcaccg cttccacccg     240
gccacgggct tcagcctgct gctcgaggtc gaggacgcgg cgctgaacaa ccgcccaac      300
gacgccacgg tcgacgcgca aggccgtctg tggttcggca ccatgcacga cggggaagag     360
aacaatagcg gctcgctcta tcggatggac ctcaccggcg tcgcccggat ggaccgcgac     420
atctgcatca ccaacggccc gtgcgtctcg cccgacggca agaccttcta ccacaccgac     480
accctggaaa agacgatcta cgccttcgac ctggccgagg acggcctgct gtcgaacaag     540
cgcgtcttcg tgcagttcgc cctgggcgac gatgtctatc cggacggttc ggtcgtcgat     600
tccgaaggct atctgtggac cgccctgtgg gcggtttcg cgcgcgtccg cttctcgccg     660
caaggcgacg ccgtgacgcg catcgaactg cccgccccca acgtcaccaa gccctgcttc     720
ggcgggcctg acctgaagac cctctatttc accaccgccc gcaagggcct gagcgacgag     780
accctggccc agtacccgct ggccggcggt gtgttcgccg ttccggtcga tgtggccggc     840
caaccccagc atgaggtccg ccttgtctaa                                       870
```

<210> SEQ ID NO 67
<211> LENGTH: 289
<212> TYPE: PRT
<213> ORGANISM: Caulobacter crescentus

<400> SEQUENCE: 67

Met Thr Ala Gln Val Thr Cys Val Trp Asp Leu Lys Ala Thr Leu Gly
1               5                   10                  15

Glu Gly Pro Ile Trp His Gly Asp Thr Leu Trp Phe Val Asp Ile Lys
                20                  25                  30

Gln Arg Lys Ile His Asn Tyr His Pro Ala Thr Gly Glu Arg Phe Ser
        35                  40                  45

Phe Asp Ala Pro Asp Gln Val Thr Phe Leu Ala Pro Ile Val Gly Ala
 50                  55                  60

Thr Gly Phe Val Val Gly Leu Lys Thr Gly Ile His Arg Phe His Pro
 65                  70                  75                  80

Ala Thr Gly Phe Ser Leu Leu Leu Glu Val Glu Asp Ala Ala Leu Asn
                 85                  90                  95

Asn Arg Pro Asn Asp Ala Thr Val Asp Ala Gln Gly Arg Leu Trp Phe
             100                 105                 110

Gly Thr Met His Asp Gly Glu Asn Asn Ser Gly Ser Leu Tyr Arg
         115                 120                 125

Met Asp Leu Thr Gly Val Ala Arg Met Asp Arg Asp Ile Cys Ile Thr
130                 135                 140

Asn Gly Pro Cys Val Ser Pro Asp Gly Lys Thr Phe Tyr His Thr Asp
145                 150                 155                 160

Thr Leu Glu Lys Thr Ile Tyr Ala Phe Asp Leu Ala Glu Asp Gly Leu
                 165                 170                 175

Leu Ser Asn Lys Arg Val Phe Val Gln Phe Ala Leu Gly Asp Asp Val
             180                 185                 190

Tyr Pro Asp Gly Ser Val Val Asp Ser Glu Gly Tyr Leu Trp Thr Ala
         195                 200                 205

Leu Trp Gly Gly Phe Gly Ala Val Arg Phe Ser Pro Gln Gly Asp Ala
210                 215                 220

Val Thr Arg Ile Glu Leu Pro Ala Pro Asn Val Thr Lys Pro Cys Phe
225                 230                 235                 240

Gly Gly Pro Asp Leu Lys Thr Leu Tyr Phe Thr Thr Ala Arg Lys Gly
                 245                 250                 255

Leu Ser Asp Glu Thr Leu Ala Gln Tyr Pro Leu Ala Gly Gly Val Phe
             260                 265                 270

Ala Val Pro Val Asp Val Ala Gly Gln Pro Gln His Glu Val Arg Leu
         275                 280                 285

Val

<210> SEQ ID NO 68
<211> LENGTH: 1776
<212> TYPE: DNA
<213> ORGANISM: Caulobacter crescentus

<400> SEQUENCE: 68
ttgtctaacc gcacgccccg ccggttccgg tcccgcgatt ggttcgataa ccccgaccat     60
atcgacatga ccgcgctcta tctggagcgc ttcatgaact acgggatcac gccgaggag    120
ctgcgcagcg gcaagccgat catcggcatc gcccagaccg gcagcgacat ctcgccctgc    180
aaccgcatcc acctggacct ggtccagcgg gtgcgggacg ggatccgcga cgccgggggc    240
atccccatgg agttcccggt ccatccgatc ttcgagaact gccgtcgccc gacggcggcg    300
ctggaccgga acctctcgta cctgggtctc gtcgagaccc tgcacggcta ccgatcgac    360
gccgtggttc tgaccaccgg ctgcgacaag accaccccgg ccgggatcat ggccgccacc    420
acggtcaata tcccggccat cgtgctgtcg ggcggcccga tgctggacgg ctggcacgag    480
aacgagctcg tgggctcggg caccgtgatc tggcgctcgc cgcaagct ggcggccggc    540
gagatcaccg aggaagagtt catcgaccgc gccgccagct cggcgccgtc ggcgggccac    600
tgcaacacca tgggcacggc ctcgaccatg aacgccgtgg ccgaggcgct gggcctgtcg    660
ctgaccggct gcgcggccat ccccgccccc taccgcgagc gcggccagat ggcctacaag    720

```
accggccagc gcatcgtcga tctggcctat gacgacgtca aaccgctcga catcctgacc    780
aagcaagcct tcgagaacgc catcgccctg gtggcggcgg ccggcggctc gaccaacgcc    840
cagccgcaca tcgtggccat ggcccgtcac gccggcgtcg agatcaccgc cgacgactgg    900
cgcgcggcct atgacatccc gctgatcgtc aacatgcagc cggccggcaa gtatctgggc    960
gagcgcttcc accgagccgg cggcgcgccg gcggtgctgt gggagctgtt gcagcaaggc   1020
cgcctgcacg cgacgtgct gaccgtcacc ggcaagacga tgagcgagaa cctgcaaggc   1080
cgcgaaacca gcgaccgcga ggtgatcttc ccgtaccacg agccgctggc cgagaaggcc   1140
gggttcctgg ttctcaaggg caacctcttc gacttcgcga tcatgaagtc cagcgtgatc   1200
ggcgaggagt tccgcaagcg ctacctgtcg cagcccggcc aggaaggcgt gttcgaagcc   1260
cgcgccatcg tgttcgacgg ctcggacgac tatcacaagc ggatcaacga tccggccctg   1320
gagatcgacg agcgctgcat cctggtgatc cgcggcgcgg gtccgatcgg ctggcccggc   1380
tcggccgagg tcgtcaacat gcagccgccg gatcaccttc tgaagaaggg gatcatgagc   1440
ctgcccaccc tgggcgatgg ccgtcagtcg ggcaccgccg acagcccctc gatcctgaac   1500
gcctcgcccg aaagcgcgat cggcggcggc ctgtcgtggc tgcgcaccgg cgacaccatc   1560
cgcatcgacc tcaacaccgg ccgctgcgac gccctggtcg acgaggcgac gatcgccgcg   1620
cgcaagcagg acggcatccc ggcggttccc gccaccatga cgccctggca ggaaatctac   1680
cgcgcccacg ccagtcagct cgacaccggc ggcgtgctgg agttcgcggt caagtaccag   1740
gacctggcgg ccaagctgcc ccgccacaac cactga                             1776
```

<210> SEQ ID NO 69
<211> LENGTH: 591
<212> TYPE: PRT
<213> ORGANISM: Caulobacter crescentus

<400> SEQUENCE: 69

```
Met Ser Asn Arg Thr Pro Arg Arg Phe Arg Ser Arg Asp Trp Phe Asp
1               5                   10                  15

Asn Pro Asp His Ile Asp Met Thr Ala Leu Tyr Leu Glu Arg Phe Met
            20                  25                  30

Asn Tyr Gly Ile Thr Pro Glu Glu Leu Arg Ser Gly Lys Pro Ile Ile
        35                  40                  45

Gly Ile Ala Gln Thr Gly Ser Asp Ile Ser Pro Cys Asn Arg Ile His
    50                  55                  60

Leu Asp Leu Val Gln Arg Val Arg Asp Gly Ile Arg Asp Ala Gly Gly
65                  70                  75                  80

Ile Pro Met Glu Phe Pro Val His Pro Ile Phe Glu Asn Cys Arg Arg
                85                  90                  95

Pro Thr Ala Ala Leu Asp Arg Asn Leu Ser Tyr Leu Gly Leu Val Glu
            100                 105                 110

Thr Leu His Gly Tyr Pro Ile Asp Ala Val Val Leu Thr Thr Gly Cys
        115                 120                 125

Asp Lys Thr Thr Pro Ala Gly Ile Met Ala Ala Thr Thr Val Asn Ile
    130                 135                 140

Pro Ala Ile Val Leu Ser Gly Gly Pro Met Leu Asp Gly Trp His Glu
145                 150                 155                 160

Asn Glu Leu Val Gly Ser Gly Thr Val Ile Trp Arg Ser Arg Arg Lys
                165                 170                 175

Leu Ala Ala Gly Glu Ile Thr Glu Glu Glu Phe Ile Asp Arg Ala Ala
            180                 185                 190
```

```
Ser Ser Ala Pro Ser Ala Gly His Cys Asn Thr Met Gly Thr Ala Ser
        195                 200                 205

Thr Met Asn Ala Val Ala Glu Ala Leu Gly Leu Ser Leu Thr Gly Cys
        210                 215                 220

Ala Ala Ile Pro Ala Pro Tyr Arg Glu Arg Gly Gln Met Ala Tyr Lys
225                 230                 235                 240

Thr Gly Gln Arg Ile Val Asp Leu Ala Tyr Asp Val Lys Pro Leu
        245                 250                 255

Asp Ile Leu Thr Lys Gln Ala Phe Glu Asn Ala Ile Ala Leu Val Ala
        260                 265                 270

Ala Ala Gly Gly Ser Thr Asn Ala Gln Pro His Ile Val Ala Met Ala
        275                 280                 285

Arg His Ala Gly Val Glu Ile Thr Ala Asp Asp Trp Arg Ala Ala Tyr
        290                 295                 300

Asp Ile Pro Leu Ile Val Asn Met Gln Pro Ala Gly Lys Tyr Leu Gly
305                 310                 315                 320

Glu Arg Phe His Arg Ala Gly Ala Pro Ala Val Leu Trp Glu Leu
                325                 330                 335

Leu Gln Gln Gly Arg Leu His Gly Asp Val Leu Thr Val Thr Gly Lys
        340                 345                 350

Thr Met Ser Glu Asn Leu Gln Gly Arg Glu Thr Ser Asp Arg Glu Val
        355                 360                 365

Ile Phe Pro Tyr His Glu Pro Leu Ala Glu Lys Ala Gly Phe Leu Val
        370                 375                 380

Leu Lys Gly Asn Leu Phe Asp Phe Ala Ile Met Lys Ser Ser Val Ile
385                 390                 395                 400

Gly Glu Glu Phe Arg Lys Arg Tyr Leu Ser Gln Pro Gly Gln Glu Gly
                405                 410                 415

Val Phe Glu Ala Arg Ala Ile Val Phe Asp Gly Ser Asp Asp Tyr His
                420                 425                 430

Lys Arg Ile Asn Asp Pro Ala Leu Glu Ile Asp Glu Arg Cys Ile Leu
        435                 440                 445

Val Ile Arg Gly Ala Gly Pro Ile Gly Trp Pro Gly Ser Ala Glu Val
        450                 455                 460

Val Asn Met Gln Pro Pro Asp His Leu Leu Lys Lys Gly Ile Met Ser
465                 470                 475                 480

Leu Pro Thr Leu Gly Asp Gly Arg Gln Ser Gly Thr Ala Asp Ser Pro
                485                 490                 495

Ser Ile Leu Asn Ala Ser Pro Glu Ser Ala Ile Gly Gly Leu Ser
        500                 505                 510

Trp Leu Arg Thr Gly Asp Thr Ile Arg Ile Asp Leu Asn Thr Gly Arg
        515                 520                 525

Cys Asp Ala Leu Val Asp Glu Ala Thr Ile Ala Arg Lys Gln Asp
        530                 535                 540

Gly Ile Pro Ala Val Pro Ala Thr Met Thr Pro Trp Gln Glu Ile Tyr
545                 550                 555                 560

Arg Ala His Ala Ser Gln Leu Asp Thr Gly Gly Val Leu Glu Phe Ala
                565                 570                 575

Val Lys Tyr Gln Asp Leu Ala Ala Lys Leu Pro Arg His Asn His
        580                 585                 590

<210> SEQ ID NO 70
<211> LENGTH: 1968
```

<212> TYPE: DNA
<213> ORGANISM: Escherichia coli

<400> SEQUENCE: 70

```
atgtctgttc gcaatatttt tgctgacgag agccacgata tttacaccgt cagaacgcac      60
gccgatggcc cggacggcga actcccatta accgcagaga tgcttatcaa ccgcccgagc     120
ggggatctgt tcggtatgac catgaatgcc ggaatggggt ggtctccgga cgagctggat     180
cgggacggta ttttactgct cagtacactc ggtggcttac gcggcgcaga cggtaaaccc     240
gtggcgctgg cgttgcacca ggggcattac gaactggaca tccagatgaa agcggcggcc     300
gaggttatta aagccaacca tgccctgccc tatgccgtgt acgtctccga tccttgtgac     360
gggcgtactc agggtacaac ggggatgttt gattcgctac cataccgaaa tgacgcatcg     420
atggtaatgc gccgccttat tcgctctctg cccgacgcga aagcagttat tggtgtggcg     480
agttgcgata aggggcttcc ggccaccatg atggcactcg ccgcgcagca caacatcgca     540
accgtgctgg tccccggcgg cgcgacgctg cccgcaaagg atggagaaga caacggcaag     600
gtgcaaacca ttggcgcacg cttcgccaat ggcgaattat ctctacagga cgcacgccgt     660
gcgggctgta aagcctgtgc ctcttccggc ggcggctgtc aattttttgg cactgccggg     720
acatctcagg tggtggccga aggattggga ctggcaatcc cacattcagc cctggcccct     780
tccggtgagc ctgtgtggcg ggagatcgcc agagcttccg cgcgagctgc gctgaacctg     840
agtcaaaaag gcatcaccac ccgggaaatt ctcaccgata aagcgataga gaatgcgatg     900
acggtccatg ccgcgttcgg tggttcaaca aacctgctgt tacacatccc ggcaattgct     960
caccaggcag gttgccatat cccgaccgtt gatgactgga tccgcatcaa caagcgcgtg    1020
ccccgactgg tgagcgtact gcctaatggc ccggtttatc atccaacggt caatgccttt    1080
atggcaggtg gtgtgccgga agtcatgttg catctgcgca gcctcggatt gttgcatgaa    1140
gacgttatga cggttaccgg cagcacgctg aaagaaaacc tcgactggtg ggagcactcc    1200
gaacggcgtc agcggttcaa gcaactcctg ctcgatcagg aacaaatcaa cgctgacgaa    1260
gtgatcatgt ctccgcagca agcaaaagcg cgcggattaa cctcaactat caccttcccg    1320
gtgggcaata ttgcgccaga aggttcggtg atcaaatcca ccgccattga cccctcgatg    1380
attgatgagc aagtatcta ttaccataaa ggtgtggcga aggtttatct gtccgagaaa    1440
agtgcgattt acgatatcaa acatgacaag atcaaggcgg cgatattct ggtcattatt    1500
ggcgttggac cttcaggtac agggatggaa gaaacctacc aggttaccag tgccctgaag    1560
catctgtcat acggtaagca tgtttcgtta atcaccgatg cacgtttctc gggcgttct    1620
actggcgcgt gcatcggcca tgtggggcca gaagcgctgg ccggaggccc catcggtaaa    1680
ttacgcaccg gggattaat tgaaattaaa attgattgtc gcgagcttca cggcgaagtc    1740
aatttcctcg gaacccgtag cgatgaacaa ttaccttcac aggaggaggc aactgcaata    1800
ttaaatgcca gacccagcca tcaggattta cttcccgatc ctgaattgcc agatgatacc    1860
cggctatggg caatgcttca ggccgtgagt ggtgggacat ggaccggttg tatttatgat    1920
gtaaacaaaa ttggcgcggc tttgcgcgat tttatgaata aaaactga                 1968
```

<210> SEQ ID NO 71
<211> LENGTH: 1968
<212> TYPE: DNA
<213> ORGANISM: Escherichia coli

<400> SEQUENCE: 71

```
atgtctgttc gcaatatttt tgctgacgag agccacgata tttacaccgt cagaacgcac      60
gccgatggcc cggacggcga actcccatta accgcagaga tgcttatcaa ccgcccgagc     120
ggggatctgt tcggtatgac catgaatgcc ggaatgggtt ggtctccgga cgagctggat     180
cgggacggta ttttactgct cagtacactc ggtggcttac gcggcgcaga cggtaaaccc     240
gtggcgctgg cgttgcacca ggggcattac gaactggaca tccagatgaa agcggcggcc     300
gaggttatta agccaaccat gccctgccc tatgccgtgt acgtctccga tccttgtgac      360
gggcgtactc agggtacaac ggggatgttt gattcgctac ataccgaaa tgacgcatcg      420
atggtaatgc gccgccttat tcgctctctg cccgacgcga aagcagttat ggtgtggcg      480
agttgcgata aggggcttcc ggccaccatg atggcactcg ccgcgcagca acatcgca       540
accgtgctgg tccccggcgg cgcgacgctg cccgcaaagg atggagaaga caacggcaag     600
gtgcaaacca ttggcgcacg cttcgccaat ggcgaattat ctctacagga cgcacgccgt     660
gcgggctgta aagcctgtgc ctcttccggc ggcggctgtc aattttttggg cactgccggg    720
acatctcagg tggtggccga aggattggga ctggcaatcc acattcagc cctggcccct     780
tccggtgagc ctgtgtggcg ggagatcgcc agagcttccg cgcgagctgc gctgaacctg     840
agtcaaaaag gcatcaccac ccgggaaatt ctcaccgata aagcgataga gaatgcgatg    900
acggtccatg ccgcgttcgg tggttcaaca aacctgctgt tacacatccc ggcaattgct     960
caccaggcag gttgccatat cccgaccgtt gatgactgga tccgcatcaa caagcgcgtg    1020
ccccgactgg tgagcgtact gcctaatggc ccggtttatc atccaacggt caatgccttt    1080
atggcaggtg tgtgccgga agtcatgttg catctgcgca gcctcggatt gttgcatgaa     1140
gacgttatga cggttaccgg cagcacgctg aaagaaaacc tcgactggtg ggagcactcc    1200
gaacggcgtc agcggttcaa gcaactcctg ctcgatcagg aacaaatcaa cgctgacgaa    1260
gtgatcatgt ctccgcagca agcaaaagcg cgcggattaa cctcaactat caccttcccg    1320
gtgggcaata ttgcgccaga aggttcggtg atcaaatcca ccgccattga ccctcgatg     1380
attgatgagc aaggtatcta ttaccataaa ggtgtggcga aggtttatct gtccgagaaa    1440
agtgcgattt acgatatcaa acatgacaag atcaaggcgg cgatattct ggtcattatt     1500
ggcgttggac cttcaggtac agggatggaa gaaacctacc aggttaccag tgccctgaag    1560
catctgtcat acggtaagca tgtttcgtta atcaccgatg cacgtttctc gggcgttttct   1620
actggcgcgt gcatcggcca tgtggggcca gaagcgctgg ccggaggccc catcggtaaa    1680
ttacgcaccg gggatttaat tgaaattaaa attgattgtc gcgagcttca cggcgaagtc    1740
aatttcctcg gaacccgtag cgatgaacaa ttaccttcac aggaggaggc aactgcaata    1800
ttaaatgcca gacccagcca tcaggattta cttcccgatc ctgaattgcc agatgatacc    1860
cggctatggg caatgcttca ggccgtgagt ggtgggacat ggaccggttg tatttatgat    1920
gtaaacaaaa ttggcgcggc tttgcgcgat tttatgaata aaaactga                 1968
```

<210> SEQ ID NO 72
<211> LENGTH: 655
<212> TYPE: PRT
<213> ORGANISM: Escherichia coli

<400> SEQUENCE: 72

Met Ser Val Arg Asn Ile Phe Ala Asp Glu Ser His Asp Ile Tyr Thr
1               5                   10                  15

Val Arg Thr His Ala Asp Gly Pro Asp Gly Glu Leu Pro Leu Thr Ala
            20                  25                  30

```
Glu Met Leu Ile Asn Arg Pro Ser Gly Asp Leu Phe Gly Met Thr Met
         35                  40                  45

Asn Ala Gly Met Gly Trp Ser Pro Asp Glu Leu Asp Arg Asp Gly Ile
 50                  55                  60

Leu Leu Leu Ser Thr Leu Gly Gly Leu Arg Gly Ala Asp Gly Lys Pro
 65                  70                  75                  80

Val Ala Leu Ala Leu His Gln Gly His Tyr Glu Leu Asp Ile Gln Met
                 85                  90                  95

Lys Ala Ala Glu Val Ile Lys Ala Asn His Ala Leu Pro Tyr Ala
                100                 105                 110

Val Tyr Val Ser Asp Pro Cys Asp Gly Arg Thr Gln Gly Thr Thr Gly
            115                 120                 125

Met Phe Asp Ser Leu Pro Tyr Arg Asn Asp Ala Ser Met Val Met Arg
130                 135                 140

Arg Leu Ile Arg Ser Leu Pro Asp Ala Lys Ala Val Ile Gly Val Ala
145                 150                 155                 160

Ser Cys Asp Lys Gly Leu Pro Ala Thr Met Met Ala Leu Ala Ala Gln
                165                 170                 175

His Asn Ile Ala Thr Val Leu Val Pro Gly Gly Ala Thr Leu Pro Ala
            180                 185                 190

Lys Asp Gly Glu Asp Asn Gly Lys Val Gln Thr Ile Gly Ala Arg Phe
            195                 200                 205

Ala Asn Gly Glu Leu Ser Leu Gln Asp Ala Arg Arg Ala Gly Cys Lys
            210                 215                 220

Ala Cys Ala Ser Ser Gly Gly Cys Gln Phe Leu Gly Thr Ala Gly
225                 230                 235                 240

Thr Ser Gln Val Val Ala Glu Gly Leu Gly Leu Ala Ile Pro His Ser
                245                 250                 255

Ala Leu Ala Pro Ser Gly Glu Pro Val Trp Arg Glu Ile Ala Arg Ala
            260                 265                 270

Ser Ala Arg Ala Ala Leu Asn Leu Ser Gln Lys Gly Ile Thr Thr Arg
            275                 280                 285

Glu Ile Leu Thr Asp Lys Ala Ile Glu Asn Ala Met Thr Val His Ala
            290                 295                 300

Ala Phe Gly Gly Ser Thr Asn Leu Leu Leu His Ile Pro Ala Ile Ala
305                 310                 315                 320

His Gln Ala Gly Cys His Ile Pro Thr Val Asp Asp Trp Ile Arg Ile
                325                 330                 335

Asn Lys Arg Val Pro Arg Leu Val Ser Val Leu Pro Asn Gly Pro Val
            340                 345                 350

Tyr His Pro Thr Val Asn Ala Phe Met Ala Gly Gly Val Pro Glu Val
            355                 360                 365

Met Leu His Leu Arg Ser Leu Gly Leu Leu His Glu Asp Val Met Thr
370                 375                 380

Val Thr Gly Ser Thr Leu Lys Glu Asn Leu Asp Trp Trp Glu His Ser
385                 390                 395                 400

Glu Arg Arg Gln Arg Phe Lys Gln Leu Leu Leu Asp Gln Glu Gln Ile
                405                 410                 415

Asn Ala Asp Glu Val Ile Met Ser Pro Gln Gln Ala Lys Ala Arg Gly
            420                 425                 430

Leu Thr Ser Thr Ile Thr Phe Pro Val Gly Asn Ile Ala Pro Glu Gly
            435                 440                 445
```

Ser Val Ile Lys Ser Thr Ala Ile Asp Pro Ser Met Ile Asp Glu Gln
        450                 455                 460

Gly Ile Tyr Tyr His Lys Gly Val Ala Lys Val Tyr Leu Ser Glu Lys
465                 470                 475                 480

Ser Ala Ile Tyr Asp Ile Lys His Asp Lys Ile Lys Ala Gly Asp Ile
                485                 490                 495

Leu Val Ile Ile Gly Val Gly Pro Ser Gly Thr Gly Met Glu Glu Thr
                500                 505                 510

Tyr Gln Val Thr Ser Ala Leu Lys His Leu Ser Tyr Gly Lys His Val
                515                 520                 525

Ser Leu Ile Thr Asp Ala Arg Phe Ser Gly Val Ser Thr Gly Ala Cys
530                 535                 540

Ile Gly His Val Gly Pro Glu Ala Leu Ala Gly Gly Pro Ile Gly Lys
545                 550                 555                 560

Leu Arg Thr Gly Asp Leu Ile Glu Ile Lys Ile Asp Cys Arg Glu Leu
                565                 570                 575

His Gly Glu Val Asn Phe Leu Gly Thr Arg Ser Asp Glu Gln Leu Pro
                580                 585                 590

Ser Gln Glu Glu Ala Thr Ala Ile Leu Asn Ala Arg Pro Ser His Gln
                595                 600                 605

Asp Leu Leu Pro Asp Pro Glu Leu Pro Asp Asp Thr Arg Leu Trp Ala
610                 615                 620

Met Leu Gln Ala Val Ser Gly Gly Thr Trp Thr Gly Cys Ile Tyr Asp
625                 630                 635                 640

Val Asn Lys Ile Gly Ala Ala Leu Arg Asp Phe Met Asn Lys Asn
                645                 650                 655

<210> SEQ ID NO 73
<211> LENGTH: 1968
<212> TYPE: DNA
<213> ORGANISM: Escherichia coli

<400> SEQUENCE: 73
atgaccattg agaaaatttt caccccgcag gacgacgcgt tttatgcggt gatcacccac      60
gcggcggggc cgcagggcgc tctgccgctg accccgcaga tgctgatgga atctcccagc     120
ggcaacctgt tcggcatgac gcagaacgcc gggatgggct gggacgccaa caagctcacc     180
ggcaaagagg tgctgattat cggcactcag gcggcatcc gcgccggaga cggacgccca     240
atcgcgctgg gctaccacac cgggcattgg gagatcggca tgcagatgca ggcggcggcg     300
aaggagatca cccgcaatgg cgggatcccg ttcgcggcct tcgtcagcga tccgtgcgac     360
gggcgctcgc agggcacgca cggtatgttc gattccctgc cgtaccgcaa cgacgcggcg     420
atcgtgtttc gccgcctgat ccgctccctg ccgacgcggc gggcggtgat cggcgtagcg     480
acctgcgata aagggctgcc cgccaccatg attgcgctgg ccgcgatgca cgacctgccg     540
actattctgg tgccgggcgg ggcgacgctg ccgccgaccg tcggggaaga cgcgggcaag     600
gtgcagacca tcggcgcgcg tttcgccaac cacgaactct ccctgcagga ggccgccgaa     660
ctgggctgtc gcgcctgcgc ctcgccgggc ggcgggtgtc agttcctcgg cacggcgggc     720
acctcgcagg tggtcgcgga ggcgctgggt ctggcgctgc cgcactccgc gctggcgccg     780
tccgggcagg cggtgtggct ggagatcgcc cgccagtcgg cgcgcgcggt cagcgagctg     840
gatagccgcg gcatcaccac gcgggatatc ctctccgata aagccatcga aaacgcgatg     900
gtgatccacg cggcgttcgg cggctccacc aatttactgc tgcacattcc ggccatcgcc     960

```
cacgcggcgg gctgcacgat cccggacgtt gagcactgga cgcgcatcaa ccgtaaagtg    1020
ccgcgtctgg tgagcgtgct gcccaacggc ccggactatc acccgaccgt gcgcgccttc    1080
ctcgcgggcg gcgtgccgga ggtgatgctc cacctgcgcg acctcggcct gctgcatctg    1140
gacgccatga ccgtgaccgg ccagacggtg ggcgagaacc ttgaatggtg gcaggcgtcc    1200
gagcgccggg cgcgcttccg ccagtgcctg cgcgagcagg acggcgtaga gccggatgac    1260
gtgatcctgc cgccggagaa ggcaaaagcg aaagggctga cctcgacggt ctgcttcccg    1320
acgggcaaca tcgctccgga aggttcggtg atcaaggcca cggcgatcga cccgtcggtg    1380
gtgggcgaag atggcgtata ccaccacacc ggcgggtgc gggtgtttgt ctcggaagcg    1440
caggcgatca aggcgatcaa gcgggaagag attgtgcagg gcgatatcat ggtggtgatc    1500
ggcggcgggc cgtccggcac cggcatggaa gagacctacc agctcacctc cgcgctaaag    1560
catatctcgt ggggcaagac ggtgtcgctc atcaccgatg cgcgcttctc gggcgtgtcg    1620
acgggcgcct gcttcggcca cgtgtcgccg gagcgctgg cgggcgggcc gattggcaag    1680
ctgcgcgata cgacatcat cgagattgcc gtggatcgtc tgacgttaac tggcagcgtg    1740
aacttcatcg gcaccgcgga caacccgctg acgccggaag agggcgcgcg cgagctggcg    1800
cggcggcaga cgcacccgga cctgcacgcc cacgactttt tgccggacga cacccggctg    1860
tgggcggcac tgcagtcggt gagcggcggc acctggaaag gctgtattta tgacaccgat    1920
aaaattatcg aggtaattaa cgccggtaaa aaagcgctcg gaatttaa                 1968

<210> SEQ ID NO 74
<211> LENGTH: 1968
<212> TYPE: DNA
<213> ORGANISM: Escherichia coli

<400> SEQUENCE: 74
atgaccattg agaaaatttt cacccccgcag acgacgcgt tttatgcggt gatcacccac      60
gcggcggggc gcagggcgc tctgccgctg accccgcaga tgctgatgga atctcccagc     120
ggcaacctgt tcggcatgac gcagaacgcc gggatgggct gggacgccaa caagctcacc     180
ggcaaagagg tgctgattat cggcactcag ggcggcatcc gcgccggaga cggacgccca     240
atcgcgctgg gctaccacac cgggcattgg gagatcggca tgcagatgca ggcggcggcg     300
aaggagatca cccgcaatgg cgggatcccg ttcgcggcct tcgtcagcga tccgtgcgac     360
gggcgctcgc agggcacgca cggtatgttc gattccctgc cgtaccgcaa cgacgcggcg     420
atcgtgtttc gccgctgat ccgctccctg ccgacgcggc gggcggtgat cggcgtagcg     480
acctgcgata aagggctgcc cgccaccatg attgcgctgg ccgcgatgca cgacctgccg     540
actattctgg tgccgggcgg ggcgacgctg ccgccgaccg tcggggaaga gcgggcaag     600 gtgcagacca tcggcgcgcg tttcgccaac cacgaactct ccctgcagga ggccgccgaa     660
ctgggctgtc gcgcctgcgc ctcgccgggc ggcgggtgtc agttcctcgg cacggcgggc     720
acctcgcagg tggtcgcgga ggcgctgggt ctggcgctgc gcactccgc gctggcgccg     780 tccgggcagg cggtgtggct ggagatcgcc cgccagtcgg cgcgcgcggt cagcgagctg     840
gatagccgcg gcatcaccac gcgggatatc ctctccgata aagccatcga aaacgcgatg     900
gtgatccacg cggcgttcgg cggctccacc aatttactgc tgcacattcc ggccatcgcc     960
cacgcggcgg gctgcacgat cccggacgtt gagcactgga cgcgcatcaa ccgtaaagtg    1020
ccgcgtctgg tgagcgtgct gcccaacggc ccggactatc acccgaccgt gcgcgccttc    1080
ctcgcgggcg gcgtgccgga ggtgatgctc cacctgcgcg acctcggcct gctgcatctg    1140
```

-continued

```
gacgccatga ccgtgaccgg ccagacggtg ggcgagaacc ttgaatggtg gcaggcgtcc    1200
gagcgccggg cgcgcttccg ccagtgcctg cgcgagcagg acggcgtaga gccggatgac    1260
gtgatcctgc cgccggagaa ggcaaaagcg aaagggctga cctcgacggt ctgcttcccg    1320
acgggcaaca tcgctccgga aggttcggtg atcaaggcca cggcgatcga cccgtcggtg    1380
gtgggcgaag atggcgtata ccaccacacc ggccgggtgc gggtgttgt ctcggaagcg    1440 caggcgatca aggcgatcaa gcgggaagag attgtgcagg gcgatatcat ggtggtgatc    1500
ggcggcgggc cgtccggcac cggcatggaa gagacctacc agctcacctc cgcgctaaag    1560
catatctcgt ggggcaagac ggtgtcgctc atcaccgatg cgcgcttctc gggcgtgtcg    1620
acgggcgcct gcttcggcca cgtgtcgccg gaggcgctgg cgggcgggcc gattggcaag    1680
ctgcgcgata cgacatcat cgagattgcc gtggatcgtc tgacgttaac tggcagcgtg    1740
aacttcatcg gcaccgcgga caacccgctg acgccggaag agggcgcgcg cgagctggcg    1800
cggcggcaga cgcaccccga cctgcacgcc cacgactttt tgccggacga cacccggctg    1860
tgggcggcac tgcagtcggt gagcggcggc acctggaaag gctgtattta tgacaccgat    1920
aaaattatcg aggtaattaa cgccggtaaa aaagcgctcg gaatttaa                1968
```

<210> SEQ ID NO 75
<211> LENGTH: 655
<212> TYPE: PRT
<213> ORGANISM: Escherichia coli

<400> SEQUENCE: 75

```
Met Thr Ile Glu Lys Ile Phe Thr Pro Gln Asp Asp Ala Phe Tyr Ala
1               5                   10                  15

Val Ile Thr His Ala Ala Gly Pro Gln Gly Ala Leu Pro Leu Thr Pro
            20                  25                  30

Gln Met Leu Met Glu Ser Pro Ser Gly Asn Leu Phe Gly Met Thr Gln
        35                  40                  45

Asn Ala Gly Met Gly Trp Asp Ala Asn Lys Leu Thr Gly Lys Glu Val
    50                  55                  60

Leu Ile Ile Gly Thr Gln Gly Gly Ile Arg Ala Gly Asp Gly Arg Pro
65                  70                  75                  80

Ile Ala Leu Gly Tyr His Thr Gly His Trp Glu Ile Gly Met Gln Met
                85                  90                  95

Gln Ala Ala Ala Lys Glu Ile Thr Arg Asn Gly Gly Ile Pro Phe Ala
            100                 105                 110

Ala Phe Val Ser Asp Pro Cys Asp Gly Arg Ser Gln Gly Thr His Gly
        115                 120                 125

Met Phe Asp Ser Leu Pro Tyr Arg Asn Asp Ala Ala Ile Val Phe Arg
    130                 135                 140

Arg Leu Ile Arg Ser Leu Pro Thr Arg Arg Ala Val Ile Gly Val Ala
145                 150                 155                 160

Thr Cys Asp Lys Gly Leu Pro Ala Thr Met Ile Ala Leu Ala Ala Met
                165                 170                 175

His Asp Leu Pro Thr Ile Leu Val Pro Gly Gly Ala Thr Leu Pro Pro
            180                 185                 190

Thr Val Gly Glu Asp Ala Gly Lys Val Gln Thr Ile Gly Ala Arg Phe
        195                 200                 205

Ala Asn His Glu Leu Ser Leu Gln Glu Ala Ala Glu Leu Gly Cys Arg
    210                 215                 220
```

```
Ala Cys Ala Ser Pro Gly Gly Gly Cys Gln Phe Leu Gly Thr Ala Gly
225                 230                 235                 240

Thr Ser Gln Val Val Ala Glu Ala Leu Gly Leu Ala Leu Pro His Ser
            245                 250                 255

Ala Leu Ala Pro Ser Gly Gln Ala Val Trp Leu Glu Ile Ala Arg Gln
            260                 265                 270

Ser Ala Arg Ala Val Ser Glu Leu Asp Ser Arg Gly Ile Thr Thr Arg
            275                 280                 285

Asp Ile Leu Ser Asp Lys Ala Ile Glu Asn Ala Met Val Ile His Ala
290                 295                 300

Ala Phe Gly Gly Ser Thr Asn Leu Leu Leu His Ile Pro Ala Ile Ala
305                 310                 315                 320

His Ala Ala Gly Cys Thr Ile Pro Asp Val Glu His Trp Thr Arg Ile
                325                 330                 335

Asn Arg Lys Val Pro Arg Leu Val Ser Val Leu Pro Asn Gly Pro Asp
                340                 345                 350

Tyr His Pro Thr Val Arg Ala Phe Leu Ala Gly Val Pro Glu Val
            355                 360                 365

Met Leu His Leu Arg Asp Leu Gly Leu Leu His Leu Asp Ala Met Thr
370                 375                 380

Val Thr Gly Gln Thr Val Gly Glu Asn Leu Glu Trp Trp Gln Ala Ser
385                 390                 395                 400

Glu Arg Arg Ala Arg Phe Arg Gln Cys Leu Arg Glu Gln Asp Gly Val
                405                 410                 415

Glu Pro Asp Asp Val Ile Leu Pro Pro Glu Lys Ala Lys Ala Lys Gly
                420                 425                 430

Leu Thr Ser Thr Val Cys Phe Pro Thr Gly Asn Ile Ala Pro Glu Gly
                435                 440                 445

Ser Val Ile Lys Ala Thr Ala Ile Asp Pro Ser Val Val Gly Glu Asp
            450                 455                 460

Gly Val Tyr His His Thr Gly Arg Val Arg Val Phe Val Ser Glu Ala
465                 470                 475                 480

Gln Ala Ile Lys Ala Ile Lys Arg Glu Glu Ile Val Gln Gly Asp Ile
                485                 490                 495

Met Val Val Ile Gly Gly Pro Ser Gly Thr Gly Met Glu Glu Thr
            500                 505                 510

Tyr Gln Leu Thr Ser Ala Leu Lys His Ile Ser Trp Gly Lys Thr Val
            515                 520                 525

Ser Leu Ile Thr Asp Ala Arg Phe Ser Gly Val Ser Thr Gly Ala Cys
            530                 535                 540

Phe Gly His Val Ser Pro Glu Ala Leu Ala Gly Gly Pro Ile Gly Lys
545                 550                 555                 560

Leu Arg Asp Asn Asp Ile Ile Glu Ile Ala Val Asp Arg Leu Thr Leu
                565                 570                 575

Thr Gly Ser Val Asn Phe Ile Gly Thr Ala Asp Asn Pro Leu Thr Pro
            580                 585                 590

Glu Glu Gly Ala Arg Glu Leu Ala Arg Arg Gln Thr His Pro Asp Leu
            595                 600                 605

His Ala His Asp Phe Leu Pro Asp Asp Thr Arg Leu Trp Ala Ala Leu
            610                 615                 620

Gln Ser Val Ser Gly Gly Thr Trp Lys Gly Cys Ile Tyr Asp Thr Asp
625                 630                 635                 640

Lys Ile Ile Glu Val Ile Asn Ala Gly Lys Lys Ala Leu Gly Ile
```

<210> SEQ ID NO 76
<211> LENGTH: 906
<212> TYPE: DNA
<213> ORGANISM: Escherichia coli

<400> SEQUENCE: 76

| | | | | | |
|---|---|---|---|---|---|
| atgaaaaaat | tcagcggcat | tattccaccg | gtatccagca | cgtttcatcg | tgacggaacc | 60 |
| cttgataaaa | aggcaatgcg | cgaagttgcc | gacttcctga | ttaataaagg | ggtcgacggg | 120 |
| ctgttttatc | tgggtaccgg | tggtgaattt | agccaaatga | atacagccca | gcgcatggca | 180 |
| ctcgccgaag | aagctgtaac | cattgtcgac | gggcgagtgc | cggtattgat | tggcgtcggt | 240 |
| tccccttcca | ctgacgaagc | ggtcaaactg | gcgcagcatg | cgcaagccta | cggcgctgat | 300 |
| ggtatcgtcg | ccatcaaccc | ctactactgg | aaagtcgcac | cacgaaatct | tgacgactat | 360 |
| taccagcaga | tcgcccgtag | cgtcacccta | ccggtgatcc | tgtacaactt | tccggatctg | 420 |
| acgggtcagg | acttaacccc | ggaaaccgtg | acgcgtctgg | ctctgcaaaa | cgagaatatc | 480 |
| gttggcatca | agacaccat | cgacagcgtt | ggtcacttgc | gtacgatgat | caacacagtt | 540 |
| aagtcggtac | gcccgtcgtt | ttcggtattc | tgcggttacg | atgatcattt | gctgaatacg | 600 |
| atgctgctgg | cggcgacgg | tgcgataacc | gccagcgcta | actttgctcc | ggaactctcc | 660 |
| gtcggcatct | accgcgcctg | gcgtgaaggc | gatctggcga | ccgctgcgac | gctgaataaa | 720 |
| aaactactac | aactgcccgc | tatttacgcc | ctcgaaacac | cgtttgtctc | actgatcaaa | 780 |
| tacagcatgc | agtgtgtcgg | gctgcctgta | gagacatatt | gcttaccacc | gattcttgaa | 840 |
| gcatctgaag | aagcaaaaga | taaagtccac | gtgctgctta | ccgcgcaggg | catttttacca | 900 |
| gtctga | | | | | | 906 |

<210> SEQ ID NO 77
<211> LENGTH: 906
<212> TYPE: DNA
<213> ORGANISM: Escherichia coli

<400> SEQUENCE: 77

| | | | | | |
|---|---|---|---|---|---|
| atgaaaaaat | tcagcggcat | tattccaccg | gtatccagca | cgtttcatcg | tgacggaacc | 60 |
| cttgataaaa | aggcaatgcg | cgaagttgcc | gacttcctga | ttaataaagg | ggtcgacggg | 120 |
| ctgttttatc | tgggtaccgg | tggtgaattt | agccaaatga | atacagccca | gcgcatggca | 180 |
| ctcgccgaag | aagctgtaac | cattgtcgac | gggcgagtgc | cggtattgat | tggcgtcggt | 240 |
| tccccttcca | ctgacgaagc | ggtcaaactg | gcgcagcatg | cgcaagccta | cggcgctgat | 300 |
| ggtatcgtcg | ccatcaaccc | ctactactgg | aaagtcgcac | cacgaaatct | tgacgactat | 360 |
| taccagcaga | tcgcccgtag | cgtcacccta | ccggtgatcc | tgtacaactt | tccggatctg | 420 |
| acgggtcagg | acttaacccc | ggaaaccgtg | acgcgtctgg | ctctgcaaaa | cgagaatatc | 480 |
| gttggcatca | agacaccat | cgacagcgtt | ggtcacttgc | gtacgatgat | caacacagtt | 540 |
| aagtcggtac | gcccgtcgtt | ttcggtattc | tgcggttacg | atgatcattt | gctgaatacg | 600 |
| atgctgctgg | cggcgacgg | tgcgataacc | gccagcgcta | actttgctcc | ggaactctcc | 660 |
| gtcggcatct | accgcgcctg | gcgtgaaggc | gatctggcga | ccgctgcgac | gctgaataaa | 720 |
| aaactactac | aactgcccgc | tatttacgcc | ctcgaaacac | cgtttgtctc | actgatcaaa | 780 |
| tacagcatgc | agtgtgtcgg | gctgcctgta | gagacatatt | gcttaccacc | gattcttgaa | 840 |
| gcatctgaag | aagcaaaaga | taaagtccac | gtgctgctta | ccgcgcaggg | catttttacca | 900 | gtctga                                                                  906

<210> SEQ ID NO 78
<211> LENGTH: 301
<212> TYPE: PRT
<213> ORGANISM: Escherichia coli

<400> SEQUENCE: 78

Met Lys Lys Phe Ser Gly Ile Ile Pro Pro Val Ser Ser Thr Phe His
1               5                   10                  15

Arg Asp Gly Thr Leu Asp Lys Lys Ala Met Arg Glu Val Ala Asp Phe
            20                  25                  30

Leu Ile Asn Lys Gly Val Asp Gly Leu Phe Tyr Leu Gly Thr Gly Gly
        35                  40                  45

Glu Phe Ser Gln Met Asn Thr Ala Gln Arg Met Ala Leu Ala Glu Glu
    50                  55                  60

Ala Val Thr Ile Val Asp Gly Arg Val Pro Val Leu Ile Gly Val Gly
65                  70                  75                  80

Ser Pro Ser Thr Asp Glu Ala Val Lys Leu Ala Gln His Ala Gln Ala
                85                  90                  95

Tyr Gly Ala Asp Gly Ile Val Ala Ile Asn Pro Tyr Tyr Trp Lys Val
            100                 105                 110

Ala Pro Arg Asn Leu Asp Asp Tyr Tyr Gln Gln Ile Ala Arg Ser Val
        115                 120                 125

Thr Leu Pro Val Ile Leu Tyr Asn Phe Pro Asp Leu Thr Gly Gln Asp
    130                 135                 140

Leu Thr Pro Glu Thr Val Thr Arg Leu Ala Leu Gln Asn Glu Asn Ile
145                 150                 155                 160

Val Gly Ile Lys Asp Thr Ile Asp Ser Val Gly His Leu Arg Thr Met
                165                 170                 175

Ile Asn Thr Val Lys Ser Val Arg Pro Ser Phe Ser Val Phe Cys Gly
            180                 185                 190

Tyr Asp Asp His Leu Leu Asn Thr Met Leu Leu Gly Gly Asp Gly Ala
        195                 200                 205

Ile Thr Ala Ser Ala Asn Phe Ala Pro Glu Leu Ser Val Gly Ile Tyr
    210                 215                 220

Arg Ala Trp Arg Glu Gly Asp Leu Ala Thr Ala Thr Leu Asn Lys
225                 230                 235                 240

Lys Leu Leu Gln Leu Pro Ala Ile Tyr Ala Leu Glu Thr Pro Phe Val
            245                 250                 255

Ser Leu Ile Lys Tyr Ser Met Gln Cys Val Gly Leu Pro Val Glu Thr
        260                 265                 270

Tyr Cys Leu Pro Pro Ile Leu Glu Ala Ser Glu Glu Ala Lys Asp Lys
    275                 280                 285

Val His Val Leu Leu Thr Ala Gln Gly Ile Leu Pro Val
290                 295                 300

<210> SEQ ID NO 79
<211> LENGTH: 909
<212> TYPE: DNA
<213> ORGANISM: Escherichia coli

<400> SEQUENCE: 79
atgccgcagt ccgcgttgtt cacgggaatc attccccctg tctccaccat ttttaccgcc      60
gacggccagc tcgataagcc gggcaccgcc gcgctgatcg acgatctgat caaagcaggc     120

```
gttgacggcc tgttcttcct gggcagcggt ggcgagttct cccagctcgg cgccgaagag      180
cgtaaagcca ttgcccgctt tgctatcgat catgtcgatc gtcgcgtgcc ggtgctgatc      240
ggcaccggcg gcaccaacgc ccgggaaacc atcgaactca gccagcacgc gcagcaggcg      300
ggcgcggacg gcatcgtggt gatcaacccc tactactgga agtgtcgga agcgaacctg      360 atccgctatt cgagcaggt ggccgacagc gtcacgctgc cggtgatgct ctataacttc      420
ccggcgctga ccgggcagga tctgactccg gcgctggtga aaaccctcgc cgactcgcgc      480
agcaatatta tcggcatcaa agacaccatc gactccgtcg cccacctgcg cagcatgatc      540
cataccgtca aaggtgccca tccgcacttc accgtgctct gcggctacga cgatcatctg      600
ttcaataccc tgctgctcgg cggcgacggg gcgatatcgg cgagcggcaa ctttgccccg      660
caggtgtcgg tgaatcttct gaaagcctgg cgcgacgggg acgtggcgaa agcggccggg      720
tatcatcaga ccttgctgca aattccgcag atgtatcagc tggatacgcc gtttgtgaac      780
gtgattaaag aggcgatcgt gctctgcggt cgtcctgtct ccacgcacgt gctgccgccc      840
gcctcgccgc tggacgagcc gcgcaaggcg cagctgaaaa ccctgctgca acagctcaag      900
ctttgctga                                                              909

<210> SEQ ID NO 80
<211> LENGTH: 909
<212> TYPE: DNA
<213> ORGANISM: Escherichia coli

<400> SEQUENCE: 80
atgccgcagt ccgcgttgtt cacgggaatc attcccctg tctccaccat ttttaccgcc       60
gacggccagc tcgataagcc gggcaccgcc gcgctgatcg acgatctgat caaagcaggc     120
gttgacggcc tgttcttcct gggcagcggt ggcgagttct cccagctcgg cgccgaagag      180
cgtaaagcca ttgcccgctt tgctatcgat catgtcgatc gtcgcgtgcc ggtgctgatc      240
ggcaccggcg gcaccaacgc ccgggaaacc atcgaactca gccagcacgc gcagcaggcg      300
ggcgcggacg gcatcgtggt gatcaacccc tactactgga agtgtcgga agcgaacctg      360 atccgctatt cgagcaggt ggccgacagc gtcacgctgc cggtgatgct ctataacttc      420
ccggcgctga ccgggcagga tctgactccg gcgctggtga aaaccctcgc cgactcgcgc      480
agcaatatta tcggcatcaa agacaccatc gactccgtcg cccacctgcg cagcatgatc      540
cataccgtca aaggtgccca tccgcacttc accgtgctct gcggctacga cgatcatctg      600
ttcaataccc tgctgctcgg cggcgacggg gcgatatcgg cgagcggcaa ctttgccccg      660
caggtgtcgg tgaatcttct gaaagcctgg cgcgacgggg acgtggcgaa agcggccggg      720
tatcatcaga ccttgctgca aattccgcag atgtatcagc tggatacgcc gtttgtgaac      780
gtgattaaag aggcgatcgt gctctgcggt cgtcctgtct ccacgcacgt gctgccgccc      840
gcctcgccgc tggacgagcc gcgcaaggcg cagctgaaaa ccctgctgca acagctcaag      900
ctttgctga                                                              909

<210> SEQ ID NO 81
<211> LENGTH: 302
<212> TYPE: PRT
<213> ORGANISM: Escherichia coli

<400> SEQUENCE: 81

Met Pro Gln Ser Ala Leu Phe Thr Gly Ile Ile Pro Pro Val Ser Thr
1               5                   10                  15
```

Ile Phe Thr Ala Asp Gly Gln Leu Asp Lys Pro Gly Thr Ala Ala Leu
                20                  25                  30

Ile Asp Asp Leu Ile Lys Ala Gly Val Asp Gly Leu Phe Phe Leu Gly
            35                  40                  45

Ser Gly Gly Glu Phe Ser Gln Leu Gly Ala Glu Arg Lys Ala Ile
 50                  55                  60

Ala Arg Phe Ala Ile Asp His Val Asp Arg Val Pro Val Leu Ile
 65                  70                  75                  80

Gly Thr Gly Gly Thr Asn Ala Arg Glu Thr Ile Glu Leu Ser Gln His
                85                  90                  95

Ala Gln Gln Ala Gly Ala Asp Gly Ile Val Val Ile Asn Pro Tyr Tyr
                100                 105                 110

Trp Lys Val Ser Glu Ala Asn Leu Ile Arg Tyr Phe Glu Gln Val Ala
            115                 120                 125

Asp Ser Val Thr Leu Pro Val Met Leu Tyr Asn Phe Pro Ala Leu Thr
130                 135                 140

Gly Gln Asp Leu Thr Pro Ala Leu Val Lys Thr Leu Ala Asp Ser Arg
145                 150                 155                 160

Ser Asn Ile Ile Gly Ile Lys Asp Thr Ile Asp Ser Val Ala His Leu
                165                 170                 175

Arg Ser Met Ile His Thr Val Lys Gly Ala His Pro His Phe Thr Val
            180                 185                 190

Leu Cys Gly Tyr Asp Asp His Leu Phe Asn Thr Leu Leu Leu Gly Gly
        195                 200                 205

Asp Gly Ala Ile Ser Ala Ser Gly Asn Phe Ala Pro Gln Val Ser Val
    210                 215                 220

Asn Leu Leu Lys Ala Trp Arg Asp Gly Asp Val Ala Lys Ala Ala Gly
225                 230                 235                 240

Tyr His Gln Thr Leu Leu Gln Ile Pro Gln Met Tyr Gln Leu Asp Thr
                245                 250                 255

Pro Phe Val Asn Val Ile Lys Glu Ala Ile Val Leu Cys Gly Arg Pro
            260                 265                 270

Val Ser Thr His Val Leu Pro Pro Ala Ser Pro Leu Asp Glu Pro Arg
        275                 280                 285

Lys Ala Gln Leu Lys Thr Leu Leu Gln Gln Leu Lys Leu Cys
    290                 295                 300

<210> SEQ ID NO 82
<211> LENGTH: 957
<212> TYPE: DNA
<213> ORGANISM: Scheffersomyces stipitis

<400> SEQUENCE: 82
atgccttcta ttaagttgaa ctctggttac gacatgccag ccgtcggttt cggctgttgg    60
aaagtcgacg tcgacaccctg ttctgaacag atctaccgtg ctatcaagac cggttacaga   120
ttgttcgacg gtgccgaaga ttacgccaac gaaaagttag ttggtgccgg tgtcaagaag   180
gccattgacg aaggtatcgt caagcgtgaa gatttgttcc ttacctccaa gttgtggaac   240
aactaccacc acccagacaa cgtcgaaaag gccttgaaca gaacccttc tgacttgcaa    300 gttgactacg ttgacttgtt cttgatccac ttcccagtca ccttcaagtt cgttccatta   360
gaagaaaagt accccaccag gattctactgt ggtaagggtg acaacttcga ctacgaagat   420
gttccaattt tagagacttg gaaggctctt gaaaagttgg tcaaggccgg taagatcaga   480

```
tctatcggtg tttctaactt cccaggtgct tgctcttgg acttgttgag aggtgctacc      540
atcaagccat ctgtcttgca agttgaacac cacccatact tgcaacaacc aagattgatc      600
gaattcgctc aatcccgtgg tattgctgtc accgcttact cttcgttcgg tcctcaatct      660
ttcgttgaat tgaaccaagg tagagctttg aacacttctc cattgttcga gaacgaaact      720
atcaaggcta tcgctgctaa gcacggtaag tctccagctc aagtcttgtt gagatggtca      780
tcccaaagag gcattgccat cattccaaag tccaacactg tcccaagatt gttggaaaac      840
aaggacgtca acagcttcga cttggacgaa caagatttcg ctgacattgc caagttggac      900
atcaacttga gattcaacga cccatgggac tgggacaaga ttcctatctt cgtctaa         957

<210> SEQ ID NO 83
<211> LENGTH: 957
<212> TYPE: DNA
<213> ORGANISM: Scheffersomyces stipitis

<400> SEQUENCE: 83
atgccatcta tcaagttaaa ttccggttac gacatgcctg ctgttggttt cggttgctgg       60
aaggttgatg tcgatacttg ttccgagcaa atttaccgtg ctatcaagac tggttacaga      120
ttgttcgatg gtgctgaaga ctacgccaac gaaaagttag tcggtgctgg tgttaaaaag      180
gctatcgacg aaggtattgt taaaagagaa gacttgttct tgacttctaa gttgtggaac      240
aactaccacc atcctgataa cgtcgaaaaa gctttgaacc gtaccttgtc cgatttgcaa      300
gtcgattacg ttgatttgtt cttgattcat ttcccagtta ccttcaagtt cgttccattg      360
gaagagaagt atccaccagg tttctactgt ggtaagggtg ataacttcga ttacgaagat      420
gtcccaatct tagaaacctg gaaggcttta gaaaagttgg ttaaggctgg taagatcaga      480
tccatcggtg tttctaactt cccaggtgcc ttattgttag acttattgag aggtgctacc      540
attaagcctt ccgttttgca agttgaacat catccttact tgcaacaacc aagattgatc      600
gaattcgctc aatctagagg tatcgctgtt actgcctact cttccttcgg tccacaatct      660
ttcgttgagt tgaaccaagg tagagctttg aacacctctc cattgttcga aaacgaaact      720
attaaggcca ttgctgctaa gcatggtaag tctccagccc aagttttgtt gagatggtct      780
tctcaaagag gtatcgctat tcccaaagt ctaatactg tcccaagatt gttggaaaac      840
aaggacgtta actcctttga tttggatgaa caagactttg ctgacatcgc taaattggac      900
atcaacttga gattcaacga cccatgggac tgggacaaga ttccaatttt tgtttaa         957

<210> SEQ ID NO 84
<211> LENGTH: 318
<212> TYPE: PRT
<213> ORGANISM: Scheffersomyces stipitis

<400> SEQUENCE: 84

Met Pro Ser Ile Lys Leu Asn Ser Gly Tyr Asp Met Pro Ala Val Gly
1               5                  10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80
```

```
Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 85
<211> LENGTH: 984
<212> TYPE: DNA
<213> ORGANISM: Saccharomyces cerevisiae

<400> SEQUENCE: 85

```
atgtcttcac tggttactct taataacggt ctgaaaatgc ccctagtcgg cttagggtgc    60
tggaaaattg acaaaaaagt ctgtgcgaat caaatttatg aagctatcaa attaggctac   120
cgtttattcg atggtgcttg cgactacggc aacgaaaagg aagttggtga aggtatcagg   180
aaagccatct ccgaaggtct tgtttctaga aggatatat ttgttgtttc aaagttatgg   240
aacaattttc accatcctga tcatgtaaaa ttagctttaa agaagacctt aagcgatatg   300
ggacttgatt atttagacct gtattatatt cacttcccaa tcgccttcaa atatgttcca   360
tttgaagaga ataccctcc aggattctat acgggcgcag atgacgagaa aaaggtcac    420
atcaccgaag cacatgtacc aatcatagat acgtaccggg ctctggaaga atgtgttgat   480
gaaggcttga ttaagtctat tggtgttttcc aactttcagg gaagcttgat tcaagattta   540
ttacgtggtt gtagaatcaa gcccgtggct ttgcaaattg aacaccatcc ttatttgact   600
caagaacacc tagttgagtt ttgtaaatta cacgatatcc aagtagttgc ttactcctcc   660
ttcggtcctc aatcattcat tgagatggac ttacagttgg caaaaccac gccaactctg   720
ttcgagaatg atgtaatcaa gaaggtctca caaaaccatc caggcagtac cacttcccaa   780
```

```
gtattgctta gatgggcaac tcagagaggc attgccgtca ttccaaaatc ttccaagaag    840
gaaaggttac ttggcaacct agaaatcgaa aaaaagttca ctttaacgga gcaagaattg    900
aaggatattt ctgcactaaa tgccaacatc agatttaatg atccatggac ctggttggat    960
ggtaaattcc ccacttttgc ctga                                          984
```

<210> SEQ ID NO 86
<211> LENGTH: 984
<212> TYPE: DNA
<213> ORGANISM: Saccharomyces cerevisiae

<400> SEQUENCE: 86

```
atgtcttcac tggttactct taataacggt ctgaaaatgc ccctagtcgg cttagggtgc     60
tggaaaattg acaaaaaagt ctgtgcgaat caaatttatg aagctatcaa attaggctac    120
cgtttattcg atggtgcttg cgactacggc aacgaaaagg aagttggtga aggtatcagg    180
aaagccatct ccgaaggtct tgtttctaga aaggatatat ttgttgtttc aaagttatgg    240
aacaattttc accatcctga tcatgtaaaa ttagctttaa agaagacctt aagcgatatg    300
ggacttgatt atttagacct gtattatatt cacttcccaa tcgccttcaa atatgttcca    360
tttgaagaga ataccctcc aggattctat acgggcgcag atgacgagaa gaaggtcac     420 atcaccgaag cacatgtacc aatcatagat acgtaccggg ctctggaaga atgtgttgat    480
gaaggcttga ttaagtctat tggtgttccc aactttcagg aagcttgat tcaagattta     540 ttacgtggtt gtagaatcaa gcccgtggct ttgcaaattg aacaccatcc ttatttgact    600
caagaacacc tagttgagtt ttgtaaatta acgatatcc aagtagttgc ttactcctcc    660
ttcggtcctc aatcattcat tgagatggac ttacagttgg caaaaaccac gccaactctg    720
ttcgagaatg atgtaatcaa gaaggtctca caaaaccatc caggcagtac cacttcccaa    780
gtattgctta gatgggcaac tcagagaggc attgccgtca ttccaaaatc ttccaagaag    840
gaaaggttac ttggcaacct agaaatcgaa aaaaagttca ctttaacgga gcaagaattg    900
aaggatattt ctgcactaaa tgccaacatc agatttaatg atccatggac ctggttggat    960
ggtaaattcc ccacttttgc ctga                                          984
```

<210> SEQ ID NO 87
<211> LENGTH: 327
<212> TYPE: PRT
<213> ORGANISM: Saccharomyces cerevisiae

<400> SEQUENCE: 87

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110
```

```
Pro Ile Ala Phe Lys Tyr Val Pro Phe Glu Glu Lys Tyr Pro Pro Gly
            115                 120                 125

Phe Tyr Thr Gly Ala Asp Asp Glu Lys Lys Gly His Ile Thr Glu Ala
        130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 88
<211> LENGTH: 1092
<212> TYPE: DNA
<213> ORGANISM: Scheffersomyces stipitis

<400> SEQUENCE: 88
atgactgcta accccttcctt ggtgttgaac aagatcgacg acatttcgtt cgaaacttac      60
gatgccccag aaatctctga acctaccgat gtcctcgtcc aggtcaagaa aaccggtatc     120
tgtggttccg acatccactt ctacgcccat ggtagaatcg gtaacttcgt tttgaccaag     180
ccaatggtct tgggtcacga atccgccggt actgttgtcc aggttggtaa gggtgtcacc     240
tctcttaagg ttggtgacaa cgtcgctatc gaaccaggta ttccatccag attctccgac     300
gaatacaaga gcggtcacta caacttgtgt cctcacatgg ccttcgccgc tactcctaac     360
tccaaggaag gcgaaccaaa cccaccaggt accttatgta agtacttcaa gtcgccagaa     420
gacttcttgg tcaagttgcc agaccacgtc agcttggaac tcggtgctct tgttgagcca     480
ttgtctgttg gtgtccacgc ctctaagttg ggttccgttg ctttcggcga ctacgttgcc     540
gtctttggtg ctggtcctgt tggtctttttg gctgctgctg tcgccaagac cttcggtgct     600
aagggtgtca tcgtcgttga catttttcgac aacaagttga agatggccaa ggacattggt     660
gctgctactc acaccttcaa ctccaagacc ggtggttctg aagaattgat caaggctttc     720
ggtggtaacg tgccaaacgt cgttttggaa tgtactggtg ctgaaccttg tatcaagttg     780
ggtgttgacg ccattgcccc aggtggtcgt ttcgttcaag tcggtaacgc tgctggtcca     840
gtcagcttcc caatcaccgt tttcgccatg aaggaattga ctttgttcgg ttcttttcaga     900
```

```
tacggattca acgactacaa gactgctgtt ggaatctttg acactaacta ccaaaacggt    960
agagaaaatg ctccaattga ctttgaacaa ttgatcaccc acagatacaa gttcaaggac   1020
gctattgaag cctacgactt ggtcagagcc ggtaagggtg ctgtcaagtg tctcattgac   1080
ggccctgagt aa                                                       1092

<210> SEQ ID NO 89
<211> LENGTH: 1092
<212> TYPE: DNA
<213> ORGANISM: Scheffersomyces stipitis

<400> SEQUENCE: 89
atgactgcta acccttcctt ggtgttgaac aagatcgacg acatttcgtt cgaaacttac     60
gatgccccag aaatctctga acctaccgat gtcctcgtcc aggtcaagaa aaccggtatc    120
tgtggttccg acatccactt ctacgcccat ggtagaatcg gtaacttcgt tttgaccaag    180
ccaatggtct tgggtcacga atccgccggt actgttgtcc aggttggtaa gggtgtcacc    240
tctcttaagg ttggtgacaa cgtcgctatc gaaccaggta ttccatccag attctccgac    300
gaatacaaga gcggtcacta caacttgtgt cctcacatgg ccttcgccgc tactcctaac    360
tccaaggaag gcgaaccaaa cccaccaggt accttatgta agtacttcaa gtcgccagaa    420
gatttcttgg tcaagttgcc agaccacgtc agcttggaac tcggtgctct tgttgagcca    480
ttgtctgttg gtgtccacgc tctaagttg ggttccgttg ctttcggcga ctacgttgcc    540
gtctttggag caggtcctgt tggtctttg gctgctgctg tcgccaagac cttcggtgct    600
aagggtgtca tcgtcgttga catttcgac aacaagttga gatggccaa ggacattgga    660 gctgctactc acaccttcaa ctccaagacc ggtggttctg aagaattgat caaggctttc    720
ggtggtaacg tgccaaacgt cgttttggaa tgtacaggtg cagaaccttg tatcaagttg    780
ggtgttgacg ccattgcccc aggtggtcgt ttcgttcaag tcggtaacgc tgctggtcca    840
gtcagcttcc caatcaccgt tttcgccatg aaggaattga ctttgttcgg ttctttcaga    900
tacggattca acgactacaa gactgctgtt ggaatctttg acactaacta ccaaaacggt    960
agagaaaatg ctccaattga ctttgaacaa ttgatcaccc acagatacaa gttcaaggac   1020
gctattgaag cctacgactt ggtcagagcc ggtaagggtg ctgtcaagtg tctcattgac   1080
ggccctgagt aa                                                       1092

<210> SEQ ID NO 90
<211> LENGTH: 363
<212> TYPE: PRT
<213> ORGANISM: Scheffersomyces stipitis

<400> SEQUENCE: 90

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
```

```
                    85                  90                  95
Arg Phe Ser Asp Glu Tyr Lys Ser Gly His Tyr Asn Leu Cys Pro His
                100                 105                 110
Met Ala Phe Ala Ala Thr Pro Asn Ser Lys Glu Gly Glu Pro Asn Pro
                115                 120                 125
Pro Gly Thr Leu Cys Lys Tyr Phe Lys Ser Pro Glu Asp Phe Leu Val
            130                 135                 140
Lys Leu Pro Asp His Val Ser Leu Glu Leu Gly Ala Leu Val Glu Pro
145                 150                 155                 160
Leu Ser Val Gly Val His Ala Ser Lys Leu Gly Ser Val Ala Phe Gly
                165                 170                 175
Asp Tyr Val Ala Val Phe Gly Ala Gly Pro Val Gly Leu Leu Ala Ala
                180                 185                 190
Ala Val Ala Lys Thr Phe Gly Ala Lys Gly Val Ile Val Val Asp Ile
                195                 200                 205
Phe Asp Asn Lys Leu Lys Met Ala Lys Asp Ile Gly Ala Ala Thr His
            210                 215                 220
Thr Phe Asn Ser Lys Thr Gly Gly Ser Glu Glu Leu Ile Lys Ala Phe
225                 230                 235                 240
Gly Gly Asn Val Pro Asn Val Val Leu Glu Cys Thr Gly Ala Glu Pro
                245                 250                 255
Cys Ile Lys Leu Gly Val Asp Ala Ile Ala Pro Gly Gly Arg Phe Val
                260                 265                 270
Gln Val Gly Asn Ala Ala Gly Pro Val Ser Phe Pro Ile Thr Val Phe
            275                 280                 285
Ala Met Lys Glu Leu Thr Leu Phe Gly Ser Phe Arg Tyr Gly Phe Asn
290                 295                 300
Asp Tyr Lys Thr Ala Val Gly Ile Phe Asp Thr Asn Tyr Gln Asn Gly
305                 310                 315                 320
Arg Glu Asn Ala Pro Ile Asp Phe Glu Gln Leu Ile Thr His Arg Tyr
                325                 330                 335
Lys Phe Lys Asp Ala Ile Glu Ala Tyr Asp Leu Val Arg Ala Gly Lys
            340                 345                 350
Gly Ala Val Lys Cys Leu Ile Asp Gly Pro Glu
            355                 360

<210> SEQ ID NO 91
<211> LENGTH: 1092
<212> TYPE: DNA
<213> ORGANISM: Trichoderma reesei

<400> SEQUENCE: 91
atggcgactc aaacgatcaa caaggatgcg atcagcaacc tctccttcgt cctcaacaag      60
cccggcgacg tgacctttga ggagcggccg aagccgacca tcacggaccc caacgacgtc     120
ctcgtcgccg tcaactacac gggcatctgc ggctccgacg tgcactactg ggtgcacggc     180
gccatcgggc acttcgtcgt caaggacccg atggtgctgg ccacgagtc ggccggcacc      240 gtcgtcgagg tcggcccggc cgtcaagagc ctcaagcccg cgaccgcgt cgccctcgag       300 cccggctacc cgtgccggcg tgctccttc tgccgcgccg caaatacaa cctgtgcccg       360 gacatggtct tcgccgccac gccgccgtac cacggcaccc tgacgggcct gtgggcggcg     420
cccgccgact tctgctacaa gctgccggac ggcgtgtcgc tgcaggaggg cgcgctgatc     480
gagccgctgg ccgtggccgt ccacattgtc aagcaggccc gcgtccagcc gggccagtcc     540
```

-continued

```
gtcgtcgtca tgggcgccgg ccccgtcggc ctgctgtgcg ccgccgtggc caaggcgtac    600
ggcgcctcca ccattgtcag cgtcgacatc gtgcagtcca agctcgactt tgcgcgcggc    660
ttctgctcga cgcacacgta cgtctcgcag cgcatctcgg ctgaggacaa cgcaaaggcc    720
atcaaggagc tggcgggcct gcccggcggc gccgacgtcg tgattgacgc cagcggcgcg    780
gagccgtcga tccagacgag cattcacgtc gtccgcatgg gcggcacgta cgtccagggc    840
ggcatgggca gagcgacat cacgttcccc atcatggcca tgtgcctcaa ggaggtgacg    900
gtccggggct cgttccgcta cggcgccggc gactacgagc tggcggtcga gctggtccgg    960
acggggcggg tggacgtcaa gaagctgatt acgggcaccg tcagcttcaa gcaggcggag   1020
gaggcgttcc aaaaggtcaa gtctggggag gccatcaaga ttctgattgc cgggcccaac   1080
gagaaggtgt aa                                                       1092
```

<210> SEQ ID NO 92
<211> LENGTH: 363
<212> TYPE: PRT
<213> ORGANISM: Trichoderma reesei

<400> SEQUENCE: 92

```
Met Ala Thr Gln Thr Ile Asn Lys Asp Ala Ile Ser Asn Leu Ser Phe
1               5                  10                  15

Val Leu Asn Lys Pro Gly Asp Val Thr Phe Glu Glu Arg Pro Lys Pro
            20                  25                  30

Thr Ile Thr Asp Pro Asn Asp Val Leu Ala Val Asn Tyr Thr Gly
        35                  40                  45

Ile Cys Gly Ser Asp Val His Tyr Trp Val His Gly Ala Ile Gly His
    50                  55                  60

Phe Val Val Lys Asp Pro Met Val Leu Gly His Glu Ser Ala Gly Thr
65                  70                  75                  80

Val Val Glu Val Gly Pro Ala Val Lys Ser Leu Lys Pro Gly Asp Arg
                85                  90                  95

Val Ala Leu Glu Pro Gly Tyr Pro Cys Arg Arg Cys Ser Phe Cys Arg
            100                 105                 110

Ala Gly Lys Tyr Asn Leu Cys Pro Asp Met Val Phe Ala Ala Thr Pro
        115                 120                 125

Pro Tyr His Gly Thr Leu Thr Gly Leu Trp Ala Ala Pro Ala Asp Phe
    130                 135                 140

Cys Tyr Lys Leu Pro Asp Gly Val Ser Leu Gln Glu Gly Ala Leu Ile
145                 150                 155                 160

Glu Pro Leu Ala Val Ala Val His Ile Val Lys Gln Ala Arg Val Gln
                165                 170                 175

Pro Gly Gln Ser Val Val Val Met Gly Ala Gly Pro Val Gly Leu Leu
            180                 185                 190

Cys Ala Ala Val Ala Lys Ala Tyr Gly Ala Ser Thr Ile Val Ser Val
        195                 200                 205

Asp Ile Val Gln Ser Lys Leu Asp Phe Ala Arg Gly Phe Cys Ser Thr
    210                 215                 220

His Thr Tyr Val Ser Gln Arg Ile Ser Ala Glu Asp Asn Ala Lys Ala
225                 230                 235                 240

Ile Lys Glu Leu Ala Gly Leu Pro Gly Gly Ala Asp Val Val Ile Asp
                245                 250                 255

Ala Ser Gly Ala Glu Pro Ser Ile Gln Thr Ser Ile His Val Val Arg
            260                 265                 270
```

```
Met Gly Gly Thr Tyr Val Gln Gly Gly Met Gly Lys Ser Asp Ile Thr
            275                 280                 285
Phe Pro Ile Met Ala Met Cys Leu Lys Glu Val Thr Val Arg Gly Ser
        290                 295                 300
Phe Arg Tyr Gly Ala Gly Asp Tyr Glu Leu Ala Val Glu Leu Val Arg
305                 310                 315                 320
Thr Gly Arg Val Asp Val Lys Lys Leu Ile Thr Gly Thr Val Ser Phe
                325                 330                 335
Lys Gln Ala Glu Ala Phe Gln Lys Val Lys Ser Gly Glu Ala Ile
            340                 345                 350
Lys Ile Leu Ile Ala Gly Pro Asn Glu Lys Val
        355                 360

<210> SEQ ID NO 93
<211> LENGTH: 1314
<212> TYPE: DNA
<213> ORGANISM: Pyromyces sp.

<400> SEQUENCE: 93
atggctaagg aatatttccc acaaattcaa aagattaagt tcgaaggtaa ggattctaag      60
aatccattag ccttccacta ctacgatgct gaaaaggaag tcatgggtaa gaaaatgaag     120
gattggttac gtttcgccat ggcctggtgg cacactcttt gcgccgaagg tgctgaccaa     180
ttcggtggag gtacaaagtc tttcccatgg aacgaaggta ctgatgctat tgaaattgcc     240
aagcaaaagg ttgatgctgg tttcgaaatc atgcaaaagc ttggtattcc atactactgt     300
ttccacgatg ttgatcttgt ttccgaaggt aactctattg aagaatacga atccaacctt     360
aaggctgtcg ttgcttacct caaggaaaag caaaaggaaa ccggtattaa gcttctctgg     420
agtactgcta acgtcttcgg tcacaagcgt tacatgaacg gtgcctccac taacccagac     480
tttgatgttg tcgcccgtgc tattgttcaa attaagaacg ccatagacgc cggtattgaa     540
cttggtgctg aaaactacgt cttctggggt ggtcgtgaag gttacatgag tctccttaac     600
actgaccaaa agcgtgaaaa ggaacacatg gccactatgc ttaccatggc tcgtgactac     660
gctcgttcca agggattcaa gggtactttc tcattgaaca aaagccaatg gaaccaacc      720
aagcaccaat acgatgttga cactgaaacc gctattggtt tccttaaggc ccacaactta     780
gacaaggact caaggtcaa cattgaagtt aaccacgcta ctcttgctgg tcacactttc     840
gaacacgaac ttgcctgtgc tgttgatgct ggtatgctcg gttccattga tgctaaccgt     900
ggtgactacc aaaacggttg ggatactgat caattcccaa ttgatcaata cgaactcgtc     960
caagcttgga tggaaatcat ccgtggtggt ggtttcgtta ctggtggtac caacttcgat    1020
gccaagactc gtcgtaactc tactgacctc gaagacatca tcattgccca cgtttctggt    1080
atggatgcta tggctcgtgc tcttgaaaac gctgccaagc tcctccaaga atctccatac    1140
accaagatga agaaggaacg ttacgcttcc ttcgacagtg tattggtaa ggactttgaa    1200
gatggtaagc tcaccctcga acaagtttac gaatacggta gaagaacgg tgaaccaaag    1260
caaacttctg gtaagcaaga actctacgaa gctattgttg ccatgtacca ataa          1314

<210> SEQ ID NO 94
<211> LENGTH: 1314
<212> TYPE: DNA
<213> ORGANISM: Pyromyces sp.

<400> SEQUENCE: 94
atggccaagg aatacttccc acaaatccaa aagattaaat tcgaaggtaa agattccaag      60
```

```
aacccattgg cttttcacta ctacgatgct gagaaggaag ttatgggtaa gaagatgaag      120
gattggttga gattcgctat ggcttggtgg cacactttgt gcgctgaagg tgctgaccaa      180
ttcggtggtg gtactaagtc tttcccatgg aacgaaggta ctgatgctat tgaaatcgct      240
aagcaaaaag tcgatgctgg ttttgagatt atgcaaaaat tgggtatccc atactactgt      300
ttccacgacg tcgacttggt ttctgaaggt aattctatcg aagaatacga atctaatttg      360
aaggctgttg tcgcttactt aaaagaaaag caaaaggaga ctggtattaa gttgttgtgg      420
tccaccgcta acgtctttgg tcataaaaga tacatgaacg gtgcttccac caacccagac      480
ttcgatgtcg tcgccagagc tatcgttcaa attaaaaacg ccatcgacgc tggtattgaa      540
ttgggtgctg aaaattacgt cttttggggt ggtcgtgaag ttacatgtc tttgttgaac       600 actgaccaaa agagagaaaa agaacacatg gccactatgt tgaccatggc cagagattac      660
gccagatcta agggtttcaa gggtaccttc ttaattgaac caaaacctat ggaaccaact      720
aagcaccaat acgacgttga cactgaaact gctatcggtt ttttgaaggc tcacaacttg      780
gataaggatt ttaaagtcaa cattgaagtt aaccatgcta ctttggctgg tcacactttt      840
gaacatgaat tggcctgtgc tgttgatgct ggtatgttgg ttctatcga tgctaataga      900 ggtgactatc aaaacggttg gacactgat caattcccaa tcgatcaata tgaattagtt       960
caagcttgga tggaaattat cagaggtggt ggtttcgtta ctggtggtac taacttcgat     1020
gctaagacca agaaaactc tactgatttg gaagatatta tcattgccca cgtttccggt      1080
atggatgcca tggccagagc tttggaaaac gccgccaagt tattgcaaga gtccccatac     1140
accaagatga aaaaggaacg ttacgcttct ttcgactctg gtatcggtaa agacttcgaa     1200
gatggtaagt tgaccttgga acaagtttac gaatacggta agaagaacgg tgaacctaaa     1260
caaacctctg gtaaacaaga attgtatgaa gctattgttg ccatgtacca ataa           1314
```

<210> SEQ ID NO 95
<211> LENGTH: 437
<212> TYPE: PRT
<213> ORGANISM: Pyromyces sp.

<400> SEQUENCE: 95

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
                20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
```

```
                145                 150                 155                 160
        Phe Asp Val Val Ala Arg Ala Ile Val Gln Ile Lys Asn Ala Ile Asp
                        165                 170                 175

Ala Gly Ile Glu Leu Gly Ala Glu Asn Tyr Val Phe Trp Gly Gly Arg
                    180                 185                 190

Glu Gly Tyr Met Ser Leu Leu Asn Thr Asp Gln Lys Arg Glu Lys Glu
                195                 200                 205

His Met Ala Thr Met Leu Thr Met Ala Arg Asp Tyr Ala Arg Ser Lys
            210                 215                 220

Gly Phe Lys Gly Thr Phe Leu Ile Glu Pro Lys Pro Met Glu Pro Thr
        225                 230                 235                 240

Lys His Gln Tyr Asp Val Asp Thr Glu Thr Ala Ile Gly Phe Leu Lys
                        245                 250                 255

Ala His Asn Leu Asp Lys Asp Phe Lys Val Asn Ile Glu Val Asn His
                    260                 265                 270

Ala Thr Leu Ala Gly His Thr Phe Glu His Glu Leu Ala Cys Ala Val
                275                 280                 285

Asp Ala Gly Met Leu Gly Ser Ile Asp Ala Asn Arg Gly Asp Tyr Gln
            290                 295                 300

Asn Gly Trp Asp Thr Asp Gln Phe Pro Ile Asp Gln Tyr Glu Leu Val
        305                 310                 315                 320

Gln Ala Trp Met Glu Ile Ile Arg Gly Gly Phe Val Thr Gly Gly
                        325                 330                 335

Thr Asn Phe Asp Ala Lys Thr Arg Arg Asn Ser Thr Asp Leu Glu Asp
                    340                 345                 350

Ile Ile Ile Ala His Val Ser Gly Met Asp Ala Met Ala Arg Ala Leu
                355                 360                 365

Glu Asn Ala Ala Lys Leu Leu Gln Glu Ser Pro Tyr Thr Lys Met Lys
            370                 375                 380

Lys Glu Arg Tyr Ala Ser Phe Asp Ser Gly Ile Gly Lys Asp Phe Glu
        385                 390                 395                 400

Asp Gly Lys Leu Thr Leu Glu Gln Val Tyr Glu Tyr Gly Lys Lys Asn
                        405                 410                 415

Gly Glu Pro Lys Gln Thr Ser Gly Lys Gln Glu Leu Tyr Glu Ala Ile
                    420                 425                 430

Val Ala Met Tyr Gln
                435

<210> SEQ ID NO 96
<211> LENGTH: 657
<212> TYPE: DNA
<213> ORGANISM: Clostridium acetobutylicum

<400> SEQUENCE: 96
atgaactcta aaataattag atttgaaaat ttaaggtcat tctttaaaga tgggatgaca      60
attatgattg gaggtttttt aaactgtggc actccaacca aattaattga tttttttagtt    120 aatttaaata taagaatttt aacgattata agtaatgata catgttatcc taatacaggt     180
attggtaagt taatatcaaa taatcaagta aaaaagctta ttgcttcata taggcagc       240 aacccagata ctgcaaaaaa acttttttaat aatgaacttg aagtagagct ctctccccaa   300
ggaactctag tggaaagaat acgtgcaggc ggatctggct taggtggtgt actaactaaa    360
acaggtttag gaactttgat tgaaaaagga agaaaaaaa tatctataaa tggaacggaa     420
tatttgttag agctacctct tacagccgat gtagcattaa ttaaaggtag tattgtagat    480
```

```
gaggccggaa acaccttcta taaaggtact actaaaaact ttaatcccta tatggcaatg    540
gcagctaaaa ccgtaatagt tgaagctgaa aatttagtta gctgtgaaaa actagaaaag    600
gaaaaagcaa tgaccccgg agttcttata aattatatag taaaggagcc tgcataa        657
```

<210> SEQ ID NO 97
<211> LENGTH: 218
<212> TYPE: PRT
<213> ORGANISM: Clostridium acetobutylicum

<400> SEQUENCE: 97

```
Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
            20                  25                  30

Thr Lys Leu Ile Asp Phe Leu Val Asn Leu Asn Ile Lys Asn Leu Thr
        35                  40                  45

Ile Ile Ser Asn Asp Thr Cys Tyr Pro Asn Thr Gly Ile Gly Lys Leu
    50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
        115                 120                 125

Lys Gly Lys Lys Lys Ile Ser Ile Asn Gly Thr Glu Tyr Leu Leu Glu
    130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
            180                 185                 190

Val Ser Cys Glu Lys Leu Glu Lys Glu Lys Ala Met Thr Pro Gly Val
        195                 200                 205

Leu Ile Asn Tyr Ile Val Lys Glu Pro Ala
    210                 215
```

<210> SEQ ID NO 98
<211> LENGTH: 666
<212> TYPE: DNA
<213> ORGANISM: Clostridium acetobutylicum

<400> SEQUENCE: 98

```
atgattaatg ataaaaacct agcgaaagaa ataatagcca aaagagttgc aagagaatta     60
aaaaatggtc aacttgtaaa cttaggtgta ggtcttccta ccatggttgc agattatata    120
ccaaaaaatt tcaaaattac tttccaatca gaaaacggaa tagttggaat gggcgctagt    180
cctaaaataa atgaggcaga taagatgta gtaaatgcag gaggagacta tacaacagta    240
cttcctgacg gcacattttt cgatagctca gtttcgtttt cactaatccg tggtggtcac    300
gtagatgtta ctgttttagg ggctctccag gtagatgaaa agggtaatat agccaattgg    360
attgttcctg gaaaaatgct ctctggtatg ggtggagcta tggatttagt aaatggagct    420
```

-continued

```
aagaaagtaa taattgcaat gagacataca aataaaggtc aacctaaaat tttaaaaaaa    480
tgtacacttc ccctcacggc aaagtctcaa gcaaatctaa ttgtaacaga acttggagta    540
attgaggtta ttaatgatgg tttacttctc actgaaatta ataaaaacac aaccattgat    600
gaaataaggt ctttaactgc tgcagattta ctcatatcca atgaacttag acccatggct    660
gtttag                                                               666
```

<210> SEQ ID NO 99
<211> LENGTH: 221
<212> TYPE: PRT
<213> ORGANISM: Clostridium acetobutylicum

<400> SEQUENCE: 99

```
Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220
```

<210> SEQ ID NO 100
<211> LENGTH: 651
<212> TYPE: DNA
<213> ORGANISM: Escherichia coli

<400> SEQUENCE: 100

```
atggatgcga acaacgtat tgcgcgccgt gtggcgcaag agcttcgtga tggtgacatc    60
gttaacttag ggatcggttt acccacaatg gtcgccaatt atttaccgga gggtattcat    120
atcactctgc aatcggaaaa cggcttcctc ggtttaggcc cggtcacgac agcgcatcca    180
gatctggtga acgctggcgg gcaaccgtgc ggtgttttac ccggtgcagc catgtttgat    240
agcgccatgt catttgcgct aatccgtggc ggtcatattg atgcctgcgt gctcggcggt    300
ttgcaagtag acgaagaagc aaacctcgcg aactgggtag tgcctgggaa aatggtgccc    360
```

```
ggtatgggtg gcgcgatgga tctggtgacc gggtcgcgca aagtgatcat cgccatggaa    420
cattgcgcca aagatggttc agcaaaaatt ttgcgccgct gcaccatgcc actcactgcg    480
caacatgcgg tgcatatgct ggttactgaa ctggctgtct ttcgttttat tgacggcaaa    540
atgtggctca ccgaaattgc cgacgggtgt gatttagcca ccgtgcgtgc caaaacagaa    600
gctcggtttg aagtcgccgc cgatctgaat acgcaacggg gtgatttatg a             651
```

<210> SEQ ID NO 101
<211> LENGTH: 216
<212> TYPE: PRT
<213> ORGANISM: Escherichia coli

<400> SEQUENCE: 101

```
Met Asp Ala Lys Gln Arg Ile Ala Arg Val Ala Gln Glu Leu Arg
1               5                  10                  15

Asp Gly Asp Ile Val Asn Leu Gly Ile Gly Leu Pro Thr Met Val Ala
                20                  25                  30

Asn Tyr Leu Pro Glu Gly Ile His Ile Thr Leu Gln Ser Glu Asn Gly
            35                  40                  45

Phe Leu Gly Leu Gly Pro Val Thr Thr Ala His Pro Asp Leu Val Asn
        50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu
        115                 120                 125

Val Thr Gly Ser Arg Lys Val Ile Ile Ala Met Glu His Cys Ala Lys
    130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
        195                 200                 205

Leu Asn Thr Gln Arg Gly Asp Leu
    210                 215
```

<210> SEQ ID NO 102
<211> LENGTH: 663
<212> TYPE: DNA
<213> ORGANISM: Escherichia coli

<400> SEQUENCE: 102

```
atgaaaacaa aattgatgac attacaagac gccaccggct tctttcgtga cggcatgacc    60
atcatggtgg gcggatttat ggggattggc actccatccc gctggttgaa agcattactg    120
gaatctggtg ttcgcgacct gacattgata gccaatgata ccgcgtttgt tgataccggc    180
atcggtccgc tcatcgtcaa tggtcgagtc cgcaaagtga ttgcttcaca tatcggcacc    240 aaccccggaaa caggtcggcg catgatatct ggtgagatgg acgtcgttct ggtgccgcaa    300
```

```
ggtacgctaa tcgagcaaat tcgctgtggt ggagctggac ttggtggttt tctcacccca    360
acgggtgtcg gcaccgtcgt agaggaaggc aaacagacac tgacactcga cggtaaaacc    420
tggctgctcg aacgcccact gcgcgccgac ctggcgctaa ttcgcgctca tcgttgcgac    480
acacttggca acctgaccta tcaacttagc gcccgcaact ttaacccccct gatagccctt    540 gcggctgata tcacgctggt agagccagat gaactggtcg aaaccggcga gctgcaacct    600
gaccatattg tcaccctgg tgccgttatc gaccacatca tcgtttcaca ggagagcaaa    660
taa                                                                  663
```

<210> SEQ ID NO 103
<211> LENGTH: 220
<212> TYPE: PRT
<213> ORGANISM: Escherichia coli

<400> SEQUENCE: 103

```
Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys
    210                 215                 220
```

<210> SEQ ID NO 104
<211> LENGTH: 1056
<212> TYPE: DNA
<213> ORGANISM: Clostridium beijerinckii

<400> SEQUENCE: 104

```
atgaaaggtt ttgcaatgct aggtattaat aagttaggat ggatcgaaaa agaaaggcca    60
gttgcgggtt catatgatgc tattgtacgc ccattagcag tatctccgtg tacatcagat    120
atacatactg ttttttgaggg agctcttgga gataggaaga atatgatttt agggcatgaa    180
gctgtaggtg aagttgttga agtaggaagt gaagtgaagg attttaaacc tggtgacaga    240
```

```
gttatagttc cttgtacaac tccagattgg agatctttgg aagttcaagc tggttttcaa    300
cagcactcaa acggtatgct cgcaggatgg aaattttcaa atttcaagga tggagttttt    360
ggtgaatatt ttcatgtaaa tgatgcggat atgaatcttg cgattctacc taaagacatg    420
ccattagaaa atgctgttat gataacagat atgatgacta ctggatttca tggagcagaa    480
cttgcagata ttcaaatggg ttcaagtgtt gtggtaattg gcattggagc tgttggctta    540
atgggaatag caggtgctaa attacgtgga gcaggtagaa taattggagt ggggagcagg    600
ccgatttgtg ttgaggctgc aaaattttat ggagcaacag atattctaaa ttataaaaat    660
ggtcatatag ttgatcaagt tatgaaatta acgaatggaa aaggcgttga ccgcgtaatt    720
atggcaggcg gtggttctga aacattatcc caagcagtat ctatggttaa accaggagga    780
ataatttcta atataaatta tcatggaagt ggagatgctt tactaatacc acgtgtagaa    840
tggggatgtg gaatggctca caagactata aaaggaggtc tttgtcctgg gggacgtttg    900
agagcagaaa tgttaagaga tatggtagta tataatcgtg ttgatctaag taaattagtt    960
acacatgtat atcatggatt tgatcacata gaagaagcac tgttattaat gaaagacaag   1020
ccaaaagact taattaaagc agtagttata ttataa                             1056
```

<210> SEQ ID NO 105
<211> LENGTH: 1056
<212> TYPE: DNA
<213> ORGANISM: Clostridium beijerinckii

<400> SEQUENCE: 105

```
atgaaagggt ttgccatgtt aggtatcaat aaactgggct ggattgaaaa agagcgcccg     60
gtggcgggtt catacgatgc aattgttcgt ccgctggccg tcagtccgtg caccagcgac    120
atccatacag tctttgaagg tgccctgggt gatcggaaaa acatgattct gggccatgaa    180
gccgtaggcg aagtagtgga agtgggcagc gaggtaaagg atttcaaacc gggtgatcgc    240
gtaattgttc cttgcacgac cccagattgg cgctcactgg aagttcaggc tggttttcag    300
cagcatagta acggtatgtt agcaggctgg aagtttagca attttaaaga cggggtgttc    360
ggggagtatt ttcatgtcaa cgatgcggac atgaatctgg ctattttacc taaagatatg    420
ccgctggaga acgcagtgat gattaccgac atgatgacga caggctttca cggtgcagaa    480
ctggctgaca tccaaatggg ctccagtgtg gtggttatcg gtattggtgc ggtcgggctg    540
atgggtatcg cgggcgcgaa attacggggc gctggtcgca tcatcggtgt cggcagccgt    600
ccaatttgcg ttgaagcagc taaattctat ggtgccacgg acattctgaa ctataaaaat    660
ggtcacatcg tcgatcaggt gatgaaactg accaatggca aaggtgtgga ccgcgtgatc    720
atggcgggcg gcggctcaga gactttatct caagcggtgt ctatggttaa acctgggggc    780
atcatttcta atattaacta tcatggctcc ggcgacgcat tactgatccc gcgtgttgaa    840
tggggctgtg ggatggccca caaaaccatt aaagggggtt tatgtccggg tggtcgcctg    900
cgtgccgaaa tgctgcgtga catggtggtt tacaaccgtg tggatctgtc caaactggta    960
actcacgtat accacggttt cgatcacatt gaagaggcgc tgctgctgat gaaggataag   1020
ccaaaggatc tgattaaggc ggttgttatc ctgtaa                             1056
```

<210> SEQ ID NO 106
<211> LENGTH: 351
<212> TYPE: PRT
<213> ORGANISM: Clostridium beijerinckii

<400> SEQUENCE: 106

Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
            340                 345                 350

<210> SEQ ID NO 107
<211> LENGTH: 2580
<212> TYPE: DNA
<213> ORGANISM: Clostridium carboxidivorans

<400> SEQUENCE: 107
atgaaggtaa ctaatgttga agaactgatg aaaaaaatgc aggaagtgca aaatgctcaa      60
aaaaaatttg ggagttttac tcaggaacaa gtagatgaaa ttttcaggca agcagcacta     120

```
gcagctaaca gtgccagaat agatctagct aaaatggcag tggaagaaac taaaatggga      180
attgtagagg ataaggttat aaaaaatcat tttgttgcag aatacatata taataagtat      240
aaaaatgaaa aaacttgtgg gattttggaa gaagatgaag gctttggaat ggttaaaatt      300
gcagaacctg taggtgtgat tgcagcagta attccaacaa caaatccaac atctacagca      360
atatttaaag cattattagc tttgaaaaca agaaatggta taattttttc accacatcca      420
agagcaaaaa agtgtactat tgcagcagct aagttagttc ttgatgctgc agttaaagca      480
ggtgctccta aaggaattat aggttggata gatgaaccct ctattgaact ttcacagata      540
gtaatgaaag aagctgatat aatccttgca acaggtggtc caggtatggt aaaagcagct      600
tattcttcag gtaaacctgc tatagggggtt ggtcctggta acacacctgc tttaattgat      660
gaaagtgctg atattaaaat ggcagtaaat tcaatacttc tttccaaaac ttttgataat      720
ggtatgattt gtgcttcaga gcagtcggta gtagttgtag attcaatata tgaagaagtt      780
aagaaagaat ttgctcatag aggagcttat attttaagta aggatgaaac aactaaagtt      840
ggaaaaatac tcttagttaa tggtacatta aatgctggta tcgttggtca gagtgcttat      900
aaaatagcag aaatggcagg agttaaagtt ccagaagatg ctaaagttct tataggagaa      960
gtaaaatcag tggagcattc agaagagcca ttttcacatg aaaagttatc tccagtttta     1020
gctatgtata gagctaaaaa ttttgatgaa gctctttttaa aagctggaag attagttgaa     1080
ctcggtggaa tggtcatac atctgtatta tatgtaaatg caataactga aaaagtaaaa      1140
gtagaaaaat ttagagaaac tatgaagact ggtagaacat taataaatat gccttcagca     1200
caaggtgcta taggagacat atataacttt aaactagctc cttcattaac attaggttgt     1260
ggttcatggg gaggaaactc cgtatcagaa aatgttggac taaacactt attaaatata      1320 aaaagtgttg ctgagaggag agaaaatatg ctttggttta gagttcctga aaaggtttat     1380
tttaaatatg gtagtcttgg agttgcatta aaagaattag atattttgga taagaaaaaa     1440
gtatttatag taacagataa agttctttat caattaggtt atatagatag agttacaaag     1500
attcttgaag aattgaaaat ttcatataaa atatttacag atgtagaacc agatccaacc     1560
ctagctacag ctaaaaaagg tgcagaagaa ttgttatcat ttaatccaga tactattata     1620
gcagttggtg gtggttcagc aatggatgct gctaagatta tgtgggtaat gtatgaacat     1680
ccggaagtaa gatttgaaga tttagctatg agatttatgg atataagaaa gagagtatat     1740
acttttccta agatgggtga aaaagcaatg atgatttctg ttgcaacatc agcaggaaca     1800
ggatcagaag taacacccttt tgcagtaatt actgatgaaa aaacaggagc taaatatcca     1860
ttagctgatt atgaattaac tccaaatatg gctataattg atgctgaact tatgatgggt     1920
atgccaaaag gattaacagc agcttcagga atagatgcac taactcatgc aatagaagct     1980
tatgtatcaa taatggcttc agaatatact aatggattag cgttagaagc aataagattg     2040
atatttaagt atttaccaat agcttacagt gaaggaacaa caagtataaa ggcaagagaa     2100
aaaatggcgc atgcttcaac aatagctggt atggcatttg ctaatgcatt tttaggagta     2160
tgtcattcaa tggcacataa attaggatca actcatcacg taccacatgg cattgccaat     2220
gcactactta taaatgaagt tataaaattt aatgcagtag aaaatccaag aaaacaagct     2280
gcatttccac aatataagta tccaaatata aaaagagat atgctagaat agcagattac     2340
cttaacttag gtgggtcaac agacgatgaa aaagtacaat tattaataaa tgctatagat     2400
gaattaaaag ctaagataaa tattccagaa agtattaaag aagcaggagt aacagaagaa     2460
```

```
aaatttatg ctactttaga taaaatgtca gaattagctt ttgatgatca atgtacaggt   2520 gcaaaccta gatatccatt aataagtgaa ataaaacaaa tgtatgtaaa tgcattttaa   2580
```

<210> SEQ ID NO 108
<211> LENGTH: 859
<212> TYPE: PRT
<213> ORGANISM: Clostridium carboxidivorans

<400> SEQUENCE: 108

```
Met Lys Val Thr Asn Val Glu Glu Leu Met Lys Met Gln Glu Val
1               5                   10                  15

Gln Asn Ala Gln Lys Lys Phe Gly Ser Phe Thr Gln Glu Gln Val Asp
            20                  25                  30

Glu Ile Phe Arg Gln Ala Ala Leu Ala Ala Asn Ser Ala Arg Ile Asp
        35                  40                  45

Leu Ala Lys Met Ala Val Glu Glu Thr Lys Met Gly Ile Val Glu Asp
    50                  55                  60

Lys Val Ile Lys Asn His Phe Val Ala Glu Tyr Ile Tyr Asn Lys Tyr
65                  70                  75                  80

Lys Asn Glu Lys Thr Cys Gly Ile Leu Glu Glu Asp Glu Gly Phe Gly
                85                  90                  95

Met Val Lys Ile Ala Glu Pro Val Gly Val Ile Ala Ala Val Ile Pro
            100                 105                 110

Thr Thr Asn Pro Thr Ser Thr Ala Ile Phe Lys Ala Leu Leu Ala Leu
        115                 120                 125

Lys Thr Arg Asn Gly Ile Ile Phe Ser Pro His Pro Arg Ala Lys Lys
    130                 135                 140

Cys Thr Ile Ala Ala Ala Lys Leu Val Leu Asp Ala Ala Val Lys Ala
145                 150                 155                 160

Gly Ala Pro Lys Gly Ile Ile Gly Trp Ile Asp Glu Pro Ser Ile Glu
                165                 170                 175

Leu Ser Gln Ile Val Met Lys Glu Ala Asp Ile Ile Leu Ala Thr Gly
            180                 185                 190

Gly Pro Gly Met Val Lys Ala Ala Tyr Ser Ser Gly Lys Pro Ala Ile
        195                 200                 205

Gly Val Gly Pro Gly Asn Thr Pro Ala Leu Ile Asp Glu Ser Ala Asp
    210                 215                 220

Ile Lys Met Ala Val Asn Ser Ile Leu Leu Ser Lys Thr Phe Asp Asn
225                 230                 235                 240

Gly Met Ile Cys Ala Ser Glu Gln Ser Val Val Val Asp Ser Ile
                245                 250                 255

Tyr Glu Glu Val Lys Lys Glu Phe Ala His Arg Gly Ala Tyr Ile Leu
            260                 265                 270

Ser Lys Asp Glu Thr Thr Lys Val Gly Lys Ile Leu Leu Val Asn Gly
        275                 280                 285

Thr Leu Asn Ala Gly Ile Val Gly Gln Ser Ala Tyr Lys Ile Ala Glu
    290                 295                 300

Met Ala Gly Val Lys Val Pro Glu Asp Ala Lys Val Leu Ile Gly Glu
305                 310                 315                 320

Val Lys Ser Val Glu His Ser Glu Glu Pro Phe Ser His Glu Lys Leu
                325                 330                 335

Ser Pro Val Leu Ala Met Tyr Arg Ala Lys Asn Phe Asp Glu Ala Leu
            340                 345                 350
```

```
Leu Lys Ala Gly Arg Leu Val Glu Leu Gly Met Gly His Thr Ser
            355                 360                 365

Val Leu Tyr Val Asn Ala Ile Thr Glu Lys Val Lys Val Glu Lys Phe
        370                 375                 380

Arg Glu Thr Met Lys Thr Gly Arg Thr Leu Ile Asn Met Pro Ser Ala
385                 390                 395                 400

Gln Gly Ala Ile Gly Asp Ile Tyr Asn Phe Lys Leu Ala Pro Ser Leu
                405                 410                 415

Thr Leu Gly Cys Gly Ser Trp Gly Gly Asn Ser Val Ser Glu Asn Val
            420                 425                 430

Gly Pro Lys His Leu Leu Asn Ile Lys Ser Val Ala Glu Arg Arg Glu
        435                 440                 445

Asn Met Leu Trp Phe Arg Val Pro Glu Lys Val Tyr Phe Lys Tyr Gly
    450                 455                 460

Ser Leu Gly Val Ala Leu Lys Glu Leu Asp Ile Leu Asp Lys Lys Lys
465                 470                 475                 480

Val Phe Ile Val Thr Asp Lys Val Leu Tyr Gln Leu Gly Tyr Ile Asp
                485                 490                 495

Arg Val Thr Lys Ile Leu Glu Glu Leu Lys Ile Ser Tyr Lys Ile Phe
            500                 505                 510

Thr Asp Val Glu Pro Asp Pro Thr Leu Ala Thr Ala Lys Lys Gly Ala
        515                 520                 525

Glu Glu Leu Leu Ser Phe Asn Pro Asp Thr Ile Ile Ala Val Gly Gly
    530                 535                 540

Gly Ser Ala Met Asp Ala Ala Lys Ile Met Trp Val Met Tyr Glu His
545                 550                 555                 560

Pro Glu Val Arg Phe Glu Asp Leu Ala Met Arg Phe Met Asp Ile Arg
                565                 570                 575

Lys Arg Val Tyr Thr Phe Pro Lys Met Gly Glu Lys Ala Met Met Ile
            580                 585                 590

Ser Val Ala Thr Ser Ala Gly Thr Gly Ser Glu Val Thr Pro Phe Ala
        595                 600                 605

Val Ile Thr Asp Glu Lys Thr Gly Ala Lys Tyr Pro Leu Ala Asp Tyr
    610                 615                 620

Glu Leu Thr Pro Asn Met Ala Ile Ile Asp Ala Glu Leu Met Met Gly
625                 630                 635                 640

Met Pro Lys Gly Leu Thr Ala Ala Ser Gly Ile Asp Ala Leu Thr His
                645                 650                 655

Ala Ile Glu Ala Tyr Val Ser Ile Met Ala Ser Glu Tyr Thr Asn Gly
            660                 665                 670

Leu Ala Leu Glu Ala Ile Arg Leu Ile Phe Lys Tyr Leu Pro Ile Ala
        675                 680                 685

Tyr Ser Glu Gly Thr Thr Ser Ile Lys Ala Arg Glu Lys Met Ala His
    690                 695                 700

Ala Ser Thr Ile Ala Gly Met Ala Phe Ala Asn Ala Phe Leu Gly Val
705                 710                 715                 720

Cys His Ser Met Ala His Lys Leu Gly Ser Thr His His Val Pro His
                725                 730                 735

Gly Ile Ala Asn Ala Leu Leu Ile Asn Glu Val Ile Lys Phe Asn Ala
            740                 745                 750

Val Glu Asn Pro Arg Lys Gln Ala Ala Phe Pro Gln Tyr Lys Tyr Pro
        755                 760                 765
```

Asn Ile Lys Lys Arg Tyr Ala Arg Ile Ala Asp Tyr Leu Asn Leu Gly
    770             775                 780

Gly Ser Thr Asp Asp Glu Lys Val Gln Leu Leu Ile Asn Ala Ile Asp
785                 790                 795                 800

Glu Leu Lys Ala Lys Ile Asn Ile Pro Glu Ser Ile Lys Glu Ala Gly
                805                 810                 815

Val Thr Glu Glu Lys Phe Tyr Ala Thr Leu Asp Lys Met Ser Glu Leu
            820                 825                 830

Ala Phe Asp Asp Gln Cys Thr Gly Ala Asn Pro Arg Tyr Pro Leu Ile
                835                 840                 845

Ser Glu Ile Lys Gln Met Tyr Val Asn Ala Phe
    850                 855

<210> SEQ ID NO 109
<211> LENGTH: 1401
<212> TYPE: DNA
<213> ORGANISM: Escherichia coli

<400> SEQUENCE: 109
atgccacatt cctacgatta cgatgccata gtaataggtt ccggccccgg cggcgaaggc        60
gctgcaatgg gcctggttaa gcaaggtgcg cgcgtcgcag ttatcgagcg ttatcaaaat       120
gttggcggcg gttgcaccca ctggggcacc atcccgtcga agctctccg tcacgccgtc        180
agccgcatta tagaattcaa tcaaaaccca ctttacagcg accattcccg actgctccgc       240
tcttcttttg ccgatatcct taaccatgcc gataacgtga ttaatcaaca acgcgcatg        300
cgtcagggat tttacgaacg taatcactgt gaaatattgc agggaaacgc tcgctttgtt       360
gacgagcata cgttggcgct ggattgcccg gacggcagcg ttgaaacact aaccgctgaa       420
aaatttgtta ttgcctgcgg ctctcgtcca tatcatccaa cagatgttga tttcacccat       480
ccacgcattt acgacagcga ctcaattctc agcatgcacc acgaaccgcg ccatgtactt       540
atctatggtg ctggagtgat cggctgtgaa atgcgctcga tcttccgcgg tatggatgta       600
aaagtggatc tgatcaacac ccgcgatcgc ctgctggcat ttctcgatca agagatgtca       660
gattctctct cctatcactt ctggaacagt ggcgtagtga ttcgtcacaa cgaagagtac       720
gagaagatcg aaggctgtga cgatggtgtg atcatgcatc tgaagtcggg taaaaaactg       780
aaagctgact gcctgctcta tgccaacggt cgcaccggta ataccgattc gctggcgtta       840
cagaacattg gctagaaac tgacagccgc ggacagctga aggtcaacag catgtatcag       900
accgcacagc cacacgttta cgcggtgggc gacgtgattg gttatccgag cctggcgtcg       960
gcggcctatg accaggggcg cattgccgcg caggcgctgg taaaaggcga agccaccgca      1020
catctgattg aagatatccc taccggtatt tacaccatcc cggaaatcag ctctgtgggc      1080
aaaaccgaac agcagctgac cgcaatgaaa gtgccatatg aagtgggccg cgcccagttt      1140
aaacatctgg cacgcgcaca aatcgtcggc atgaacgtgg cacgctgaa attttgttc       1200
catcgggaaa caaaagagat tctgggtatt cactgctttg gcgagcgcgc tgccgaaatt      1260
attcatatcg gtcaggcgat tatggaacag aaaggtggcg gcaacactat tgagtacttc      1320
gtcaacacca ccttttaacta cccgacgatg gcggaagcct atcgggtagc tgcgttaaac      1380
ggtttaaacc gcctgttta a                                                 1401

<210> SEQ ID NO 110
<211> LENGTH: 466
<212> TYPE: PRT
<213> ORGANISM: Escherichia coli

<400> SEQUENCE: 110

```
Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
            115                 120                 125

Cys Pro Asp Gly Ser Val Glu Thr Leu Thr Ala Glu Lys Phe Val Ile
        130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Glu Gln Gln Leu Thr Ala
        355                 360                 365

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415
```

-continued

Ala Ala Glu Ile Ile His Ile Gly Gln Ala Ile Met Glu Gln Lys Gly
            420                 425                 430

Gly Gly Asn Thr Ile Glu Tyr Phe Val Asn Thr Thr Phe Asn Tyr Pro
        435                 440                 445

Thr Met Ala Glu Ala Tyr Arg Val Ala Ala Leu Asn Gly Leu Asn Arg
    450                 455                 460

Leu Phe
465

<210> SEQ ID NO 111
<211> LENGTH: 41
<212> TYPE: DNA
<213> ORGANISM: artificial
<220> FEATURE:
<223> OTHER INFORMATION: Forward primer to amplify fucA and fucO

<400> SEQUENCE: 111
cctttaataa ggagatatac catggaacga aataaacttg c                   41

<210> SEQ ID NO 112
<211> LENGTH: 56
<212> TYPE: DNA
<213> ORGANISM: artificial
<220> FEATURE:
<223> OTHER INFORMATION: Reverse primer to amplify fucA and fucO

<400> SEQUENCE: 112
ggttattcct ccttatttag agctctaaac gaattcttac caggcggtat ggtaaa    56

<210> SEQ ID NO 113
<211> LENGTH: 56
<212> TYPE: DNA
<213> ORGANISM: artificial
<220> FEATURE:
<223> OTHER INFORMATION: Forward primer to amplify fucK

<400> SEQUENCE: 113
gaattcgttt agagctctaa ataaggagga ataaccatga tgaaacaaga agttat    56

<210> SEQ ID NO 114
<211> LENGTH: 40
<212> TYPE: DNA
<213> ORGANISM: artificial
<220> FEATURE:
<223> OTHER INFORMATION: Reverse primer to amplify fucK

<400> SEQUENCE: 114
gagctcggta cccgggggatc caaaaaaccc ctcaagaccc                    40

<210> SEQ ID NO 115
<211> LENGTH: 39
<212> TYPE: DNA
<213> ORGANISM: artificial
<220> FEATURE:
<223> OTHER INFORMATION: Forward primer to amplify thl

<400> SEQUENCE: 115
ctgttgttat attgtaatga tgtatgcaag agggataaa                      39

<210> SEQ ID NO 116
<211> LENGTH: 38
<212> TYPE: DNA
<213> ORGANISM: artificial
<220> FEATURE:
<223> OTHER INFORMATION: Reverse primer to amplify thl

```
<400> SEQUENCE: 116
tatatctcct tcttaaagtt cataaatcac cccgttgc                            38

<210> SEQ ID NO 117
<211> LENGTH: 21
<212> TYPE: DNA
<213> ORGANISM: artificial
<220> FEATURE:
<223> OTHER INFORMATION: Forward primer to amplify fucO

<400> SEQUENCE: 117
atggctaaca gaatgattct g                                              21

<210> SEQ ID NO 118
<211> LENGTH: 23
<212> TYPE: DNA
<213> ORGANISM: artificial
<220> FEATURE:
<223> OTHER INFORMATION: Reverse primer to amplify fucO

<400> SEQUENCE: 118
ttaccaggcg gtatggtaaa gct                                            23

<210> SEQ ID NO 119
<211> LENGTH: 39
<212> TYPE: DNA
<213> ORGANISM: artificial
<220> FEATURE:
<223> OTHER INFORMATION: Forward primer to amplify atoA/D

<400> SEQUENCE: 119
ctgttgttat attgtaatga tgtatgcaag agggataaa                           39

<210> SEQ ID NO 120
<211> LENGTH: 38
<212> TYPE: DNA
<213> ORGANISM: artificial
<220> FEATURE:
<223> OTHER INFORMATION: Reverse primer to amplify atoA/D

<400> SEQUENCE: 120
tatatctcct tcttaaagtt cataaatcac cccgttgc                            38
```

MICROORGANISMS AND METHODS FOR THE CO-PRODUCTION OF ETHYLENE GLYCOL AND THREE CARBON COMPOUNDS

CROSS REFERENCE TO RELATED APPLICATIONS

This application is a Continuation Application of U.S. application Ser. No. 15/453,094, filed on Mar. 8, 2017, which claims benefit of priority to U.S. Provisional Application No. 62/305,814, filed Mar. 9, 2016, and to U.S. Provisional Application No. 62/430,742, filed Dec. 6, 2016, the contents of each of which are incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BRAS_001_02 US_ST25.txt, date recorded: Mar. 7, 2017, file size about 231 kilobytes).

TECHNICAL FIELD

This application relates to recombinant microorganisms useful in the biosynthesis of monoethylene glycol and one or more three-carbon compounds. The application further relates to methods of producing monoethylene glycol and one or more three-carbon compound using the recombinant microorganisms, as well as compositions comprising one or more of these compounds and/or the recombinant microorganisms.

BACKGROUND

Organic compounds such as monoethylene glycol (MEG), acetone, isopropanol (IPA) and propene are valuable as raw material in the production of products like polyethylene terephthalate (PET) resins (from MEG) and the plastic polypropylene (from propene). These compounds also find use directly for industrial or household purposes.

However, the compounds are currently produced from precursors that originate from fossil fuels, which contribute to climate change. To develop more environmentally friendly processes for the production of MEG and three-carbon compounds such as isopropanol, researchers have engineered microorganisms with biosynthetic pathways to produce MEG or IPA separately. However, these pathways are challenging to implement, with loss of product yield, redox balance and excess biomass formation being some major obstacles to overcome.

Thus there exists a need for improved biosynthesis pathways for the production of MEG and three-carbon compounds such as IPA.

SUMMARY OF THE DISCLOSURE

The present application relates to recombinant microorganisms having one or more biosynthesis pathways for the production of monoethylene glycol and one or more three-carbon compounds.

The present disclosure provides a combination of an easy to implement, high yield C2 branch pathway for MEG production from xylose with an easy to implement C3 branch pathway for production of one or more three-carbon compounds from DHAP or pyruvate.

The presently disclosed process of co-producing MEG and one or more three-carbon compounds is synergistic by utilizing the excess NADH produced in the C3 branch pathway to feed the NADH requirement of the C2 branch pathway.

In one aspect, the present application provides a recombinant microorganism co-producing monoethylene glycol (MEG) and one or more three-carbon compounds. In one embodiment, the MEG and one or more three-carbon compounds are co-produced from xylose. In another embodiment, the recombinant microorganism comprises a deletion, insertion, or loss of function mutation in a gene encoding a D-xylulose-5-kinase and/or in a gene encoding a glycoaldehyde dehydrogenase. In some embodiments, the gene encoding the D-xylulose-5-kinase is xylB. In some embodiments, the gene encoding the glycoaldehyde dehydrogenase is aldA. In some embodiments, MEG is produced through the conversion of glycolaldehyde in a C2 branch pathway and one or more three-carbon compounds is produced through the conversion of DHAP or pyruvate in a C3 branch pathway. In other embodiments, at least a portion of the excess NADH produced in the C3 branch pathway is used as a source of reducing equivalents in the C2 branch pathway. In further embodiments, at least a portion of the excess NADH produced in the C3 branch pathway is used to produce ATP. In yet further embodiments, excess biomass formation is minimized and production of MEG and one or more three-carbon compounds is maximized.

In one embodiment, MEG is produced from xylose via ribulose-1-phosphate. In another embodiment, MEG is produced from xylose via xylulose-1-phosphate. In a further embodiment, MEG is produced from xylose via xylonate.

In one embodiment, the one or more three-carbon compounds is acetone. In another embodiment, the one or more three-carbon compounds is isopropanol. In a further embodiment, the one or more three-carbon compounds is propene.

In one preferred embodiment, MEG and acetone are co-produced from xylose using a ribulose-1-phosphate pathway for the conversion of xylose to MEG and a C3 branch pathway for the conversion of dihydroxyacetone-phosphate (DHAP) to acetone.

In one aspect, the present application relates to a recombinant microorganism capable of co-producing monoethylene glycol (MEG) and acetone from exogenous D-xylose, wherein the recombinant microorganism expresses one or more of the following:

(a) at least one endogenous or exogenous nucleic acid molecule encoding an enzyme that catalyzes the conversion of D-xylulose to D-ribulose;

(b) at least one endogenous or exogenous nucleic acid molecule encoding an enzyme that catalyzes the conversion of D-ribulose from (a) to D-ribulose-1-phosphate;

(c) at least one endogenous or exogenous nucleic acid molecule encoding an enzyme that catalyzes the conversion of D-ribulose-1-phosphate from (b) to glycolaldehyde and dihydroxyacetonephosphate (DHAP);

(d) at least one endogenous or exogenous nucleic acid molecule encoding an enzyme that catalyzes the conversion of glycolaldehyde from (c) to MEG;

(e) at least one endogenous or exogenous nucleic acid molecule encoding an enzyme that catalyzes the conversion of acetyl-CoA to acetoacetyl-CoA;

(f) at least one endogenous or exogenous nucleic acid molecule encoding an enzyme that catalyzes the conversion of acetoacetyl-CoA from (e) to acetoacetate; and/or (g) at least one endogenous or exogenous nucleic acid molecule encoding an enzyme that catalyzes the conversion of acetoacetate from (f) to acetone;

wherein the produced intermediate DHAP is converted to acetyl-CoA through the endogenous glycolysis pathway in the microorganism, and wherein MEG and acetone are co-produced.

In one embodiment, the enzyme that catalyzes the conversion of D-xylulose to D-ribulose is a D-tagatose 3-epimerase. In a further embodiment, the enzyme that catalyzes the conversion of D-xylulose to D-ribulose is encoded by one or more endogenous nucleic acid molecules. In an alternative embodiment, the enzyme that catalyzes the conversion of D-xylulose to D-ribulose is encoded by one or more exogenous nucleic acid molecules. In another embodiment, the enzyme is a D-tagatose 3-epimerase that is encoded by a nucleic acid molecule obtained from a microorganism selected from *Pseudomonas* sp., *Mesorhizobium* sp. and *Rhodobacter* sp. In some embodiments, the nucleic acid molecule encoding D-tagatose 3-epimerase is obtained from a microorganism selected from *Pseudomonas cichorii, Pseudomonas* sp. ST-24, *Mesorhizobium loti* and *Rhodobacter sphaeroides*. In some embodiments, the nucleic acid molecule encoding D-tagatose 3-epimerase is dte, C1KKR1, or homolog thereof. In some embodiments, the one or more nucleic acid molecules is FJ851309.1 or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

In one embodiment, the enzyme that catalyzes the conversion of D-ribulose to D-ribulose-1-phosphate is a D-ribulokinase. In a further embodiment, the enzyme that catalyzes the conversion of D-ribulose to D-ribulose-1-phosphate is encoded by one or more endogenous nucleic acid molecules. In an alternative embodiment, the enzyme that catalyzes the conversion of D-ribulose to D-ribulose-1-phosphate is encoded by one or more exogenous nucleic acid molecules. In another embodiment, the enzyme is a D-ribulokinase that is encoded by a nucleic acid molecule obtained from *E. coli*. In some embodiments, the nucleic acid molecule encoding D-ribulokinase is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

In one embodiment, the enzyme that catalyzes the conversion of D-ribulose-1-phosphate to glycolaldehyde and dihydroxyacetonephosphate (DHAP) is a D-ribulose-1-phosphate aldolase. In a further embodiment, the enzyme that catalyzes the conversion of D-ribulose-1-phosphate to glycolaldehyde and DHAP is encoded by one or more endogenous nucleic acid molecules. In an alternative embodiment, the enzyme that catalyzes the conversion of D-ribulose-1-phosphate to glycolaldehyde and DHAP is encoded by one or more exogenous nucleic acid molecules. In another embodiment, the enzyme is a D-ribulose-1-phosphate aldolase that is encoded by a nucleic acid molecule obtained from *E. coli*. In some embodiments, the nucleic acid molecule encoding D-ribulose-1-phosphate aldolase is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

In one embodiment, the enzyme that catalyzes the conversion of glycolaldehyde to MEG is a glycolaldehyde reductase or aldehyde reductase. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme is a glycolaldehyde reductase or aldehyde reductase that is encoded by a nucleic acid molecule obtained from a microorganism selected from *E. coli* or *S. cerevisiae*. In some embodiments, the nucleic acid molecule encoding glycolaldehyde reductase or aldehyde reductase is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment, the enzyme that catalyzes the conversion of acetyl-CoA to acetoacetyl-CoA is a thiolase or acetyl coenzyme A acetyltransferase. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is a thiolase or acetyl coenzyme A acetyltransferase that is encoded by a nucleic acid molecule obtained from a microorganism selected from *Clostridium* sp., *Bacillus* sp., *E. coli, Saccharomyces* sp. and *Marinobacter* sp. In some embodiments, the nucleic acid molecule encoding thiolase or acetyl coenzyme A acetyltransferase is obtained from a microorganism selected from *Clostridium acetobutylicum, Clostridium thermosaccharolyticum, Bacillus cereus, E. coli, Saccharomyces cerevisiae* and *Marinobacter hydrocarbonoclasticus*. In some embodiments, the nucleic acid molecule encoding thiolase or acetyl coenzyme A acetyltransferase is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment, the enzyme that catalyzes the conversion of acetoacetyl-CoA to acetoacetate is an acetate:acetoacetyl-CoA transferase or hydrolase. In some embodiments, the transferase is an acetyl-CoA:acetoacetate-CoA transferase. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme is an acetate:acetoacetyl-CoA transferase or hydrolase that is encoded by a nucleic acid molecule obtained from a microorganism selected from *Clostridium* sp. and *E. coli*. In some embodiments, the nucleic acid molecule encoding acetate:acetoacetyl-CoA hydrolase is obtained from *Clostridium acetobutylicum*. In some embodiments, the nucleic acid molecules encoding acetate:acetoacetyl-CoA transferase is obtained from *E. coli*. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment, the enzyme that catalyzes the conversion of acetoacetate to acetone is an acetoacetate decarboxylase. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme is an acetoacetate decarboxylase that is encoded by a nucleic acid molecule obtained from a microorganism selected from *Clostridium* sp., *Bacillus* sp., *Chromobacterium* sp. and *Pseudomonas* sp. In some embodiments, the nucleic acid molecule encoding acetoacetate decarboxylase is obtained from a microorganism selected from *Clostridium acetobutylicum, Clostridium beijerinckii, Clostridium cellulolyticum, Bacillus polymyxa, Chromobacterium violaceum* and *Pseudomonas putida*. In some embodiments, the nucleic acid molecule encoding acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment, the recombinant microorganism further comprises one or more modifications selected from the group consisting of:
(a) a deletion, insertion, or loss of function mutation in a gene encoding an enzyme that catalyzes the conversion of D-xylulose to D-xylulose-5-phosphate;
(b) a deletion, insertion, or loss of function mutation in a gene encoding an enzyme that catalyzes the conversion of glycolaldehyde to glycolic acid; and
(c) a deletion, insertion, or loss of function mutation in a gene encoding an enzyme that catalyzes the conversion of pyruvate to lactate.

In one embodiment, the enzyme that catalyzes the conversion of D-xylulose to D-xylulose-5-phosphate is a D-xylulose-5-kinase. In some embodiments, the D-xylulose-5-kinase is from *Escherichia coli*. In some embodiments, the D-xylulose-5-kinase is encoded by the xylB gene, or homolog thereof.

In some embodiments, a recombinant microorganism producing MEG and a three-carbon compound comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

In one embodiment, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene, or homolog thereof.

In some embodiments, a recombinant microorganism producing MEG and a three-carbon compound comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

In some embodiments, a recombinant microorganism producing MEG and a three-carbon compound comprises a deletion, insertion, or loss of function mutation in a gene encoding a lactate dehydrogenase to prevent the production of lactate from pyruvate and instead shunt the reaction toward production of a three-carbon compound.

In one embodiment, the recombinant microorganism further comprises an endogenous enzyme that catalyzes the conversion of D-xylose to D-xylulose.

In one preferred embodiment, MEG and acetone are co-produced from xylose using a xylulose-1-phosphate pathway for the conversion of xylose to MEG and a C3 branch pathway for the conversion of dihydroxyacetonephosphate (DHAP) to acetone.

In another aspect, the present application relates to a recombinant microorganism capable of co-producing monoethylene glycol (MEG) and acetone from exogenous D-xylose, wherein the recombinant microorganism expresses one or more of the following:
(a) at least one endogenous or exogenous nucleic acid molecule encoding an enzyme that catalyzes the conversion of D-xylulose to D-xylulose-1-phosphate;
(b) at least one endogenous or exogenous nucleic acid molecule encoding an enzyme that catalyzes the conversion of D-xylulose-1-phosphate from (a) to glycolaldehyde and dihydroxyacetonephosphate (DHAP);
(c) at least one endogenous or exogenous nucleic acid molecule encoding an enzyme that catalyzes the conversion of glycolaldehyde from (b) to MEG;
(d) at least one endogenous or exogenous nucleic acid molecule encoding an enzyme that catalyzes the conversion of acetyl-CoA to acetoacetyl-CoA;
(e) at least one endogenous or exogenous nucleic acid molecule encoding an enzyme that catalyzes the conversion of acetoacetyl-CoA from (d) to acetoacetate; and/or
(f) at least one endogenous or exogenous nucleic acid molecule encoding an enzyme that catalyzes the conversion of acetoacetate from (e) to acetone;

wherein the produced intermediate DHAP is converted to acetyl-CoA through the endogenous glycolysis pathway in the microorganism, and wherein MEG and acetone are co-produced.

In one embodiment, the enzyme that catalyzes the conversion of D-xylulose to D-xylulose-1-phosphate is a D-xylulose 1-kinase. In a further embodiment, the enzyme that catalyzes the conversion of D-xylulose to D-xylulose-1-phosphate is encoded by one or more endogenous nucleic acid molecules. In an alternative embodiment, the enzyme that catalyzes the conversion of D-xylulose to D-xylulose-1-phosphate is encoded by one or more exogenous nucleic acid molecules. In another embodiment, the enzyme is a D-xylulose 1-kinase that is encoded by a nucleic acid molecule obtained from *Homo sapiens*. In one embodiment, the *Homo sapiens* D-xylulose 1-kinase is a ketohexokinase C. In some embodiments, the nucleic acid molecule encoding human ketohexokinase C is khk-C, or homolog thereof. In another embodiment, the one or more nucleic acid molecules encoding the D-xylulose 1-kinase comprises an amino acid sequence set forth in SEQ ID NO: 55. In a further embodiment, the one or more nucleic acid molecules encoding the D-xylulose 1-kinase is encoded by a nucleic acid sequence selected from the group consisting of SEQ ID NOs: 53 and 54.

In one embodiment, the enzyme that catalyzes the conversion of D-xylulose-1-phosphate to glycolaldehyde and dihydroxyacetonephosphate (DHAP) is a D-xylulose-1-phosphate aldolase. In a further embodiment, the enzyme that catalyzes the conversion of D-xylulose-1-phosphate to glycolaldehyde and DHAP is encoded by one or more endogenous nucleic acid molecules. In an alternative embodiment, the enzyme that catalyzes the conversion of D-xylulose-1-phosphate to glycolaldehyde and DHAP is encoded by one or more exogenous nucleic acid molecules. In another embodiment, the enzyme is a D-xylulose-1-phosphate aldolase that is encoded by a nucleic acid molecule obtained from *Homo sapiens*. In one embodiment, the *Homo sapiens* D-xylulose 1-phosphate aldolase is an aldolase B. In some embodiments, the nucleic acid molecule encoding human aldolase B is ALDOB, or homolog thereof. In some embodiments, the one or more nucleic acid molecules encoding the D-xylulose-1-phosphate aldolase comprises an amino acid sequence set forth in SEQ ID NO: 58. In some embodiments, the one or more nucleic acid molecules encoding the D-xylulose-1-phosphate aldolase is encoded by a nucleic acid sequence selected from the group consisting of SEQ ID NOs: 56 and 57.

In one embodiment, the enzyme that catalyzes the conversion of glycolaldehyde to MEG is a glycolaldehyde reductase or aldehyde reductase. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme is a glycolaldehyde reductase or aldehyde reductase that is encoded by a nucleic acid molecule obtained from a microorganism selected from *E. coli* or *S. cerevisiae*. In some embodiments, the nucleic acid molecule encoding glycolaldehyde reductase or aldehyde reductase is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment, the enzyme that catalyzes the conversion of acetyl-CoA to acetoacetyl-CoA is a thiolase or acetyl coenzyme A acetyltransferase. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is a thiolase or acetyl coenzyme A acetyltransferase that is encoded by a nucleic acid molecule obtained from a microorganism selected from *Clostridium* sp., *Bacillus* sp., *E. coli*, *Saccharomyces* sp. and *Marinobacter* sp. In some embodiments, the nucleic acid molecule encoding thiolase or acetyl coenzyme A acetyltransferase is obtained from a microorganism selected from *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the nucleic acid molecule encoding thiolase or acetyl coenzyme A acetyltransferase is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment, the enzyme that catalyzes the conversion of acetoacetyl-CoA to acetoacetate is a acetate:acetoacetyl-CoA transferase or hydrolase. In some embodiments, the transferase is an acetyl-CoA:acetoacetate-CoA transferase. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme is an acetate:acetoacetyl-CoA transferase or hydrolase that is encoded by a nucleic acid molecule obtained from a microorganism selected from *Clostridium* sp. and *E. coli*. In some embodiments, the nucleic acid molecule encoding acetate:acetoacetyl-CoA hydrolase is obtained from *Clostridium acetobutylicum*. In some embodiments, the nucleic acid molecules encoding acetate:acetoacetyl-CoA transferase is obtained from *E. coli*. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment, the enzyme that catalyzes the conversion of acetoacetate to acetone is an acetoacetate decarboxylase. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme is an acetoacetate decarboxylase that is encoded by a nucleic acid molecule obtained from a microorganism selected from *Clostridium* sp., *Bacillus* sp., *Chromobacterium* sp. and *Pseudomonas* sp. In some embodiments, the nucleic acid molecule encoding acetoacetate decarboxylase is obtained from a microorganism selected from *Clostridium acetobutylicum, Clostridium beijerinckii, Clostridium cellulolyticum, Bacillus polymyxa, Chromobacterium violaceum* and *Pseudomonas putida*. In some embodiments, the nucleic acid molecule encoding acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment, the recombinant microorganism further comprises one or more modifications selected from the group consisting of:
  (a) a deletion, insertion, or loss of function mutation in a gene encoding an enzyme that catalyzes the conversion of D-xylulose to D-xylulose-5-phosphate;
  (b) a deletion, insertion, or loss of function mutation in a gene encoding an enzyme that catalyzes the conversion of glycolaldehyde to glycolic acid; and
  (c) a deletion, insertion, or loss of function mutation in a gene encoding an enzyme that catalyzes the conversion of pyruvate to lactate.

In one embodiment, the enzyme that catalyzes the conversion of D-xylulose to D-xylulose-5-phosphate is a D-xylulose-5-kinase. In some embodiments, the D-xylulose-5-kinase is from *Escherichia coli*. In some embodiments, the D-xylulose-5-kinase is encoded by the xylB gene, or homolog thereof.

In some embodiments, a recombinant microorganism producing MEG and a three-carbon compound comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

In one embodiment, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene, or homolog thereof.

In some embodiments, a recombinant microorganism producing MEG and a three-carbon compound comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

In some embodiments, a recombinant microorganism producing MEG and a three-carbon compound comprises a deletion, insertion, or loss of function mutation in a gene encoding a lactate dehydrogenase to prevent the production of lactate from pyruvate and instead shunt the reaction toward production of a three-carbon compound.

In one embodiment, the recombinant microorganism further comprises an endogenous enzyme that catalyzes the conversion of D-xylose to D-xylulose.

In another aspect, the present application relates to a recombinant microorganism capable of co-producing monoethylene glycol (MEG) and acetone from exogenous D-xylose and glucose, wherein the recombinant microorganism expresses one or more of the following:
  (a) at least one exogenous nucleic acid molecule encoding an enzyme that catalyzes the conversion of D-xylose to xylitol and at least one exogenous nucleic acid molecule encoding an enzyme that catalyzes the conversion of xylitol to D-xylulose;
  (b) at least one exogenous nucleic acid molecule encoding an enzyme that catalyzes the conversion of D-xylose to D-xylulose, and
wherein the microorganism further expresses one or more of the following:
  (c) at least one endogenous or exogenous nucleic acid molecule encoding a D-tagatose 3-epimerase that catalyzes the conversion of D-xylulose from (a) or (b) to D-ribulose;
  (d) at least one endogenous or exogenous nucleic acid molecule encoding a D-ribulokinase that catalyzes the conversion of D-ribulose from (c) to D-ribulose-1-phosphate;
  (e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);
  (f) at least one endogenous or exogenous nucleic acid molecule encoding a glycolaldehyde reductase or methylglyoxal reductase that catalyzes the conversion of glycolaldehyde from (e) to MEG;
  (g) at least one endogenous or exogenous nucleic acid molecule encoding a thiolase that catalyzes the conversion of acetyl-CoA to acetoacetyl-CoA;
  (h) at least one endogenous or exogenous nucleic acid molecule encoding an acetate:acetoacetyl-CoA transferase or hydrolase that catalyzes the conversion of acetoacetyl-CoA from (g) to acetoacetate; and/or
  (i) at least one endogenous or exogenous nucleic acid molecule encoding an acetoacetate decarboxylase that catalyzes the conversion of acetoacetate from (h) to acetone;
wherein the produced intermediate DHAP is converted to acetyl-CoA through the endogenous glycolysis pathway in the microorganism, and wherein MEG and acetone are co-produced.

In one embodiment, the enzyme that catalyzes the conversion of D-xylose to xylitol is a xylose reductase or aldose reductase. In a further embodiment, the enzyme that catalyzes the conversion of D-xylose to xylitol is encoded by one or more endogenous nucleic acid molecules. In an alternative embodiment, the enzyme that catalyzes the conversion of D-xylose to xylitol is encoded by one or more exogenous nucleic acid molecules. In another embodiment, the enzyme is a xylose reductase or aldose reductase that is encoded by a nucleic acid molecule obtained from a microorganism selected from *Hypocrea* sp., *Scheffersomyces* sp., *Saccha-* romyces sp., Pachysolen sp., Pichia sp., Candida sp., Aspergillus sp., Neurospora sp., and Cryptococcus sp. In some embodiments, the nucleic acid molecule encoding the xylose reductase or aldose reductase is obtained from a microorganism selected from Hypocrea jecorina, Scheffersomyces stipitis, S. cerevisiae, Pachysolen tannophilus, Pichia stipitis, Pichia quercuum, Candida shehatae, Candida tenuis, Candida tropicalis, Aspergillus niger, Neurospora crassa and Cryptococcus lactativorus. In some embodiments, the nucleic acid molecule encoding xylose reductase or aldose reductase is xyl1, GRE3, or homolog thereof. In some embodiments, the one or more nucleic acid molecules encoding the xylose reductase or aldose reductase comprises an amino acid sequence selected from the group consisting of SEQ ID NOs: 84 and 87. In some embodiments, the one or more nucleic acid molecules encoding the xylose reductase or aldose reductase is encoded by a nucleic acid sequence selected from the group consisting of SEQ ID NOs: 82, 83, 85 and 86.

In one embodiment, the enzyme that catalyzes the conversion of xylitol to D-xylulose is a xylitol dehydrogenase. In a further embodiment, the enzyme that catalyzes the conversion of xylitol to D-xylulose is encoded by one or more endogenous nucleic acid molecules. In an alternative embodiment, the enzyme that catalyzes the conversion of xylitol to D-xylulose is encoded by one or more exogenous nucleic acid molecules. In another embodiment, the enzyme is a xylitol dehydrogenase that is encoded by a nucleic acid molecule obtained from a microorganism selected from Scheffersomyces sp., Trichoderma sp., Pichia sp., Saccharomyces sp., Gluconobacter sp., Galactocandida sp., Neurospora sp., and Serratia sp. In some embodiments, the nucleic acid molecule encoding the xylitol dehydrogenase is obtained from a microorganism selected from Scheffersomyces stipitis, Trichoderma reesei, Pichia stipitis, S. cerevisiae, Gluconobacter oxydans, Galactocandida mastotermitis, Neurospora crassa and Serratia marcescens. In some embodiments, the one or more nucleic acid molecule encoding xylitol dehydrogenase is xyl2, xdh1, or homolog thereof. In some embodiments, the one or more nucleic acid molecules encoding the xylitol dehydrogenase comprises an amino acid sequence selected from the group consisting of SEQ ID NOs: 90 and 92. In some embodiments, the one or more nucleic acid molecules encoding the xylitol dehydrogenase is encoded by a nucleic acid sequence selected from the group consisting of SEQ ID NOs: 88, 89 and 91.

In one embodiment, the enzyme that catalyzes the conversion of D-xylose to D-xylulose is a D-xylose isomerase. In a further embodiment, the enzyme that catalyzes the conversion of D-xylose to D-xylulose is encoded by one or more endogenous nucleic acid molecules. In an alternative embodiment, the enzyme that catalyzes the conversion of D-xylose to D-xylulose is encoded by one or more exogenous nucleic acid molecules. In another embodiment, the enzyme is a D-xylose isomerase that is encoded by a nucleic acid molecule obtained from E. coli. In another embodiment, the xylose isomerase is encoded by one or more nucleic acid molecules obtained from Pyromyces sp. In some embodiments, the nucleic acid molecule encoding D-xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

In one embodiment, the enzyme that catalyzes the conversion of D-xylulose to D-ribulose is a D-tagatose 3-epimerase. In a further embodiment, the enzyme that catalyzes the conversion of D-xylulose to D-ribulose is encoded by one or more endogenous nucleic acid molecules. In an alternative embodiment, the enzyme that catalyzes the conversion of D-xylulose to D-ribulose is encoded by one or more exogenous nucleic acid molecules. In another embodiment, the enzyme is a D-tagatose 3-epimerase that is encoded by a nucleic acid molecule obtained from a microorganism selected from Pseudomonas sp., Mesorhizobium sp. and Rhodobacter sp. In some embodiments, the nucleic acid molecule encoding D-tagatose 3-epimerase is obtained from a microorganism selected from Pseudomonas cichorii, Pseudomonas sp. ST-24, Mesorhizobium loti and Rhodobacter sphaeroides. In some embodiments, the nucleic acid molecule encoding D-tagatose 3-epimerase is dte, C1KKR1, or homolog thereof. In some embodiments, the one or more nucleic acid molecules is FJ851309.1 or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

In one embodiment, the enzyme that catalyzes the conversion of D-ribulose to D-ribulose-1-phosphate is a D-ribulokinase. In a further embodiment, the enzyme that catalyzes the conversion of D-ribulose to D-ribulose-1-phosphate is encoded by one or more endogenous nucleic acid molecules. In an alternative embodiment, the enzyme that catalyzes the conversion of D-ribulose to D-ribulose-1-phosphate is encoded by one or more exogenous nucleic acid molecules. In another embodiment, the enzyme is a D-ribulokinase that is encoded by a nucleic acid molecule obtained from E. coli. In some embodiments, the nucleic acid molecule encoding D-ribulokinase is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

In one embodiment, the enzyme that catalyzes the conversion of D-ribulose-1-phosphate to glycolaldehyde and dihydroxyacetonephosphate (DHAP) is a D-ribulose-1-phosphate aldolase. In a further embodiment, the enzyme that catalyzes the conversion of D-ribulose-1-phosphate to glycolaldehyde and DHAP is encoded by one or more endogenous nucleic acid molecules. In an alternative embodiment, the enzyme that catalyzes the conversion of D-ribulose-1-phosphate to glycolaldehyde and DHAP is encoded by one or more exogenous nucleic acid molecules. In another embodiment, the enzyme is a D-ribulose-1-phosphate aldolase that is encoded by a nucleic acid molecule obtained from E. coli. In some embodiments, the nucleic acid molecule encoding D-ribulose-1-phosphate aldolase is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

In one embodiment, the enzyme that catalyzes the conversion of glycolaldehyde to MEG is a glycolaldehyde reductase or aldehyde reductase. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme is a glycolaldehyde reductase or aldehyde reductase that is encoded by a nucleic acid molecule obtained from a microorganism selected from *E. coli* or *S. cerevisiae*. In some embodiments, the nucleic acid molecule encoding glycolaldehyde reductase or aldehyde reductase is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment, the enzyme that catalyzes the conversion of acetyl-CoA to acetoacetyl-CoA is a thiolase or acetyl coenzyme A acetyltransferase. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is a thiolase or acetyl coenzyme A acetyltransferase that is encoded by a nucleic acid molecule obtained from a microorganism selected from *Clostridium* sp., *Bacillus* sp., *E. coli*, *Saccharomyces* sp. and *Marinobacter* sp. In some embodiments, the nucleic acid molecule encoding thiolase or acetyl coenzyme A acetyltransferase is obtained from a microorganism selected from *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the nucleic acid molecule encoding thiolase or acetyl coenzyme A acetyltransferase is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment, the enzyme that catalyzes the conversion of acetoacetyl-CoA to acetoacetate is a acetate: acetoacetyl-CoA transferase or hydrolase. In some embodiments, the transferase is an acetyl-CoA:acetoacetate-CoA transferase. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme is an acetate:acetoacetyl-CoA transferase or hydrolase that is encoded by one or more nucleic acid molecule obtained from a microorganism selected from *Clostridium* sp. and *E. coli*. In some embodiments, the nucleic acid molecules encoding acetate:acetoacetyl-CoA hydrolase is obtained from *Clostridium acetobutylicum*. In some embodiments, the nucleic acid molecules encoding acetate:acetoacetyl-CoA transferase is obtained from *E. coli*. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment, the enzyme that catalyzes the conversion of acetoacetate to acetone is an acetoacetate decarboxylase. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme is an acetoacetate decarboxylase that is encoded by a nucleic acid molecule obtained from a microorganism selected from *Clostridium* sp., *Bacillus* sp., *Chromobacterium* sp. and *Pseudomonas* sp. In some embodiments, the nucleic acid molecule encoding acetoacetate decarboxylase is obtained from a microorganism selected from *Clostridium acetobutylicum*, *Clostridium beijerinckii*, *Clostridium cellulolyticum*, *Bacillus polymyxa*, *Chromobacterium violaceum* and *Pseudomonas putida*. In some embodiments, the nucleic acid molecule encoding acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment, the recombinant microorganism further comprises one or more modifications selected from the group consisting of:
  (a) a deletion, insertion, or loss of function mutation in a gene encoding an enzyme that catalyzes the conversion of D-xylulose to D-xylulose-5-phosphate; and
  (b) a deletion, insertion, or loss of function mutation in a gene encoding an enzyme that catalyzes the conversion of D-xylulose-5-phosphate to D-xylulose.

In one embodiment, the enzyme that catalyzes the conversion of D-xylulose to D-xylulose-5-phosphate is a D-xylulose-5-kinase. In some embodiments, the D-xylulose-5-kinase is from *Saccharomyces cerevisiae*. In some embodiments the D-xylulose-5-kinase is encoded by the XKS1 gene, or homolog thereof. In some embodiments, the D-xylulose-5-kinase is from *Pichia stipitis*. In some embodiments the D-xylulose-5-kinase is encoded by the XYL3 gene, or homolog thereof.

In some embodiments, a recombinant microorganism producing MEG and a three-carbon compound comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

In one embodiment, the enzyme that catalyzes the conversion of D-xylulose-5-phosphate to D-xylulose is an alkaline phosphatase. In some embodiments, the alkaline phosphatase is from *S. cerevisiae*. In some embodiments, the alkaline phosphatase is encoded by the PHO13 gene, or homolog thereof.

In some embodiments, a recombinant microorganism producing MEG and a three-carbon compound comprises a deletion, insertion, or loss of function mutation in a gene encoding an alkaline phosphatase to prevent the production of D-xylulose from D-xylulose-5-phosphate.

In one embodiment, the recombinant microorganism capable of co-producing monoethylene glycol (MEG) and acetone from exogenous D-xylose and glucose is a fungus.

In one preferred embodiment, MEG and acetone are co-produced from xylose using a xylonate pathway for the conversion of xylose to MEG and a C3 branch pathway for the conversion of dihydroxyacetone-phosphate (DHAP) to acetone.

In another aspect, the present application relates to a recombinant microorganism capable of co-producing monoethylene glycol (MEG) and acetone from exogenous D-xylose, wherein the recombinant microorganism expresses one or more of the following:
  (a) at least one endogenous or exogenous nucleic acid molecule encoding an enzyme that catalyzes the conversion of D-xylose to D-xylonolactone;
  (b) at least one endogenous or exogenous nucleic acid molecule encoding an enzyme that catalyzes the conversion of D-xylonolactone from (a) to D-xylonate;
  (c) at least one endogenous or exogenous nucleic acid molecule encoding an enzyme that catalyzes the conversion of D-xylonate from (b) to 2-keto-3-deoxy-xylonate;
  (d) at least one endogenous or exogenous nucleic acid molecule encoding an enzyme that catalyzes the conversion of 2-keto-3-deoxy-xylonate from (c) to glycolaldehyde and pyruvate;
  (e) at least one endogenous or exogenous nucleic acid molecule encoding an enzyme that catalyzes the conversion of glycolaldehyde from (d) to MEG;
  (f) at least one exogenous nucleic acid molecule encoding an enzyme that catalyzes the conversion of acetyl-CoA to acetoacetyl-CoA;
  (g) at least one endogenous or exogenous nucleic acid molecule encoding an enzyme that catalyzes the conversion of acetoacetyl-CoA from (f) to acetoacetate; and/or
  (h) at least one exogenous nucleic acid molecule encoding an enzyme that catalyzes the conversion of acetoacetate from (g) to acetone;
wherein the produced intermediate pyruvate is converted to acetyl-CoA through the endogenous glycolysis pathway in the microorganism, and wherein MEG and acetone are co-produced.

In one embodiment, the enzyme that catalyzes the conversion of D-xylose to D-xylonolactone is a xylose dehydrogenase. In a further embodiment, the enzyme that catalyzes the conversion of D-xylose to D-xylonolactone is encoded by one or more endogenous nucleic acid molecules. In an alternative embodiment, the enzyme that catalyzes the conversion of D-xylose to D-xylonolactone is encoded by one or more exogenous nucleic acid molecules. In another embodiment, the enzyme is a xylose dehydrogenase that is encoded by a nucleic acid molecule obtained from a microorganism selected from *Caulobacter* sp., *Haloarcula* sp., *Haloferax* sp., *Halorubrum* sp. and *Trichoderma* sp. In some embodiments, the nucleic acid molecule encoding the xylose dehydrogenase is obtained from a microorganism selected from *Caulobacter crescentus, Haloarcula marismortui,* *Haloferax volcanii, Halorubrum lacusprofundi* and *Trichoderma reesei*. In some embodiments, the nucleic acid molecule encoding xylose dehydrogenase is selected from xylB, xdh (HVO_B0028), xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the enzyme that catalyzes the conversion of D-xylonolactone to D-xylonate is a xylonolactonase. In a further embodiment, the enzyme that catalyzes the conversion of D-xylonolactone to D-xylonate is encoded by one or more endogenous nucleic acid molecules. In an alternative embodiment, the enzyme that catalyzes the conversion of D-xylonolactone to D-xylonate is encoded by one or more exogenous nucleic acid molecules. In another embodiment, the enzyme is a xylonolactonase that is encoded by a nucleic acid molecule obtained from a microorganism selected from *Caulobacter* sp. and *Haloferax* sp. In some embodiments, the nucleic acid molecule encoding the xylonolactonase is obtained from a microorganism selected from *Caulobacter crescentus, Haloferax volcanii* and *Haloferax gibbonsii*. In some embodiments, the nucleic acid molecule encoding xylonolactonase is xylC, or homolog thereof. In a further embodiment, the one or more nucleic acid molecules encoding the xylonolactonase comprises an amino acid sequence set forth in SEQ ID NO: 67. In yet another embodiment, the one or more nucleic acid molecules encoding the xylonolactonase is encoded by a nucleic acid sequence set forth in SEQ ID NO: 66.

In one embodiment, the enzyme that catalyzes the conversion of D-xylonate to 2-keto-3-deoxy-xylonate is a xylonate dehydratase. In a further embodiment, the enzyme that catalyzes the conversion of D-xylonate to 2-keto-3-deoxy-xylonate is encoded by one or more endogenous nucleic acid molecules. In an alternative embodiment, the enzyme that catalyzes the conversion of D-xylonate to 2-keto-3-deoxy-xylonate is encoded by one or more exogenous nucleic acid molecules. In another embodiment, the enzyme is a xylonate dehydratase that is encoded by a nucleic acid molecule obtained from a microorganism selected from *Caulobacter* sp., *Haloferax* sp., *Sulfolobus* sp. and *E. coli*. In some embodiments, the nucleic acid molecule encoding the xylonate dehydratase is obtained from a microorganism selected from *Caulobacter crescentus, Haloferax volcanii, E. coli* and *Suffolobus soffataricus*. In some embodiments, the nucleic acid molecule encoding xylonate dehydratase is selected from xylD, yjhG, yagF, xad, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the enzyme that catalyzes the conversion of 2-keto-3-deoxy-xylonate to glycolaldehyde and pyruvate is a 2-keto-3-deoxy-D-pentonate aldolase. In a further embodiment, the enzyme that catalyzes the conversion of 2-keto-3-deoxy-xylonate to glycolaldehyde and pyruvate is encoded by one or more endogenous nucleic acid molecules. In an alternative embodiment, the enzyme that catalyzes the conversion of 2-keto-3-deoxy-xylonate to glycolaldehyde and pyruvate is encoded by one or more exogenous nucleic acid molecules. In another embodiment, the enzyme is a 2-keto-3-deoxy-D-pentonate aldolase that is encoded by a nucleic acid molecule obtained from a microorganism selected from *Pseudomonas* sp. and *E. coli*. In some embodiments, the nucleic acid molecule encoding 2-keto-3-deoxy-D-pentonate aldolase is selected from yjhH, yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the enzyme that catalyzes the conversion of glycolaldehyde to MEG is a glycolaldehyde reductase or aldehyde reductase. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme is a glycolaldehyde reductase or aldehyde reductase that is encoded by a nucleic acid molecule obtained from a microorganism selected from *E. coli* or *S. cerevisiae*. In some embodiments, the nucleic acid molecule encoding glycolaldehyde reductase or aldehyde reductase is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment, the enzyme that catalyzes the conversion of acetyl-CoA to acetoacetyl-CoA is a thiolase or acetyl coenzyme A acetyltransferase. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is a thiolase or acetyl coenzyme A acetyltransferase that is encoded by a nucleic acid molecule obtained from a microorganism selected from *Clostridium* sp., *Bacillus* sp., *E. coli, Saccharomyces* sp. and *Marinobacter* sp. In some embodiments, the nucleic acid molecule encoding thiolase or acetyl coenzyme A acetyltransferase is obtained from a microorganism selected from *Clostridium acetobutylicum, Clostridium thermosaccharolyticum, Bacillus cereus, E. coli, Saccharomyces cerevisiae* and *Marinobacter hydrocarbonoclasticus*. In some embodiments, the nucleic acid molecule encoding thiolase or acetyl coenzyme A acetyltransferase is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment, the enzyme that catalyzes the conversion of acetoacetyl-CoA to acetoacetate is a acetate:acetoacetyl-CoA transferase or hydrolase. In some embodiments, the transferase is an acetyl-CoA:acetoacetate-CoA transferase. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme is an acetate:acetoacetyl-CoA transferase or hydrolase that is encoded by one or more nucleic acid molecules obtained from a microorganism selected from *Clostridium* sp. and *E. coli*. In some embodiments, the nucleic acid molecules encoding acetate:acetoacetyl-CoA hydrolase are obtained from *Clostridium acetobutylicum*. In some embodiments, the nucleic acid molecules encoding acetate:acetoacetyl-CoA transferase are obtained from *E. coli*. In some embodiments, the nucleic acid molecules encoding acetate:acetoacetyl-CoA transferase subunits are atoA and atoD, or homologs thereof. In some embodiments, the one or more nucleic acid molecules encoding acetate:acetoacetyl-CoA hydrolase subunits are ctfA and ctfB, or homologs thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment, the enzyme that catalyzes the conversion of acetoacetate to acetone is an acetoacetate decarboxylase. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme is an acetoacetate decarboxylase that is encoded by one or more nucleic acid molecule obtained from a microorganism selected from *Clostridium* sp., *Bacillus* sp., *Chromobacterium* sp. and *Pseudomonas* sp. In some embodiments, the nucleic acid molecule encoding acetoacetate decarboxylase is obtained from a microorganism selected from *Clostridium acetobutylicum, Clostridium beijerinckii, Clostridium cellulolyticum, Bacillus polymyxa, Chromobacterium violaceum* and *Pseudomonas putida*. In some embodiments, the nucleic acid molecule encoding acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment, the recombinant microorganism further comprises one or more modifications selected from the group consisting of:
(a) a deletion, insertion, or loss of function mutation in a gene encoding an enzyme that catalyzes the conversion of D-xylose to D-xylulose;

(b) a deletion, insertion, or loss of function mutation in a gene encoding an enzyme that catalyzes the conversion of glycolaldehyde to glycolic acid; and (c) a deletion, insertion, or loss of function mutation in a gene encoding an enzyme that catalyzes the conversion of pyruvate to lactate.

In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a recombinant microorganism producing MEG and a three-carbon compound comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene, or homolog thereof.

In some embodiments, a recombinant microorganism producing MEG and a three-carbon compound comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

In some embodiments, a recombinant microorganism producing MEG and a three-carbon compound comprises a deletion, insertion, or loss of function mutation in a gene encoding a lactate dehydrogenase to prevent the production of lactate from pyruvate and instead shunt the reaction toward production of a three-carbon compound.

In another aspect, the present application relates to a recombinant microorganism capable of co-producing monoethylene glycol (MEG) and acetone from exogenous D-xylose, wherein the recombinant microorganism expresses one or more of the following:

(a) at least one endogenous or exogenous nucleic acid molecule encoding an enzyme that catalyzes the conversion of D-xylose to D-xylonate;

(b) at least one endogenous or exogenous nucleic acid molecule encoding an enzyme that catalyzes the conversion of D-xylonate from (a) to 2-keto-3-deoxy-xylonate;

(c) at least one endogenous or exogenous nucleic acid molecule encoding an enzyme that catalyzes the conversion of 2-keto-3-deoxy-xylonate from (b) to glycolaldehyde and pyruvate;

(d) at least one exogenous nucleic acid molecule encoding an enzyme that catalyzes the conversion of glycolaldehyde from (c) to MEG;

(e) at least one exogenous nucleic acid molecule encoding an enzyme that catalyzes the conversion of acetyl-CoA to acetoacetyl-CoA;

(f) at least one endogenous or exogenous nucleic acid molecule encoding an enzyme that catalyzes the conversion of acetoacetyl-CoA from (e) to acetoacetate; and/or (g) at least one exogenous nucleic acid molecule encoding an enzyme that catalyzes the conversion of acetoacetate from (f) to acetone;

wherein the produced intermediate pyruvate is converted to acetyl-CoA through the endogenous glycolysis pathway in the microorganism, and wherein MEG and acetone are co-produced.

In one embodiment, the enzyme that catalyzes the conversion of D-xylose to D-xylonate is a xylose dehydrogenase. In a further embodiment, the enzyme that catalyzes the conversion of D-xylose to D-xylonate is encoded by one or more endogenous nucleic acid molecules. In an alternative embodiment, the enzyme that catalyzes the conversion of D-xylose to D-xylonate is encoded by one or more exogenous nucleic acid molecules. In another embodiment, the enzyme is a xylose dehydrogenase that is encoded by a nucleic acid molecule obtained from a microorganism selected from *Caulobacter* sp., *Haloarcula* sp., *Haloferax* sp., *Halorubrum* sp. and *Trichoderma* sp. In some embodiments, the nucleic acid molecule encoding the xylose dehydrogenase is obtained from a microorganism selected from *Caulobacter crescentus*, *Haloarcula marismortui*, *Haloferax volcanii*, *Halorubrum lacusprofundi* and *Trichoderma reesei*. In some embodiments, the nucleic acid molecule encoding xylose dehydrogenase is selected from xylB, xdh (HVO_B0028), xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the enzyme that catalyzes the conversion of D-xylonate to 2-keto-3-deoxy-xylonate is a xylonate dehydratase. In a further embodiment, the enzyme that catalyzes the conversion of D-xylonate to 2-keto-3-deoxy-xylonate is encoded by one or more endogenous nucleic acid molecules. In an alternative embodiment, the enzyme that catalyzes the conversion of D-xylonate to 2-keto-3-deoxy-xylonate is encoded by one or more exogenous nucleic acid molecules. In another embodiment, the enzyme is a xylonate dehydratase that is encoded by a nucleic acid molecule obtained from a microorganism selected from *Caulobacter* sp., *Haloferax* sp., *Sulfolobus* sp. and *E. coli*. In some embodiments, the nucleic acid molecule encoding the xylonate dehydratase is obtained from a microorganism selected from *Caulobacter crescentus, Haloferax volcanii, E. coli* and *Suffolobus soffataricus*. In some embodiments, the nucleic acid molecule encoding xylonate dehydratase is selected from xylD, yjhG, yagF, xad, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the enzyme that catalyzes the conversion of 2-keto-3-deoxy-xylonate to glycolaldehyde and pyruvate is a 2-keto-3-deoxy-D-pentonate aldolase. In a further embodiment, the enzyme that catalyzes the conversion of 2-keto-3-deoxy-xylonate to glycolaldehyde and pyruvate is encoded by one or more endogenous nucleic acid molecules. In an alternative embodiment, the enzyme that catalyzes the conversion of 2-keto-3-deoxy-xylonate to glycolaldehyde and pyruvate is encoded by one or more exogenous nucleic acid molecules. In another embodiment, the enzyme is a 2-keto-3-deoxy-D-pentonate aldolase that is encoded by a nucleic acid molecule obtained from a microorganism selected from *Pseudomonas* sp. and *E. coli*. In some embodiments, the nucleic acid molecule encoding the 2-keto-3-deoxy-D-pentonate aldolase is obtained from a microorganism selected from *E. coli*. In some embodiments, the nucleic acid molecule encoding 2-keto-3-deoxy-D-pentonate aldolase is selected from yjhH, yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the enzyme that catalyzes the conversion of glycolaldehyde to MEG is a glycolaldehyde reductase or aldehyde reductase. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme is a glycolaldehyde reductase or aldehyde reductase that is encoded by a nucleic acid molecule obtained from a microorganism selected from *E. coli* or *S. cerevisiae*. In some embodiments, the nucleic acid molecule encoding glycolaldehyde reductase or aldehyde reductase is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment, the enzyme that catalyzes the conversion of acetyl-CoA to acetoacetyl-CoA is a thiolase or acetyl coenzyme A acetyltransferase. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is a thiolase or acetyl coenzyme A acetyltransferase that is encoded by a nucleic acid molecule obtained from a microorganism selected from *Clostridium* sp., *Bacillus* sp., *E. coli*, *Saccharomyces* sp. and *Marinobacter* sp. In some embodiments, the nucleic acid molecule encoding thiolase or acetyl coenzyme A acetyltransferase is obtained from a microorganism selected from *Clostridium acetobutylicum, Clostridium thermosaccharolyticum, Bacillus cereus, E. coli, Saccharomyces cerevisiae* and *Marinobacter hydrocarbonoclasticus*. In some embodiments, the nucleic acid molecule encoding thiolase or acetyl coenzyme A acetyltransferase is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment, the enzyme that catalyzes the conversion of acetoacetyl-CoA to acetoacetate is a acetate:acetoacetyl-CoA transferase or hydrolase. In some embodiments, the transferase is an acetyl-CoA:acetoacetate-CoA transferase. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme is an acetate:acetoacetyl-CoA transferase or hydrolase that is encoded by one or more nucleic acid molecules obtained from a microorganism selected from *Clostridium* sp. and *E. coli*. In some embodiments, the nucleic acids molecule encoding acetate:acetoacetyl-CoA hydrolase are obtained from *Clostridium acetobutylicum*. In some embodiments, the nucleic acid molecules encoding acetate:acetoacetyl-CoA transferase are obtained from *E. coli*. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment, the enzyme that catalyzes the conversion of acetoacetate to acetone is an acetoacetate decarboxylase. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme is an acetoacetate decarboxylase that is encoded by a nucleic acid molecule obtained from a microorganism selected from *Clostridium* sp., *Bacillus* sp., *Chromobacterium* sp. and *Pseudomonas* sp. In some embodiments, the nucleic acid molecule encoding acetoacetate decarboxylase is obtained from a microorganism selected from *Clostridium acetobutylicum, Clostridium beijerinckii, Clostridium cellulolyticum, Bacillus polymyxa, Chromobacterium violaceum* and *Pseudomonas putida*. In some embodiments, the nucleic acid molecule encoding acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment, the recombinant microorganism further comprises one or more modifications selected from the group consisting of:

(a) a deletion, insertion, or loss of function mutation in a gene encoding an enzyme that catalyzes the conversion of D-xylose to D-xylulose;

(b) a deletion, insertion, or loss of function mutation in a gene encoding an enzyme that catalyzes the conversion of glycolaldehyde to glycolic acid; and (c) a deletion, insertion, or loss of function mutation in a gene encoding an enzyme that catalyzes the conversion of pyruvate to lactate.

In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a recombinant microorganism producing MEG and a three-carbon compound comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene, or homolog thereof.

In some embodiments, a recombinant microorganism producing MEG and a three-carbon compound comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

In some embodiments, a recombinant microorganism producing MEG and a three-carbon compound comprises a deletion, insertion, or loss of function mutation in a gene encoding a lactate dehydrogenase to prevent the production of lactate from pyruvate and instead shunt the reaction toward production of a three-carbon compound.

In any of the above-described aspects and embodiments, the recombinant microorganism may further comprise at least one nucleic acid molecule encoding an enzyme that catalyzes the conversion of acetone to isopropanol. In one embodiment, the enzyme that catalyzes the conversion of acetone to isopropanol is encoded by one or more endogenous nucleic acid molecules. In an alternative embodiment, the enzyme that catalyzes the conversion of acetone to isopropanol is encoded by one or more exogenous nucleic acid molecules. In one embodiment, the enzyme that catalyzes the conversion of acetone to isopropanol is a secondary alcohol dehydrogenase (S-ADH). In another embodiment, the enzyme is a secondary alcohol dehydrogenase that is encoded by a nucleic acid molecule obtained from a microorganism selected from *Burkholderia* sp, *Alcaligenes* sp., *Clostridium* sp., *Thermoanaerobacter* sp., *Phytomonas* sp., *Rhodococcus* sp., *Methanobacterium* sp., *Methanogenium* sp., *Entamoeba* sp., *Trichomonas* sp., and *Tritrichomonas* sp. In some embodiments, the nucleic acid molecule encoding the secondary alcohol dehydrogenase is obtained from a microorganism selected from *Burkholderia* sp. AIU 652, *Alcaligenes eutrophus*, *Clostridium ragsdalei*, *Clostridium beijerinckii*, *Clostridium carboxidivorans*, *Thermoanaerobacter brockii*, *Thermoanaerobacter ethanolicus* (*Clostridium thermohydrosulfuricum*), *Rhodococcus ruber*, *Methanobacterium palustre*, methanogenic archaea *Methanogenium liminatans*, parasitic protist *Entamoeba histolytica*, parasitic protozoan *Tritrichomonas foetus* and human parasite *Trichomonas vaginalis*. In some embodiments, the one or more nucleic acid molecule encoding secondary alcohol dehydrogenase is adh, adhB, EhAdh1, or homolog thereof. In some embodiments, the S-ADH is predicted from homology and can be from *Thermoanaerobacter mathranii*, *Micrococcus luteus*, *Nocardiopsis alba*, *Mycobacterium hassiacum*, *Helicobacter suis*, *Candida albicans*, *Candida parapsilosis*, *Candida orthopsilosis*, *Candida metapsilosis*, *Grosmannia clavigera* and *Scheffersomyces stipitis*. In a further embodiment, the alcohol dehydrogenase comprises an amino acid sequence selected from the group consisting of SEQ ID NOs: 106 and 108. In yet another embodiment, the alcohol dehydrogenase is encoded by a nucleic acid sequence selected from the group consisting of SEQ ID NOs: 104, 105 and 107.

In any of the above-described aspects and embodiments, the recombinant microorganism may further comprise at least one nucleic acid molecule encoding an enzyme that catalyzes the conversion of isopropanol to propene. In one embodiment, the enzyme that catalyzes the conversion of isopropanol to propene is encoded by one or more endogenous nucleic acid molecules. In an alternative embodiment, the enzyme that catalyzes the conversion of isopropanol to propene is encoded by one or more exogenous nucleic acid molecules. In one embodiment, the enzyme that catalyzes the conversion of isopropanol to propene is a dehydratase.

In one embodiment, MEG is produced through the conversion of glycolaldehyde in a C-2 branch pathway and acetone is produced through the conversion of DHAP or pyruvate in a C-3 branch pathway. In another embodiment, MEG is produced through the conversion of glycolaldehyde in a C-2 branch pathway and IPA is produced through the conversion of DHAP or pyruvate in a C-3 branch pathway. In a further embodiment, MEG is produced through the conversion of glycolaldehyde in a C-2 branch pathway and propene is produced through the conversion of DHAP or pyruvate in a C-3 branch pathway.

In one embodiment, at least a portion of the excess NADH produced in the C-3 branch is used as a source of reducing equivalents in the C-2 branch. In another embodiment, at least a portion of the excess NADH produced in the C-3 branch is used to produce ATP.

In one embodiment, the co-produced MEG and acetone comprise a yield potential greater than 90% of the theoretical maximum yield potential without carbon fixation. In another embodiment, the co-produced MEG and IPA comprise a yield potential greater than 90% of the theoretical maximum yield potential without carbon fixation. In a further embodiment, the co-produced MEG and propene comprise a yield potential greater than 90% of the theoretical maximum yield potential without carbon fixation.

In one embodiment, excess biomass formation is minimized and production of MEG and acetone is maximized. In another embodiment, excess biomass formation is minimized and production of MEG and IPA is maximized. In a further embodiment, excess biomass formation is minimized and production of MEG and propene is maximized.

In yet another aspect, the present application provides a method of producing MEG and a three carbon compound using a recombinant microorganism as described above, wherein the method comprises cultivating the recombinant microorganism in a culture medium containing a feedstock providing a carbon source until the MEG and the three carbon compound is produced. In some embodiments, the three carbon compound is selected from acetone, isopropanol, and propene.

In yet another aspect, the present application provides a method of producing a recombinant microorganism that co-produces, produces or accumulates MEG and a three carbon compound. In some embodiments, the three carbon compound is selected from acetone, isopropanol, and propene.

In yet another aspect, the present application provides a recombinant microorganism co-producing monoethylene glycol (MEG) and a three carbon compound. In some embodiments, the three carbon compound is selected from acetone, isopropanol, and propene.

BRIEF DESCRIPTION OF DRAWINGS

Illustrative embodiments of the disclosure are illustrated in the drawings, in which.

SEQUENCES

Figure 1:
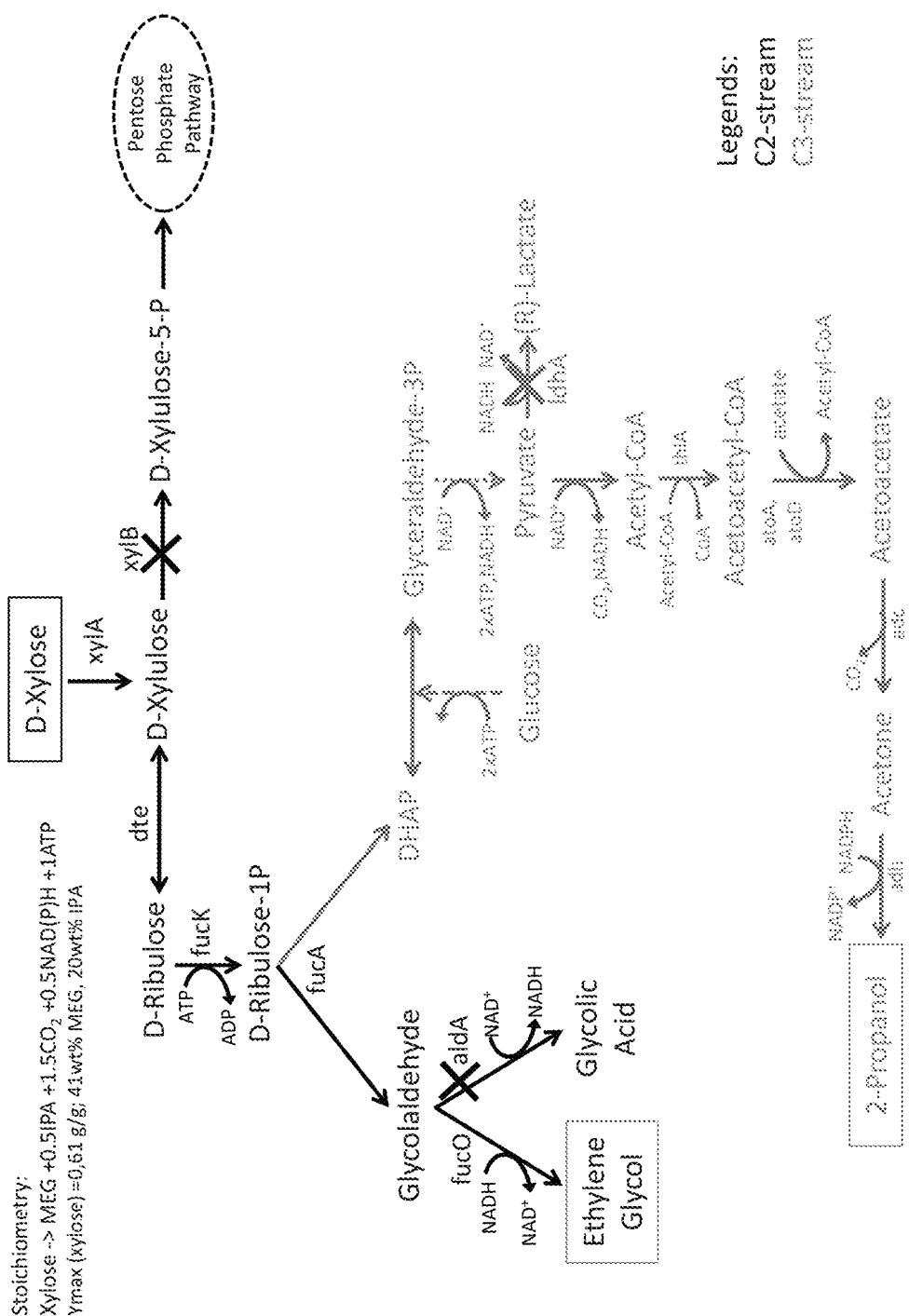
FIG. 1 illustrates MEG and isopropanol co-production pathway via ribulose-1-phosphate.

A sequence listing for SEQ ID NO: 1-SEQ ID NO: 120 is part of this application and is incorporated by reference herein. The sequence listing is provided at the end of this document.

DETAILED DESCRIPTION

Definitions

The following definitions and abbreviations are to be used for the interpretation of the disclosure.

As used herein and in the appended claims, the singular forms "a," "an," and "the" include plural referents unless the context clearly dictates otherwise. Thus, for example, reference to "a three-carbon compound" includes a plurality of such three-carbon compounds and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9× to 1.1×, or, in some embodiments, a value from 0.95× to 1.05λ. Any reference to "about X" or "around X" specifically indicates at least the values X, 0.95×, 0.96×, 0.97×, 0.98×, 0.99×, 1.01×, 1.02×, 1.03×, 1.04×, and 1.05×. Thus, "about X" and "around X" are intended to teach and provide written description support for a claim limitation of, e.g., "0.98×."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic +non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, a linalool dehydratase/isomerase enzyme may be a "variant" relative to a reference linalool dehydratase/isomerase enzyme by virtue of alteration(s) in any part of the polypeptide sequence encoding the reference linalool dehydratase/isomerase enzyme. A variant of a reference linalool dehydratase/isomerase enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference linalool dehydratase/isomerase enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed linalool dehydratase/isomerase enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed linalool dehydratase/isomerase enzymes of the present disclosure.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

The term "yield potential" as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway.

If a specific pathway towards a product has a lower yield than the thermodynamic maximum yield, then it loses mass and can most likely be improved upon or substituted with a more efficient pathway towards the product.

The term "redox balanced" refers to a set of reactions, which taken together produce as much redox cofactors as they consume. Designing metabolic pathways and engineering an organism such that the redox cofactors are balanced or close to being balanced usually results in a more efficient, higher yield production of the desired compounds. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. Biological energy is frequently stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide (NAD+), which then contributes to the creation of a proton gradient, which drives the synthesis of adenosine triphosphate (ATP) and is maintained by the reduction of oxygen. The term redox state is often used to describe the balance of GSH/GSSG, NAD+/NADH and NADP+/NADPH in a biological system such as a cell or organ. The redox state is reflected in the balance of several sets of metabolites (e.g., lactate and pyruvate, beta-hydroxybutyrate, and acetoacetate), whose interconversion is dependent on these ratios. An abnormal redox state can develop in a variety of deleterious situations, such as hypoxia, shock, and sepsis.

The terms "C2 pathway", "C2 branch pathway" or "C2 stream" as used herein refers to a biochemical pathway wherein MEG can be produced via glycolaldehyde.

The terms "C3 pathway", "C3 branch pathway" or "C3 stream" as used herein refers to a biochemical pathway wherein MEG or one or more three-carbon compounds can be produced via pyruvate or dihydroxyacetonephosphate (DHAP).

INTRODUCTION

The present disclosure combines the production of monoethylene glycol (MEG) and one or more three carbon compounds in different hosts. In some embodiments, the three carbon compound is isopropanol (IPA). The present disclosure thereby avoids some of the biggest pathway engineering challenges for known MEG and IPA pathways demonstrated so far. Surprisingly, the combination of a pathway for MEG production and a pathway for production of a three carbon compound complements each other and is highly synergistic, avoiding or overcoming the biggest challenges and shortcomings of each pathway alone, establishing a good redox balance but also delivering required ATP, without production of excess ATP.

A demonstrated fermentative production of MEG from xylose (WO2013126721A1, which is herein referenced in its entirety), via ribulose-1-phosphate, has a high yield potential (82 wt %=0.82 g MEG/g xylose). MEG is produced via two different pathways which are active in parallel, a 2-carbon (C2) stream (via glycolaldehyde) and a 3-carbon (C3) stream (via dihydroxyacetonephosphate (DHAP)). The C2 stream is easy to implement at high efficiency, but the C3 stream is very difficult to implement at high efficiency via metabolic engineering. Several pathway options for DHAP→MEG exist, all of which are difficult to implement. Furthermore, the overall process is ATP neutral. Thus, some glucose and therefore yield will be lost in order to obtain some surplus ATP required for cell growth and maintenance.

A further demonstrated fermentative production of MEG from xylose (Alkim et al., Microb Cell Fact (2015) 14:127), via xylulose-1-phosphate, is very similar to the route described by WO2013126721A1. It has the same high yield potential (82 wt %), but the C3 stream for MEG production via DHAP is difficult to implement and there is an ATP shortage.

A further fermentative production of MEG was demonstrated from glucose (Chen et al., Met. Eng. (2016) 33:12-18). It uses exclusively a pathway identical to one of the C3 stream solutions of WO2013126721A1, going via DHAP and then ethanolamine to glyceraldehyde to MEG. Only in this case, DHAP is derived from glucose, not from xylose. Thus it suffers even more from the technical difficulty to implement a high productivity and high yield pathway from DHAP to MEG. It furthermore has a reduced total yield potential of 69 wt % versus the thermodynamic maximum yield for the product MEG derived from glucose (82 wt %). The pathway is furthermore ATP neutral, not generating any ATP that the cells need for growth and maintenance. This pathway is also not redox balanced and has a high excess of 2 mol NADH per mol of consumed glucose, all of which needs to be re-oxidized for the cell to be viable. In an aerobic fermentation, this NADH can be used to generate ATP, which however would be in high excess (2 NADH→6 ATP), leading to excess biomass formation during the production phase and therefore reduced product formation and yield. The only described solution for the loss of yield potential for MEG production from glucose is the production of MEG from xylose with a high yield potential. The only described solution for the excess NADH production in the MEG from glucose process is the production of MEG from xylose which can be redox neutral.

A demonstrated fermentative production of IPA via acetoacetyl-CoA (US 2010/0311135, which is herein referenced in its entirety) has excess NADH (2 mol per mol of consumed glucose) and low yield potential (34 wt %). This pathway has excess ATP (2 mol per mol of consumed glucose), more than is required for cell maintenance during the production phase, thereby favoring biomass formation over production. If the NADH is not utilized via carbon fixation, it needs to be re-oxidized for the cell to stay viable, further losing glucose in this process. Alternatively, NADH can be oxidized through ATP production, which would lead to even more unwanted excess ATP.

Other potential solutions exist for reducing NADH excess and increasing IPA yield potential (thermodynamic max yield=47 wt %): re-capturing $CO_2$ produced in excess during the fermentation and in doing so also re-oxidizing excess NADH ($CO_2$ fixation). Or avoid excess CO2 and NADH release altogether by diverting some flux from glycolysis to a phosphoketolase (PK)/phosphotransacetylase (PTA) pathway to generate more acetyl-CoA and less $CO_2$ and NADH. However, so far none of these options have been technically demonstrated in the context of IPA production and are generally known to be very challenging.

The present disclosure combines one of three easy to implement, high yield C2-streams for MEG production from xylose with an easy to implement IPA production stream via the DHAP pathway. Surprisingly, the problem of the IPA pathway, excess NADH production, complements the NADH requiring C2 part of MEG production. The combination of these pathways leads to a high total yield potential of 61 wt %, which is close to the maximum energetic yield of 65 wt % for degradation of xylose into MEG and IPA, assuming these products are produced in a 2:1 ratio. This high yield potential stems from the synergies of coupling the IPA pathway with the C2-branch of MEG production from xylose.

The proposed pathway in its basic form is not redox neutral, but has a small excess of 0.5 mol NADH per mol of consumed xylose. In an aerobic fermentation, oxidation of NADH can deliver just enough ATP to obtain sufficient, but not excessive, ATP required for growth and maintenance during the production phase without having a significantly negative impact on product formation.

The present disclosure solves a number of problems associated with MEG and/or IPA production. In one embodiment, the problem of a difficult to implement C3 pathway in production of MEG from xylose is solved. In another embodiment, the problem of ATP shortage in production of MEG from xylose is solved. In another embodiment, the problem of loss of yield potential in production of MEG from glucose is solved. In another embodiment, the problem of ATP shortage in production of MEG from glucose is solved. In another embodiment, the problem of excess NADH production in production of MEG from glucose is solved. In another embodiment, the problem of loss of yield potential in production of IPA from glucose is solved. In another embodiment, the problem of excess NADH production in production of IPA from glucose is solved.

In one embodiment, the pathway for MEG+IPA co-production in E. coli comprises the following enzymes for IPA production: thiolase, acetate:acetoacetyl-CoA transferase or hydrolase, acetoacetate decarboxylase and secondary alcohol dehydrogenase. The MEG pathway via ribulose-1-phosphate comprises the following enzymes: D-tagatose 3-epimerase, D-ribulokinase, D-ribulose-phosphate aldolase and glycolaldehyde reductase. In order to increase carbon flux to the desired pathway, three specific genes that could divert carbon flux were identified and deleted: xylB gene coding for a xylulokinase (this enzyme can divert carbon flux into the pentose phosphate pathway), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

Figure 4:
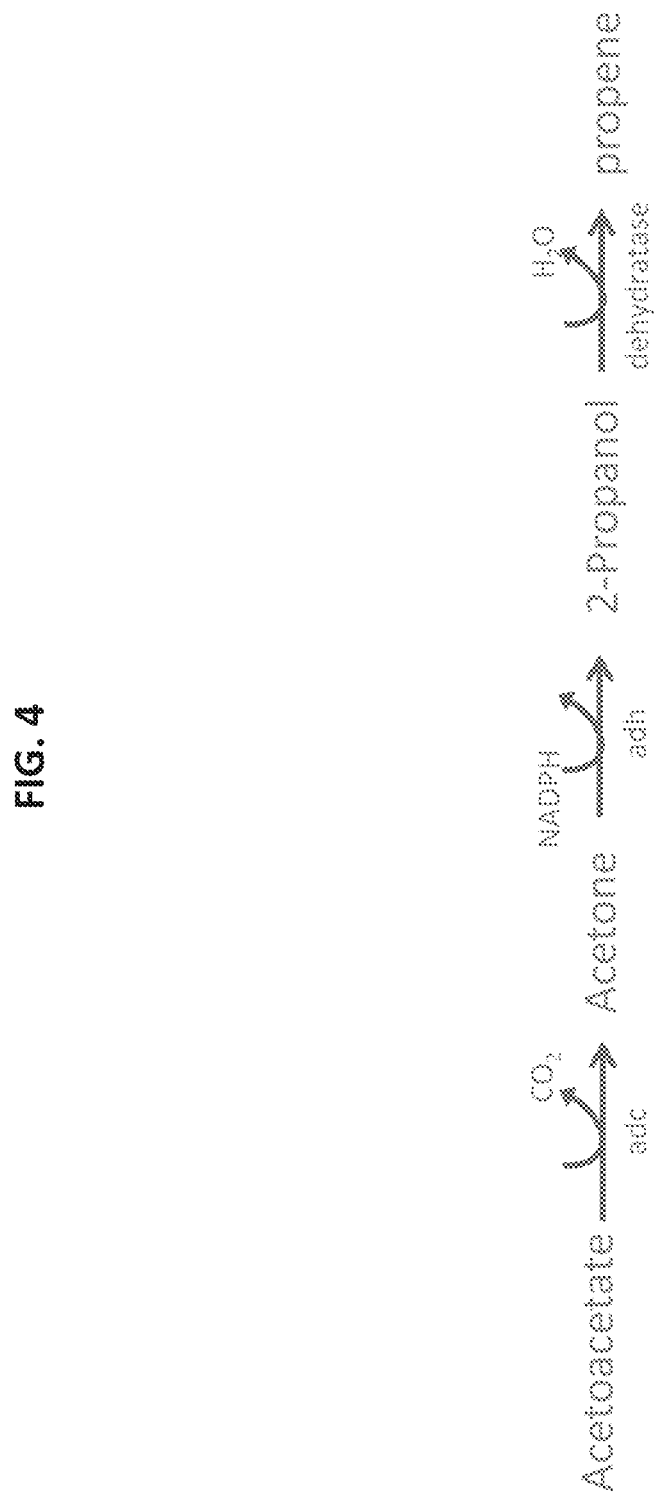
FIG. 4 illustrates possible three carbon co-products for MEG.

The first step of the pathway (FIG. 1) is the natural conversion of D-xylose into D-xylulose. D-xylulose normally enters the pentose phosphate pathway for energy and biomass generation, which is inhibited by the deletion of the xylB gene. In the engineered pathway, all carbon will be re-directed to D-ribulose by the D-tagatose 3-epimerase enzyme. D-ribulose is them converted to D-Ribulose-1-phosphate by the native E. coli enzyme D-ribulokinase. D-Ribulose-1-phosphate is cleaved into glycolaldehyde and dihydroxy acetone phosphate (DHAP) by D-ribulose-phosphate aldolase. The further degradation of DHAP is termed the C3 branch, leading to IPA production. Degradation of glycolaldehyde, termed the C2-branch, can lead to ethylene glycol or glycolate formation. Glycolate is the undesired by-product that can be produced by the aldA gene product. Ethylene glycol can be produced from glycolaldehyde using the enzyme glycolaldehyde reductase. The conversion of DHAP to acetyl-CoA (through glyceraldehyde-3-phosphate and pyruvate) is part of natural E. coli metabolism. One molecule of acetyl-CoA is condensed to another molecule of acetyl-CoA by the enzyme thiolase to produce acetoacetyl-CoA. The CoA from acetoacetyl-CoA is recycled to a molecule of acetate by acetate:acetoacetyl-CoA transferase or hydrolase, generating acetyl-CoA and acetoacetate. Acetoacetate is decarboxylated by acetoacetate decarboxylase to acetone which is further reduced to IPA by a secondary alcohol dehydrogenase enzyme. IPA can further be converted to propene by a dehydratase (FIG. 4).

In another embodiment, the pathway for MEG+IPA co-production in E. coli comprises the following enzymes for IPA production: thiolase, acetate: acetoacetyl-CoA transferase or hydrolase, acetoacetate decarboxylase and secondary alcohol dehydrogenase. The MEG pathway via D-xylulose-1-phosphate comprises the following enzymes: D-xylulose 1-kinase, D-xylulose-1-phosphate aldolase and glycolaldehyde reductase. In order to increase carbon flux to the desired pathway, three specific genes that could divert carbon flux were identified and deleted: xylB gene coding for a xylulokinase (this enzyme can divert carbon flux into the pentose phosphate pathway), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

Figure 2:
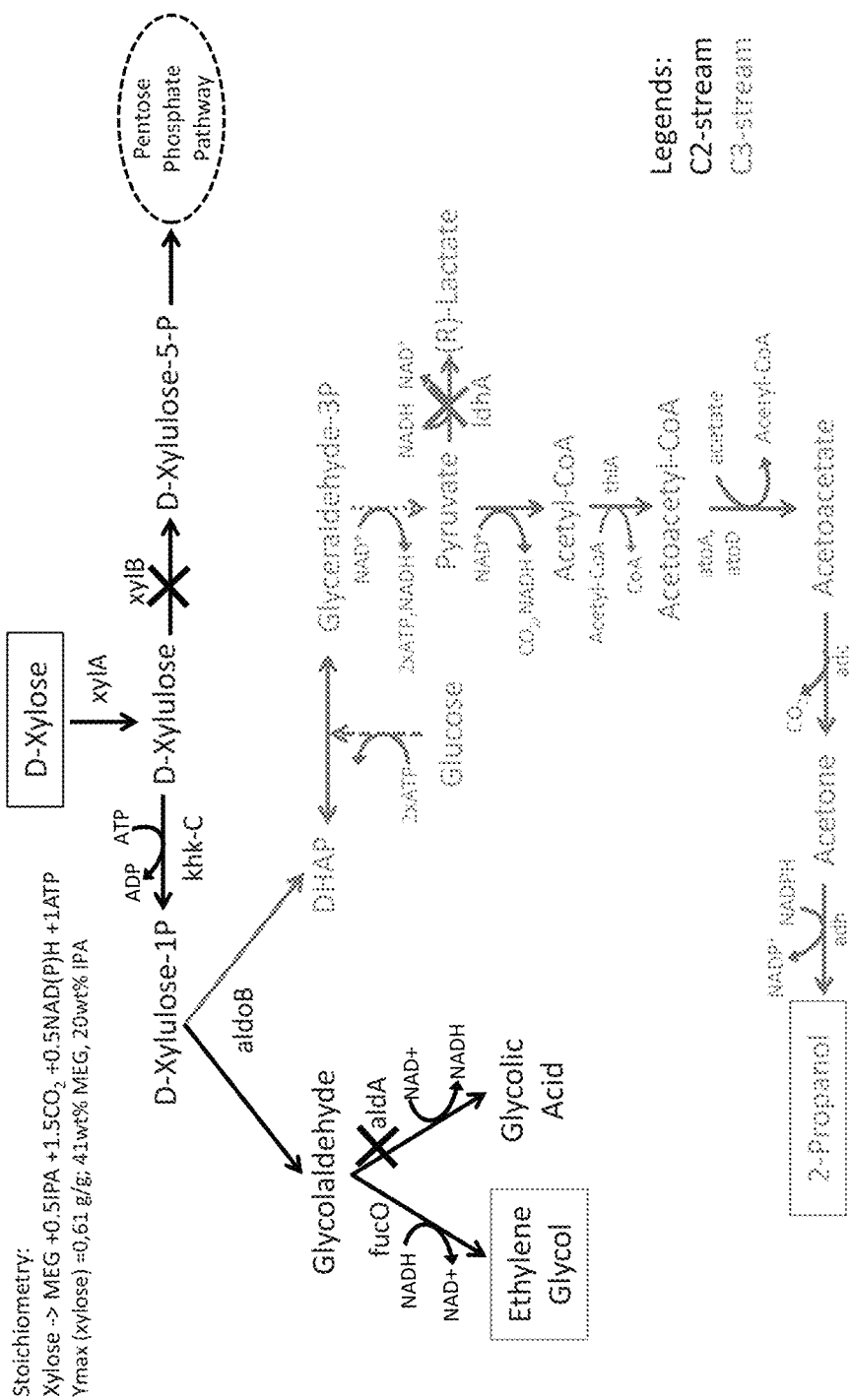
FIG. 2 illustrates MEG and isopropanol co-production pathway via xylulose-1-phosphate.

The first step of the pathway (FIG. 2) is the natural conversion of D-xylose into D-xylulose. D-xylulose normally enters the pentose phosphate pathway for energy and biomass generation, which is inhibited by the deletion of the xylB gene. In the engineered pathway, all carbon will be re-directed to D-xylulose-1-phosphate by the D-xylulose 1-kinase enzyme. D-xylulose-1-phosphate is then cleaved into glycolaldehyde and dihydroxy acetone phosphate (DHAP) by D-xylulose-1-phosphate aldolase. Production of MEG from glycolaldehyde and a three carbon compound from DHAP (for example, acetone, IPA and/or propene) proceeds as described for FIG. 1.

In another embodiment, the pathway for MEG+IPA co-production in E. coli comprises the following enzymes for IPA production: thiolase, acetate:acetoacetyl-CoA transferase or hydrolase, acetoacetate decarboxylase and secondary alcohol dehydrogenase. The MEG pathway via D-xylonate comprises the following enzymes: xylose dehydrogenase, optionally xylonolactonase, xylonate dehydratase, 2-keto-3-deoxy-D-xylonate aldolase and glycolaldehyde reductase. In order to increase carbon flux to the desired pathway, three specific genes that could divert carbon flux were identified and deleted: xylA gene coding for a D-xylose isomerase (this enzyme can divert carbon flux from D-xylose to D-xylulose instead of to D-xylonate or D-xylonolactone), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

Figure 3:
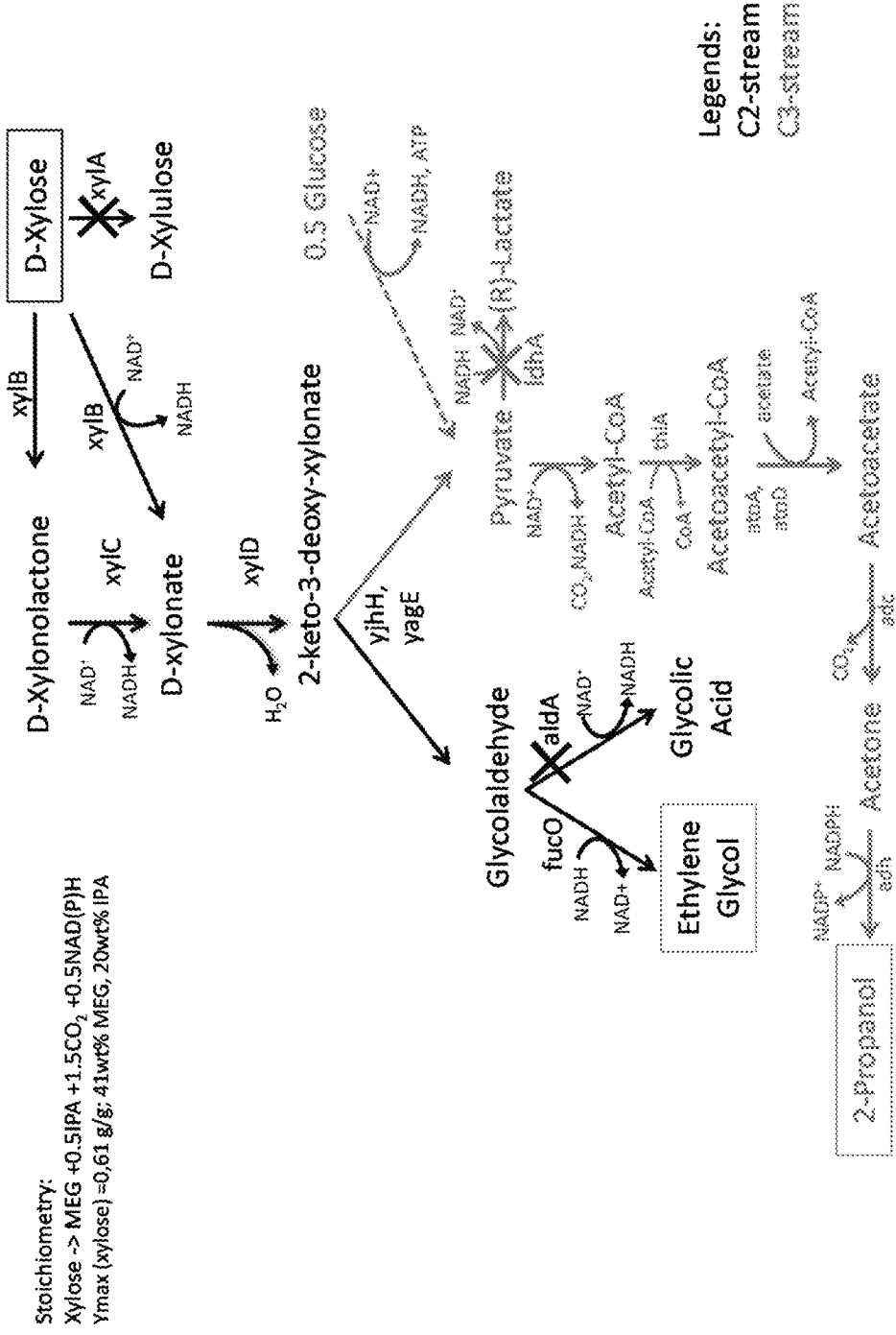
FIG. 3 illustrates MEG and isopropanol co-production pathway via xylonate.

The first step of the pathway (FIG. 3) is the conversion of D-xylose into D-xylonate, either by a two-step process using a xylose dehydrogenase to convert D-xylose to D-xylonolactone followed by conversion of D-xylonolactone to D-xylonate with a xylonolactonase enzyme, or by a one-step process using a xylose dehydrogenase to convert D-xylose directly to D-xylonate. The conversion of D-xylose to D-xylulose is inhibited by the deletion of the xylA gene. D-xylonate is then converted to 2-keto-3-deoxy-xylonate by a xylonate dehydratase. 2-keto-3-deoxy-xylonate is then cleaved into glycolaldehyde and pyruvate by 2-keto-3-deoxy-D-xylonate aldolase. Production of MEG from glycolaldehyde and a three carbon compound from pyruvate (for example, acetone, IPA and/or propene) proceeds as described for FIG. 1.

Figure 5:
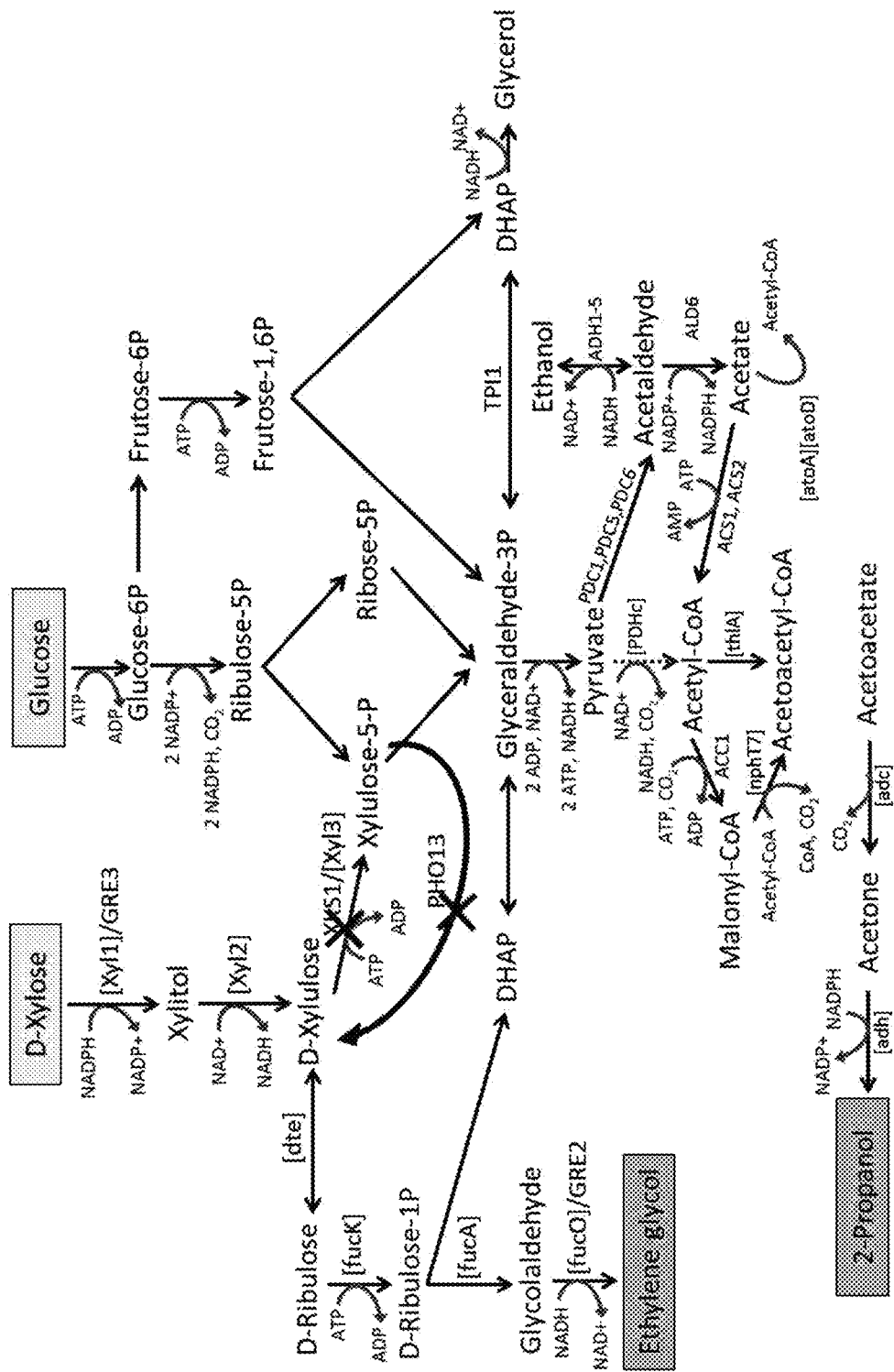
FIG. 5 illustrates MEG and isopropanol co-production pathway from xylose and glucose, via ribulose-1-phosphate, in *S. cerevisiae*.

The pathway for MEG+IPA co-production in S. cerevisiae (FIG. 5) comprises the following enzymes for IPA production: thiolase, acetate:acetoacetyl-CoA transferase or hydrolase, acetoacetate decarboxylase and secondary alcohol dehydrogenase. The MEG pathway via D-ribulose-1-phosphate comprises the following enzymes: D-tagatose 3-epimerase, D-ribulokinase, D-ribulose-phosphate aldolase and glycolaldehyde reductase. Besides the two main pathways, S. cerevisiae is not capable of consuming xylose, so two different pathways were tested for xylose consumption. Pathway 1 comprises 2 genes: Xyl1 converts D-Xylose to xylitol, and Xyl2 converts Xylitol to D-xylulose. Pathway 2 comprises only one gene: XylA that directly converts D-xylose to D-xylulose. In order to increase carbon flux to the desired pathway, two specific genes that could divert carbon flux were identified and deleted: XKS1 gene coding for a xylulokinase (this enzyme can divert carbon flux into the pentose phosphate pathway) and PHO13 gene coding for alkaline phosphatase (can divert carbon from pentose phosphate pathway).

The first step of the pathway is the conversion of D-xylose into D-xylulose, directly or via the intermediate xylitol. D-xylulose is converted to D-ribulose by the D-tagatose 3-epimerase enzyme. D-ribulose is then converted to D-Ribulose-1-phosphate by D-ribulokinase. D-Ribulose-1-phosphate is cleaved into glycolaldehyde and DHAP by D-ribulose-phosphate aldolase. DHAP enters the C3 branch for IPA production and glycolaldehyde can be converted to ethylene glycol using glycolaldehyde reductase. The conversion of DHAP to acetyl-CoA (through glyceraldehyde-3-phosphate and pyruvate) is part of the natural S. cerevisiae metabolism. One molecule of acetyl-CoA is condensed to another molecule of acetyl-CoA by thiolase, producing acetoacetyl-CoA. The CoA from acetoacetyl-CoA is recycled to a molecule of acetate by acetate:acetoacetyl-CoA transferase or hydrolase, generating one molecule of acetyl-CoA and one of acetoacetate. Acetoacetate is further decarboxylated by acetoacetate decarboxylase to acetone, which is further converted to IPA by a secondary alcohol dehydrogenase enzyme. IPA can further be converted to propene by a dehydratase-isomerase (FIG. 4).

Surprisingly, the main problem of the IPA pathway, excess NADH production, is highly synergistic with a C2-stream for MEG production by complementing the NADH requirement of the C2 branch, while leaving just enough NADH to generate required ATP in an aerobic process, without excess ATP production.

The described IPA process of US 2010/0311135 and other applications, without carbon fixation, can only achieve 34 wt % versus the energetic maximum yield potential of 47 wt %. Thus, this IPA pathway, even if implemented perfectly, can only achieve 72% of the energetic maximum yield. In the present disclosure, the synergy of coupling IPA with MEG production is such that, without necessity of $CO_2$ fixation, the combined products' yield potential of 61 wt % is very close (94%) to the energetic (=theoretic, pathway independent) maximum yield potential of 65 wt %.

In a further embodiment, the inventive co-production pathway from xylose is implemented in an organism with natural or added capability to fix $CO_2$ using excess reducing agents, thereby providing even higher yield potential. Various $CO_2$ fixation pathways are known and have been implemented in E. coli or other hosts. Acetogens, such as Clostridium ljungdahlii, can naturally utilize excess NADH generated in the presented xylose fermentation pathway especially efficient to re-capture released $CO_2$ in the Wood-Ljungdahl pathway to produce the intermediate acetyl-CoA, which can then be used to produce more acetone or related products. $CO_2$ is released for instance in the pyruvate+CoA+NAD+→acetyl-CoA+$CO_2$+2 NADH or acetoacetone→acetone+$CO_2$ reactions. Furthermore, adding a second feedstock, such as hydrogen gas ($H_2$) or syngas (a composition of $H_2$, CO, $CO_2$) or methanol, can provide more reducing agents and even allow acetogens or similarly enabled organisms to re-capture all $CO_2$ released in the xylose fermentation pathway or $CO_2$ present in the second feedstock. Such a mixotrophic fermentation can thus further increase yield potential. In the case of MEG+ acetone from xylose, $CO_2$ fixation can lead to an increase of 25% relative acetone or 8% total MEG+ acetone product yield. With externally added reducing agents, calculated for full capture of all xylose carbon, the yield potential is +100% for acetone which equals +32% total product yield.

Yield potentials without $CO_2$ fixation:

1 xylose→1 MEG+1/2 acetone+3/2 $CO_2$+1 NADH 1 xylose→1 MEG+1/2 IPA+3/2 $CO_2$+1/2 NADH Yield potentials with $CO_2$ fixation:

1 xylose→1 MEG+5/8 acetone+9/8 $CO_2$ 1 xylose→1 MEG+10/18 IPA+4/3 $CO_2$

Yield potentials with externally added reducing agents, calculated for fixation of $CO_2$ equivalent to all $CO_2$ released during xylose fermentation:

1 xylose→1 MEG+1 acetone 1 xylose→1 MEG+1 IPA

While this present disclosure is theoretically sound and synergistic, it surprisingly also avoids the biggest metabolic engineering and technical challenges of both MEG and IPA fermentation processes: C3-stream MEG fermentation and carbon fixation for IPA process.

In one embodiment, MEG is produced through the conversion of glycolaldehyde in a C-2 branch pathway and acetone is produced through the conversion of DHAP or pyruvate in a C-3 branch pathway. In another embodiment, MEG is produced through the conversion of glycolaldehyde in a C-2 branch pathway and IPA is produced through the conversion of DHAP or pyruvate in a C-3 branch pathway. In a further embodiment, MEG is produced through the conversion of glycolaldehyde in a C-2 branch pathway and propene is produced through the conversion of DHAP or pyruvate in a C-3 branch pathway.

In one embodiment, at least a portion of the excess NADH produced in the C-3 branch is used as a source of reducing equivalents in the C-2 branch. In another embodiment, at least a portion of the excess NADH produced in the C-3 branch is used to produce ATP.

In one embodiment, the co-produced MEG and acetone comprise a yield potential greater than 90% of the theoretical maximum yield potential without carbon fixation. In another embodiment, the co-produced MEG and IPA comprise a yield potential greater than 90% of the theoretical maximum yield potential without carbon fixation. In a further embodiment, the co-produced MEG and propene comprise a yield potential greater than 90% of the theoretical maximum yield potential without carbon fixation.

In one embodiment, excess biomass formation is minimized and production of MEG and acetone is maximized. In another embodiment, excess biomass formation is minimized and production of MEG and IPA is maximized. In a further embodiment, excess biomass formation is minimized and production of MEG and propene is maximized.

Monoethylene Glycol (MEG)

Monoethylene glycol (MEG) is an important raw material for industrial applications. A primary use of MEG is in the manufacture of polyethylene terephthalate (PET) resins, films and fibers. In addition, MEG is important in the production of antifreezes, coolants, aircraft anti-icer and deicers and solvents. MEG is also known as ethane-1,2-diol.

Ethylene glycol is also used as a medium for convective heat transfer in, for example, automobiles and liquid cooled computers.

Because of its high boiling point and affinity for water, ethylene glycol is a useful desiccant. Ethylene glycol is widely used to inhibit the formation of natural gas clathrates (hydrates) in long multiphase pipelines that convey natural gas from remote gas fields to a gas processing facility. Ethylene glycol can be recovered from the natural gas and reused as an inhibitor after purification treatment that removes water and inorganic salts.

Minor uses of ethylene glycol include in the manufacture of capacitors, as a chemical intermediate in the manufacture of 1,4-dioxane, and as an additive to prevent corrosion in liquid cooling systems for personal computers. Ethylene glycol is also used in the manufacture of some vaccines; as a minor ingredient in shoe polish, inks and dyes; as a rot and fungal treatment for wood; and as a preservative for biological specimens.

Acetone

Acetone (also known as propanone) is an organic compound with the formula $(CH3)_2CO$. It is a colorless, volatile, flammable liquid, and is the simplest ketone.

Acetone is miscible with water and serves as an important solvent, typically for cleaning purposes in the laboratory. Over 6.7 million tonnes are produced worldwide, mainly for use as a solvent and production of methyl methacrylate and bisphenol A. It is a common building block in organic chemistry. Familiar household uses of acetone are as the active ingredient in nail polish remover and as paint thinner.

Isopropanol

Isopropyl alcohol (IUPAC name 2-propanol), also called isopropanol, is a compound with the chemical formula $C_3H_8O$ or $C_3H_7OH$ or $CH_3CHOHCH_3$. It is a colorless, flammable chemical compound with a strong odor. It is the simplest example of a secondary alcohol, where the alcohol carbon atom is attached to two other carbon atoms sometimes shown as $(CH3)_2CHOH$. It is a structural isomer of propanol. It has a wide variety of industrial and household uses.

Propene, also known as propylene or methyl ethylene, is an unsaturated organic compound having the chemical formula $C_3H_6$. It has one double bond, and is the second simplest member of the alkene class of hydrocarbons.

Propene is produced from fossil fuels—petroleum, natural gas, and, to a much lesser extent, coal. Propene is a byproduct of oil refining and natural gas processing.

Propene is the second most important starting product in the petrochemical industry after ethylene. It is the raw material for a wide variety of products. Manufacturers of the plastic polypropylene account for nearly two thirds of all demand. Polypropylene is, for example, needed for the production of films, packaging, caps and closures as well as for other applications. Propene is also used for the production of important chemicals such as propylene oxide, acrylonitrile, cumene, butyraldehyde, and acrylic acid. Over 85 million tonnes of propene is processed worldwide.

Enzymes

Exemplary enzymes that may be used in the MEG and three-carbon compound co-production pathways disclosed herein are listed in Table 1.

TABLE 1

| Described Reaction | EC no. | Required enzyme activity | Gene candidate | Source Organism | Natural/annotated function |
|---|---|---|---|---|---|
| Isomerases that may be used in all xylulose dependent MEG pathways | | | | | |
| D-xylose + NAD(P)H <=> Xylitol + NAD(P)+ | 1.1.1.307 | xylose reductase | xyl1 | *Scheffersomyces stipitis* | D-xylose reductase |
| D-xylose + NAD(P)H <=> Xylitol + NAD(P)+ | 1.1.1.307 | xylose reductase | GRE3 | *Saccharomyces cerevisiae* | aldose reductase |
| Xylitol + NAD+ <=> D-xylulose + NADH | 1.1.1.9 | xylitol dehydrogenase | xyl2 | *Scheffersomyces stipitis* | D-xylulose reductase |
| Xylitol + NAD+ <=> D-xylulose + NADH | 1.1.1.9 | xylitol dehydrogenase | xdh1 | *Trichoderma reesei* | Xylitol dehydrogenase |
| D-xylopyranose <=> D-xylulose | 5.3.1.5 | xylose isomerase | xylA | *Pyromyces* sp. | xylose isomerase |
| Glycolaldehyde reductases that may be used in all MEG pathways | | | | | |
| glycolaldehyde + NAD(P)H <=> monoethylene glycol + NAD(P)+ | 1.1.1.- | glycolaldehyde reductase | gldA | *Escherichia coli* | glycerol dehydrogenase |
| glycolaldehyde + NAD(P)H <=> monoethylene glycol + NAD(P)+ | 1.1.1.- | glycolaldehyde reductase | GRE2 | *Saccharomyces cerevisiae* | methylglyoxal reductase |
| glycolaldehyde + NAD(P)H <=> monoethylene glycol + NAD(P)+ | 1.1.1.- | glycolaldehyde reductase | GRE3 | *Saccharomyces cerevisiae* | aldose reductase |

TABLE 1-continued

| Reaction | EC | Enzyme | Gene | Organism | Description |
|---|---|---|---|---|---|
| glycolaldehyde + NAD(P)H <=> monoethylene glycol + NAD(P)+ | 1.1.1.- | glycolaldehyde reductase | yqhD* | Escherichia coli | Alcohol dehydrogenase |
| glycolaldehyde + NAD(P)H <=> monoethylene glycol + NAD(P)+ | 1.1.1.- | glycolaldehyde reductase | yqhD | Escherichia coli | Alcohol dehydrogenase |
| glycolaldehyde + NAD(P)H <=> monoethylene glycol + NAD(P)+ | 1.1.1.- | glycolaldehyde reductase | ydjg | Escherichia coli | methylglyoxal reductase |
| glycolaldehyde + NAD(P)H <=> monoethylene glycol + NAD(P)+ | 1.1.1.- | glycolaldehyde reductase | fucO | Escherichia coli | lactaldehyde reductase |
| glycolaldehyde + NAD(P)H <=> monoethylene glycol + NAD(P)+ | 1.1.1.- | glycolaldehyde reductase | yafB (dkgB) | Escherichia coli | methylglyoxal reductase [multifunctional] |
| glycolaldehyde + NAD(P)H <=> monoethylene glycol + NAD(P)+ | 1.1.1.- | glycolaldehyde reductase | yqhE (dkgA) | Escherichia coli | 2,5-diketo-D-gluconic acid reductase A |
| Enzymes that may be used in D-ribulose-1-phosphate pathway to MEG | | | | | |
| D-xylulose <=> D-ribulose | 5.1.3.- | D-ribulose-3-epimerase | DTE | Pseudomonas cichorii | D-tagatose 3-epimerase |
| D-xylulose <=> D-ribulose | 5.1.3.- | D-ribulose-3-epimerase | C1KKR1 | Rhodobacter sphaeroides | D-tagatose 3-epimerase |
| D-ribulose + ATP <=> D-ribulose-1-phosphate + ADP | 2.7.1.- | D-ribulose-1-kinase | fucK | Escherichia coli | L-fuculokinase |
| D-ribulose-1-phosphate <=> glyceraldehyde + dihydroxyacetonephosphate | 4.1.2.- | D-ribulose-1-phosphate aldolase | fucA | Escherichia coli | L-fuculose phosphate aldolase |
| Enzymes that may be used in D-xylulose-1-phosphate pathway to MEG | | | | | |
| D-xylulose + ATP <=> D-xylulose-1-phosphate + ADP | 2.7.1.- | D-xylulose 1-kinase | khk-C (cDNA) | Homo sapiens | ketohexokinase C |
| D-xylulose-1-phosphate <=> glyceraldehyde + dihydroxyacetonephosphate | 4.1.2.- | D-xylulose-1-phosphate aldolase | aldoB (cDNA) | Homo sapiens | Fructose-bisphosphate aldolase B |
| Enzymes that may be used in xylonate pathway to MEG | | | | | |
| D-xylose + NAD+ <=> D-xylonolactone + NADH, or D-xylose + NAD+ <=> D-xylonate + NADH | 1.1.1.175 | xylose dehydrogenase | xylB | Caulobacter crescentus | D-xylose 1-dehydrogenase |
| D-xylose + NADP+ <=> D-xylonolactone + NADPH, or D-xylose + NADP+ <=> D-xylonate + NADPH | 1.1.1.179 | xylose dehydrogenase | xdh1, HVO_B0028 | Haloferax volcanii | D-xylose 1-dehydrogenase |
| D-xylose + NADP+ <=> D-xylonolactone + NADPH, or D-xylose + NADP+ <=> D-xylonate + NADPH | 1.1.1.179 | xylose dehydrogenase | xyd1 | Trichoderma reesei | D-xylose 1-dehydrogenase |
| D-xylonolactone + H2O <=> D-xylonate | 3.1.1.68 | xylonolactonase | xylC | Caulobacter crescentus | Xylonolactonase |
| D-xylonate <=> 2-keto-3-deoxy-xylonate + H2O | 4.2.1.82 | xylonate dehydratase | xylD | Caulobacter crescentus | xylonate dehydratase |
| D-xylonate <=> 2-keto-3-deoxy-xylonate + H2O | 4.2.1.82 | xylonate dehydratase | yjhG | Escherichia coli | xylonate dehydratase |
| D-xylonate <=> 2-keto-3-deoxy-xylonate + H2O | 4.2.1.82 | xylonate dehydratase | yagF | Escherichia coli | xylonate dehydratase |
| 2-keto-3-deoxy-xylonate <=> glycolaldehyde + pyruvate | 4.1.2.- | 2-keto-3-deoxy-D-pentonate aldolase | yjhH | Escherichia coli | Uncharacterized lyase |
| 2-keto-3-deoxy-xylonate <=> glycolaldehyde + pyruvate | 4.1.2.- | 2-keto-3-deoxy-D-pentonate aldolase | yagE | Escherichia coli | Probable 2-keto-3-deoxy-galactonate aldolase |
| Enzymes that may be used in pathway to produce one or more three-carbon compounds | | | | | |
| 2 acetyl-Coa -> acetoacetyl-CoA + CoA | 2.3.1.9 | acetyl coenzyme A acetyltransferase | thlA | Clostridium acetobutylicum | acetyl coenzyme A acetyltransferase |

TABLE 1-continued

| | | | | | |
|---|---|---|---|---|---|
| 2 acetyl-Coa -> acetoacetyl-CoA + CoA | 2.3.1.9 | acetyl coenzyme A acetyltransferase | atoB | Escherichia coli | acetyl coenzyme A acetyltransferase |
| 2 acetyl-Coa -> acetoacetyl-CoA + CoA | 2.3.1.9 | acetyl coenzyme A acetyltransferase | ERG10 | Saccharomyces cerevisiae | acetyl coenzyme A acetyltransferase |
| acetoacetyl-CoA + acetate -> acetoacetate + acetyl-CoA | 2.8.3.8 | Acetyl-CoA: acetoacetate-CoA transferase subunit | atoA | Escherichia coli | Acetyl-CoA: acetoacetate-CoA transferase subunit |
| acetoacetyl-CoA + acetate -> acetoacetate + acetyl-CoA | 2.8.3.8 | Acetyl-CoA: acetoacetate-CoA transferase subunit | atoD | Escherichia coli | Acetyl-CoA: acetoacetate-CoA transferase subunit |
| acetoacetate -> acetone + CO2 | 4.1.1.4 | acetoacetate decarboxylase | adc | Clostridium acetobutylicum | acetoacetate decarboxylase |
| acetoacetate -> acetone + CO2 | 4.1.1.4 | acetoacetate decarboxylase | adc | Clostridium beijerinckii | acetoacetate decarboxylase |
| acetone + NAD(P)H -> 2-propanol + NAD(P)+ | 1.1.1.2 | secondary alcohol dehydrogenase | adh | Clostridium beijerinckii | secondary alcohol dehydrogenase |
| acetone + NAD(P)H -> 2-propanol + NAD(P)+ | 1.1.1.2 | secondary alcohol dehydrogenase | adh | Clostridium carboxidivorans | alcohol dehydrogenase |
| NADH + NADP+ <--> NAD+ + NADPH | 1.6.1.1. | Soluble pyridine nucleotide transhydrogenase | udhA | Escherichia coli | Soluble pyridine nucleotide transhydrogenase |
| Hydrolases that may be used in pathway to produce one or more three-carbon compounds | | | | | |
| Acetoacetyl-CoA + H(2)O <=> CoA + acetoacetate | 3.1.2.11 | acetate: acetoacetyl-CoA hydrolase | ctfA | Clostridium acetobutylicum | butyrate-acetoacetate CoA-transferase, complex A |
| Acetoacetyl-CoA + H(2)O <=> CoA + acetoacetate | 3.1.2.11 | acetate: acetoacetyl-CoA hydrolase | ctfB | Clostridium acetobutylicum | butyrate-acetoacetate CoA-transferase, subunit B |
| Acetoacetyl-CoA + H(2)O <=> CoA + acetoacetate | 3.1.2.11 | acetate: acetoacetyl-CoA hydrolase | atoA | Escherichia coli (strain K12) | Acetyl-CoA: acetoacetate-CoA transferase subunit |
| Acetoacetyl-CoA + H(2)O <=> CoA + acetoacetate | 3.1.2.11 | acetate: acetoacetyl-CoA hydrolase | atoD | Escherichia coli (strain K12) | Acetyl-CoA: acetoacetate-CoA transferase subunit |

| | Described Reaction | Gene Identifier (nt) | SEQ ID NO (nt) | Uniprot ID | SEQ ID NO (AA) |
|---|---|---|---|---|---|
| Isomerases that may be used in all xylulose dependent MEG pathways | | | | | |
| | D-xylose + NAD(P)H <=> Xylitol + NAD(P)+ | GeneID: 4839234 | 82, 83 | P31867 | 84 |
| | D-xylose + NAD(P)H <=> Xylitol + NAD(P)+ | GeneID: 856504 | 85, 86 | P38715 | 87 |
| | Xylitol + NAD+ <=> D-xylulose + NADH | GeneID: 4852013 | 88, 89 | P22144 | 90 |
| | Xylitol + NAD+ <=> D-xylulose + NADH | ENA Nr.: AF428150.1 | 91 | Q876R2 | 92 |
| | D-xylopyranose <=> D-xylulose | ENA Nr.: CAB76571.1 | 93, 94 | Q9P8C9 | 95 |
| Glycolaldehyde reductases that may be used in all MEG pathways | | | | | |
| | glycolaldehyde + NAD(P)H <=> monoethylene glycol + NAD(P)+ | GeneID: 12933659 | 12 | P0A9S5 | 13 |
| | glycolaldehyde + NAD(P)H <=> monoethylene glycol + NAD(P)+ | GeneID: 854014 | 14 | Q12068 | 15 |
| | glycolaldehyde + NAD(P)H <=> monoethylene glycol + NAD(P)+ | GeneID: 856504 | 16 | P38715 | 17 |
| | glycolaldehyde + NAD(P)H <=> monoethylene glycol + NAD(P)+ | GeneID: 947493 | 18, 19 | Modified version of Q46856; G149E | 20 |

TABLE 1-continued

| | | | | |
|---|---|---|---|---|
| glycolaldehyde + NAD(P)H <=> monoethylene glycol + NAD(P)+ | GeneID: 947493 | 21, 22 | Q46856 | 23 |
| glycolaldehyde + NAD(P)H <=> monoethylene glycol + NAD(P)+ | GeneID: 12930149 | 24 | P77256 | 25 |
| glycolaldehyde + NAD(P)H <=> monoethylene glycol + NAD(P)+ | GeneID: 947273 | 26, 27 | P0A9S1 | 28 |
| glycolaldehyde + NAD(P)H <=> monoethylene glycol + NAD(P)+ | 545778205 | 29 | P30863 | 30 |
| glycolaldehyde + NAD(P)H <=> monoethylene glycol + NAD(P)+ | GeneID: 947495 | 31 | Q46857 | 32 |

Enzymes that may be used in D-ribulose-1-phosphate pathway to MEG

| | | | | |
|---|---|---|---|---|
| D-xylulose <=> D-ribulose | ENA Nr.: BAA24429.1 | 1, 2 | O50580 | 3 |
| D-xylulose <=> D-ribulose | ENA Nr.: FJ851309.1 | 4 | C1KKR1 | 5 |
| D-ribulose + ATP <=> D-ribulose-1-phosphate + ADP | GeneID: 946022 | 6, 7 | P11553 | 8 |
| D-ribulose-1-phosphate <=> glyceraldehyde + dihydroxyacetonephosphate | GeneID: 947282 | 9, 10 | P0AB87 | 11 |

Enzymes that may be used in D-xylulose-1-phosphate pathway to MEG

| | | | | |
|---|---|---|---|---|
| D-xylulose + ATP <=> D-xylulose-1-phosphate + ADP | GenBank: CR456801.1 | 53, 54 | P50053 | 55 |
| D-xylulose-1-phosphate <=> glyceraldehyde + dihydroxyacetonephosphate | CCDS6756.1 | 56, 57 | P05062 | 58 |

Enzymes that may be used in xylonate pathway to MEG

| | | | | |
|---|---|---|---|---|
| D-xylose + NAD+ <=> D-xylonolactone + NADH, or D-xylose + NAD+ <=> D-xylonate + NADH | GeneID: 7329904 | 59, 60 | B8H1Z0 | 61 |
| D-xylose + NADP+ <=> D-xylonolactone + NADPH, or D-xylose + NADP+ <=> D-xylonate + NADPH | GeneID: 8919161 | 62 | D4GP29 | 63 |
| D-xylose + NADP+ <=> D-xylonolactone + NADPH, or D-xylose + NADP+ <=> D-xylonate + NADPH | ENA Nr.: EF136590.1 | 64 | A0A024SMV2 | 65 |
| D-xylonolactone + H2O <=> D-xylonate | GeneID: 7329903 | 66 | A0A0H3C6P8 | 67 |
| D-xylonate <=> 2-keto-3-deoxy-xylonate + H2O | GeneID: 7329902 | 68 | A0A0H3C6H6 | 69 |
| D-xylonate <=> 2-keto-3-deoxy-xylonate + H2O | GeneID: 946829 | 70, 71 | P39358 | 72 |
| D-xylonate <=> 2-keto-3-deoxy-xylonate + H2O | GeneID: 944928 | 73, 74 | P77596 | 75 |
| 2-keto-3-deoxy-xylonate <=> glycolaldehyde + pyruvate | GeneID: 948825 | 76, 77 | P39359 | 78 |
| 2-keto-3-deoxy-xylonate <=> glycolaldehyde + pyruvate | GeneID: 944925 | 79, 80 | P75682 | 81 |

Enzymes that may be used in pathway to produce one or more three-carbon compounds

| | | | | |
|---|---|---|---|---|
| 2 acetyl-Coa -> acetoacetyl-CoA + CoA | 3309200 | 33, 34 | P45359 | 35 |
| 2 acetyl-Coa -> acetoacetyl-CoA + CoA | GeneID: 946727 | 36 | P76461 | 37 |
| 2 acetyl-Coa -> acetoacetyl-CoA + CoA | 856079 | 38 | P41338 | 39 |

TABLE 1-continued

| | | | | |
|---|---|---|---|---|
| acetoacetyl-CoA + acetate -> acetoacetate + acetyl-CoA | 48994873 | 41, 42 | P76459 | 43 |
| acetoacetyl-CoA + acetate -> acetoacetate + acetyl-CoA | 48994873 | 44, 45 | P76458 | 46 |
| acetoacetate -> acetone + CO2 | 6466901 | 47, 48 | P23670 | 49 |
| acetoacetate -> acetone + CO2 | 149901357 | 50, 51 | A6M020 | 52 |
| acetone + NAD(P)H -> 2-propanol + NAD(P)+ | 60592972 | 104, 105 | P25984 | 106 |
| acetone + NAD(P)H -> 2-propanol + NAD(P)+ | 308066805 | 107 | C6PZV5 | 108 |
| NADH + NADP+ <--> NAD+ + NADPH | GeneID: 948461 | 109 | P27306 | 110 |
| Hydrolases that may be used in pathway to produce one or more three-carbon compounds | | | | |
| Acetoacetyl-CoA + H(2)O <=> CoA + acetoacetate | NCBI-GeneID: 1116168 | 96 | P33752 | 97 |
| Acetoacetyl-CoA + H(2)O <=> CoA + acetoacetate | NCBI-GeneID: 1116169 | 98 | P23673 | 99 |
| Acetoacetyl-CoA + H(2)O <=> CoA + acetoacetate | GeneID: 946719 | 100 | P76459 | 101 |
| Acetoacetyl-CoA + H(2)O <=> CoA + acetoacetate | GeneID: 947525 | 102 | P76458 | 103 |

D-Tagatose 3-Epimerase (EC 5.1.3.31)

The present disclosure describes enzymes that can catalyze the epimerization of various ketoses at the C-3 position, interconverting D-fructose and D-psicose, D-tagatose and D-sorbose, D-ribulose and D-xylulose, and L-ribulose and L-xylulose. The specificity depends on the species. The enzymes from *Pseudomonas cichorii* and *Rhodobacter sphaeroides* require $Mn^{2+}$. In one embodiment, the enzyme is D-tagatose 3-epimerase (dte). In another embodiment, the D-tagatose 3-epimerase catalyzes the conversion of D-xylulose to D-ribulose.

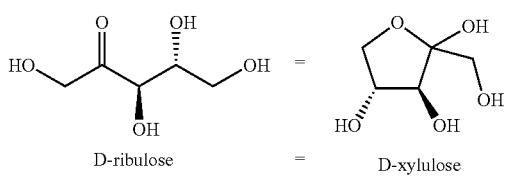 [SMILES: O=C(CO)[C@H](O)[C@H](O)CO ; OCC1(O)OC[C@@H](O)[C@@H]1O]
D-ribulose

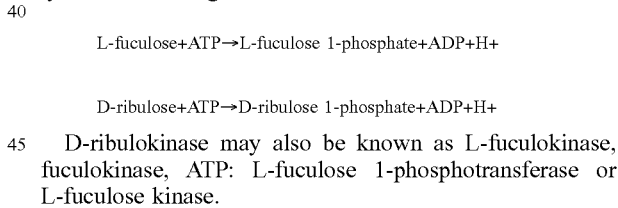
D-xylulose

In some embodiments, the D-tagatose 3-epimerase is from *Pseudomonas* spp. In another embodiment, the D-tagatose 3-epimerase is from *Pseudomonas cichorii*. In another embodiment, the D-tagatose 3-epimerase is from *Pseudomonas* sp. ST-24. In another embodiment, the D-tagatose 3-epimerase is from *Mesorhizobium loti*. In another embodiment, the D-tagatose 3-epimerase is from *Rhodobacter sphaeroides* (C1KKR1).

In one embodiment, the D-tagatose 3-epimerase is encoded by one or more nucleic acid molecules obtained from a microorganism selected from the group consisting of *Pseudomonas* sp., *Mesorhizobium* sp. and *Rhodobacter* sp. In some embodiments, the D-tagatose 3-epimerase is encoded by one or more nucleic acid molecules obtained from a microorganism selected from the group consisting of *Pseudomonas cichorii*, *Pseudomonas* sp. ST-24, *Mesorhizobium loti* and *Rhodobacter sphaeroides*. In some embodiments, the one or more nucleic acid molecules is dte and/or FJ851309.1, or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

D-tagatose 3-epimerase may also be known as L-ribulose 3-epimerase or ketose 3-epimerase.

D-Ribulokinase (EC 2.7.1.16)

The present disclosure describes enzymes that can catalyze the following reactions:

L-fuculose+ATP→L-fuculose 1-phosphate+ADP+H+

D-ribulose+ATP→D-ribulose 1-phosphate+ADP+H+

D-ribulokinase may also be known as L-fuculokinase, fuculokinase, ATP: L-fuculose 1-phosphotransferase or L-fuculose kinase.

Thus, in some embodiments, the disclosure provides for an enzyme that plays roles in the fucose degradation pathway, the super pathway of fucose and rhamnose degradation and/or the D-arabinose degradation I pathway.

In some embodiments, the enzyme can function as both an L-fucolokinase and a D-ribulokinase, the second enzyme of the L-fucose and D-arabinose degradation pathways, respectively.

In particular embodiments, the enzyme converts D-ribulose to D-ribulose-1-phosphate. In some embodiments, the D-ribulokinase is from *Escherichia coli*. In some embodiments, the D-ribulokinase is encoded by the fucK gene. In one embodiment, the D-ribulokinase is encoded by one or more nucleic acid molecules obtained from *E. coli*. In some embodiments, the one or more nucleic acid molecules is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

D-Ribulose-1-Phosphate Aldolase (EC 4.1.2.17)

The present disclosure describes enzymes that can catalyze the following reversible reactions:

L-fuculose 1-phosphate⇌(S)-lactaldehyde+dihydroxy acetone phosphate (DHAP)

D-ribulose 1-phosphate⇌glycolaldehyde+dihydroxy acetone phosphate (DHAP)

D-ribulose-1-phosphate aldolase may also be known as L-fuculose-phosphate aldolase, L-fuculose 1-phosphate aldolase or L-fuculose-1-phosphate (S)-lactaldehyde-lyase.

Thus, in some embodiments, the disclosure provides for an enzyme that plays roles in the fucose degradation pathway, the super pathway of fucose and rhamnose degradation and/or the D-arabinose degradation I pathway. In one embodiment, the enzyme may use $Zn^{2+}$ as a cofactor. In another embodiment, an inhibitor of this enzyme may be phosphoglycolohydroxamate.

In some embodiments, the enzyme can function as both an L-fuculose-phosphate aldolase and a D-ribulose-phosphate aldolase, the third enzyme of the L-fucose and D-arabinose degradation pathways, respectively.

The substrate specificity of the enzyme has been tested with a partially purified preparation from an E. coli strain.

Crystal structures of the enzyme and a number of point mutants have been solved. The combination of structural data and enzymatic activity of mutants allowed modelling and refinement of the catalytic mechanism of the enzyme. The enantiomeric selectivity of the enzyme has been studied.

In particular embodiments, the enzyme converts D-ribulose-1-phosphate to glycolaldehyde and DHAP. In some embodiments, the D-ribulose-1-phosphate aldolase is from Escherichia coli. In some embodiments, the D-ribulose-1-phosphate aldolase is encoded by the fucA gene. In one embodiment, the D-ribulose-1-phosphate aldolase is encoded by one or more nucleic acid molecules obtained from E. coli. In some embodiments, the one or more nucleic acid molecules is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

Glycolaldehyde Reductase (EC 1.1.1.77)

The present disclosure describes enzymes that can catalyze the following reversible reactions:

ethylene glycol+NAD+⇌glycolaldehyde+NADH+H+

(S)-propane-1,2-diol+NAD+⇌(S)-lactaldehyde+NADH+H+

Glycolaldehyde reductase may also be known as lactaldehyde reductase, propanediol oxidoreductase, (R) [or(S)]-propane-1,2-diol:NAD+ oxidoreductase or L-1,2-propanediol oxidoreductase.

Thus, in some embodiments, the disclosure provides for an enzyme that plays roles in the ethylene glycol degradation pathway, the super pathway of glycol metabolism and degradation, the anaerobic L-lactaldehyde degradation pathway and/or the super pathway of fucose and rhamnose degradation. In one embodiment, the enzyme may use $Fe^{2+}$ as a cofactor.

L-1,2-propanediol oxidoreductase is an iron-dependent group III dehydrogenase. It anaerobically reduces L-lactaldehyde, a product of both the L-fucose and L-rhamnose catabolic pathways, to L-1,2-propanediol, which is then excreted from the cell.

Crystal structures of the enzyme have been solved, showing a domain-swapped dimer in which the metal, cofactor and substrate binding sites could be located. An aspartate and three conserved histidine residues are required for $Fe^{2+}$ binding and enzymatic activity.

In vitro, the enzyme can be reactivated by high concentrations of NAD+ and efficiently inactivated by a mixture of $Fe^{3+}$ and ascorbate or $Fe^{2+}$ and $H_2O_2$. Metal-catalyzed oxidation of the conserved His277 residue is proposed to be the cause of the inactivation.

Expression of FucO enables engineered one-turn reversal of the β-oxidation cycle. FucO activity contributes to the conversion of isobutyraldehyde to isobutanol in an engineered strain.

In particular embodiments, the enzyme converts glycolaldehyde to MEG. In some embodiments, the glycolaldehyde reductase is from Escherichia coli. In some embodiments, the glycolaldehyde reductase is encoded by the fucO gene. In one embodiment, the glycolaldehyde reductase is encoded by one or more nucleic acid molecules obtained from a microorganism selected from E. coli and S. cerevisiae. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

Aldehyde Reductases

A number of aldehyde reductases may be used to convert glycolaldehyde to MEG.

An NADPH-dependent aldehyde reductase (YqhD) can catalyze the following reactions:

acetol+NADP+⇌methylglyoxal+NADPH+H+(reversible, EC 1.1.1.-)

an alcohol+NADP+⇌an aldehyde+NADPH+H+(reversibility unspecified, EC 1.1.1.2)

an aldehyde+NADP++$H_2O$→a carboxylate+NADPH+2 H+(EC 1.2.1.4)

1,3-propanediol+NADP+⇌3-hydroxypropionaldehyde+NADPH+H+(reversibility unspecified, EC 1.1.1.-)

D-3,4-dihydroxybutanal+NADPH⇌1,3,4-butanetriol+NADP+(reversibility unspecified)

YqhD is an NADPH-dependent aldehyde reductase that may be involved in glyoxal detoxification and/or be part of a glutathione-independent response to lipid peroxidation.

It has been reported that various alcohols, aldehydes, amino acids, sugars and α-hydroxy acids have been tested as substrates for YqhD. The purified protein only shows NADP-dependent alcohol dehydrogenase activity, with a preference for alcohols longer than C(3), but with Km values in the millimolar range, suggesting that they are not the physiological substrates. In contrast, YqhD does exhibit short-chain aldehyde reductase activity with substrates such as propanaldehyde, acetaldehyde, and butanaldehyde, as well as acrolein and malondialdehyde. In a metabolically engineered strain, phenylacetaldehyde and 4-hydroxyphenylacetaldehyde are reduced to 2-phenylethanol and 2-(4-hydroxyphenyl)ethanol by the endogenous aldehyde reductases YqhD, YjgB, and YahK.

Overexpression of YqhD increases 1,3-propanediol oxidoreductase activity of the cell. *E. coli* has been engineered to express YqhD for the industrial production of 1,3-propanediol. YqhD activity contributes to the production of isobutanol, 1,2-propanediol, 1,2,4-butanetriol and acetol as well. Mutation of yqhD enables production of butanol by an engineered one-turn reversal of the β-oxidation cycle.

YqhD has furfural reductase activity, which appears to cause growth inhibition due to depletion of NADPH in metabolically engineered strains that produce alcohol from lignocellulosic biomass.

The crystal structure of YqhD has been solved at 2 Å resolution. YqhD is an asymmetric dimer of dimers, and the active site contains a $Zn^{2+}$ ion. The NADPH cofactor is modified by hydroxyl groups at positions 5 and 6 in the nicotinamide ring.

Overexpression of yqhD leads to increased resistance to reactive oxygen-generating compounds such as hydrogen peroxide, paraquat, chromate and potassium tellurite. A yqhD deletion mutant shows increased sensitivity to these compounds and to glyoxal, and contains increased levels of reactive aldehydes that are generated during lipid peroxidation. Conversely, yqhD deletion leads to increased furfural tolerance.

In particular embodiments, an NADPH-dependent aldehyde reductase converts glycolaldehyde to MEG. In some embodiments, the NADPH-dependent aldehyde reductase is from *Escherichia coli*. In some embodiments, the NADPH-dependent aldehyde reductase is encoded by the yqhD gene.

A multi-functional methylglyoxal reductase (DkgA) can catalyze the following reactions:

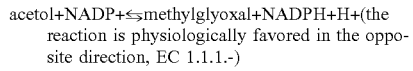
acetol+NADP+⇌methylglyoxal+NADPH+H+(the reaction is physiologically favored in the opposite direction, EC 1.1.1.-)

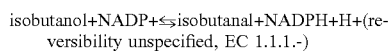
isobutanol+NADP+⇌isobutanal+NADPH+H+(reversibility unspecified, EC 1.1.1.-)

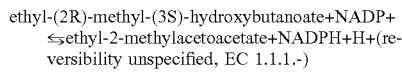
ethyl-(2R)-methyl-(3S)-hydroxybutanoate+NADP+⇌ethyl-2-methylacetoacetate+NADPH+H+(reversibility unspecified, EC 1.1.1.-)

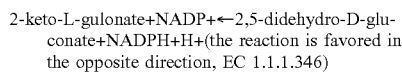
2-keto-L-gulonate+NADP+←2,5-didehydro-D-gluconate+NADPH+H+(the reaction is favored in the opposite direction, EC 1.1.1.346)

DkgA (YqhE) belongs to the aldo-keto reductase (AKR) family and has been shown to have methylglyoxal reductase and beta-keto ester reductase activity.

dkgA is reported to encode a 2,5-diketo-D-gluconate reductase (25DKGR) A, one of two 25DKG reductases in *E. coli*. The enzyme uses NADPH as the preferred electron donor and is thought to be involved in ketogluconate metabolism. The specific activity of the enzyme towards 2,5-diketo-D-gluconate is reported to be almost 1000-fold lower than its activity towards methylglyoxal.

Due to its low Km for NADPH, reduction of furans by DkgA may deplete NADPH pools and thereby limit cellular biosynthesis. A broad survey of aldehyde reductases showed that DkgA was one of several endogenous aldehyde reductases that contribute to the degradation of desired aldehyde end products of metabolic engineering.

A crystal structure of DkgA has been solved at 2.16 Å resolution.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgA gene.

A multi-functional methylglyoxal reductase (DkgB) can catalyze the following reactions:

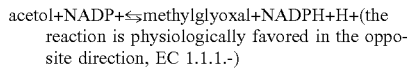
acetol+NADP+⇌methylglyoxal+NADPH+H+(the reaction is physiologically favored in the opposite direction, EC 1.1.1.-)

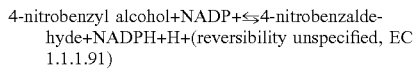
4-nitrobenzyl alcohol+NADP+⇌4-nitrobenzaldehyde+NADPH+H+(reversibility unspecified, EC 1.1.1.91)

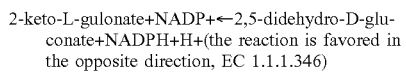
2-keto-L-gulonate+NADP+←2,5-didehydro-D-gluconate+NADPH+H+(the reaction is favored in the opposite direction, EC 1.1.1.346)

DkgB (YafB) is a member of the aldo-keto reductase (AKR) subfamily 3F. DkgB was shown to have 2,5-diketo-D-gluconate reductase, methylglyoxal reductase and 4-nitrobenzaldehyde reductase activities.

dkgB is reported to encode 2,5-diketo-D-gluconate reductase (25DKGR) B, one of two 25DKG reductases in *E. coli*. The enzyme uses NADPH as the preferred electron donor and is thought to be involved in ketogluconate metabolism. However, the specific activity of the enzyme towards 2,5-diketo-D-gluconate is reported to be almost 1000-fold lower than its activity towards methylglyoxal.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgB gene.

A methylglyoxal reductase (YeaE) can catalyze the following reaction:

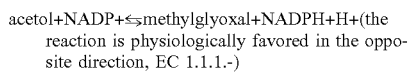
acetol+NADP+⇌methylglyoxal+NADPH+H+(the reaction is physiologically favored in the opposite direction, EC 1.1.1.-)

YeaE has been shown to have methylglyoxal reductase activity.

The subunit structure of YeaE has not been determined, but its amino acid sequence similarity to the aldo-keto reductases DkgA (YqhE) and DkgB (YafB) suggests that it may be monomeric.

In particular embodiments, a methylglyoxal reductase converts glycolaldehyde to MEG. In some embodiments, the methylglyoxal reductase is from *Escherichia coli*. In some embodiments, the methylglyoxal reductase is encoded by the yeaE gene.

A L-glyceraldehyde 3-phosphate reductase (yghZ) can catalyze the following reactions:

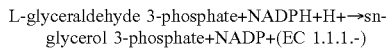
L-glyceraldehyde 3-phosphate+NADPH+H+→sn-glycerol 3-phosphate+NADP+(EC 1.1.1.-)

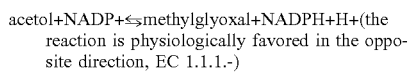
acetol+NADP+⇌methylglyoxal+NADPH+H+(the reaction is physiologically favored in the opposite direction, EC 1.1.1.-)

YghZ is an L-glyceraldehyde 3-phosphate (L-GAP) reductase. The enzyme is also able to detoxify methylglyoxal at a low rate. YghZ defines the AKR14 (aldo-keto reductase 14) protein family.

L-GAP is not a natural metabolite and is toxic to *E. coli*. L-GAP is a substrate of both the glycerol-3-phosphate and hexose phosphate transport systems of *E. coli* K-12. It has been postulated that the physiological role of YghZ is the detoxification of L-GAP, which may be formed by non-enzymatic racemization of GAP or by an unknown cellular process.

The crystal structure of the *E. coli* enzyme has been determined and is suggested to be a tetramer. However, others have found that the protein forms an octamer based on gel filtration and electron microscopy studies.

In particular embodiments, a L-glyceraldehyde 3-phosphate reductase converts glycolaldehyde to MEG. In some embodiments, the L-glyceraldehyde 3-phosphate reductase is from *Escherichia coli*. In some embodiments, the L-glyceraldehyde 3-phosphate reductase is encoded by the yghZ gene.

An L-1,2-propanediol dehydrogenase/glycerol dehydrogenase (GldA) can catalyze the following reactions:

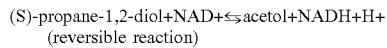
(S)-propane-1,2-diol+NAD+⇌acetol+NADH+H+ (reversible reaction)

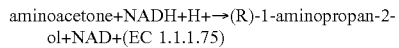
aminoacetone+NADH+H+→(R)-1-aminopropan-2-ol+NAD+ (EC 1.1.1.75)

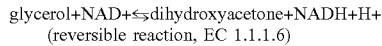
glycerol+NAD+⇌dihydroxyacetone+NADH+H+ (reversible reaction, EC 1.1.1.6)

The physiological function of the GldA enzyme has long been unclear. The enzyme was independently isolated as a glycerol dehydrogenase and a D-1-amino-2-propanol: NAD+ oxidoreductase. At that time, D-1-amino-2-propanol was thought to be an intermediate for the biosynthesis of vitamin B12, and although *E. coli* is unable to synthesize vitamin B12 de novo, enzymes catalyzing the synthesis of this compound were sought. It was later found that GldA was responsible for both activities.

The primary in vivo role of GldA was recently proposed to be the removal of dihydroxyacetone by converting it to glycerol. However, a dual role in the fermentation of glycerol has also recently been established. Glycerol dissimilation in *E. coli* can be accomplished by two different pathways. The glycerol and glycerophosphodiester degradation pathway requires the presence of a terminal electron acceptor and utilizes an ATP-dependent kinase of the Glp system, which phosphorylates glycerol to glycerol-3-phosphate. However, upon inactivation of the kinase and selection for growth on glycerol, it was found that an NAD+-linked dehydrogenase, GldA, was able to support glycerol fermentation. Recently, it was shown that GldA was involved in glycerol fermentation both as a glycerol dehydrogenase, producing dihydroxyacetone, and as a 1,2-propanediol dehydrogenase, regenerating NAD+ by producing 1,2-propanediol from acetol.

The enzyme is found in two catalytically active forms, a large form of eight subunits and a small form of two subunits. The large form appears to be the major species.

In particular embodiments, an L-1,2-propanediol dehydrogenase/glycerol dehydrogenase converts glycolaldehyde to MEG. In some embodiments, the L-1,2-propanediol dehydrogenase/glycerol dehydrogenase is from *Escherichia coli*. In some embodiments, the L-1,2-propanediol dehydrogenase/glycerol dehydrogenase is encoded by the gldA gene.

An NADPH-dependent methylglyoxal reductase (GRE2) from *Saccharomyces cerevisiae* can catalyze the following reactions:

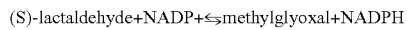
(S)-lactaldehyde+NADP+⇌methylglyoxal+NADPH

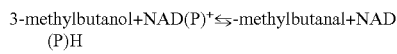
3-methylbutanol+NAD(P)+⇌-methylbutanal+NAD(P)H

Gre2 is a versatile enzyme that catalyzes the stereoselective reduction of a broad range of substrates including aliphatic and aromatic ketones, diketones, as well as aldehydes, using NADPH as the cofactor.

The crystal structures of Gre2 from *S. cerevisiae* in an apo-form at 2.00 Å and NADPH-complexed form at 2.40 Å resolution have been solved. Gre2 forms a homodimer, each subunit of which contains an N-terminal Rossmann-fold domain and a variable C-terminal domain, which participates in substrate recognition. The induced fit upon binding to the cofactor NADPH makes the two domains shift toward each other, producing an interdomain cleft that better fits the substrate. Computational simulation combined with site-directed mutagenesis and enzymatic activity analysis enabled characterization of a potential substrate-binding pocket that determines the stringent substrate stereoselectivity for catalysis.

Gre2 catalyzes the irreversible reduction of the cytotoxic compound methylglyoxal (MG) to (S)-lactaldehyde as an alternative to detoxification of MG by glyoxalase I GLO1. MG is synthesized via a bypath of glycolysis from dihydroxyacetone phosphate and is believed to play a role in cell cycle regulation and stress adaptation. GRE2 also catalyzes the reduction of isovaleraldehyde to isoamylalcohol. The enzyme serves to suppress isoamylalcohol-induced filamentation by modulating the levels of isovaleraldehyde, the signal to which cells respond by filamentation. GRE2 is also involved in ergosterol metabolism.

In particular embodiments, an NADPH-dependent methylglyoxal reductase converts glycolaldehyde to MEG. In some embodiments, the NADPH-dependent methylglyoxal reductase is from *S. cerevisiae*. In some embodiments, the NADPH-dependent methylglyoxal reductase is encoded by the GRE2 gene.

Thiolase/Acetyl Coenzyme A Acetyltransferase (EC 2.3.1.9)

The present disclosure describes enzymes that can catalyze the following reaction:

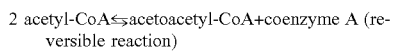
2 acetyl-CoA⇌acetoacetyl-CoA+coenzyme A (reversible reaction)

Thiolase/Acetyl coenzyme A acetyltransferase may also be known as acetyl-CoA-C-acetyltransferase, acetoacetyl-CoA thiolase, acetyl-CoA:acetyl-CoA C-acetyltransferase or thiolase II.

Thus, in some embodiments, the disclosure provides for an enzyme that plays a role in acetoacetate degradation (to acetyl CoA). In one embodiment, an inhibitor of this enzyme may be acetoacetyl-CoA.

In particular embodiments, the enzyme converts acetyl-CoA to acetoacetyl-CoA. In some embodiments, the thiolase/acetyl coenzyme A acetyltransferase is from *Clostridium* spp. In some embodiments, the thiolase/acetyl coenzyme A acetyltransferase is from *Clostridium acetobutylicum*. In some embodiments, the thiolase/acetyl coenzyme A acetyltransferase is from *Clostridium thermosaccharolyticum*. In some embodiments, the thiolase/acetyl coenzyme A acetyltransferase is from *Bacillus cereus*. In some embodiments, the thiolase/acetyl coenzyme A acetyltransferase is from *Marinobacter hydrocarbonoclasticus* ATCC 49840. In some embodiments, the thiolase/acetyl coenzyme A acetyltransferase is encoded by the thlA gene. In some embodiments, the thiolase/acetyl coenzyme A acetyltransferase is from *Escherichia coli*. In some embodiments, the thiolase/acetyl coenzyme A acetyltransferase is encoded by the atoB gene.

In one embodiment, the thiolase or acetyl coenzyme A acetyltransferase is encoded by one or more nucleic acid molecules obtained from a microorganism selected from the group consisting of *Clostridium* sp., *Bacillus* sp., *E. coli*, *Saccharomyces* sp. and *Marinobacter* sp. In some embodiments, the thiolase or acetyl coenzyme A acetyltransferase is encoded by one or more nucleic acid molecules obtained from a microorganism selected from the group consisting of *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the one or more nucleic acid molecules is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

Acetate:Acetoacetyl-CoA Transferase (EC 2.8.3.-)

The present disclosure describes enzymes that can catalyze the following reaction:

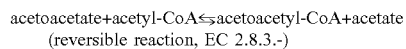
(reversible reaction, EC 2.8.3.-)

Acetate:Acetoacetyl-CoA transferase may also be known as acetoacetyl-CoA transferase or acetyl-CoA:acetoacetate-CoA transferase.

Thus, in some embodiments, the disclosure provides for an enzyme that plays a role in acetoacetate degradation (to acetyl CoA). In one embodiment, inhibitors of this enzyme may include acetyl-CoA and coenzyme A.

The growth of *E. coli* on short-chain fatty acids (C3-C6) requires the activation of the acids to their respective thioesters. This activation is catalyzed by acetoacetyl-CoA transferase. The reaction takes place in two half-reactions which involves a covalent enzyme-CoA. The enzyme undergoes two detectable conformational changes during the reaction. It is thought likely that the reaction proceeds by a ping-pong mechanism. The enzyme can utilize a variety of short-chain acyl-CoA and carboxylic acid substrates but exhibits maximal activity with normal and 3-keto substrates.

In particular embodiments, the enzyme converts acetoacetyl-CoA to acetoacetate. In some embodiments, the acetate:acetoacetyl-CoA transferase is from *Clostridium* spp. In some embodiments, the acetate:acetoacetyl-CoA transferase is from *Clostridium acetobutylicum*. In some embodiments, the acetate:acetoacetyl-CoA transferase is from *Escherichia coli*. In some embodiments, the acetate:acetoacetyl-CoA transferase is encoded by the atoA and atoD genes. In another embodiment, the subunit composition of acetoacetyl-CoA transferase is [(AtoA)₂][(AtoD)₂], with (AtoA)₂ being the β complex and (AtoD)₂ being the α complex. In one embodiment, the acetate:acetoacetyl-CoA transferase is a fused acetate:acetoacetyl-CoA transferase: α subunit/β subunit. In another embodiment, the acetate:acetoacetyl-CoA transferase is encoded by the ydiF gene.

Acetate:Acetoacetyl-CoA Hydrolase (EC 3.1.2.11)

The present disclosure describes enzymes that can catalyze the following reaction:

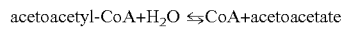

Acetoacetyl-CoA hydrolase may also be known as acetoacetyl coenzyme A hydrolase, acetoacetyl CoA deacylase or acetoacetyl coenzyme A deacylase.

This enzyme belongs to the family of hydrolases, specifically those acting on thioester bonds.

In particular embodiments, the enzyme converts acetoacetyl-CoA to acetoacetate. In some embodiments, the acetate:acetoacetyl-CoA hydrolase is from *Clostridium* spp. In some embodiments, the acetate:acetoacetyl-CoA hydrolase is from *Clostridium acetobutylicum*. In another embodiment, the Acetoacetyl-CoA hydrolase is encoded by the ctfA (subunit A) and/or ctfB (subunit B) genes.

In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

Acetoacetate Decarboxylase (EC 4.1.1.4)

The present disclosure describes enzymes that can catalyze the following reaction:

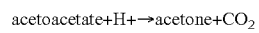

Acetoacetate decarboxylase may also be known as ADC, AADC or acetoacetate carboxy-lyase.

Thus, in some embodiments, the disclosure provides for an enzyme that plays roles in isopropanol biosynthesis, pyruvate fermentation to acetone, the super pathway of *Clostridium acetobutylicum* acidogenic and solventogenic fermentation and/or the super pathway of *Clostridium acetobutylicum* solventogenic fermentation.

Acetoacetate decarboxylase (ADC) plays a key role in solvent production in *Clostridium acetobutylicum*. During the acidogenic phase of growth, acids accumulate causing a metabolic shift to solvent production. In this phase acids are re-assimilated and metabolized to produce acetone, butanol and ethanol.

Preliminary purification and crystallization of the enzyme has revealed that a lysine residue is implicated in the active site. The enzyme is a large complex composed of 12 copies of a single type of subunit.

The enzyme of *Clostridium acetobutylicum* ATCC 824 has been purified and the adc gene encoding it cloned. The enzyme has also been purified from the related strain *Clostridium acetobutylicum* DSM 792 and the gene cloned and sequenced. The decarboxylation reaction proceeds by the formation of a Schiff base intermediate.

ADC is a key enzyme in acid uptake, effectively pulling the CoA-transferase reaction in the direction of acetoacetate formation.

In particular embodiments, the enzyme converts acetoacetate to acetone. In some embodiments, the acetoacetate decarboxylase is from *Clostridium* spp. In some embodiments, the acetoacetate decarboxylase is from *Clostridium acetobutylicum*. In some embodiments, the acetoacetate decarboxylase is from *Clostridium beijerinckii*. In some embodiments, the acetoacetate decarboxylase is from *Clostridium cellulolyticum*. In some embodiments, the acetoacetate decarboxylase is from *Bacillus polymyxa*. In some embodiments, the acetoacetate decarboxylase is from *Chromobacterium violaceum*. In some embodiments, the acetoacetate decarboxylase is from *Pseudomonas putida*. In another embodiment, the acetoacetate decarboxylase is encoded by the adc gene.

In one embodiment, the acetoacetate decarboxylase is encoded by one or more nucleic acid molecules obtained from a microorganism selected from the group consisting of *Clostridium* sp., *Bacillus* sp., *Chromobacterium* sp. and *Pseudomonas* sp. In another embodiment, the acetoacetate decarboxylase is encoded by one or more nucleic acid molecules obtained from a microorganism selected from the group consisting of *Clostridium acetobutylicum*,

*Clostridium beijerinckii, Clostridium cellulolyticum, Bacillus polymyxa, Chromobacterium violaceum* and *Pseudomonas putida*. In some embodiments, the one or more nucleic acid molecules encoding the acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

Alcohol Dehydrogenase (EC 1.1.1.-)

The present disclosure describes enzymes that can catalyze the reversible oxidation of primary or secondary alcohols to aldehydes or ketones, respectively. In one embodiment, the enzyme is a secondary alcohol dehydrogenase (S-ADH) and catalyzes the reduction of ketones such as acetone into secondary alcohols such as 2-propanol (isopropanol).

In some embodiments the S-ADH is from *Burkholderia* sp. In some embodiments, the S-ADH is from *Burkholderia* sp. AIU 652. In some embodiments, the S-ADH is from *Alcaligenes* sp. In some embodiments, the S-ADH is from *Alcaligenes eutrophus*. In some embodiments, the S-ADH is from *Clostridium* sp. In some embodiments, the S-ADH is from *Clostridium ragsdalei*. In some embodiments, the S-ADH is from *Clostridium beijerinckii*. In some embodiments, the S-ADH is from *Thermoanaerobacter* sp. In some embodiments, the S-ADH is from *Thermoanaerobacter brockii*. In some embodiments, the S-ADH is from *Thermoanaerobacter ethanolicus* (*Clostridium thermohydrosulfuricum*). In some embodiments, the S-ADH is encoded by the adhB gene. In some embodiments, the S-ADH is from the *trypanosomatid Phytomonas* sp. In some embodiments, the S-ADH is from *Rhodococcus* sp. In some embodiments, the S-ADH is from *Rhodococcus ruber*. In some embodiments, the S-ADH is from *Methanobacterium palustre*. In some embodiments, the S-ADH is from methanogenic archaea *Methanogenium* liminatans. In some embodiments, the S-ADH is from the parasitic protist *Entamoeba histolytica* (EhAdh1). In some embodiments, the S-ADH is from parasitic protozoan *Tritrichomonas foetus*. In some embodiments, the S-ADH is from human parasite *Trichomonas vaginalis*.

In some embodiments, the S-ADH is predicted from homology and can be from *Thermoanaerobacter mathranii, Micrococcus luteus, Nocardiopsis alba, Mycobacterium hassiacum, Helicobacter suis, Candida albicans, Candida parapsilosis, Candida orthopsilosis, Candida metapsilosis, Grosmannia clavigera* and *Scheffersomyces stipitis*.

In a further embodiment, the alcohol dehydrogenase comprises an amino acid sequence selected from the group consisting of SEQ ID NOs: 106 and 108. In yet another embodiment, the alcohol dehydrogenase is encoded by a nucleic acid sequence selected from the group consisting of SEQ ID NOs: 104, 105 and 107.

Dehydratase (EC 4.2.1.-)

The present disclosure describes enzymes that can catalyze the following reactions:

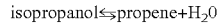

D-Xylulose 1-Kinase (EC 2.7.1.-)

The present disclosure describes enzymes that can catalyze the conversion of D-xylulose to D-xylulose-1-phosphate. In some embodiments, the conversion can be catalyzed by a human ketohexokinase C (khk-C), also known as fructokinase.

Ketohexokinase, or fructokinase, phosphorylates fructose to fructose-1-phosphate. The enzyme is involved in fructose metabolism, which is part of carbohydrate metabolism. It is found in the liver, intestine and kidney cortex.

In human liver, purified fructokinase, when coupled with aldolase, has been discovered to contribute to an alternative mechanism to produce oxalate from xylitol. In coupled sequence, fructokinase and aldolase produce glycolaldehyde, a precursor to oxalate, from D-xylulose via D-xylulose 1-phosphate.

In particular embodiments, the enzyme converts D-xylulose to D-xylulose-1-phosphate. In some embodiments, the D-xylulose 1-kinase is a ketohexokinase C. In some embodiments, the ketohexokinase C is from *Homo sapiens*. In some embodiments, the human ketohexokinase C is encoded by the khk-C gene.

In one embodiment, the D-xylulose 1-kinase is encoded by one or more nucleic acid molecules obtained from *Homo sapiens*. In some embodiments, the one or more nucleic acid molecules encoding the D-xylulose 1-kinase is ketohexokinase C (khk-C), or homolog thereof. In another embodiment, the one or more nucleic acid molecules encoding the D-xylulose 1-kinase comprises an amino acid sequence set forth in SEQ ID NO: 55. In a further embodiment, the one or more nucleic acid molecules encoding the D-xylulose 1-kinase is encoded by a nucleic acid sequence selected from the group consisting of SEQ ID NOs: 53 and 54.

D-Xylulose-1-Phosphate Aldolase (EC 4.1.2.-)

The present disclosure describes enzymes that can catalyze the conversion of D-xylulose-1-phosphate to glycolaldehyde and DHAP. In some embodiments, the conversion can be catalyzed by a human aldolase B, which is also known as fructose-bisphosphate aldolase B or liver-type aldolase.

Aldolase B is one of three isoenzymes (A, B, and C) of the class I fructose 1,6-bisphosphate aldolase enzyme (EC 4.1.2.13), and plays a key role in both glycolysis and gluconeogenesis. The generic fructose 1,6-bisphosphate aldolase enzyme catalyzes the reversible cleavage of fructose 1,6-bisphosphate (FBP) into glyceraldehyde 3-phosphate and dihydroxyacetone phosphate (DHAP) as well as the reversible cleavage of fructose 1-phosphate (F1P) into glyceraldehyde and dihydroxyacetone phosphate. In mammals, aldolase B is preferentially expressed in the liver, while aldolase A is expressed in muscle and erythrocytes and aldolase C is expressed in the brain. Slight differences in isozyme structure result in different activities for the two substrate molecules: FBP and fructose 1-phosphate. Aldolase B exhibits no preference and thus catalyzes both reactions, while aldolases A and C prefer FBP.

Aldolase B is a homotetrameric enzyme, composed of four subunits. Each subunit has a molecular weight of 36 kDa and contains an eight-stranded α/β barrel, which encloses lysine 229 (the Schiff-base forming amino acid that is key for catalysis).

In particular embodiments, the enzyme converts D-xylulose-1-phosphate to glycolaldehyde and DHAP. In some embodiments, the D-xylulose-1-phosphate aldolase is an aldolase B. In some embodiments, the aldolase B is from *Homo sapiens*. In some embodiments, the human aldolase B is encoded by the ALDOB gene.

In one embodiment, the D-xylulose-1-phosphate aldolase is encoded by one or more nucleic acid molecules obtained from *Homo sapiens*. In another embodiment, the one or more nucleic acid molecules encoding the D-xylulose-1-phosphate aldolase is aldolase B (ALDOB), or homolog thereof. In some embodiments, the one or more nucleic acid molecules encoding the D-xylulose-1-phosphate aldolase comprises an amino acid sequence set forth in SEQ ID NO: 58. In some embodiments, the one or more nucleic acid molecules encoding the D-xylulose-1-phosphate aldolase is encoded by a nucleic acid sequence selected from the group consisting of SEQ ID NOs: 56 and 57.

D-Xylose Isomerase (EC 5.3.1.5)

The present disclosure describes enzymes that can catalyze the following reversible reaction:

D-xylopyranose⇌D-xylulose

D-xylose isomerase may also be known as xylose isomerase or D-xylose ketol-isomerase.

Thus, in some embodiments, the disclosure provides for an enzyme that plays a role in xylose degradation.

Xylose isomerase catalyzes the first reaction in the catabolism of D-xylose.

Two conserved histidine residues, H101 and H271, were shown to be essential for catalytic activity. The fluorescence of two conserved tryptophan residues, W49 and W188, is quenched during binding of xylose, and W49 was shown to be essential for catalytic activity. The presence of $Mg^{2+}$, $Mn^{2+}$ or $Co^{2+}$ protects the enzyme from thermal denaturation.

The subunit composition has not been established experimentally.

In particular embodiments, the enzyme converts D-xylose to D-xylulose. In some embodiments, the D-xylose isomerase is from *Escherichia coli*. In some embodiments, the D-xylose isomerase is encoded by the xylA gene.

In some embodiments, a recombinant microorganism producing MEG and a three-carbon compound comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the recombinant microorganism comprises an endogenous or exogenous xylose isomerase that catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

D-Xylulose-5-Kinase/Xylulokinase

The present disclosure describes enzymes that can catalyze the following reactions:

D-xylulose+ATP→D-xylulose 5-phosphate+ADP+H+ (EC 2.7.1.17)

ATP+1-deoxy-D-xylulose→1-deoxy-D-xylulose 5-phosphate+ADP+H+(EC 2.7.1.-)

D-xylulose-5-kinase may also be known as xylulose kinase or xylulokinase.

Xylulokinase catalyzes the phosphorylation of D-xylulose, the second step in the xylose degradation pathway, producing D-xylulose-5-phosphate, an intermediate of the pentose phosphate pathway.

In the absence of substrate, xylulokinase has weak ATPase activity. Xylulokinase can also catalyze the phosphorylation of 1-deoxy-D-xylulose. This would allow a potential salvage pathway for generating 1-deoxy-D-xylulose 5-phosphate for use in the biosynthesis of terpenoids, thiamine and pyridoxal. The rate of phosphorylation of 1-deoxy-D-xylulose is 32-fold lower than the rate of phosphorylation of D-xylulose.

The kinetic mechanism of the bacterial enzyme has been studied, suggesting a predominantly ordered reaction mechanism. The enzyme undergoes significant conformational changes upon binding of the substrate and of ATP. Two conserved aspartate residues, D6 and D233, were found to be essential for catalytic activity, and a catalytic mechanism has been proposed.

Crystal structures of bacterial xylulokinase in the apo form and bound to D-xylulose have been determined at 2.7 and 2.1 Å resolution, respectively.

In particular embodiments, the enzyme converts D-xylulose to D-xylulose-5-phosphate. In some embodiments, the D-xylulose-5-kinase is from *Escherichia coli*. In some embodiments, the D-xylulose-5-kinase is encoded by the xylB gene. In some embodiments, the D-xylulose-5-kinase is from *Saccharomyces cerevisiae*. In some embodiments the D-xylulose-5-kinase is encoded by the XKS1 gene. In some embodiments, the D-xylulose-5-kinase is from *Pichia stipitis*. In some embodiments the D-xylulose-5-kinase is encoded by the XYL3 gene.

In some embodiments, a recombinant microorganism producing MEG and a three-carbon compound comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

Xylose Dehydrogenase (EC 1.1.1.175 or EC 1.1.1.179)

The present disclosure describes enzymes that can catalyze the following reactions:

aldehydo-D-xylose+NAD++$H_2O$→D-xylonate+ NADH+2 H+

α-D-xylopyranose+NAD+⇌D-xylonolactone+ NADH+H+(reversibility unspecified, EC 1.1.1.175)

Xylose dehydrogenase may also be known as D-xylose dehydrogenase, D-xylose 1-dehydrogenase, (NAD+)-linked D-xylose dehydrogenase, NAD+-D-xylose dehydrogenase, D-xylose: NAD+ 1-oxidoreductase D-Xylose dehydrogenase catalyzes the NAD+-dependent oxidation of D-xylose to D-xylonolactone. This is the first reaction in the oxidative, non-phosphorylative pathway for the degradation of D-xylose in *Caulobacter crescentus*. This pathway is similar to the pathway for L-arabinose degradation in *Azospirillum brasilense*. The amino acid sequence of the *C. crescentus* enzyme is unrelated to that of xylose dehydrogenase from the archaeon *Haloarcula marismortui*, or the L-arabinose 1-dehydrogenase of *Azospirillum brasilense*.

D-xylose is the preferred substrate for recombinant D-xylose dehydrogenase from *Caulobacter crescentus*. The enzyme can use L-arabinose, but it is a poorer substrate. The Km for L-arabinose is 166 mM. Other substrates such as D-arabinose, L-xylose, D-ribose, D-galactose, D-glucose and D-glucose-6-phosphate showed little or no activity in the assay, as measured by NADH production. *C. crescentus* D-xylose dehydrogenase can convert D-xylose to D-xylonate directly.

Partially purified, native D-xylose dehydrogenase from *C. crescentus* had a Km of 70 μM for D-xylose. This value was lower than the Km of 760 μM for the recombinant, His-tagged enzyme.

In some embodiments, the D-Xylose dehydrogenase is from the halophilic archaeon *Haloferax volcanii*. The *Haloferax volcanii* D-Xylose dehydrogenase catalyzes the first reaction in the oxidative xylose degradation pathway of the halophilic archaeon *Haloferax volcanii*. The *H. volcanii* D-Xylose dehydrogenase shows 59% amino acid sequence identity to a functionally characterized xylose dehydrogenase from *Haloarcula marismortui* and 56% identity to an ortholog in *Halorubrum lacusprofundi*, but is only 11% identical to the bacterial NAD+-dependent xylose dehydrogenase from *Caulobacter crescentus* CB15.

In particular embodiments, the enzyme converts D-xylose to D-xylonolactone. In some embodiments, the D-Xylose dehydrogenase is from *Caulobacter crescentus*. In some embodiments, the D-Xylose dehydrogenase is encoded by the xylB gene. In some embodiments, the D-Xylose dehydrogenase is from *Haloferax volcanii*. In some embodiments, the D-Xylose dehydrogenase is from *Haloarcula marismortui*. In some embodiments, the D-Xylose dehydrogenase is from *Halorubrum lacusprofundi*. In some embodiments, the D-Xylose dehydrogenase is encoded by the xdh gene.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

Xylonolactonase (3.1.1.68)

The present disclosure describes enzymes that can catalyze the following reaction:

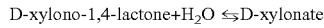

D-xylono-1,4-lactone+H₂O ⇌ D-xylonate

This enzyme belongs to the family of hydrolases, specifically those acting on carboxylic ester bonds. This enzyme participates in pentose and glucuronate interconversions.

Xylonolactonase may also be known as D-xylonolactonase, xylono-1,4-lactonase, xylono-gamma-lactonase or D-xylono-1,4-lactone lactonohydrolase.

In particular embodiments, the enzyme converts D-xylonolactone to D-xylonate. In some embodiments, the D-xylonolactonase is from *Haloferax* sp. In some embodiments, the D-xylonolactonase is from *Haloferax volcanii*. In some embodiments, the D-xylonolactonase is from *Haloferax gibbonsii*. In some embodiments, the D-xylonolactonase is from *Caulobacter crescentus*. In some embodiments, the D-xylonolactonase is encoded by the xylC gene.

In one embodiment, the xylonolactonase is encoded by one or more nucleic acid molecules obtained from a microorganism selected from *Caulobacter* sp. and *Haloferax* sp. In another embodiment, the xylonolactonase is encoded by one or more nucleic acid molecules obtained from a microorganism selected from the group consisting of *Caulobacter crescentus, Haloferax volcanii* and *Haloferax gibbonsii*. In some embodiments, the one or more nucleic acid molecules encoding the xylonolactonase is xylC, or homolog thereof. In a further embodiment, the one or more nucleic acid molecules encoding the xylonolactonase comprises an amino acid sequence set forth in SEQ ID NO: 67. In yet another embodiment, the one or more nucleic acid molecules encoding the xylonolactonase is encoded by a nucleic acid sequence set forth in SEQ ID NO: 66.

Xylonate Dehydratase (EC 4.2.1.82)

The present disclosure describes enzymes that can catalyze the following reaction:

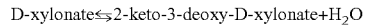

D-xylonate ⇌ 2-keto-3-deoxy-D-xylonate+H₂O

This enzyme belongs to the family of lyases, specifically the hydro-lyases, which cleave carbon-oxygen bonds. This enzyme participates in pentose and glucuronate interconversions.

Xylonate dehydratase may also be known as D-xylonate hydro-lyase, D-xylo-aldonate dehydratase or D-xylonate dehydratase.

In particular embodiments, the enzyme converts D-xylonate to 2-keto-3-deoxy-D-xylonate. In some embodiments, the xylonate dehydratase is from *Caulobacter crescentus*. In some embodiments, the xylonate dehydratase is encoded by the xylD gene. In some embodiments, the xylonate dehydratase is from *Escherichia coli*. In some embodiments, the xylonate dehydratase is encoded by the yjhG gene. In some embodiments, the xylonate dehydratase is encoded by the yagF gene. In some embodiments, the xylonate dehydratase is from *Haloferax volcanii*. In some embodiments, the xylonate dehydratase is encoded by the xad gene. In some embodiments, the xylonate dehydratase is from *Sulfolobus solfataricus*.

In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

2-Keto-3-Deoxy-D-Pentonate Aldolase (4.1.2.28)

The present disclosure describes enzymes that can catalyze the following reaction:

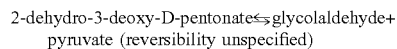

2-dehydro-3-deoxy-D-pentonate ⇌ glycolaldehyde+ pyruvate (reversibility unspecified)

This enzyme belongs to the family of lyases, specifically the aldehyde-lyases, which cleave carbon-carbon bonds. This enzyme participates in pentose and glucuronate interconversions.

2-keto-3-deoxy-D-pentonate aldolase may also be known as 2-dehydro-3-deoxy-D-pentonate glycolaldehyde-lyase (pyruvate-forming), 2-dehydro-3-deoxy-D-pentonate aldolase, 3-deoxy-D-pentulosonic acid aldolase, and 2-dehydro-3-deoxy-D-pentonate glycolaldehyde-lyase.

YjhH appears to be a 2-dehydro-3-deoxy-D-pentonate aldolase. Genetic evidence suggests that YagE may also function as a 2-dehydro-3-deoxy-D-pentonate aldolase. yagE is part of the prophage CP4-6.

A yjhH yagE double mutant cannot use D-xylonate as the sole source of carbon, and crude cell extracts do not contain 2-dehydro-3-deoxy-D-pentonate aldolase activity. Both phenotypes are complemented by providing yjhH on a plasmid.

ArcA appears to activate yjhH gene expression under anaerobiosis. Two putative ArcA binding sites were identified 211 and 597 bp upstream of this gene, but no promoter upstream of it has been identified.

The crystal structure of YagE suggests that the protein is a homotetramer. Co-crystal structures of YagE in the presence of pyruvate and 2-keto-3-deoxygalactonate have been solved.

In particular embodiments, the enzyme converts 2-keto-3-deoxy-xylonate to glycolaldehyde and pyruvate. In some embodiments, the 2-keto-3-deoxy-D-pentonate aldolase is from *Pseudomonas* sp. In some embodiments, the 2-keto-3-deoxy-D-pentonate aldolase is from *Escherichia coli*. In some embodiments, the 2-keto-3-deoxy-D-pentonate aldolase is encoded by the yjhH gene. In some embodiments, the 2-keto-3-deoxy-D-pentonate aldolase is encoded by the yagE gene.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

Glycolaldehyde Dehydrogenase (1.2.1.21)

The present disclosure describes enzymes that can catalyze the following reaction:

glycolaldehyde+NAD$^+$+H$_2$O ⇌ glycolate+NADH+2H$^+$

This enzyme belongs to the family of oxidoreductases, specifically those acting on the aldehyde or oxo group of donor with NAD+ or NADP+ s acceptor. This enzyme participates in glyoxylate and dicarboxylate metabolism.

Glycolaldehyde dehydrogenase may also be known as glycolaldehyde:NAD+ oxidoreductase or glycol aldehyde dehydrogenase.

In *E. coli* aldehyde dehydrogenase A (AldA) is an enzyme of relatively broad substrate specificity for small α-hydroxy-aldehyde substrates. It is thus utilized in several metabolic pathways.

L-fucose and L-rhamnose are metabolized through parallel pathways which converge after their corresponding aldolase reactions yielding the same products: dihydroxy-acetone phosphate and L-lactaldehyde. Aerobically, aldehyde dehydrogenase A oxidizes L-lactaldehyde to L-lactate.

In parallel pathways utilizing the same enzymes, D-arabinose and L-xylose can be metabolized to dihydroxy-acetone phosphate and glycolaldehyde, which is oxidized to glycolate by aldehyde dehydrogenase A.

Crystal structures of the enzyme alone and in ternary and binary complexes have been solved.

Aldehyde dehydrogenase A is only present under aerobic conditions and is most highly induced by the presence of fucose, rhamnose or glutamate. The enzyme is inhibited by NADH, which may act as a switch to shift from oxidation of lactaldehyde to its reduction by propanediol oxidoreductase. AldA is upregulated during short-term adaptation to glucose limitation.

Based on sequence similarity, AldA was predicted to be a succinate-semialdehyde dehydrogenase.

Regulation of aldA expression has been investigated. The gene is regulated by catabolite repression, repression under anaerobic conditions via ArcA, and induction by the carbon source.

In particular embodiments, the enzyme converts glycolaldehyde to glycolate. In some embodiments, the glycolaldehyde dehydrogenase is from *Escherichia coli*. In some embodiments, the glycolaldehyde dehydrogenase is encoded by the aldA gene.

In some embodiments, a recombinant microorganism producing MEG and a three-carbon compound comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

Lactate Dehydrogenase (1.1.1.28)

The present disclosure describes enzymes that can catalyze the following reaction:

(R)-lactate+NAD+ ⇌ pyruvate+NADH+H+

Lactate dehydrogenase (LDH) is an enzyme found in nearly all living cells such as in animals, plants and prokaryotes. LDH catalyzes the conversion of lactate to pyruvic acid and back, as it converts NADH to NAD+ and back. A dehydrogenase is an enzyme that transfers a hydride from one molecule to another.

LDH exist in four distinct enzyme classes. The most common one is NAD(P)-dependent L-lactate dehydrogenase. Other LDHs act on D-lactate and/or are dependent on cytochrome c: D-lactate dehydrogenase (cytochrome) and L-lactate dehydrogenase (cytochrome).

LDH has been of medical significance because it is found extensively in body tissues, such as blood cells and heart muscle. Because it is released during tissue damage, it is a marker of common injuries and disease such as heart failure.

Lactate dehydrogenase may also be known as lactic acid dehydrogenase, (R)-lactate:NAD+ oxidoreductase or D-lactate dehydrogenase-fermentative.

In *E. coli*, lactate dehydrogenase (LdhA) is a soluble NAD-linked lactate dehydrogenase (LDH) that is specific for the production of D-lactate. LdhA is a homotetramer and shows positive homotropic cooperativity under higher pH conditions.

*E. coli* contains two other lactate dehydrogenases: D-lactate dehydrogenase and L-lactate dehydrogenase. Both are membrane-associated flavoproteins required for aerobic growth on lactate.

LdhA is present under aerobic conditions but is induced when *E. coli* is grown on a variety of sugars under anaerobic conditions at acidic pH. Unlike most of the genes involved in anaerobic respiration, ldhA is not activated by Fnr; rather the ArcAB system and several genes involved in the control of carbohydrate metabolism (csrAB and mlc) appear to regulate expression. The expression of IdhA is negatively affected by the transcriptional regulator ArcA. IdhA belongs to the σ32 regulon.

The IdhA gene is a frequent target for mutations in metabolic engineering, most often to eliminate production of undesirable fermentation side products, but also to specifically produce D-lactate.

In particular embodiments, the enzyme converts pyruvate to lactate. In some embodiments, the lactate dehydrogenase is from *Escherichia coli*. In some embodiments, the lactate dehydrogenase is encoded by the IdhA gene.

In some embodiments, a recombinant microorganism producing MEG and a three-carbon compound comprises a deletion, insertion, or loss of function mutation in a gene encoding a lactate dehydrogenase to prevent the production of lactate from pyruvate and instead shunt the reaction toward production of a three-carbon compound.

Xylose Reductase or Aldose Reductase (EC 1.1.1.21)

The present disclosure describes enzymes that can catalyze the following reactions:

α-D-xylose+NADPH+H+⇌xylitol+NADP

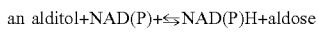

an alditol+NAD(P)+⇌NAD(P)H+aldose

Aldose reductase may also be known as alditol:NAD(P)+ 1-oxidoreductase, polyol dehydrogenase or aldehyde reductase.

Aldose reductase is a cytosolic oxidoreductase that catalyzes the reduction of a variety of aldehydes and carbonyls, including monosaccharides.

Aldose reductase may be considered a prototypical enzyme of the aldo-keto reductase enzyme superfamily. The enzyme comprises 315 amino acid residues and folds into a β/α-barrel structural motif composed of eight parallel β strands. Adjacent strands are connected by eight peripheral α-helical segments running anti-parallel to the β sheet. The catalytic active site is situated in the barrel core. The NADPH cofactor is situated at the top of the β/α barrel, with the nicotinamide ring projecting down in the center of the barrel and pyrophosphate straddling the barrel lip.

The reaction mechanism of aldose reductase in the direction of aldehyde reduction follows a sequential ordered path where NADPH binds, followed by the substrate. Binding of NADPH induces a conformational change (Enzyme•NADPH->Enzyme*•NADPH) that involves hinge-like movement of a surface loop (residues 213-217) so as to cover a portion of the NADPH in a manner similar to that of a safety belt. The alcohol product is formed via a transfer of the pro-R hydride of NADPH to the face of the substrate's carbonyl carbon. Following release of the alcohol product, another conformational change occurs (E*•NAD(P)+->E•NAD(P)+) in order to release NADP+. Kinetic studies have shown that reorientation of this loop to permit release of NADP+ appears to represent the rate-limiting step in the direction of aldehyde reduction. As the rate of coenzyme release limits the catalytic rate, it can be seen that perturbation of interactions that stabilize coenzyme binding can have dramatic effects on the maximum velocity (Vmax).

D-xylose-fermenting *Pichia stipitis* and *Candida shehatae* were shown to produce one single aldose reductase (ALR) that is active both with NADPH and NADH. Other yeasts such as *Pachysolen tannophilus* and *C. tropicalis* synthesize multiple forms of ALR with different coenzyme specificities. The significant dual coenzyme specificity distinguishes the *P. stipitis* and the *C. shehatae* enzymes from most other ALRs so far isolated from mammalian or microbial sources. The yeast *Candida tenuis* CBS 4435 produces comparable NADH- and NADPH-linked aldehyde-reducing activities during growth on D-xylose.

In particular embodiments, the enzyme converts D-xylose to xylitol. In some embodiments, the xylose reductase or aldose reductase is from *Hypocrea jecorina*. In some embodiments, the xylose reductase or aldose reductase is encoded by the xyl1 gene. In some embodiments, the xylose reductase or aldose reductase is from *Saccharomyces cerevisiae*. In some embodiments, the xylose reductase or aldose reductase is encoded by the GRE3 gene. In some embodiments, the xylose reductase or aldose reductase is from *Pachysolen tannophilus*. In some embodiments, the xylose reductase or aldose reductase is from *Pichia* sp. In some embodiments, the xylose reductase or aldose reductase is from *Pichia stipitis*. In some embodiments, the xylose reductase or aldose reductase is from *Pichia quercuum*. In some embodiments, the xylose reductase or aldose reductase is from *Candida* sp. In some embodiments, the xylose reductase or aldose reductase is from *Candida shehatae*. In some embodiments, the xylose reductase or aldose reductase is from *Candida tenuis*. In some embodiments, the xylose reductase or aldose reductase is from *Candida tropicalis*. In some embodiments, the xylose reductase or aldose reductase is from *Aspergillus niger*. In some embodiments, the xylose reductase or aldose reductase is from *Neurospora crassa*. In some embodiments, the xylose reductase or aldose reductase is from *Cryptococcus lactativorus*.

In some embodiments, the xylose reductase or aldose reductase is encoded by one or more nucleic acid molecules obtained from a microorganism selected from the group consisting of *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the xylose reductase or aldose reductase is encoded by one or more nucleic acid molecules obtained from a microorganism selected from the group consisting of *Hypocrea jecorina*, *Scheffersomyces stipitis*, *Saccharomyces cerevisiae*, *Pachysolen tannophilus*, *Pichia stipitis*, *Pichia quercuum*, *Candida shehatae*, *Candida tenuis*, *Candida tropicalis*, *Aspergillus niger*, *Neurospora crassa* and *Cryptococcus lactativorus*. In another embodiment, the one or more nucleic acid molecules encoding the xylose reductase or aldose reductase is xyl1 and/or GRE3 or homolog thereof. In some embodiments, the one or more nucleic acid molecules encoding the xylose reductase or aldose reductase comprises an amino acid sequence selected from the group consisting of SEQ ID NOs: 84 and 87. In some embodiments, the one or more nucleic acid molecules encoding the xylose reductase or aldose reductase is encoded by a nucleic acid sequence selected from the group consisting of SEQ ID NOs: 82, 83, 85 and 86.

Xylitol Dehydrogenase (1.1.1.9)

The present disclosure describes enzymes that can catalyze the following reaction:

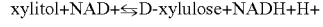

xylitol+NAD+⇌D-xylulose+NADH+H+

Xylitol dehydrogenase may also be known as D-xylulose reductase, NAD+-dependent xylitol dehydrogenase, erythritol dehydrogenase, 2,3-cis-polyol(DPN) dehydrogenase (C3-5), pentitol-DPN dehydrogenase, xylitol-2-dehydrogenase or xylitol: NAD+ 2-oxidoreductase (D-xylulose-forming).

Xylitol dehydrogenase (XDH) is one of several enzymes responsible for assimilating xylose into eukaryotic metabolism and is useful for fermentation of xylose contained in agricultural byproducts to produce ethanol. For efficient xylose utilization at high flux rates, cosubstrates should be recycled between the NAD+-specific XDH and the NADPH-preferring xylose reductase, another enzyme in the pathway.

In particular embodiments, the enzyme converts xylitol to D-xylulose. In some embodiments, the xylitol dehydrogenase is from yeast. In some embodiments, the xylitol dehydrogenase is from *Pichia* sp., *Saccharomyces* sp., *Gluconobacter* sp., *Galactocandida* sp., *Neurospora* sp. or *Serratia* sp. In some embodiments, the xylitol dehydrogenase is from *Pichia stipitis*, *S. cerevisiae*, *Gluconobacter oxydans*, *Galactocandida mastotermitis*, *Neurospora crassa* or *Serratia marcescens*. In some embodiments, the xylitol dehydrogenase is encoded by xyl2 or xdh1.

In one embodiment, the xylitol dehydrogenase is encoded by one or more nucleic acid molecules obtained from a microorganism selected from the group consisting of *Scheffersomyces* sp., *Trichoderma* sp., *Pichia* sp., *Saccharomyces* sp., *Gluconobacter* sp., *Galactocandida* sp., *Neurospora* sp., and *Serratia* sp. In another embodiment, the xylitol dehydrogenase is encoded by one or more nucleic acid molecules obtained from a microorganism selected from the group consisting of *Scheffersomyces stipitis*, *Trichoderma reesei*, *Pichia stipitis*, *Saccharomyces cerevisiae*, *Gluconobacter oxydans*, *Galactocandida mastotermitis*, *Neurospora crassa* and *Serratia marcescens*. In another embodiment, the one or more nucleic acid molecules encoding the xylitol dehydrogenase is xyl2 and/or xdh1, or homolog thereof. In some embodiments, the one or more nucleic acid molecules encoding the xylitol dehydrogenase comprises an amino acid sequence selected from the group consisting of SEQ ID NOs: 90 and 92. In some embodiments, the one or more nucleic acid molecules encoding the xylitol dehydrogenase is encoded by a nucleic acid sequence selected from the group consisting of SEQ ID NOs: 88, 89 and 91.

Alkaline Phosphatase (EC 3.1.3.1)

Alkaline phosphatase is a hydrolase enzyme responsible for removing phosphate groups from many types of molecules, including nucleotides, proteins, and alkaloids. As the name suggests, alkaline phosphatases are most effective in an alkaline environment. It is sometimes used synonymously as basic phosphatase.

The *S. cerevisiae* Pho13 alkaline phosphatase enzyme is a monomeric protein with molecular mass of 60 kDa and hydrolyzes p-nitrophenyl phosphate with maximal activity at pH 8.2 with strong dependence on Mg2+ ions and an apparent Km of 3.6×10(−5) M. No other substrates tested except phosphorylated histone II-A and casein were hydrolyzed at any significant rate. These data suggest that the physiological role of the p-nitrophenyl phosphate-specific phosphatase may involve participation in reversible protein phosphorylation.

In particular embodiments, the enzyme converts D-xylulose-5-phosphate to D-xylulose. In some embodiments, the alkaline phosphatase is from yeast. In some embodiments, the alkaline phosphatase is from *Saccharomyces* sp. In some embodiments, the alkaline phosphatase is from *S. cerevisiae*. In some embodiments, the alkaline phosphatase is encoded by the PHO13 gene.

In some embodiments, a recombinant microorganism producing MEG and a three-carbon compound comprises a deletion, insertion, or loss of function mutation in a gene encoding an alkaline phosphatase to prevent the conversion of D-xylulose-5-phosphate to D-xylulose.

Soluble Pyridine Nucleotide Transhydrogenase (EC 1.6.1.1.)

The present disclosure describes enzymes that can catalyze the following reaction:

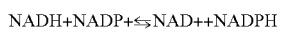

Soluble pyridine nucleotide transhydrogenase may also be known as NAD(P)+transhydrogenase (B-specific), STH, pyridine nucleotide transhydrogenase, or transhydrogenase.

*E. coli* contains both a soluble and a membrane-bound pyridine nucleotide transhydrogenase. The soluble pyridine nucleotide transhydrogenase is the sthA or udhA gene product; its primary physiological role appears to be the reoxidation of NADPH (Canonaco F. et al. (2001) Metabolic flux response to phosphoglucose isomerase knock-out in *Escherichia coli* and impact of overexpression of the soluble transhydrogenase UdhA. FEMS Microbiol Lett 204(2): 247-252; Sauer U. et al. (2004) The soluble and membrane-bound transhydrogenases UdhA and PntAB have divergent functions in NADPH metabolism of *Escherichia coli*. J Biol Chem 279(8): 6613-6619). The membrane-bound proton-translocating transhydrogenase is the pntAB gene product; PntAB is a major source of NADPH (Sauer et al. 2004).

UdhA contains noncovalently bound FAD and is present in a form consisting of seven or eight monomers (Boonstra B. et al. (1999) The udhA gene of *Escherichia coli* encodes a soluble pyridine nucleotide transhydrogenase. J Bacteriol 181(3): 1030-1034).

Moderate overexpression of UdhA (SthA) allows an increased maximal growth rate of a phosphoglucose isomerase mutant (Canonaco et al. 2001), and a pgi sthA double mutant is not viable (Sauer et al. 2004). These phenotypes may be due to the ability of UdhA to restore the cellular redox balance under conditions of excess NADPH formation (Canonaco et al. 2001; Sauer et al. 2004). Mutations in sthA appear during adaptation of a pgi mutant strain to growth on glucose minimal medium (Charusanti P. et al. (2010) Genetic basis of growth adaptation of *Escherichia coli* after deletion of pgi, a major metabolic gene." PLoS Genet 6(11): e1001186).

Transcription of sthA is downregulated by growth on glycerol (Sauer et al. 2004).

In some embodiments, expression of a transhydrogenase can increase activity of a NADPH-dependent alcohol dehydrogenase, leading to improved acetone to 2-propanol conversion. In one embodiment, the soluble pyridine nucleotide transhydrogenase is encoded by one or more nucleic acid molecules obtained from *E. coli*. In another embodiment, the one or more nucleic acid molecules encoding the soluble pyridine nucleotide transhydrogenase is udhA, or homolog thereof. In some embodiments, the one or more nucleic acid molecules encoding the soluble pyridine nucleotide transhydrogenase comprises an amino acid sequence set forth in SEQ ID NO: 110. In some embodiments, the one or more nucleic acid molecules encoding the soluble pyridine nucleotide transhydrogenase is encoded by a nucleic acid sequence set forth in SEQ ID NO: 109.

Biosynthesis of MEG and One or More Three-Carbon Compound Using a Recombinant Microorganism As discussed above, the present application provides a recombinant microorganism co-producing monoethylene glycol (MEG) and one or more three-carbon compounds. In one embodiment, the MEG and one or more three-carbon compounds are co-produced from xylose. In another embodiment, the recombinant microorganism comprises a deletion, insertion, or loss of function mutation in a gene encoding a D-xylulose-5-kinase and/or in a gene encoding a glycoaldehyde dehydrogenase. In some embodiments, the gene encoding the D-xylulose-5-kinase is xylB. In some embodiments, the gene encoding the glycoaldehyde dehydrogenase is aldA.

In one embodiment, MEG is produced from xylose via ribulose-1-phosphate. In another embodiment, MEG is produced from xylose via xylulose-1-phosphate. In a further embodiment, MEG is produced from xylose via xylonate.

In one embodiment, one or more three-carbon compounds is produced from DHAP or pyruvate. In one embodiment, the one or more three-carbon compounds is acetone. In another embodiment, the one or more three-carbon compounds is isopropanol. In a further embodiment, the one or more three-carbon compounds is propene.

In one preferred embodiment, MEG and one or more three-carbon compounds are produced from xylose using a ribulose-1-phosphate pathway for the conversion of xylose to MEG and dihydroxyacetone-phosphate (DHAP), and using a C3 branch pathway for the conversion of DHAP to one or more three-carbon compounds.

As discussed above, in a first aspect, the present disclosure relates to a recombinant microorganism capable of co-producing monoethylene glycol (MEG) and acetone from exogenous D-xylose, wherein the recombinant microorganism expresses one or more of the following:
(a) at least one endogenous or exogenous nucleic acid molecule encoding a D-tagatose 3-epimerase that catalyzes the conversion of D-xylulose to D-ribulose;
(b) at least one endogenous or exogenous nucleic acid molecule encoding a D-ribulokinase that catalyzes the conversion of D-ribulose from (a) to D-ribulose-1-phosphate;
(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);
(d) at least one endogenous or exogenous nucleic acid molecule encoding a glycolaldehyde reductase that catalyzes the conversion of glycolaldehyde from (c) to MEG;
(e) at least one exogenous nucleic acid molecule encoding a thiolase that catalyzes the conversion of acetyl-CoA to acetoacetyl-CoA;
(f) at least one endogenous or exogenous nucleic acid molecule encoding an acetate:acetoacetyl-CoA transferase or hydrolase that catalyzes the conversion of acetoacetyl-CoA from (e) to acetoacetate; and/or
(g) at least one endogenous or exogenous nucleic acid molecule encoding an acetoacetate decarboxylase that catalyzes the conversion of acetoacetate from (f) to acetone;
wherein the produced intermediate DHAP is converted to acetyl-CoA through the endogenous glycolysis pathway in the microorganism, and wherein MEG and acetone are co-produced.

In one embodiment, the D-tagatose 3-epimerase is encoded by one or more nucleic acid molecules obtained from a microorganism selected from the group consisting of *Pseudomonas* sp., *Mesorhizobium* sp. and *Rhodobacter* sp. In some embodiments, the D-tagatose 3-epimerase is encoded by one or more nucleic acid molecules obtained from a microorganism selected from the group consisting of *Pseudomonas cichorii, Pseudomonas* sp. ST-24, *Mesorhizobium loti* and *Rhodobacter sphaeroides*. In some embodiments, the one or more nucleic acid molecules is dte and/or FJ851309.1, or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

In one embodiment, the D-ribulokinase is encoded by one or more nucleic acid molecules obtained from *E. coli*. In some embodiments, the one or more nucleic acid molecules is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

In one embodiment, the D-ribulose-1-phosphate aldolase is encoded by one or more nucleic acid molecules obtained from *E. coli*. In some embodiments, the one or more nucleic acid molecules is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

In one embodiment, the recombinant microorganism further comprises at least one endogenous or exogenous nucleic acid molecule encoding a secondary alcohol dehydrogenase that catalyzes the conversion of acetone from (g) to isopropanol.

In another embodiment, the recombinant microorganism further comprises at least one endogenous or exogenous nucleic acid molecule encoding a dehydratase that catalyzes the conversion of isopropanol to propene.

In another embodiment, the recombinant microorganism further comprises one or more modifications selected from the group consisting of:
(a) a deletion, insertion, or loss of function mutation in a gene encoding a D-xylulose-5-kinase that catalyzes the conversion of D-xylulose to D-xylulose-5-phosphate;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

In one preferred embodiment, MEG and acetone are co-produced from xylose using a xylulose-1-phosphate pathway for the conversion of xylose to MEG and a C3 branch pathway for the conversion of dihydroxyacetone-phosphate (DHAP) to acetone.

As discussed above, in a second aspect, the present disclosure relates to a recombinant microorganism capable of co-producing monoethylene glycol (MEG) and acetone from exogenous D-xylose, wherein the recombinant microorganism expresses one or more of the following:
(a) at least one endogenous or exogenous nucleic acid molecule encoding a D-xylulose 1-kinase that catalyzes the conversion of D-xylulose to D-xylulose-1-phosphate;
(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);
(c) at least one endogenous or exogenous nucleic acid molecule encoding a glycolaldehyde reductase that catalyzes the conversion of glycolaldehyde from (b) to MEG;
(d) at least one endogenous or exogenous nucleic acid molecule encoding a thiolase that catalyzes the conversion of acetyl-CoA to acetoacetyl-CoA;
(e) at least one endogenous or exogenous nucleic acid molecule encoding an acetate:acetoacetyl-CoA transferase or hydrolase that catalyzes the conversion of acetoacetyl-CoA from (d) to acetoacetate; and/or
(f) at least one endogenous or exogenous nucleic acid molecule encoding an acetoacetate decarboxylase that catalyzes the conversion of acetoacetate from (e) to acetone;
wherein the produced intermediate DHAP is converted to acetyl-CoA through the endogenous glycolysis pathway in the microorganism, and wherein MEG and acetone are co-produced.

In one embodiment, the D-xylulose 1-kinase is encoded by one or more nucleic acid molecules obtained from *Homo sapiens*. In some embodiments, the one or more nucleic acid molecules encoding the D-xylulose 1-kinase is ketohexokinase C (khk-C), or homolog thereof. In another embodiment, the one or more nucleic acid molecules encoding the D-xylulose 1-kinase comprises an amino acid sequence set forth in SEQ ID NO: 55. In a further embodiment, the one or more nucleic acid molecules encoding the D-xylulose 1-kinase is encoded by a nucleic acid sequence selected from the group consisting of SEQ ID NOs: 53 and 54.

In one embodiment, the D-xylulose-1-phosphate aldolase is encoded by one or more nucleic acid molecules obtained from *Homo sapiens*. In another embodiment, the one or more nucleic acid molecules encoding the D-xylulose-1-phosphate aldolase is aldolase B (ALDOB), or homolog thereof. In some embodiments, the one or more nucleic acid molecules encoding the D-xylulose-1-phosphate aldolase comprises an amino acid sequence set forth in SEQ ID NO: 58. In some embodiments, the one or more nucleic acid molecules encoding the D-xylulose-1-phosphate aldolase is encoded by a nucleic acid sequence selected from the group consisting of SEQ ID NOs: 56 and 57.

In one embodiment, the recombinant microorganism further comprises at least one endogenous or exogenous nucleic acid molecule encoding a secondary alcohol dehydrogenase that catalyzes the conversion of acetone from (f) to isopropanol.

In another embodiment, the recombinant microorganism further comprises at least one endogenous or exogenous nucleic acid molecule encoding a dehydratase-isomerase that catalyzes the conversion of isopropanol to propene.

In another embodiment, the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

In some embodiments of any aspect disclosed above, a recombinant microorganism producing MEG and one or more three-carbon compounds comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate. In some embodiments, the D-xylulose-5-kinase is from *Escherichia coli*. In some embodiments, the D-xylulose-5-kinase is encoded by the xylB gene, or homolog thereof.

In some embodiments of any aspect disclosed above, a recombinant microorganism producing MEG and one or more three-carbon compounds comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In some embodiments, the glycolaldehyde dehydrogenase is from *Escherichia coli*. In some embodiments, the glycolaldehyde dehydrogenase is encoded by the aldA gene, or homolog thereof.

In some embodiments of any aspect disclosed above, a recombinant microorganism producing MEG and one or more three-carbon compounds comprises a deletion, insertion, or loss of function mutation in a gene encoding a lactate dehydrogenase to prevent the production of lactate from pyruvate and instead shunt the reaction toward production of one or more three-carbon compounds. In some embodiments, the lactate dehydrogenase is from *Escherichia* coil. In some embodiments, the lactate dehydrogenase is encoded by the IdhA gene, or homolog thereof.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

As discussed above, in a third aspect, the present application relates to a recombinant microorganism capable of co-producing monoethylene glycol (MEG) and acetone from exogenous D-xylose and glucose, wherein the recombinant microorganism expresses one or more of the following:
(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;
(b) at least one exogenous nucleic acid molecule encoding a D-xylose isomerase that catalyzes the conversion of D-xylose to D-xylulose, and wherein the microorganism further expresses one or more of the following:
(c) at least one endogenous or exogenous nucleic acid molecule encoding a D-tagatose 3-epimerase that catalyzes the conversion of D-xylulose from (a) or (b) to D-ribulose;
(d) at least one endogenous or exogenous nucleic acid molecule encoding a D-ribulokinase that catalyzes the conversion of D-ribulose from (c) to D-ribulose-1-phosphate;
(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);
(f) at least one endogenous or exogenous nucleic acid molecule encoding a glycolaldehyde reductase or methylglyoxal reductase that catalyzes the conversion of glycolaldehyde from (e) to MEG;
(g) at least one endogenous or exogenous nucleic acid molecule encoding a thiolase that catalyzes the conversion of acetyl-CoA to acetoacetyl-CoA;
(h) at least one endogenous or exogenous nucleic acid molecule encoding an acetate:acetoacetyl-CoA transferase or hydrolase that catalyzes the conversion of acetoacetyl-CoA from (g) to acetoacetate; and/or
(i) at least one endogenous or exogenous nucleic acid molecule encoding an acetoacetate decarboxylase that catalyzes the conversion of acetoacetate from (h) to acetone;

wherein the produced intermediate DHAP is converted to acetyl-CoA through the endogenous glycolysis pathway in the microorganism, and wherein MEG and acetone are co-produced.

In some embodiments, the xylose reductase or aldose reductase is encoded by one or more nucleic acid molecules obtained from a microorganism selected from the group consisting of *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the xylose reductase or aldose reductase is encoded by one or more nucleic acid molecules obtained from a microorganism selected from the group consisting of *Hypocrea jecorina, Scheffersomyces stipitis, Saccharomyces cerevisiae, Pachysolen tannophilus, Pichia stipitis, Pichia quercuum, Candida shehatae, Candida tenuis, Candida tropicalis, Aspergillus niger, Neurospora crassa* and *Cryptococcus lactativorus*. In another embodiment, the one or more nucleic acid molecules encoding the xylose reductase or aldose reductase is xyl1 and/or GRE3 or homolog thereof. In some embodiments, the one or more nucleic acid molecules encoding the xylose reductase or aldose reductase comprises an amino acid sequence selected from the group consisting of SEQ ID NOs: 84 and 87. In some embodiments, the one or more nucleic acid molecules encoding the xylose reductase or aldose reductase is encoded by a nucleic acid sequence selected from the group consisting of SEQ ID NOs: 82, 83, 85 and 86.

In one embodiment, the xylitol dehydrogenase is encoded by one or more nucleic acid molecules obtained from a microorganism selected from the group consisting of *Scheffersomyces* sp., *Trichoderma* sp., *Pichia* sp., *Saccharomyces* sp., *Gluconobacter* sp., *Galactocandida* sp., *Neurospora* sp., and *Serratia* sp. In another embodiment, the xylitol dehydrogenase is encoded by one or more nucleic acid molecules obtained from a microorganism selected from the group consisting of *Scheffersomyces stipitis, Trichoderma reesei, Pichia stipitis, Saccharomyces cerevisiae, Gluconobacter oxydans, Galactocandida mastotermitis, Neurospora crassa* and *Serratia marcescens*. In another embodiment, the one or more nucleic acid molecules encoding the xylitol dehydrogenase is xyl2 and/or xdh1, or homolog thereof. In some embodiments, the one or more nucleic acid molecules encoding the xylitol dehydrogenase comprises an amino acid sequence selected from the group consisting of SEQ ID NOs: 90 and 92. In some embodiments, the one or more nucleic acid molecules encoding the xylitol dehydrogenase is encoded by a nucleic acid sequence selected from the group consisting of SEQ ID NOs: 88, 89 and 91.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

In one embodiment, the recombinant microorganism further comprises at least one endogenous or exogenous nucleic acid molecule encoding a secondary alcohol dehydrogenase that catalyzes the conversion of acetone from (i) to isopropanol.

In another embodiment, the recombinant microorganism further comprises at least one endogenous or exogenous nucleic acid molecule encoding a dehydratase that catalyzes the conversion of isopropanol to propene.

In another embodiment, the recombinant microorganism further comprises one or more modifications selected from the group consisting of:
(a) a deletion, insertion, or loss of function mutation in a gene encoding a D-xylulose-5-kinase that catalyzes the conversion of D-xylulose to D-xylulose-5-phosphate; and
(b) a deletion, insertion, or loss of function mutation in a gene encoding an alkaline phosphatase that catalyzes the conversion of D-xylulose-5-phosphate to D-xylulose.

In one embodiment, the enzyme that catalyzes the conversion of D-xylulose to D-xylulose-5-phosphate is a D-xylulose-5-kinase. In some embodiments, the D-xylulose-5-kinase is from *Saccharomyces cerevisiae*. In some embodiments the D-xylulose-5-kinase is encoded by the XKS1 gene, or homolog thereof. In some embodiments, the D-xylulose-5-kinase is from *Pichia stipitis*. In some embodiments the D-xylulose-5-kinase is encoded by the XYL3 gene, or homolog thereof.

In a further embodiment, the microorganism is a fungus.

In one preferred embodiment, MEG and acetone are co-produced from xylose using a xylonate pathway for the conversion of xylose to MEG and a C3 branch pathway for the conversion of dihydroxyacetone-phosphate (DHAP) to acetone.

As discussed above, in a fourth aspect, the present application relates to a recombinant microorganism capable of co-producing monoethylene glycol (MEG) and acetone from exogenous D-xylose, wherein the recombinant microorganism expresses one or more of the following:
(a) at least one endogenous or exogenous nucleic acid molecule encoding a xylose dehydrogenase that catalyzes the conversion of D-xylose to D-xylonolactone;
(b) at least one endogenous or exogenous nucleic acid molecule encoding a xylonolactonase that catalyzes the conversion of D-xylonolactone from (a) to D-xylonate;
(c) at least one endogenous or exogenous nucleic acid molecule encoding a xylonate dehydratase that catalyzes the conversion of D-xylonate from (b) to 2-keto-3-deoxy-xylonate;
(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;
(e) at least one endogenous or exogenous nucleic acid molecule encoding a glycolaldehyde reductase that catalyzes the conversion of glycolaldehyde from (d) to MEG;
(f) at least one exogenous nucleic acid molecule encoding a thiolase that catalyzes the conversion of acetyl-CoA to acetoacetyl-CoA;
(g) at least one endogenous or exogenous nucleic acid molecule encoding an acetate:acetoacetyl-CoA transferase or hydrolase that catalyzes the conversion of acetoacetyl-CoA from (f) to acetoacetate; and/or
(h) at least one exogenous nucleic acid molecule encoding an acetoacetate decarboxylase that catalyzes the conversion of acetoacetate from (g) to acetone;
wherein the produced intermediate pyruvate is converted to acetyl-CoA through the endogenous glycolysis pathway in the microorganism, and wherein MEG and acetone are co-produced.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the xylonolactonase is encoded by one or more nucleic acid molecules obtained from a microorganism selected from *Caulobacter* sp. and *Haloferax* sp. In another embodiment, the xylonolactonase is encoded by one or more nucleic acid molecules obtained from a microorganism selected from the group consisting of *Caulobacter crescentus, Haloferax volcanii* and *Haloferax gibbonsii*. In some embodiments, the one or more nucleic acid molecules encoding the xylonolactonase is xylC, or homolog thereof.

In a further embodiment, the one or more nucleic acid molecules encoding the xylonolactonase comprises an amino acid sequence set forth in SEQ ID NO: 67. In yet another embodiment, the one or more nucleic acid molecules encoding the xylonolactonase is encoded by a nucleic acid sequence set forth in SEQ ID NO: 66.

In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the recombinant microorganism further comprises at least one endogenous or exogenous nucleic acid molecule encoding a secondary alcohol dehydrogenase that catalyzes the conversion of acetone from (h) to isopropanol.

In another embodiment, the recombinant microorganism further comprises at least one endogenous or exogenous nucleic acid molecule encoding a dehydratase that catalyzes the conversion of isopropanol to propene.

In another embodiment, the recombinant microorganism further comprises one or more modifications selected from the group consisting of:
(a) a deletion, insertion, or loss of function mutation in a gene encoding a D-xylose isomerase that catalyzes the conversion of D-xylose to D-xylulose;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

In some embodiments, a recombinant microorganism producing MEG and one or more three-carbon compounds comprises a deletion, insertion, or loss of function mutation in a gene encoding a D-xylose isomerase to prevent conversion of D-xylose to D-xylulose and instead shunt the reaction toward the conversion of D-xylose to D-xylonate. In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a recombinant microorganism producing MEG and one or more three-carbon compounds comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In one embodiment, the glycolaldehyde dehydrogenase is from *Escherichia coli*. In some embodiments, the glycolaldehyde dehydrogenase is encoded by the aldA gene, or homolog thereof.

In some embodiments, a recombinant microorganism producing MEG and one or more three-carbon compounds comprises a deletion, insertion, or loss of function mutation in a gene encoding a lactate dehydrogenase to prevent the production of lactate from pyruvate and instead shunt the reaction toward production of one or more three-carbon compounds. In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the IdhA gene, or homolog thereof.

As discussed above, in a fifth aspect, the present application relates to a recombinant microorganism capable of co-producing monoethylene glycol (MEG) and acetone from exogenous D-xylose, wherein the recombinant microorganism expresses one or more of the following:
 (a) at least one endogenous or exogenous nucleic acid molecule encoding a xylose dehydrogenase that catalyzes the conversion of D-xylose to D-xylonate;
 (b) at least one endogenous or exogenous nucleic acid molecule encoding a xylonate dehydratase that catalyzes the conversion of D-xylonate from (a) to 2-keto-3-deoxy-xylonate;
 (c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;
 (d) at least one exogenous nucleic acid molecule encoding a glycolaldehyde reductase that catalyzes the conversion of glycolaldehyde from (c) to MEG;
 (e) at least one exogenous nucleic acid molecule encoding a thiolase that catalyzes the conversion of acetyl-CoA to acetoacetyl-CoA;
 (f) at least one endogenous or exogenous nucleic acid molecule encoding an acetate:acetoacetyl-CoA transferase or hydrolase that catalyzes the conversion of acetoacetyl-CoA from (e) to acetoacetate; and/or
 (g) at least one exogenous nucleic acid molecule encoding an acetoacetate decarboxylase that catalyzes the conversion of acetoacetate from (f) to acetone;
wherein the produced intermediate pyruvate is converted to acetyl-CoA through the endogenous glycolysis pathway in the microorganism, and wherein MEG and acetone are co-produced.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the recombinant microorganism further comprises at least one endogenous or exogenous nucleic acid molecule encoding a secondary alcohol dehydrogenase that catalyzes the conversion of acetone from (g) to isopropanol.

In another embodiment, the recombinant microorganism further comprises at least one endogenous or exogenous nucleic acid molecule encoding a dehydratase that catalyzes the conversion of isopropanol to propene.

In another embodiment, the recombinant microorganism further comprises one or more modifications selected from the group consisting of:
 (a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In some embodiments, a recombinant microorganism producing MEG and one or more three-carbon compounds comprises a deletion, insertion, or loss of function mutation in a gene encoding a D-xylose isomerase to prevent conversion of D-xylose to D-xylulose and instead shunt the reaction toward the conversion of D-xylose to D-xylonate. In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a recombinant microorganism producing MEG and one or more three-carbon compounds comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In one embodiment, the glycolaldehyde dehydrogenase is from *Escherichia coli*. In some embodiments, the glycolaldehyde dehydrogenase is encoded by the aldA gene, or homolog thereof.

In some embodiments, a recombinant microorganism producing MEG and one or more three-carbon compounds comprises a deletion, insertion, or loss of function mutation in a gene encoding a lactate dehydrogenase to prevent the production of lactate from pyruvate and instead shunt the reaction toward production of one or more three-carbon compounds. In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the IdhA gene, or homolog thereof.

In one embodiment of any aspect disclosed above, the glycolaldehyde reductase is encoded by one or more nucleic acid molecules obtained from a microorganism selected from *E. coli* and *S. cerevisiae*. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment of any aspect disclosed above, the thiolase or acetyl coenzyme A acetyltransferase is encoded by one or more nucleic acid molecules obtained from a microorganism selected from the group consisting of *Clostridium* sp., *Bacillus* sp., *E. coli*, *Saccharomyces* sp. and *Marinobacter* sp. In some embodiments, the thiolase or acetyl coenzyme A acetyltransferase is encoded by one or more nucleic acid molecules obtained from a microorganism selected from the group consisting of *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the one or more nucleic acid molecules is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment of any aspect disclosed above, the acetyl-CoA:acetoacetate-CoA transferase or acetate:acetoacetyl-CoA hydrolase is encoded by one or more nucleic acid molecules obtained from a microorganism selected from *Clostridium* sp. and *E. coli*. In another embodiment, the acetyl-CoA:acetoacetate-CoA transferase or acetate:acetoacetyl-CoA hydrolase is encoded by one or more nucleic acid molecules obtained from *E. coli*. In some embodiments, the one or more nucleic acid molecules encoding the acetyl-CoA:acetoacetate-CoA transferase is atoA and/or atoD, or homolog thereof. In another embodiment, the acetyl-CoA:acetoacetate-CoA transferase or acetate:acetoacetyl-CoA hydrolase is encoded by one or more nucleic acid molecules obtained from *Clostridium acetobutylicum*. In some embodiments, the one or more nucleic acid molecules encoding the acetate:acetoacetyl-CoA hydrolase is ctfA and/or ctfB, or homolog thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment of any aspect disclosed above, the acetoacetate decarboxylase is encoded by one or more nucleic acid molecules obtained from a microorganism selected from the group consisting of *Clostridium* sp., *Bacillus* sp., *Chromobacterium* sp. and *Pseudomonas* sp. In another embodiment, the acetoacetate decarboxylase is encoded by one or more nucleic acid molecules obtained from a microorganism selected from the group consisting of *Clostridium acetobutylicum*, *Clostridium beijerinckii*, *Clostridium cellulolyticum*, *Bacillus polymyxa*, *Chromobacterium violaceum* and *Pseudomonas putida*. In some embodiments, the one or more nucleic acid molecules encoding the acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment of any aspect disclosed above, the enzyme that catalyzes the conversion of acetone to isopropanol is a secondary alcohol dehydrogenase (S-ADH). In another embodiment, the enzyme is a secondary alcohol dehydrogenase that is encoded by a nucleic acid molecule obtained from a microorganism selected from *Burkholderia* sp, *Alcaligenes* sp., *Clostridium* sp., *Thermoanaerobacter* sp., *Phytomonas* sp., *Rhodococcus* sp., *Methanobacterium* sp., *Methanogenium* sp., *Entamoeba* sp., *Trichomonas* sp., and *Tritrichomonas* sp. In some embodiments, the nucleic acid molecule encoding the secondary alcohol dehydrogenase is obtained from a microorganism selected from *Burkholderia* sp. AIU 652, *Alcaligenes eutrophus*, *Clostridium*

*ragsdalei, Clostridium beijerinckii, Clostridium carboxidivorans, Thermoanaerobacter brockii, Thermoanaerobacter ethanolicus* (*Clostridium thermohydrosulfuricum*), *Rhodococcus ruber, Methanobacterium palustre*, methanogenic archaea *Methanogenium* liminatans, parasitic protist *Entamoeba histolytica*, parasitic protozoan *Tritrichomonas foetus* and human parasite *Trichomonas vaginalis*. In some embodiments, the one or more nucleic acid molecule encoding secondary alcohol dehydrogenase is adh, adhB, EhAdh1, or homolog thereof. In some embodiments, the S-ADH is predicted from homology and can be from *Thermoanaerobacter mathranii, Micrococcus luteus, Nocardiopsis alba, Mycobacterium hassiacum, Helicobacter suis, Candida albicans, Candida parapsilosis, Candida orthopsilosis, Candida metapsilosis, Grosmannia clavigera* and *Scheffersomyces stipitis*. In a further embodiment, the alcohol dehydrogenase comprises an amino acid sequence selected from the group consisting of SEQ ID NOs: 106 and 108. In yet another embodiment, the alcohol dehydrogenase is encoded by a nucleic acid sequence selected from the group consisting of SEQ ID NOs: 104, 105 and 107.

Recombinant Microorganism

The disclosure provides microorganisms that can be engineered to express various endogenous or exogenous enzymes.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*.

In some embodiments, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium*.

In some embodiments, the recombinant microorganism is used to produce monoethylene glycol (MEG) disclosed herein.

Accordingly, in another aspect, the present inventions provide a method of producing MEG and one or more three-carbon compounds using a recombinant microorganism described herein. In one embodiment, the method comprises cultivating the recombinant microorganism in a culture medium containing a feedstock providing a carbon source until MEG and one or more three-carbon compounds is produced. In a further embodiment, the MEG and one or more three-carbon compounds is recovered. Recovery can be by methods known in the art, such as distillation, membrane-based separation gas stripping, solvent extraction, and expanded bed adsorption. In an exemplary embodiment, the three carbon compound is selected from acetone, isopropanol, and propene.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In an exemplary embodiment, the carbon source is a sugar. In a further exemplary embodiment, the sugar is D-xylose. In alternative embodiments, the sugar is selected from the group consisting of glucose, fructose, and sucrose.

Methods of Producing a Recombinant Microorganism that Produces or Accumulates MEG and One or More Three-Carbon Compounds As discussed above, the present application provides a method of producing a recombinant microorganism that produces or accumulates MEG and one or more three-carbon compounds. In one embodiment, the MEG and one or more three-carbon compounds are co-produced from xylose. In another embodiment, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylulose-5-kinase and/or in a gene encoding a glycoaldehyde dehydrogenase. In some embodiments, the gene encoding the D-xylulose-5-kinase is xylB. In some embodiments, the gene encoding the glycoaldehyde dehydrogenase is aldA.

In one embodiment, MEG is produced from xylose via ribulose-1-phosphate. In another embodiment, MEG is produced from xylose via xylulose-1-phosphate. In a further embodiment, MEG is produced from xylose via xylonate.

In one embodiment, one or more three-carbon compounds is produced from DHAP or pyruvate. In one embodiment, the one or more three-carbon compounds is acetone. In another embodiment, the one or more three-carbon compounds is isopropanol. In a further embodiment, the one or more three-carbon compounds is propene.

As discussed above, in one aspect, the present disclosure provides a method of producing a recombinant microorganism that produces or accumulates MEG and acetone from exogenous D-xylose, comprising introducing into the recombinant microorganism and/or overexpressing one or more of the following:

(a) at least one endogenous or exogenous nucleic acid molecule encoding a D-tagatose 3-epimerase that catalyzes the conversion of D-xylulose to D-ribulose;

(b) at least one endogenous or exogenous nucleic acid molecule encoding a D-ribulokinase that catalyzes the conversion of D-ribulose from (a) to D-ribulose-1-phosphate;

(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

(d) at least one endogenous or exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate; and/or (g) at least one endogenous or exogenous nucleic acid molecule encoding an acetoacetate decarboxylase that catalyzes the conversion of acetoacetate from (f) to acetone;

wherein the produced intermediate DHAP is converted to acetyl-CoA through the endogenous glycolysis pathway in the microorganism, and wherein MEG and acetone are co-produced.

In one embodiment, the D-tagatose 3-epimerase is encoded by one or more nucleic acid molecules obtained from a microorganism selected from the group consisting of *Pseudomonas* sp., *Mesorhizobium* sp. and *Rhodobacter* sp. In some embodiments, the D-tagatose 3-epimerase is encoded by one or more nucleic acid molecules obtained from a microorganism selected from the group consisting of *Pseudomonas cichorii, Pseudomonas* sp. ST-24, *Mesorhizobium loti* and *Rhodobacter sphaeroides*. In some embodiments, the one or more nucleic acid molecules is dte and/or FJ851309.1, or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

In one embodiment, the D-ribulokinase is encoded by one or more nucleic acid molecules obtained from *E. coli*. In some embodiments, the one or more nucleic acid molecules is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

In one embodiment, the D-ribulose-1-phosphate aldolase is encoded by one or more nucleic acid molecules obtained from *E. coli*. In some embodiments, the one or more nucleic acid molecules is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (g) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:
(a) a deletion, insertion, or loss of function mutation in a gene encoding a D-xylulose-5-kinase that catalyzes the conversion of D-xylulose to D-xylulose-5-phosphate;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

As discussed above, in another aspect, the present disclosure provides a method of producing a recombinant microorganism that produces or accumulates MEG and acetone from exogenous D-xylose, comprising introducing into the recombinant microorganism and/or overexpressing one or more of the following:
(a) at least one endogenous or exogenous nucleic acid molecule encoding a D-xylulose 1-kinase that catalyzes the conversion of D-xylulose to D-xylulose-1-phosphate,
(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);
(c) at least one endogenous or exogenous nucleic acid molecule encoding a glycolaldehyde reductase that catalyzes the conversion of glycolaldehyde from (b) to MEG;
(d) at least one endogenous or exogenous nucleic acid molecule encoding a thiolase that catalyzes the conversion of acetyl-CoA to acetoacetyl-CoA;
(e) at least one endogenous or exogenous nucleic acid molecule encoding an acetate:acetoacetyl-CoA transferase or hydrolase that catalyzes the conversion of acetoacetyl-CoA from (d) to acetoacetate; and/or
(f) at least one endogenous or exogenous nucleic acid molecule encoding an acetoacetate decarboxylase that catalyzes the conversion of acetoacetate from (e) to acetone;
wherein the produced intermediate DHAP is converted to acetyl-CoA through the endogenous glycolysis pathway in the microorganism, and wherein MEG and acetone are co-produced.

In one embodiment, the D-xylulose 1-kinase is encoded by one or more nucleic acid molecules obtained from *Homo sapiens*. In some embodiments, the one or more nucleic acid molecules encoding the D-xylulose 1-kinase is ketohexokinase C (khk-C), or homolog thereof. In another embodiment, the one or more nucleic acid molecules encoding the D-xylulose 1-kinase comprises an amino acid sequence set forth in SEQ ID NO: 55. In a further embodiment, the one or more nucleic acid molecules encoding the D-xylulose 1-kinase is encoded by a nucleic acid sequence selected from the group consisting of SEQ ID NOs: 53 and 54.

In one embodiment, the D-xylulose-1-phosphate aldolase is encoded by one or more nucleic acid molecules obtained from *Homo sapiens*. In another embodiment, the one or more nucleic acid molecules encoding the D-xylulose-1-phosphate aldolase is aldolase B (ALDOB), or homolog thereof. In some embodiments, the one or more nucleic acid molecules encoding the D-xylulose-1-phosphate aldolase comprises an amino acid sequence set forth in SEQ ID NO: 58. In some embodiments, the one or more nucleic acid molecules encoding the D-xylulose-1-phosphate aldolase is encoded by a nucleic acid sequence selected from the group consisting of SEQ ID NOs: 56 and 57.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (f) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:
(a) a deletion, insertion, or loss of function mutation in a gene encoding a D-xylulose-5-kinase that catalyzes the conversion of D-xylulose to D-xylulose-5-phosphate;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

In some embodiments of any aspect disclosed above, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate. In some embodiments, the D-xylulose-5-kinase is from *Escherichia coli*. In some embodiments, the D-xylulose-5-kinase is encoded by the xylB gene, or homolog thereof.

In some embodiments of any aspect disclosed above, a method of producing a recombinant microorganism that produces or accumulates MEG and one or more three-carbon compounds from exogenous D-xylose comprises introducing into the recombinant microorganism a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In some embodiments, the glycolaldehyde dehydrogenase is from *Escherichia coli*. In some embodiments, the glycolaldehyde dehydrogenase is encoded by the aldA gene, or homolog thereof.

In some embodiments of any aspect disclosed above, a method of producing a recombinant microorganism that produces or accumulates MEG and one or more three-carbon compounds from exogenous D-xylose comprises introducing into the recombinant microorganism a deletion, insertion, or loss of function mutation in a gene encoding a lactate dehydrogenase to prevent the production of lactate from pyruvate and instead shunt the reaction toward production of one or more three-carbon compounds. In some embodiments, the lactate dehydrogenase is from *Escherichia coli*. In some embodiments, the lactate dehydrogenase is encoded by the ldhA gene, or homolog thereof.

As discussed above, in another aspect, the present disclosure provides a method of producing a recombinant microorganism that produces or accumulates MEG and acetone from exogenous D-xylose and glucose, comprising introducing into the recombinant microorganism and/or overexpressing one or more of the following:
(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;
(b) at least one exogenous nucleic acid molecule encoding a D-xylose isomerase that catalyzes the conversion of D-xylose to D-xylulose, and
wherein the method further comprises introducing into the recombinant microorganism and/or overexpressing one or more of the following:
(c) at least one endogenous or exogenous nucleic acid molecule encoding a D-tagatose 3-epimerase that catalyzes the conversion of D-xylulose from (a) or (b) to D-ribulose;
(d) at least one endogenous or exogenous nucleic acid molecule encoding a D-ribulokinase that catalyzes the conversion of D-ribulose from (c) to D-ribulose-1-phosphate;
(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);
(f) at least one endogenous or exogenous nucleic acid molecule encoding a glycolaldehyde reductase or methylglyoxal reductase that catalyzes the conversion of glycolaldehyde from (e) to MEG;
(g) at least one endogenous or exogenous nucleic acid molecule encoding a thiolase that catalyzes the conversion of acetyl-CoA to acetoacetyl-CoA;
(h) at least one endogenous or exogenous nucleic acid molecule encoding an acetate:acetoacetyl-CoA transferase or hydrolase that catalyzes the conversion of acetoacetyl-CoA from (g) to acetoacetate; and/or
(i) at least one endogenous or exogenous nucleic acid molecule encoding an acetoacetate decarboxylase that catalyzes the conversion of acetoacetate from (h) to acetone;
wherein the produced intermediate DHAP is converted to acetyl-CoA through the endogenous glycolysis pathway in the microorganism, and wherein MEG and acetone are co-produced.

In some embodiments, the xylose reductase or aldose reductase is encoded by one or more nucleic acid molecules obtained from a microorganism selected from the group consisting of *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the xylose reductase or aldose reductase is encoded by one or more nucleic acid molecules obtained from a microorganism selected from the group consisting of *Hypocrea jecorina*, *Scheffersomyces stipitis*, *Saccharomyces cerevisiae*, *Pachysolen tannophilus*, *Pichia stipitis*, *Pichia quercuum*, *Candida shehatae*, *Candida tenuis*, *Candida tropicalis*, *Aspergillus niger*, *Neurospora crassa* and *Cryptococcus lactativorus*. In another embodiment, the one or more nucleic acid molecules encoding the xylose reductase or aldose reductase is xyl1 and/or GRE3 or homolog thereof. In some embodiments, the one or more nucleic acid molecules encoding the xylose reductase or aldose reductase comprises an amino acid sequence selected from the group consisting of SEQ ID NOs: 84 and 87. In some embodiments, the one or more nucleic acid molecules encoding the xylose reductase or aldose reductase is encoded by a nucleic acid sequence selected from the group consisting of SEQ ID NOs: 82, 83, 85 and 86.

In one embodiment of any aspect disclosed above, the xylitol dehydrogenase is encoded by one or more nucleic acid molecules obtained from a microorganism selected from the group consisting of *Scheffersomyces* sp., *Trichoderma* sp., *Pichia* sp., *Saccharomyces* sp., *Gluconobacter* sp., *Galactocandida* sp., *Neurospora* sp., and *Serratia* sp. In another embodiment, the xylitol dehydrogenase is encoded by one or more nucleic acid molecules obtained from a microorganism selected from the group consisting of *Scheffersomyces stipitis, Trichoderma reesei, Pichia stipitis, Saccharomyces cerevisiae, Gluconobacter oxydans, Galactocandida mastotermitis, Neurospora crassa* and *Serratia marcescens*. In another embodiment, the one or more nucleic acid molecules encoding the xylitol dehydrogenase is xyl2 and/or xdh1, or homolog thereof. In some embodiments, the one or more nucleic acid molecules encoding the xylitol dehydrogenase comprises an amino acid sequence selected from the group consisting of SEQ ID NOs: 90 and 92. In some embodiments, the one or more nucleic acid molecules encoding the xylitol dehydrogenase is encoded by a nucleic acid sequence selected from the group consisting of SEQ ID NOs: 88, 89 and 91.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (i) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:
(a) a deletion, insertion, or loss of function mutation in a gene encoding a D-xylulose-5-kinase that catalyzes the conversion of D-xylulose to D-xylulose-5-phosphate; and
(b) a deletion, insertion, or loss of function mutation in a gene encoding an alkaline phosphatase that catalyzes the conversion of D-xylulose-5-phosphate to D-xylulose.

In one embodiment, the enzyme that catalyzes the conversion of D-xylulose to D-xylulose-5-phosphate is a D-xylulose-5-kinase. In some embodiments, the D-xylulose-5-kinase is from *Saccharomyces cerevisiae*. In some embodiments the D-xylulose-5-kinase is encoded by the XKS1 gene, or homolog thereof. In some embodiments, the D-xylulose-5-kinase is from *Pichia stipitis*. In some embodiments the D-xylulose-5-kinase is encoded by the XYL3 gene, or homolog thereof.

In a further embodiment, the microorganism is a fungus.

As discussed above, in another aspect, the present application provides a method of producing a recombinant microorganism that produces or accumulates MEG and acetone from exogenous D-xylose, comprising introducing into the recombinant microorganism and/or overexpressing one or more of the following:
(a) at least one endogenous or exogenous nucleic acid molecule encoding a xylose dehydrogenase that catalyzes the conversion of D-xylose to D-xylonolactone;
(b) at least one endogenous or exogenous nucleic acid molecule encoding a xylonolactonase that catalyzes the conversion of D-xylonolactone from (a) to D-xylonate;
(c) at least one endogenous or exogenous nucleic acid molecule encoding a xylonate dehydratase that catalyzes the conversion of D-xylonate from (b) to 2-keto-3-deoxy-xylonate;
(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;
(e) at least one endogenous or exogenous nucleic acid molecule encoding a glycolaldehyde reductase that catalyzes the conversion of glycolaldehyde from (d) to MEG;
(f) at least one exogenous nucleic acid molecule encoding a thiolase that catalyzes the conversion of acetyl-CoA to acetoacetyl-CoA;
(g) at least one endogenous or exogenous nucleic acid molecule encoding an acetate:acetoacetyl-CoA transferase or hydrolase that catalyzes the conversion of acetoacetyl-CoA from (f) to acetoacetate; and/or
(h) at least one exogenous nucleic acid molecule encoding an acetoacetate decarboxylase that catalyzes the conversion of acetoacetate from (g) to acetone;
wherein the produced intermediate pyruvate is converted to acetyl-CoA through the endogenous glycolysis pathway in the microorganism, and wherein MEG and acetone are co-produced.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the xylonolactonase is encoded by one or more nucleic acid molecules obtained from a microorganism selected from *Caulobacter* sp. and *Haloferax* sp. In another embodiment, the xylonolactonase is encoded by one or more nucleic acid molecules obtained from a microorganism selected from the group consisting of *Caulobacter crescentus, Haloferax volcanii* and *Haloferax gibbonsii*. In some embodiments, the one or more nucleic acid molecules encoding the xylonolactonase is xylC, or homolog thereof. In a further embodiment, the one or more nucleic acid molecules encoding the xylonolactonase comprises an amino acid sequence set forth in SEQ ID NO: 67. In yet another embodiment, the one or more nucleic acid molecules encoding the xylonolactonase is encoded by a nucleic acid sequence set forth in SEQ ID NO: 66.

In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (h) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:

(a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylose isomerase to prevent conversion of D-xylose to D-xylulose and instead shunt the reaction toward the conversion of D-xylose to D-xylonate. In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In one embodiment, the glycolaldehyde dehydrogenase is from *Escherichia coli*. In some embodiments, the glycolaldehyde dehydrogenase is encoded by the aldA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a lactate dehydrogenase to prevent the production of lactate from pyruvate and instead shunt the reaction toward production of one or more three-carbon compounds. In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

As discussed above, in another aspect, the present application provides a method of producing a recombinant microorganism that produces or accumulates MEG and acetone from exogenous D-xylose, comprising introducing into the recombinant microorganism and/or overexpressing one or more of the following:

(a) at least one endogenous or exogenous nucleic acid molecule encoding a xylose dehydrogenase that catalyzes the conversion of D-xylose to D-xylonate;

(b) at least one endogenous or exogenous nucleic acid molecule encoding a xylonate dehydratase that catalyzes the conversion of D-xylonate from (a) to 2-keto-3-deoxy-xylonate;

(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;

(d) at least one exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate; and/or (g) at least one exogenous nucleic acid molecule encoding an acetoacetate decarboxylase that catalyzes the conversion of acetoacetate from (f) to acetone;

wherein the produced intermediate pyruvate is converted to acetyl-CoA through the endogenous glycolysis pathway in the microorganism, and wherein MEG and acetone are co-produced.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus*, *Haloarcula marismortui*, *Haloferax volcanii*, *Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus*, *Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (g) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:

(a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylose isomerase to prevent conversion of D-xylose to D-xylulose and instead shunt the reaction toward the conversion of D-xylose to D-xylonate. In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In one embodiment, the glycolaldehyde dehydrogenase is from *Escherichia coli*. In some embodiments, the glycolaldehyde dehydrogenase is encoded by the aldA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a lactate dehydrogenase to prevent the production of lactate from pyruvate and instead shunt the reaction toward production of one or more three-carbon compounds. In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

In one embodiment of any aspect disclosed above, the glycolaldehyde reductase is encoded by one or more nucleic acid molecules obtained from a microorganism selected from *E. coli* and *S. cerevisiae*. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment of any aspect disclosed above, the thiolase or acetyl coenzyme A acetyltransferase is encoded by one or more nucleic acid molecules obtained from a microorganism selected from the group consisting of *Clostridium* sp., *Bacillus* sp., *E. coli*, *Saccharomyces* sp. and *Marinobacter* sp. In some embodiments, the thiolase or acetyl coenzyme A acetyltransferase is encoded by one or more nucleic acid molecules obtained from a microorganism selected from the group consisting of *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the one or more nucleic acid molecules is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment of any aspect disclosed above, the acetyl-CoA:acetoacetate-CoA transferase or acetate:acetoacetyl-CoA hydrolase is encoded by one or more nucleic acid molecules obtained from a microorganism selected from *Clostridium* sp. and *E. coli*. In another embodiment, the acetyl-CoA:acetoacetate-CoA transferase or acetate:acetoacetyl-CoA hydrolase is encoded by one or more nucleic acid molecules obtained from *E. coli*. In some embodiments, the one or more nucleic acid molecules encoding the acetyl-CoA:acetoacetate-CoA transferase is atoA and/or atoD, or homolog thereof. In another embodiment, the acetyl-CoA:acetoacetate-CoA transferase or acetate:acetoacetyl-CoA hydrolase is encoded by one or more nucleic acid molecules obtained from *Clostridium acetobutylicum*. In some embodiments, the one or more nucleic acid molecules encoding the acetate:acetoacetyl-CoA hydrolase is ctfA and/or ctfB, or homolog thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment of any aspect disclosed above, the acetoacetate decarboxylase is encoded by one or more nucleic acid molecules obtained from a microorganism selected from the group consisting of *Clostridium* sp., *Bacillus* sp., *Chromobacterium* sp. and *Pseudomonas* sp. In another embodiment, the acetoacetate decarboxylase is encoded by one or more nucleic acid molecules obtained from a microorganism selected from the group consisting of *Clostridium acetobutylicum*, *Clostridium beijerinckii*, *Clostridium cellulolyticum*, *Bacillus polymyxa*, *Chromobacterium violaceum* and *Pseudomonas putida*. In some embodiments, the one or more nucleic acid molecules encoding the acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment of any aspect disclosed above, the enzyme that catalyzes the conversion of acetone to isopropanol is a secondary alcohol dehydrogenase (S-ADH). In another embodiment, the enzyme is a secondary alcohol dehydrogenase that is encoded by a nucleic acid molecule obtained from a microorganism selected from *Burkholderia* sp, *Alcaligenes* sp., *Clostridium* sp., *Thermoanaerobacter* sp., *Phytomonas* sp., *Rhodococcus* sp., *Methanobacterium* sp., *Methanogenium* sp., *Entamoeba* sp., *Trichomonas* sp., and *Tritrichomonas* sp. In some embodiments, the nucleic acid molecule encoding the secondary alcohol dehydrogenase is obtained from a microorganism selected from *Burkholderia* sp. AIU 652, *Alcaligenes eutrophus*, *Clostridium ragsdalei*, *Clostridium beijerinckii*, *Clostridium carboxidivorans*, *Thermoanaerobacter brockii*, *Thermoanaerobacter ethanolicus* (*Clostridium thermohydrosulfuricum*), *Rhodococcus ruber*, *Methanobacterium palustre*, methanogenic archaea *Methanogenium liminatans*, parasitic protist *Entamoeba histolytica*, parasitic protozoan *Tritrichomonas foetus* and human parasite *Trichomonas vaginalis*. In some embodiments, the one or more nucleic acid molecule encoding secondary alcohol dehydrogenase is adh, adhB, EhAdh1, or homolog thereof. In some embodiments, the S-ADH is predicted from homology and can be from *Thermoanaerobacter mathranii*, *Micrococcus luteus*, *Nocardiopsis alba*, *Mycobacterium hassiacum*, *Helicobacter suis*, *Candida albicans*, *Candida parapsilosis*, *Candida orthopsilosis*, *Candida metapsilosis*, *Grosmannia clavigera* and *Scheffersomyces stipitis*. In a further embodiment, the alcohol dehydrogenase comprises an amino acid sequence selected from the group consisting of SEQ ID NOs: 106 and 108. In yet another embodiment, the alcohol dehydrogenase is encoded by a nucleic acid sequence selected from the group consisting of SEQ ID NOs: 104, 105 and 107.

Enzyme Engineering

The enzymes in the recombinant microorganism can be engineered to improve one or more aspects of the substrate to product conversion. Non-limiting examples of enzymes that can be further engineered for use in methods of the disclosure include an aldolase, an aldehyde reductase, an acetoacetyl coenzyme A hydrolase, a xylose isomerase, a xylitol dehydrogenase and combinations thereof. These enzymes can be engineered for improved catalytic activity, improved selectivity, improved stability, improved tolerance to various fermentation conditions (temperature, pH, etc.), or improved tolerance to various metabolic substrates, products, by-products, intermediates, etc. The term "improved catalytic activity" as used herein with respect to a particular enzymatic activity refers to a higher level of enzymatic activity than that measured relative to a comparable non-engineered enzyme.

For example, engineering methods have been used to alter the stability, substrate specificity and stereospecificity of aldolases to produce excellent enzymes for biocatalytic processes. The thermostability and solvent tolerance of fructose-1,6-bisphosphate aldolase (FBP-aldolase) was increased using family DNA shuffling of the fda genes from *Escherichia coli* and *Edwardsiella ictaluri*. A fourth generation variant was identified which displayed an average 280-fold higher half-life at 53° C. than either parent. The same variant also displayed enhanced activity in various polar and non-polar organic solvents (Hao and Berry 2004 Protein Eng Des Sel 17:689-697).

As another example, acetoacetyl coenzyme A hydrolase can convert acetoacetyl-CoA to acetoacetate. However, the hydrolase is unspecific in that it also reacts with the same magnitude of order with acetyl-CoA, which is the substrate required for acetoacetyl-CoA formation by the enzyme thiolase. Thus, to create more efficient acetoacetyl-CoA hydrolases, these enzymes have been engineered to have at least 10× higher activity for the acetoacetyl-CoA substrate than for acetyl-CoA substrate by replacing several glutamic acid residues in the enzyme beta subunit that is important for catalysis (WO 2015/042588).

As another example, the *E. coli* YqhD enzyme is a broad substrate aldehyde reductase with NADPH-dependent reductase activity for more than 10 aldehyde substrates and is a useful enzyme to produce biorenewable fuels and chemicals (Jarboe 2010 *Applied Microbiology and Biotechnology* 89:249). Though YqhD enzyme activity is beneficial through its scavenging of toxic aldehydes, the enzyme is also NADPH-dependent and contributes to NADPH depletion and growth inhibition of organisms. Error-prone PCR of YqhD was performed in order to improve 1,3-propanediol production from 3-hydroxypropionaldehyde (3-HPA). This directed engineering yielded two mutants, D99QN147H and Q202A, with decreased Km and increased kcat for certain aldehydes, particularly 3-HPA (Li et al. 2008 Prog. Nat. Sci. 18 (12):1519-1524). The improved catalytic activity of the D99QN147H mutant is consistent with what is known about the structure of YqhD (Sulzenbacher et al. 2004 J. Mol. Biol. 342 (2):489-502), as residues Asp99 and Asn147 both interact with NADPH. Use of the D99QN147H mutant increased 1,3-propanediol production from 3-HPA 2-fold. Mutant YqhD enzymes with increased catalytic efficiency (increased Kcat/Km) toward NADPH have also been described in WO 2011012697 A2, which is herein incorporated in its entirety.

As another example, xylose isomerase is a metal-dependent enzyme that catalyzes the interconversion of aldose and ketose sugars, primarily between xylose to xylulose and glucose to fructose. It has lower affinity for lyxose, arabinose and mannose sugars. The hydroxyl groups of sugars may define the substrate preference of sugar isomerases. The aspartate at residue 256 of *Thermus thermophilus* xylose isomerase was replaced with arginine (Patel et al. 2012 Protein Engineering, Design & Selection vol. 25 no. 7 pp. 331-336). This mutant xylose isomerase exhibited an increase in specificity for D-lyxose, L-arabinose and D-mannose. The catalytic efficiency of the D256R xylose isomerase mutant was also higher for these 3 substrates compared to the wild type enzyme. It was hypothesized that the arginine at residue 256 in the mutant enzyme may play a role in the catalytic reaction or influence changes in substrate orientation.

As another example, the enzyme xylitol dehydrogenase plays a role in the utilization of xylose along with xylose reductase. Xylose reductase (XR) reduces xylose to xylitol and then xylitol dehydrogenase (XDH) reoxidizes xylitol to form xylulose. However, since XR prefers NADPH as cosubstrate, while XDH exclusively uses NAD+ as cosubstrate, a cosubstrate recycling problem is encountered. One solution is to engineer XDH such that its cosubstrate specificity is altered from NAD+ to NADP+ (Ehrensberger et al. 2006 Structure 14: 567-575). A crystal structure of the *Gluconobacter oxydans* holoenzyme revealed that Asp38 is largely responsible for the NAD+ specificity of XDH. Asp38 interacts with the hydroxyls of the adenosine ribose, and Met39 stacks under the purine ring and is also located near the 2' hydroxyl. A double mutant (D38S/M39R) XDH was constructed that exclusively used NADP+ without loss of enzyme activity.

Metabolic Engineering—Enzyme Overexpression or Enzyme Downregulation/Deletion for Increased Pathway Flux In various embodiments described herein, the exogenous and endogenous enzymes in the recombinant microorganism participating in the biosynthesis pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, a recombinant microorganism of the disclosure is generated from a host that contains the enzymatic capability to synthesize substrates such as D-xylulose, D-ribulose, D-ribulose-1-phosphate, D-xylulose-1-phosphate, D-xylonolactone, D-xylonate, 2-keto-3-deoxy-xylonate, glycolaldehyde, DHAP, pyruvate, acetoacetyl-CoA or acetoacetate. In some embodiments, it can be useful to increase the synthesis or accumulation of, for example, D-xylulose, D-ribulose, D-ribulose-1-phosphate, D-xylulose-1-phosphate, D-xylonolactone, D-xylonate, 2-keto-3-deoxy-xylonate, glycolaldehyde, DHAP, pyruvate, acetoacetyl-CoA or acetoacetate, to increase the production of MEG and one or more three-carbon compounds.

In some embodiments, it may be useful to increase the expression of endogenous or exogenous enzymes involved in the MEG and three-carbon compound biosynthesis pathways to increase flux from, for example, D-xylulose, D-ribulose, D-ribulose-1-phosphate, D-xylulose-1-phosphate, D-xylonolactone, D-xylonate, 2-keto-3-deoxy-xylonate, glycolaldehyde, DHAP, pyruvate, acetoacetyl-CoA or acetoacetate, thereby resulting in increased synthesis or accumulation of MEG and one or more three-carbon compounds.

Increased synthesis or accumulation can be accomplished by, for example, overexpression of nucleic acids encoding one or more of the above-described MEG and three-carbon compound biosynthesis pathway enzymes. Overexpression of a MEG and three-carbon compound biosynthesis pathway enzyme or enzymes can occur, for example, through increased expression of an endogenous gene or genes, or through the expression, or increased expression, of an exogenous gene or genes. Therefore, naturally occurring organisms can be readily modified to generate non-natural, MEG and three-carbon compound producing microorganisms through overexpression of one or more nucleic acid molecules encoding a MEG and three-carbon compound biosynthesis pathway enzyme. In addition, a non-naturally occurring organism can be generated by mutagenesis of an endogenous gene that results in an increase in activity of an enzyme in the MEG and three-carbon compound biosynthesis pathways.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding a MEG and three-carbon compound biosynthesis pathway enzyme in sufficient amounts to produce MEG and one or more three-carbon compounds.

Methods for constructing and testing the expression levels of a non-naturally occurring MEG and three-carbon compound-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more MEG and three-carbon compound biosynthesis pathway enzymes encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218).

Those of skill in the art will recognize that, due to the degenerate nature of the genetic code, a variety of nucleic acid sequences can be used to encode a given enzyme of the disclosure. The nucleic acid sequences encoding the biosynthetic enzymes are referenced herein merely to illustrate an embodiment of the disclosure, and the disclosure includes any nucleic acid sequences that encode the amino acid sequences of the polypeptides and proteins of the enzymes of the present disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the nucleic acid sequences shown herein merely illustrate embodiments of the disclosure.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., Science, 236: 1237-1245 (1987)). Exemplary expression control sequences are described in, for example, Goeddel, *Gene Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes that catalyzes a reaction in a pathway that competes with the biosynthesis pathway for the production of MEG and one or more three-carbon compounds.

In some embodiments, the recombinant microorganism is manipulated to delete, disrupt, mutate, and/or reduce the activity of one or more endogenous enzymes that catalyzes the conversion of D-xylulose to D-xylulose-5-phosphate. In some such embodiments, the enzyme that catalyzes the conversion of D-xylulose to D-xylulose-5-phosphate is a D-xylulose-5-kinase. In some embodiments, the D-xylulose-5-kinase is from *Escherichia coli*. In some embodiments, the D-xylulose-5-kinase is encoded by the xylB gene or homologs thereof. In some embodiments, the manipulation prevents the conversion of D-xylulose to D-xylulose-5-phosphate and instead shunts the reaction toward conversion of D-xylulose to D-xylulose-1-phosphate.

In some embodiments, the recombinant microorganism is manipulated to delete, disrupt, mutate, and/or reduce the activity of one or more endogenous enzymes that catalyzes the conversion of glycolaldehyde to glycolic acid. In some such embodiments, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene or homologs thereof. In some embodiments, the manipulation prevents the production of glycolic acid from glycolaldehyde and instead shunts the reaction toward conversion of glycolaldehyde to MEG.

In some embodiments, the recombinant microorganism is manipulated to delete, disrupt, mutate, and/or reduce the activity of one or more endogenous enzymes that catalyzes the conversion of pyruvate to lactate. In some such embodiments, the enzyme that catalyzes the conversion of pyruvate to lactate is a lactate dehydrogenase. In some embodiments, the lactate dehydrogenase is from *Escherichia coli*. In some embodiments, the lactate dehydrogenase is encoded by the ldhA gene or homologs thereof. In some embodiments, the manipulation prevents the production of lactate from pyruvate and instead shunts the reaction toward production of a three-carbon compound.

In some embodiments, the recombinant microorganism is manipulated to delete, disrupt, mutate, and/or reduce the activity of one or more endogenous enzymes that catalyzes the conversion of D-xylulose to D-xylulose-5-phosphate. In some such embodiments, the enzyme that catalyzes the conversion of D-xylulose to D-xylulose-5-phosphate is a D-xylulose-5-kinase. In some embodiments, the D-xylulose-5-kinase is from *Saccharomyces cerevisiae*. In some embodiments the D-xylulose-5-kinase is encoded by the XKS1 gene or homologs thereof. In some embodiments, the D-xylulose-5-kinase is from *Pichia stipitis*. In some embodiments the D-xylulose-5-kinase is encoded by the XYL3 gene or homologs thereof. In some embodiments, the manipulation prevents the conversion of D-xylulose to D-xylulose-5-phosphate and instead shunts the reaction toward conversion of D-xylulose to D-xylulose-1-phosphate.

In some embodiments, the recombinant microorganism is manipulated to delete, disrupt, mutate, and/or reduce the activity of one or more endogenous enzymes that catalyzes the conversion of D-xylulose-5-phosphate to D-xylulose. In some such embodiments, the enzyme that catalyzes the conversion of D-xylulose-5-phosphate to D-xylulose is an alkaline phosphatase. In some embodiments, the alkaline phosphatase is from *S. cerevisiae*. In some embodiments, the alkaline phosphatase is encoded by the PHO13 gene or homologs thereof. In some embodiments, the manipulation prevents the conversion of D-xylulose-5-phosphate to D-xylulose.

In some embodiments, the recombinant microorganism is manipulated to delete, disrupt, mutate, and/or reduce the activity of one or more endogenous enzymes that catalyzes the conversion of D-xylose to D-xylulose. In some such embodiments, the enzyme that catalyzes the conversion of D-xylose to D-xylulose is a D-xylose isomerase. In some embodiments, the D-xylose isomerase is from *E. coli*. In some embodiments, the D-xylose isomerase is encoded by the xylA gene or homologs thereof. In some embodiments, the manipulation prevents conversion of D-xylose to D-xylulose and instead shunts the reaction toward the conversion of D-xylose to D-xylonate.

EXAMPLES

Example 1a. Production of Ethylene Glycol in *E. coli*

Figure 7:
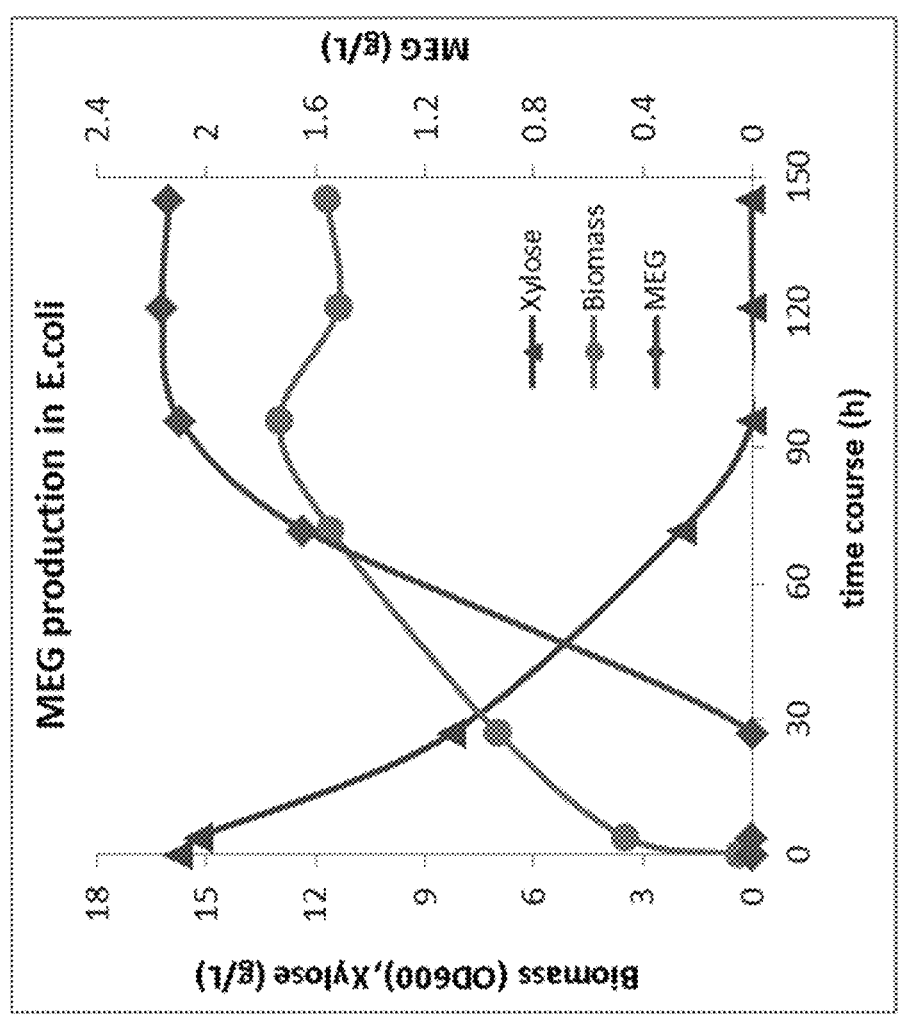
FIG. 7 illustrates MEG production from xylose in *E. coli*.

The *E. coli* K12 strain MG1655 was used as host for the deletion of two genes that could divert the carbon flux from MEG+IPA pathway: aldA and xylB. The genes were successfully deleted and deletion confirmed by sequencing. A plasmid containing the dte gene, encoding the first enzyme of the pathway (D-tagatose 3-epimerase, SEQ ID NO: 3, encoded by nucleic acid sequence SEQ ID NO: 2), was expressed under the control of the proD promoter in a pUC vector backbone. The plasmid was constructed using the MoClo system and confirmed by sequencing. The confirmed plasmid was transformed in the deleted strain. Colonies from transformations were inoculated in 3 mL of LB media for pre-culture. After 16 hours of cultivation 10% of the pre-culture was transferred to 50 mL of LB media containing 15 g/L of xylose. The flasks were incubated at 37° C., 250 rpm until complete consumption of xylose. The initial OD of the cultivation was 0.4. Xylose was fully consumed after 96 hours of cultivation. Small amounts of MEG were detected after 27 hours of cultivation. The highest MEG concentration was measured after 100 hours of cultivation, reaching 2.1 g/L. The overall yield of MEG production was 13.7 wt % (FIG. 7).

Example 1 b. Improved Production of Ethylene Glycol in *E. coli*

Figure 8:
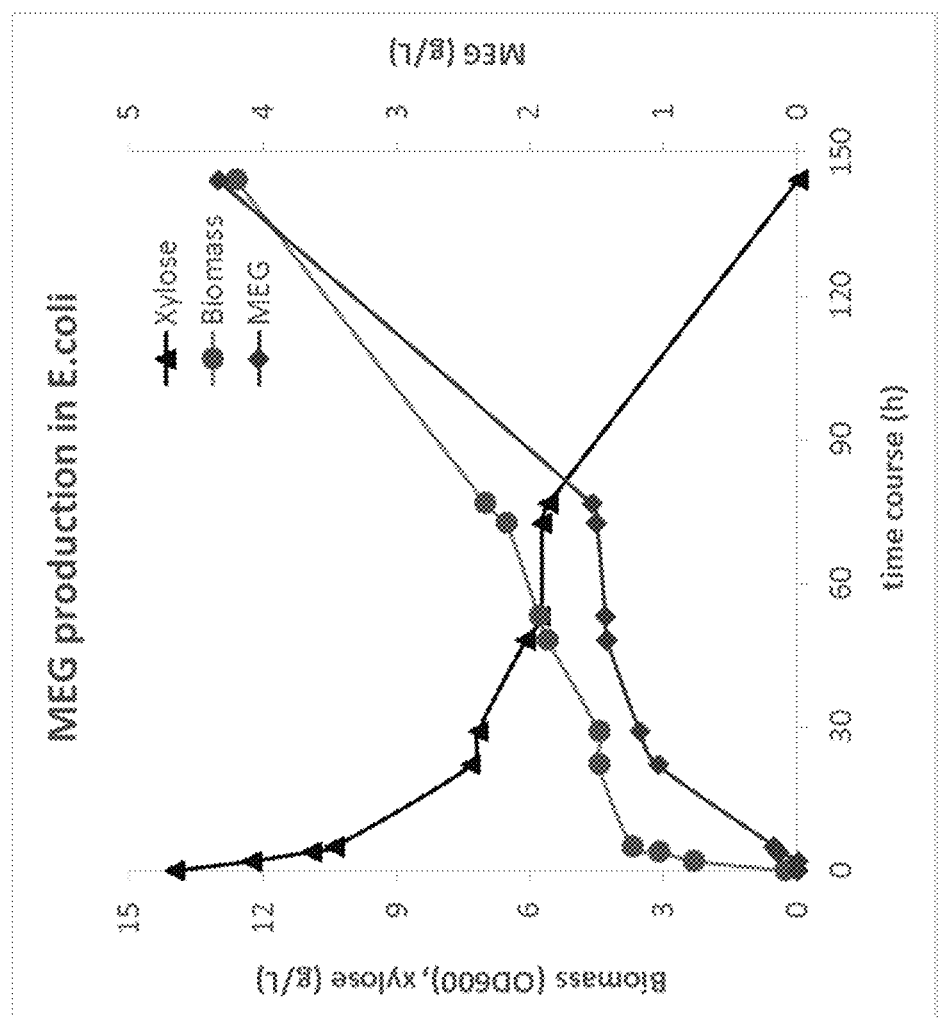
FIG. 8 illustrates improved MEG production from xylose in *E. coli*.

The *E. coli* K12 strain MG1655 with aldA and xylB genes deleted (same strains as example 1a) was used as host for the implementation of a complete MEG pathway. An operon containing dte (D-tagatose 3-epimerase enzyme, SEQ ID NO: 3, encoded by nucleic acid sequence SEQ ID NO: 2), fucA (D-ribulose-1-phosphate aldolase enzyme, SEQ ID NO: 11, encoded by nucleic acid sequence SEQ ID NO: 10), fucO (aldehyde reductase enzyme, SEQ ID NO: 28, encoded by nucleic acid sequence SEQ ID NO: 27) and fucK (D-ribulokinase enzyme, SEQ ID NO: 8, encoded by nucleic acid sequence SEQ ID NO: 7) genes under the control of the proD promoter was constructed in a pET28a backbone. The plasmid was constructed using In-fusion commercial kit and confirmed by sequencing. The confirmed plasmid was transformed in the MG1655 mutant strain. Colonies from transformation were inoculated in 3 mL of LB media for pre-culture. After 16 hours of cultivation, the pre-culture was transferred to 50 mL of LB media containing 15 g/L of xylose to an initial OD of 0.3. The flasks were incubated at 37° C., 250 rpm until complete consumption of xylose. After 4 hours of cultivation, approximately 100 mg/L of MEG could be detected. After 144 hours of cultivation, 4.3 g/L of MEG were produced and all xylose was consumed (FIG. 8). The overall yield and productivity were, respectively, 0.3 g/g and 0.03 g/L·h.

Example 2: Co-Production of Ethylene Glycol and Isopropanol in *Saccharomyces cerevisiae*

Figure 6:
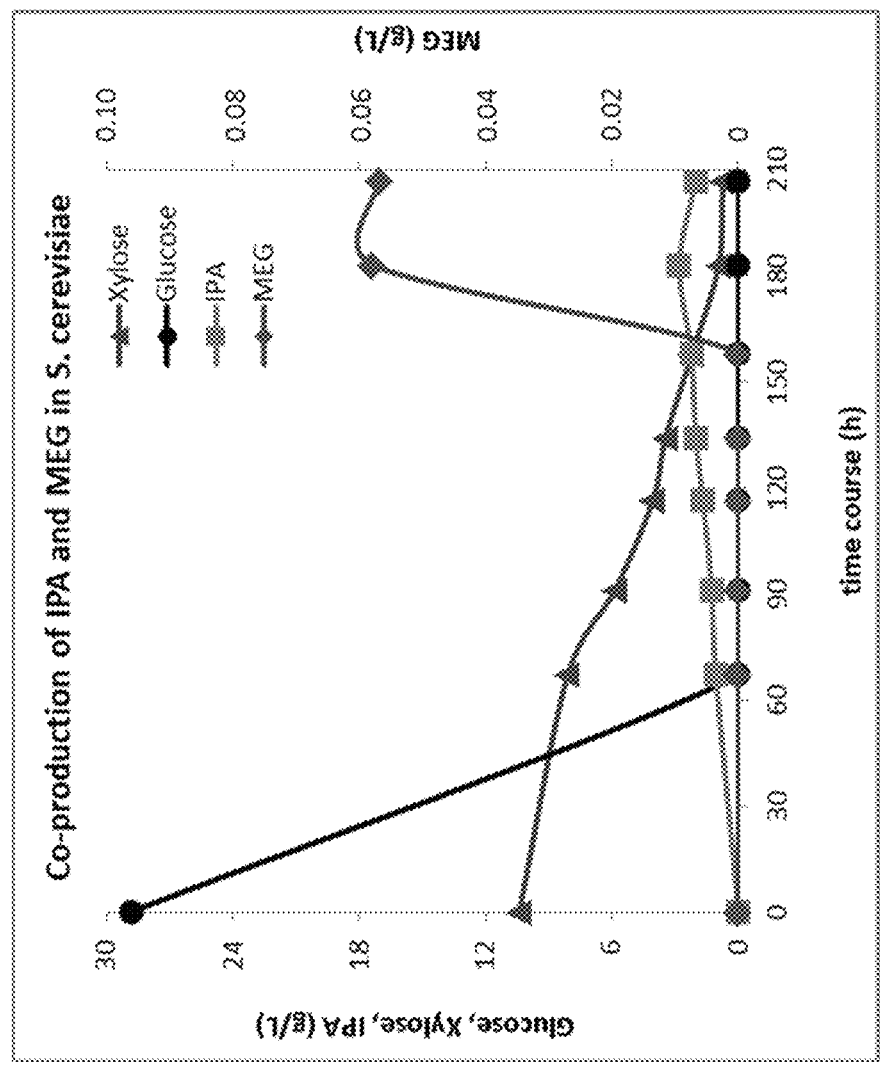
FIG. 6 illustrates MEG and isopropanol co-production from xylose and glucose in *S. cerevisiae*.

The *S. cerevisiae* laboratory strain BY4730, derived from S288c, was used as host for the expression of MEG+IPA pathways. The first step was the integration of the IPA pathway into the genome of S. cerevisiae. One copy of each gene was integrated by homologous recombination under the control of the following promoters: ADH1 for thl gene (thiolase, SEQ ID NO: 35, encoded by nucleic acid sequence SEQ ID NO: 34); TEF1 for atoA gene, PGK1 for atoD gene (acetate:acetoacetyl-CoA transferase, SEQ ID NOs: 43 and 46, encoded by nucleic acid sequences SEQ ID NOs: 42 and 45, respectively); TDH3 for adc gene (acetoacetate decarboxylase, SEQ ID NO: 49, encoded by nucleic acid sequence SEQ ID NO: 48); and TPI1 for adh gene (secondary alcohol dehydrogenase, SEQ ID NO: 106, encoded by nucleic acid sequence SEQ ID NO: 105). The integration was confirmed by PCR and sequencing. The second step was the introduction of genes capable of consuming xylose in the yeast genome. The pathway chosen for xylose consumption is composed of two genes: Xyl1 and Xyl2. Three copies of the Xyl1 gene (SEQ ID NO: 84, encoded by nucleic acid sequence SEQ ID NO: 83) under control of TEF1 promoter and three copies of the Xyl2 (SEQ ID NO: 90, encoded by nucleic acid sequence SEQ ID NO: 89) gene also under control of TEF1 promoter were integrated into the yeast genome through homologous recombination. The integration was confirmed by PCR and sequencing. The third step was the integration of the MEG pathway. Two copies of the D-tagatose 3-epimerase enzyme (dte gene, SEQ ID NO: 3, encoded by nucleic acid sequence SEQ ID NO: 2) under the control of TEF1 and TDH3 promoters, respectively, were integrated into the genome along with the following genes: one copy of fucO gene (glycolaldehyde reductase, SEQ ID NO: 28, encoded by nucleic acid sequence SEQ ID NO: 27) under control of the PGK1 promoter; one copy of the fucA gene (D-ribulose-phosphate aldolase, SEQ ID NO: 11, encoded by nucleic acid sequence SEQ ID NO: 10) using a PGK1 promoter and one copy of fucK gene (D-ribulokinase, SEQ ID NO: 8, encoded by nucleic acid sequence SEQ ID NO: 7) under a PGK1 promoter. The final strain was confirmed by PCR and sequencing. The strain was inoculated in YPD media containing 20 g/L of glucose and incubated at 30° C., 200 rpm. After 16 hours of growth, the pre-culture was inoculated in YPDX media containing 30 g/L of glucose and 10 g/L of xylose to an OD 2.0. The flasks were incubated at 30° C., 100 rpm. The typical behavior of C5 and C6 consumption in yeast was observed. 30 g/L of glucose was consumed in less than 60 hours, while 90% of the initial xylose was consumed only after 200 hours. The OD reached a value of 55 after 200 hours of cultivation. Isopropanol was already being produced in the initial 60 hours of cultivation, while MEG was only detected after 160 hours of cultivation. The highest co-production was obtained at 183 hours of cultivation, with 58 mg/L of MEG and 2.81 g/L of isopropanol. The overall yield for the co-production, from glucose and xylose, was 7.4% (FIG. 6).

Example 3. Co-Production of Ethylene Glycol (MEG), Acetone and Isopropanol (IPA) in E. coli Using Ribulose-1-Phosphate Pathway E. coli K12 strain MG1655 was used as host for the deletion of two genes that could divert the carbon flux from MEG+IPA pathway: aldA and xylB. The genes were successfully deleted and the deletion was confirmed by sequencing. Ribulose-1-phosphate pathway for MEG production was assembled in three different vectors backbones: pZA31, pZS*13 and pET28a. Production of MEG through ribulose-1-phosphate pathway requires the expression of four genes: dte (D-tagatose 3-epimerase enzyme), fucA (D-ribulose-1-phosphate aldolase enzyme), fucO (aldehyde reductase enzyme) and fucK (D-ribulokinase enzyme). dte gene was codon optimized for E. coli (Dte amino acid sequence set forth in SEQ ID NO: 3) and synthesized. All other genes are native from E. coli and were PCR amplified using the following primers: fucA and fucO (Forward Primer: CCTTTAATAAGGAGATATACCATG-GAACGAAATAAACTTGC (SEQ ID NO: 111) and Reverse Primer: GGTTATTCCTCCTTATT-TAGAGCTCTAAACGAATTCT-TACCAGGCGGTATGGTAA A (SEQ ID NO: 112)) and fucK (Forward Primer: GAATTCGTT-TAGAGCTCTAAATAAGGAGGAATAACCATGAT-GAAACAAGAAGTTA T (SEQ ID NO: 113) and Reverse Primer: GAGCT CGGTACCCGGGGATC-CAAAAAACCCCTCAAGACCC (SEQ ID NO: 114)). An operon containing dte (D-tagatose 3-epimerase enzyme), fucA (D-ribulose-1-phosphate aldolase enzyme), fucO (aldehyde reductase enzyme), fucK (D-ribulokinase enzyme) genes and T7 terminator under the control of proD promoter (constitutive promoter) was constructed in a pET28a backbone. For each gene a specific RBS sequence was utilized. The plasmid was constructed using In-fusion commercial kit and confirmed by sequencing. The entire operon under the control of proD promoter was subcloned in pZA31 and pZS*13 backbones using restriction-ligation methodology.

Isopropanol pathway was also assembled in three different vectors backbones: pZA31, pZS*13 and pET28a. Production of isopropanol requires the expression of five genes: thl (thiolase), atoA/D (acetate:acetoacetyl-CoA transferase), adc (acetoacetate decarboxylase) and adh (secondary alcohol dehydrogenase). AtoA/D gene is native from E. coli and was PCR amplified (Forward Primer: CTGTTGTTATAT-TGTAATGATGTATGCAAGAGGGATAAA (SEQ ID NO: 115) and Reverse Primer: TATATCTCCTTCTTAAAGTT-CATAAATCACCCCGTTGC (SEQ ID NO: 116)). thl (Thl amino acid sequence set forth in SEQ ID NO: 35), adc (Adc amino acid sequence set forth in SEQ ID NO: 49), and adh (Adh amino acid sequence set forth in SEQ ID NO: 106) were codon optimized for E. coli and synthesized. An operon containing thl (thiolase), adh (secondary alcohol dehydrogenase), adc (acetoacetate decarboxylase), atoA/D (acetate:acetoacetyl-CoA transferase) genes and T1 terminator under the control of the inducible promoter pLLacO was constructed in a pET28a backbone. For each gene a specific RBS sequence was utilized. The plasmid was constructed in several steps using both In-fusion commercial kit and restriction-ligation methodology. The correct assemble was confirmed by sequencing. The entire operon under the control of the inducible promoter pLLacO was subcloned in pZA31 and pZS*13 backbones using restriction-ligation methodology.

Several co-transformations of MEG and IPA plasmids were performed in the strains with xylB and aldA deleted to generate strains harboring all possible plasmid combinations. Table 2 describes the constructed strains.

TABLE 2

| Strain | Plasmids and pathways |
|---|---|
| 1 | MEG in pET28a and IPA in pZA31 |
| 2 | MEG in pET28a and IPA in pZS*13 |
| 3 | MEG in pZA31 and IPA in pZS*13 |
| 4 | MEG in pZA31 and IPA in pET28a1 |
| 5 | MEG in pZS*13 and IPA in pZA31 |
| 6 | MEG in pZS*13 and IPA in pET28a |

Colonies from transformations were inoculated in 3 mL of TB media for pre-culture. After 16 hours of cultivation, 100% of the pre-culture was transferred to 100 mL of TB media containing 15 g/L of xylose. The flasks were incubated at 37° C., 250 rpm until complete consumption of xylose. The initial OD of the cultivation was 0.3. For the induction of pLLacO promoter 1 mM of IPTG was added to the culture after 2 hours (OD=1).

Xylose was fully consumed after 32 hours of cultivation for strains 1 to 4. Strain 5 only consumed xylose completely after 55 hours and strain 6 was not able to consume all xylose after 144 hours.

Figure 9:
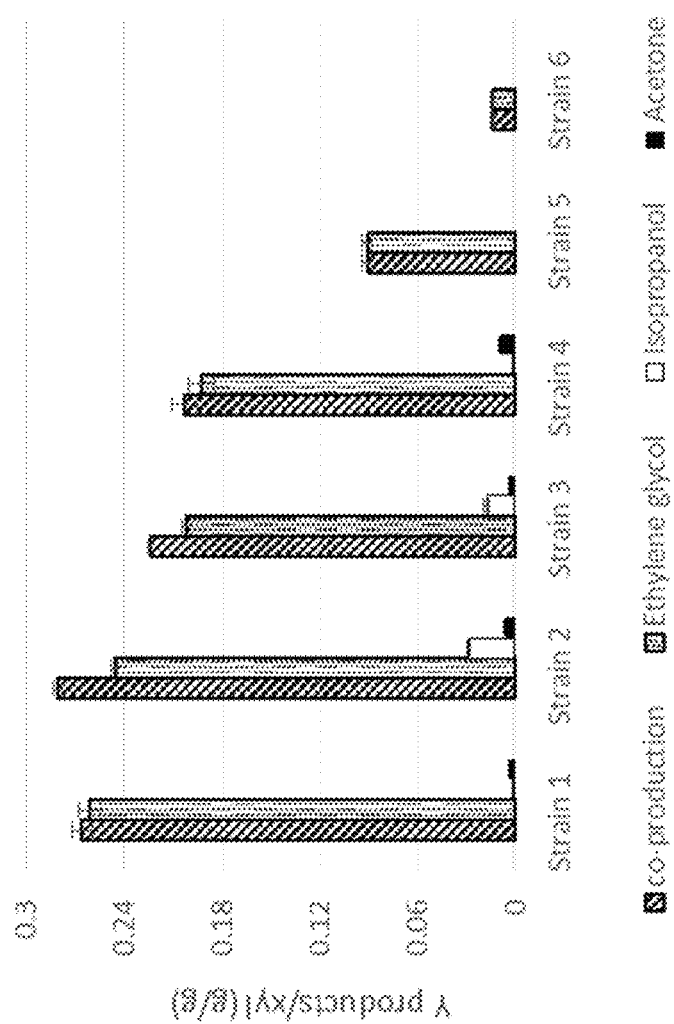
FIG. 9 illustrates overall yield (g products/g xylose) of ethylene glycol, isopropanol and/or acetone produced using a ribulose-1-phosphate pathway in six *E. coli* strains described in Example 3 and Table 2.

The overall yield of co-production was calculated considering the amount of ethylene glycol, isopropanol and acetone produced per gram of xylose consumed. The best yield was obtained after 48 hours of fermentation. The yield (g products/g xylose) of all strains is depicted in FIG. 9.

Strains 2 and 3 co-produced MEG, isopropanol and acetone while strains 1 and 4 co-produced only MEG and acetone. Strains 5 and 6 produced only MEG.

Strain 2 showed the highest overall yield (0.28 g/g), as well as the highest yield for ethylene glycol (0.25 g/g) and isopropanol (0.03 g/g) production. Strain 4 showed the highest yield for acetone production (0.01 g/g).

Example 4. Co-Production of Ethylene Glycol (MEG), Acetone and Isopropanol (IPA) in *E. coli* Using Xylulose-1-Phosphate Pathway

*E. coli* K12 strain MG1655 was used as host for the expression of MEG+IPA pathways. Two genes that could divert the carbon flux from MEG+IPA pathway were identified as target for deletion: aldA and xylB genes. A MEG pathway was integrated at xylB locus, enabling a stable integration concomitantly with xylB deletion. Production of MEG through xylulose-1-phosphate pathway requires the expression of three genes: khkC (D-xylulose-1-kinase enzyme), aldoB (D-xylulose-1-phosphate aldolase enzyme) and fucO (aldehyde reductase enzyme). khkC (KhkC amino acid sequence set forth in SEQ ID NO: 55) and aldoB (AldoB amino acid sequence set forth in SEQ ID NO: 58) genes were codon optimized for *E. coli* and synthesized. FucO gene is native from *E. coli* and was PCR amplified (Forward Primer: ATGGCTAACAGAATGATTCTG (SEQ ID NO: 117) and Reverse Primer: TTACCAGGCGGTATGGTAAAGCT (SEQ ID NO: 118)).

A MEG integration cassette was composed of an operon containing khkC (D-xylulose-1-kinase enzyme), aldoB (D-xylulose-1-phosphate aldolase enzyme), fucO (aldehyde reductase enzyme) genes and rplM terminator under the control of proD promoter (constitutive promoter) flanked by regions homologous to upstream and downstream of xylB gene. For each gene a specific RBS sequence was utilized. An antibiotic marker was also added to the cassette for the selection of transformants. The cassette was constructed using In-fusion commercial kit, confirmed by sequencing and transformed in *E. coli* K12 MG1655 strain. The proper integration of a MEG pathway at xylB locus, yielding a deleted xylB strain with a MEG pathway integrated, was confirmed by sequencing.

The strain harboring a MEG pathway at xylB locus was used as host for integration of an IPA pathway at aldA locus, enabling a stable integration concomitantly with aldA deletion. Production of isopropanol requires the expression of five genes: thl (thiolase), atoA/D (acetate:acetoacetyl-CoA transferase), adc (acetoacetate decarboxylase) and adh (secondary alcohol dehydrogenase). atoA/D gene is native from *E. coli* and was PCR amplified (Forward Primer: CTGTTGTTATATTGTAATGATGTATGCAAGAGGGA-TAAA (SEQ ID NO: 119) and Reverse Primer: TATATCTCCTTCTTAAAGTTCATAAAT-CACCCCGTTGC (SEQ ID NO: 120)). thl (Thl amino acid sequence set forth in SEQ ID NO: 35), adc (Adc amino acid sequence set forth in SEQ ID NO: 49) and adh (Adh amino acid sequence set forth in SEQ ID NO: 106) were codon optimized for *E. coli* and synthesized.

An IPA integration cassette was composed of an operon containing thl (thiolase), adh (secondary alcohol dehydrogenase), adc (acetoacetate decarboxylase), atoA/D (acetate:acetoacetyl-CoA transferase) genes and T1 terminator under the control of a medium strength constitutive promoter (modified from RecA) flanked by regions homologous to upstream and downstream of aldA gene. For each gene a specific RBS sequence was utilized. An antibiotic marker was included into the cassette for the selection of transformants. The cassette was constructed using In-fusion commercial kit, confirmed by sequencing and transformed in *E. coli* K12 MG1655 strain. The proper integration of an IPA pathway at aldA locus, yielding a deleted aldA strain with an IPA pathway integrated, was confirmed by sequencing.

The xylB aldA deleted strain with MEG and IPA pathways integrated in the genome was inoculated in 3 mL of TB media for pre-culture. After 16 hours of cultivation, 100% of the pre-culture was transferred to 100 mL of TB media containing 15 g/L of xylose. The flasks were incubated at 37° C., 250 rpm until complete consumption of xylose. The initial OD of the cultivation was 0.3.

Figure 10:
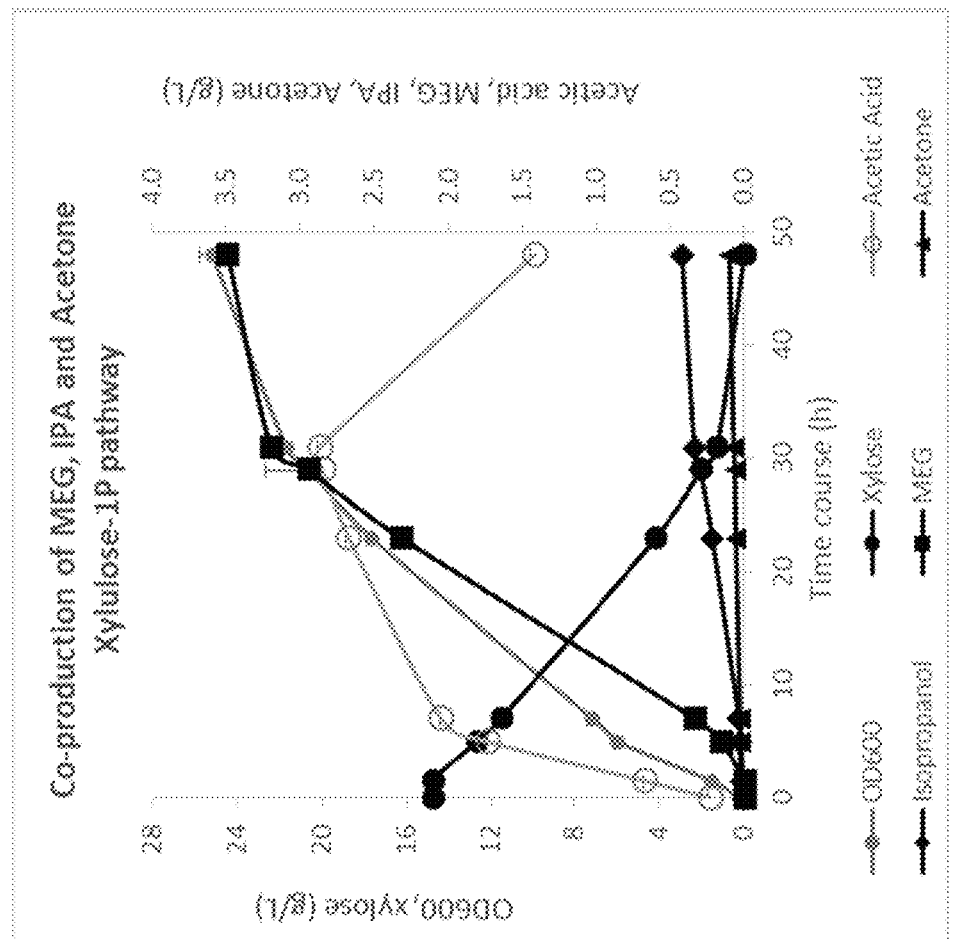
FIG. 10 illustrates co-production of MEG, isopropanol and acetone using a xylulose-1-phosphate pathway in *E. coli* as described in Example 4.

Xylose was fully consumed after 30 hours of cultivation (FIG. 10). Ethylene glycol, acetone and isopropanol reached a maximum titer of 3.5 g/L, 70 mg/L and 400 mg/L respectively.

Figure 11:
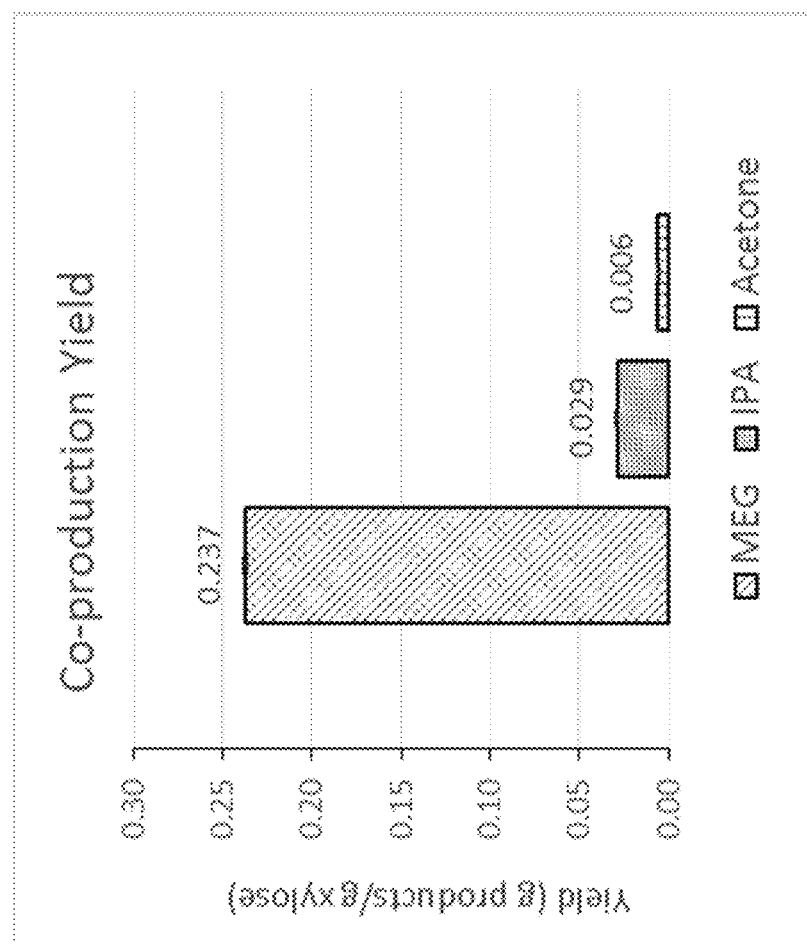
FIG. 11 illustrates overall yield (g products/g xylose) of ethylene glycol, isopropanol and acetone produced using a xylulose-1-phosphate pathway as described in Example 4.

The overall yield of co-production was calculated considering the amount of ethylene glycol, isopropanol and acetone produced per gram of xylose consumed. MEG is the product with the highest yield, 0.237 g/g, followed by isopropanol, 0.029 g/g and acetone, 0.006 g/g (FIG. 11). The best co-production yield, obtained after 48 hours of fermentation, was 0.27 g products/g xylose (44% of maximum theoretical yield).

Example 5. Co-Production of Ethylene Glycol (MEG), Acetone and Isopropanol (IPA) in *E. coli* Using Xylonate Pathway

*E. coli* K12 strain MG1655 was used as host for the expression of MEG+IPA pathways. Two genes that could divert the carbon flux from MEG+IPA pathway were identified as target for deletion: aldA and xylA genes. A MEG pathway was integrated at xylA locus, enabling a stable integration concomitantly with xylA deletion. Production of MEG through a xylonate pathway requires the expression of two genes: xdh (Xdh amino acid sequence set forth in SEQ ID NO: 61) from *Caulobacter crescentus* was codon optimized for *E. coli* and synthesized. FucO gene is native from *E. coli* and was PCR amplified (Forward Primer: ATGGCTAACAGAATGATTCTG (SEQ ID NO: 117) and Reverse Primer: TTACCAGGCGGTATGGTAAAGCT (SEQ ID NO: 118)). Two other native enzymes could be overexpressed to improve MEG production through a xylonate pathway: D-xylonate dehydratase (yjhG, yagF, or homologs thereof) and aldolase (yjhH, yagE, or homologs thereof).

A MEG integration cassette was composed of an operon containing xdh (D-xylose dehydrogenase), fucO (aldehyde reductase enzyme) genes and rnpB terminator under the control of proD promoter (constitutive promoter) flanked by regions homologous to upstream and downstream of xylA gene. For each gene a specific RBS sequence was utilized. An antibiotic marker was also added to the cassette for the selection of transformants. The cassette was constructed using In-fusion commercial kit, confirmed by sequencing and transformed in E. coli K12 MG1655 strain. The proper integration of a MEG pathway at xylA locus, yielding a deleted xylA strain with a MEG pathway integrated, was confirmed by sequencing.

The strain harboring a MEG pathway at xylA locus was used as host for integration of an IPA pathway at aldA locus, enabling a stable integration concomitantly with aldA deletion. Production of isopropanol requires the expression of five genes: thl (thiolase), atoA/D (acetate:acetoacetyl-CoA transferase), adc (acetoacetate decarboxylase) and adh (secondary alcohol dehydrogenase). AtoA/D gene is native from E. coli and was PCR amplified (Forward Primer: CTGTTGTTATATTGTAATGATGTATGCAAGAGGGA-TAAA (SEQ ID NO: 119) and Reverse Primer: TATATCTCCTTCTTAAAGTTCATAAAT-CACCCCGTTGC (SEQ ID NO: 120)). thl (Thl amino acid sequence set forth in SEQ ID NO: 35), adc (Adc amino acid sequence set forth in SEQ ID NO: 49) and adh (Adh amino acid sequence set forth in SEQ ID NO: 106) were codon optimized for E. coli and synthesized.

An IPA integration cassette was composed of an operon containing thl (thiolase), adh (secondary alcohol dehydrogenase), adc (acetoacetate decarboxylase), atoA/D (acetate:acetoacetyl-CoA transferase) genes and T1 terminator under the control of a medium strength constitutive promoter (modified from RecA) flanked by regions homologous to upstream and downstream of aldA gene. For each gene a specific RBS sequence was utilized. An antibiotic marker was included into the cassette for the selection of transformants. The cassette was constructed using In-fusion commercial kit, confirmed by sequencing and transformed in E. coli K12 MG1655 strain. The proper integration of an IPA pathway at aldA locus, yielding a deleted aldA strain with an IPA pathway integrated, was confirmed by sequencing.

The xylA aldA deleted strain with MEG and IPA pathways integrated in the genome was inoculated in 3 mL of TB media for pre-culture. After 16 hours of cultivation, 100% of the pre-culture was transferred to 100 mL of TB media containing 15 g/L of xylose. The flasks were incubated at 37° C., 250 rpm until complete consumption of xylose. The initial OD of the cultivation was 0.3.

Figure 12:
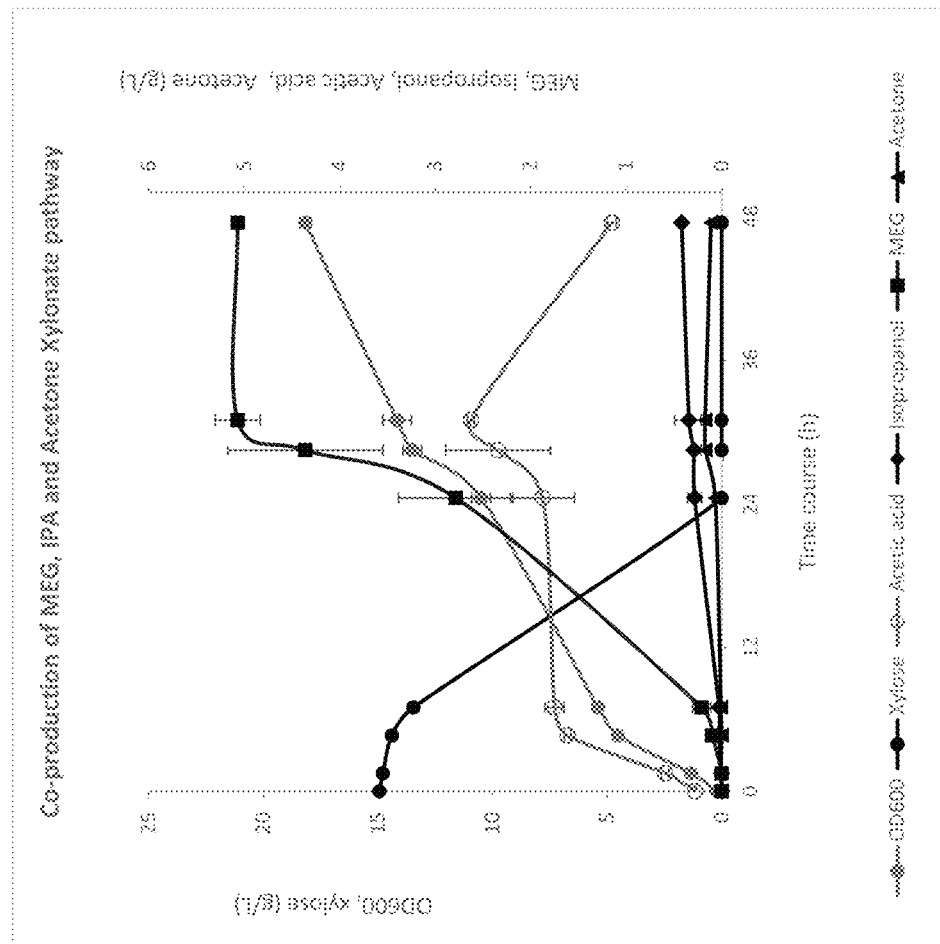
FIG. 12 illustrates co-production of MEG, isopropanol and acetone using a xylonate pathway in *E. coli* as described in Example 5.

Xylose was fully consumed before 24 hours of cultivation (FIG. 12). Ethylene glycol, acetone and isopropanol reached a maximum titer of 5 g/L, 170 mg/L and 420 mg/L respectively.

Figure 13:
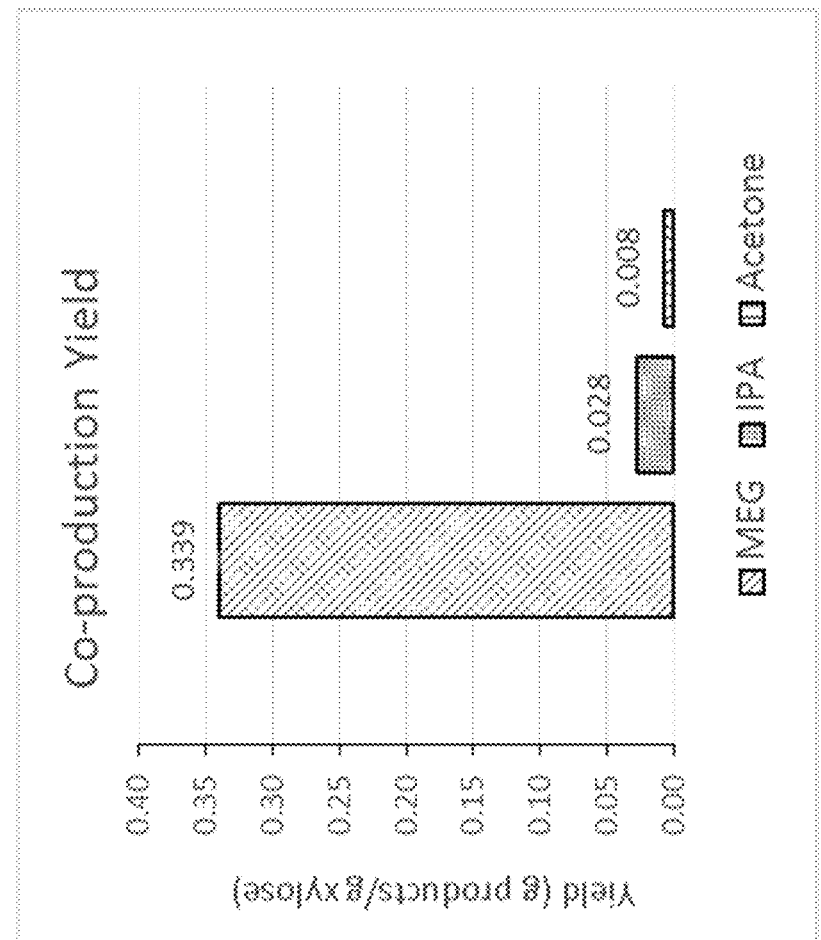
FIG. 13 illustrates overall yield (g products/g xylose) of ethylene glycol, isopropanol and acetone produced using a xylonate pathway as described in Example 5.

The overall yield of co-production was calculated considering the amount of ethylene glycol, isopropanol and acetone produced per gram of xylose consumed. MEG is the product with the highest yield, 0.339 g/g, followed by isopropanol, 0.028 g/g and acetone, 0.008 g/g (FIG. 13). The best co-production yield, obtained after 48 hours of fermentation, was 0.375 g products/g xylose (61% of maximum theoretical yield).

Example 6. Direct Production of Propylene from Glucose

Vectors pZs*13 containing an IPA pathway in an operon under plLacO promoter and pET28a containing LinD gene were co-transformed into BL21Star (DE3) using electroporation. Production of isopropanol requires the expression of five genes: thl (thiolase), atoA/D (acetate:acetoacetyl-CoA transferase), adc (acetoacetate decarboxylase) and adh (secondary alcohol dehydrogenase). atoA/D gene is native from E. coli and was PCR amplified (Forward Primer: CTGTTGTTATATTGTAATGATGTATGCAAGAGGGA-TAAA (SEQ ID NO: 119) and Reverse Primer: TATATCTCCTTCTTAAAGTTCATAAAT-CACCCCGTTGC (SEQ ID NO: 120)). thl (Thl amino acid sequence set forth in SEQ ID NO: 35), adc (Adc amino acid sequence set forth in SEQ ID NO: 49) and adh (Adh amino acid sequence set forth in SEQ ID NO: 106) were codon optimized for E. coli and synthesized. An operon containing thl (thiolase), adh (secondary alcohol dehydrogenase), adc (acetoacetate decarboxylase), atoA/D (acetate:acetoacetyl-CoA transferase) genes and T1 terminator under the control of the inducible promoter pLLacO was constructed in a pZS*13 backbone. The candidate selection was done using kanamycin and ampicillin in LB medium. The strain herein was referred to as IPA+LinD. This combination of plasmids provides a strain capable of producing isopropanol from glucose and also expressing linalool isomerase dehydratase enzyme.

One single colony of IPA+LinD, pZs*13_IPA and pET28a_LinD was inoculated in TB medium containing 10 g/L glycerol supplemented with kanamycin (50 µg/mL) and ampicillin (100 µg/mL) at 37° C., 220 rpm. After 20 hours, a new inoculation was done using optical density of 0.2 in TB medium containing 1.5 g/L glycerol supplemented with appropriate antibiotics at 37° C., 220 rpm. After 3 hours, the OD achieved 1.0 at 600 nm and IPTG was added to a final concentration of 1 mM. The flasks were incubated at 18° C., 220 rpm.

After 16 hours, the OD was measured and the cultures were concentrated to reach OD 20 using the following media as described for each assay:

(a) pZs*13_IPA in TB 20 g/L glucose (control for isopropanol production), (b) IPA+LinD in TB 10 g/L glycerol and 3 g/L isopropanol (control for propylene production), (c) IPA+LinD in TB 20 g/L glucose and 3 g/L isopropanol (control for propylene production), (d) IPA+LinD in TB 20 g/L glucose (candidate 1 for propylene production), (e) IPA+LinD in TB 20 g/L glucose (candidate 2 for propylene production)

Figure 14:
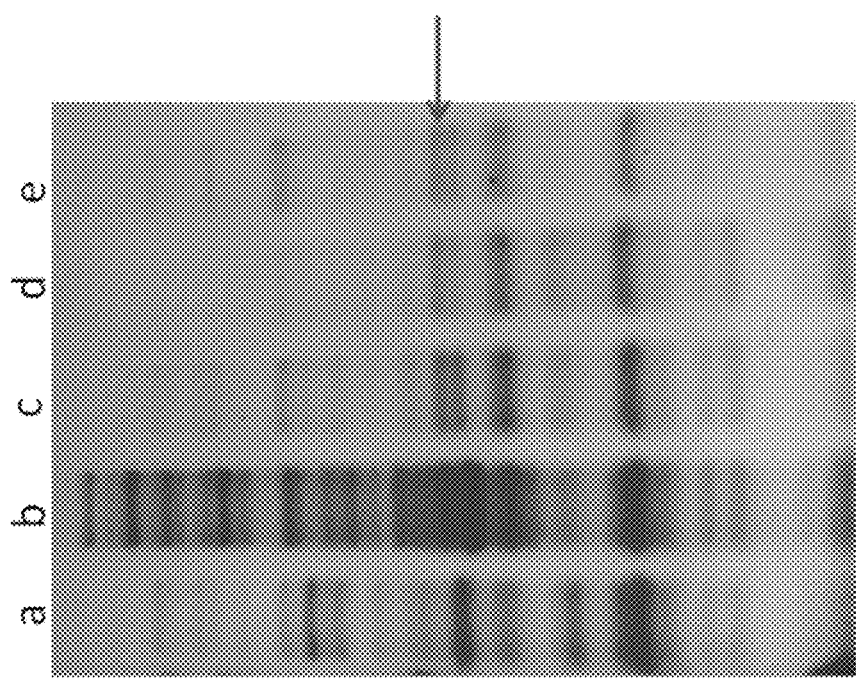
FIG. 14 shows an SDS-PAGE of soluble fraction of assays (a) to (e) as described in Example 6. The arrow indicates LinD expression in (b), (c), (d) and (e).

One aliquot of all cultures were lysate for expression analysis and the cells were collected by centrifugation at 5000 rpm for 20 min and 4° C. The pellet was kept in −80° C. for 1 hour then it was thawed on ice and ressuspended in 10% of original volume in Tris-HCl 50 mM pH 7.5. The lysis was done by sonication (3-5 cycles, 10/10 minutes, 25% amplitude) on ice after that to separate the soluble fraction it was centrifuged at 5000 rpm for 30 min at 4° C. The samples were heated at 95° C. for 10 minutes and analyzed in SDS-PAGE (FIG. 14).

1.0 mL aliquots of each culture were placed in 2 mL headspace vials in triplicate and incubated at 37° C., 225 rpm. At the end of 116 hours of incubation the vials were removed from the shaking incubator and the propylene and isopropanol concentration was analyzed in GC-MS. A control containing only TB medium 20 g/L glucose was done in order to verify contamination in the end of incubation period. 1.0 mL of the headspace phase was injected in gas chromatograph (Focus GC-Thermo) equipped with electron impact mass spectrometer detector (ISQ-Thermo). Helium was used as a carrier gas with a flow rate of 1.5 mL/min, the split rate used was 10 with a split flow of 15 mL/min. The volatile compounds were separated in a HP-Plot/Q column (Agilent) with initial temperature held at 90° C. for 1.0 min followed by a first ramp at 13.3° C./min to 130° C. and a second one at 45° C./min to 200° C. held for 1 min. The retention time of propylene under these conditions was 1.51 min and of isopropanol was 4.3 min. The product reaction was identified both by comparison with propylene and isopropanol standards and by comparison with a data base of mass fragmentation.

Figure 15:
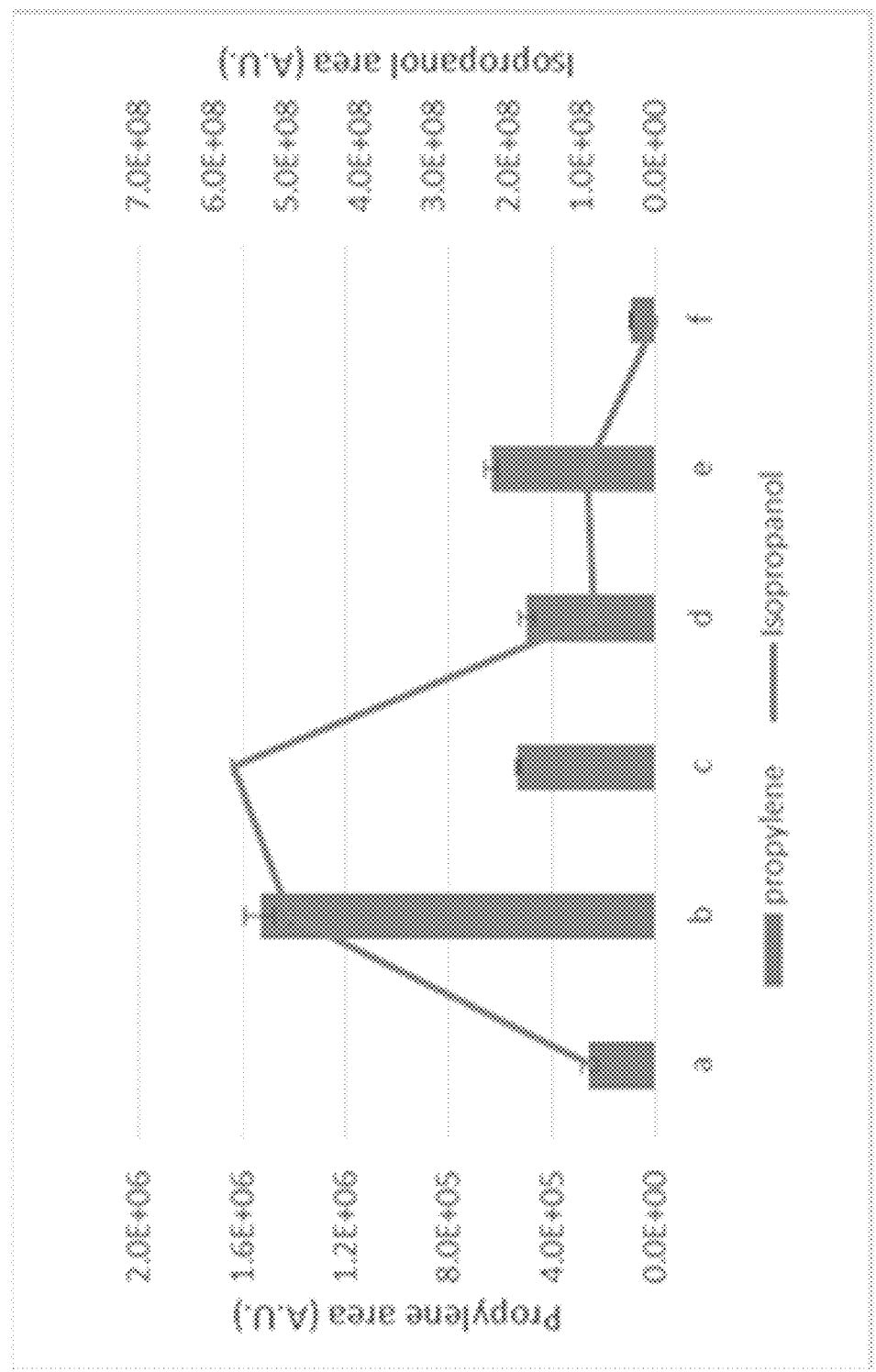
FIG. 15 illlustrates that assays (d) and (e) showed the production of propylene and isopropanol in IPA+LinD candidates. Assay (a) showed isopropanol production of pZs*13_IPA and a small amount of propylene. Assays (b) and (c) showed propylene production in medium supplemented with 3.0 g/L isopropanol using glycerol and glucose as carbon source, respectively.

The production of isopropanol in assays (a), (d) and (e) were 0.5 g/L and in (b) and (c) 3.0 g/L as expected. The production of $4 \times 10^{-5}$ mM of propylene was observed in the assay (b) positive control for propylene and a significant production was observed in the assays (d) and (e), candidates with IPA+LinD co-transformed (FIG. 15). No amount of propylene was observed in the control reaction that contained only TB medium.

| SEQUENCE LISTING |
|---|

| | | |
|---|---|---|
| SEQ ID NO: 1 | | *Pseudomonas cichorii* D-tagatose 3-epimerase DTE NT sequence |
| | | GTGAACAAAGTTGGCATGTTCTACACCTACTGGTCGACTGAGTGGATGGTCGACT |
| | | TTCCGGCGACTGCGAAGCGCATTGCCGGGCTCGGCTTCGACTTAATGGAAATCTC |
| | | GCTCGGCGAGTTTCACAATCTTTCCGACGCGAAGAAGCGTGAGCTAAAAGCCGTG |
| | | GCTGATGATCTGGGGCTCACGGTGATGTGCTGTATCGGACTGAAGTCTGAGTACG |
| | | ACTTTGCCTCGCCGGACAAGAGCGTTCGTGATGCCGGCACGGAATATGTGAAGCG |
| | | CTTGCTCGACGACTGTCACCTCCTCGGCGCGCCGGTCTTTGCTGGCCTTACGTTC |
| | | TGCGCGTGGCCCCAATCTCCGCCGCTGGACATGAAGGATAAGCGCCCTTACGTCG |
| | | ACCGTGCAATCGAAAGCGTTCGTCGTGTTATCAAGGTAGCTGAAGACTACGGGAT |
| | | TATTTATGCACTGGAAGTGGTGAACCGATTCGAGCAGTGGTTGCTTTGCAATGACGCC |
| | | AAGGAAGCAATTGCGTTTGCCGACGCGGTTGACAGTCCGGCGTGCAAGGTCCAGC |
| | | TCGACACATTCCACATGAATATCGAAGAGACTTCCTTCCGCGATGCAATCCTTGC |
| | | CTGCAAGGGCAAGATGGGCCATTTCCATTTGGGCGAAGCGAACCGTCTGCCGCCG |
| | | GGCGAGGGTCGCCTGCCGTGGGATGAAATATTCGGGGCGCTGAAGGAAATCGGAT |
| | | ATGACGGCACCATCGTTATGGAACCGTTCATGCGCAAGGGCGGCTCGGTCAGCCG |
| | | CGCGGTGGGCGTATGGCGGGATATGTCGAACGGTGCGACGGACGAAGAGATGGAC |
| | | GAGCGCGCTCGCCGCTCGTTGCAGTTTGTTCGTGACAAGCTGGCCTGA |
| | | |
| SEQ ID NO: 2 | | *Pseudomonas cichorii* D-tagatose 3-epimerase DTE codon optimized NT sequence |
| | | ATGAACAAAGTGGGTATGTTCTATACGTACTGGTCCACGGAATGGATGGTTGACT |
| | | TTCCGGCAACCGCGAAACGTATTGCGGGCCTGGGCTTCGACCTGATGGAAATTTC |
| | | TCTGGGCGAATTTCACAACCTGTCCGATGCGAAAAAGCGTGAACTGAAAGCCGTT |
| | | GCCGACGATCTGGGTCTGACTGTGATGTGCTGTATCGGCCTGAAATCTGAATACG |
| | | ATTTCGCGAGCCCGGATAAAAGCGTTCGCGACGCCGGTACTGAATATGTCAAACG |
| | | TCTGCTGGATGACTGTCACCTGCTGGGCGCACCAGTGTTCGCGGGTCTGACCTTC |
| | | TGTGCGTGGCCGCAGTCCCCACCGCTGGACATGAAGGATAAACGTCCGTACGTGG |
| | | ACCGTGCCATCGAAAGCGTGCGCCGCGTAATCAAAGTCGCTGAAGATTATGGCAT |
| | | TATTTACGCTCTGGAAGTTGTTAACCGTTTCGAACAGTGGCTGTGCAACGACGCG |
| | | AAAGAGGCCATTGCCTTCGCTGACGCGGTGGATTCTCCGGCTTGCAAAGTTCAGC |
| | | TGGACACTTTCCATATGAACATCGAGGAAACCTCCTTCCGTGACGCGATCCTGGC |
| | | TTGCAAGGGTAAAATGGGCCATTTCCATCTGGGCGAAGCAAACCGCCTGCCGCCG |
| | | GGCGAAGGTCGTCTGCCGTGGGACGAAATTTTTGGCGCTCTGAAGGAAATCGGCT |
| | | ACGATGGCACGATTGTTATGGAGCCGTTCATGCGCAAAGGTGGCTCCGTTTCCCG |
| | | TGCAGTTGGTGTTTGGCGTGATATGTCTAACGGTGCCACCGATGAAGAAATGGAC |
| | | GAACGTGCACGTCGCTCCCTGCAATTCGTTCGCGATAAACTGGCGTAA |
| | | |
| SEQ ID NO: 3 | | *Pseudomonas cichorii* D-tagatose 3-epimerase DTE AA sequence |
| | | MNKVGMFYTYWSTEWMVDFPATAKRIAGLGFDLMEISLGEFHNLSDAKKRELKAV |
| | | ADDLGLTVMCCIGLKSEYDFASPDKSVRDAGTEYVKRLLDDCHLLGAPVFAGLTF |
| | | CAWPQSPPLDMKDKRPYVDRAIESVRRVIKVAEDYGIIYALEVVNRFEQWLCNDA |
| | | KEAIAFADAVDSPACKVQLDTFHMNISETSFRDAILACKGKMGHFHLGEANRLPP |
| | | GEGRLPWDEIFGALKEIGYDGTIVMEPFMRKGGSVSRAVGVWRDMSWGATDEEMD |
| | | ERARRSLQEVRDKLA |
| | | |
| SEQ ID NO: 4 | | *Rhodobacter sphaeroides* D-tagatose 3-epimerase FJ851309.1 NT sequence |
| | | GTGAAAAATCCTGTCGGCATCATCTCGATGCAGTTCATCCGGCCCTTCACCTCGG |
| | | AGTCGCTGCATTTCCTGAAGAAGTCCCGGGCCCTGGGCTTCGATTTCATCGAGCT |
| | | TCTCGTGCCCGAGCCCGAAGACGGGCTCGACGCGGCCGAGGTGCGGCGCATCTGC |
| | | GAGGGCGAGGGCTGGGCCTCGTTCTGGCCGCGCGCGTGAACCTCCAGCGCTCGA |
| | | TCGCGAGCGAGGAGGCCGCGGCGCGGGCCGGCGGGCGCGACTATCTGAAATACTG |
| | | CATCGAGGCCGCCGAGGCGCTCGGCGCGACCATCGTCGGCGGCCCGCTCTATGGC |
| | | GAGCCGCTGGTCTTCGCCGGCCGCCCGCCCTTCCCCTGGACGGCCGAGCAGATCG |
| | | CCACCCGCGCCGCCCGCACCGTCGAGGGGCTGGCCGAAGTGGCCCCGCTCGCCGC |
| | | GAGCGCGGGCAAGGTCTTCGGGCTCGAGCCGCTGAACCGCTTCGAGACCGACATC |
| | | GTGAACACGACCGCACAGGCCATCGAGGTGGTGGATGCGGTGGGCTCGCCCGGTC |
| | | TCGGCGTCATGCTCGACACGTTCCACATGAACATGGAGGAACGCTCGATCCCCGA |
| | | TGCGATCCGCGCCACAGGCGCGCTCGTCCATTTTCAGGCCAACGAGAACCAC |
| | | CGCGGCTTCCCCGGCACCGGCACCATGGACTGGACGGCCATCGCGCGGGCGCTGG |
| | | GGCAGGCGGGCTACGCGGGTCCGGTCTCGCTCGAGCCTTTCCGGCGCGACGACGA |
| | | GCGCGTGGCGCTGCCCATCGCCCACTGGCGCGCCCCGCACGAGGACGAGGACGAG |
| | | AAGCTGCGCGCGGGGCTGGGTCTCATCCGCTCCGCGATCACCCTGGCGGAGGTGA |
| | | CCCACTGA |

| SEQUENCE LISTING | |
|---|---|
| SEQ ID NO: 5 | *Rhodobacter sphaeroides* D-tagatose 3-epimerase<br>FJ851309.1 AA sequence<br>MKNPVGIISMQFIRPPFTSESLHFLKESRALGFDFIELLVPEPEDGLDAAEVRRIC<br>EGEGLGLVLAARVNLQRSIASEEAAARAGGRDYLKYCIEAAEALGATIVGGPLYG<br>EPLVFAGRPPFPWTAEQIATRAARTVEGLAEVAPLAASAGKVFGLEPLNRFETDI<br>VNTTAQAIEVVDAVGSPGLGVMLDTFHMNMEERSIPDAIRATGARLVHFQANENH<br>RGFPGTGTMDWTAIARALGQAGYAGPVSLEPFRRDDERVALPIAHWRAPHEDEDE<br>KLRAGLGLIRSAITLAEVTH |
| SEQ ID NO: 6 | *Escherichia coli* L-fuculokinase FucK NT sequence<br>ATGATGAAACAAGAAGTTATCCTGGTACTCGACTGTGGCGCGACCAATGTCAGGG<br>CCATCGCGGTTAATCGGCAGGGCAAAATTGTTGCCCGCGCCTCAACGCCTAATGC<br>CAGCGATATCGCGATGGAAAACAACACCTGGCACCAGTGGTCTTTAGACGCCATT<br>TTGCAACGCTTTGCTGATTGCTGTCGGCAAATCAATAGTGAACTGACTGAATGCC<br>ACATCCGCGGTATCGCCGTCACCACCTTTGGTGTGGATGGCGCTCTGGTAGATAA<br>GCAAGGCAATCTGCTCTATCCGATTATTAGCTGGAAATGTCCGCGAACAGCAGCG<br>GTTATGGACAATATTGAACGGTTAATCTCCGCACAGCGGTTGCAGGCTATTTCTG<br>GCGTCGGAGCCTTTAGTTTCAATACGTTATATAAGTTGGTGTGGTTGAAAGAAAA<br>TCATCCACAACTGCTGGAACGCGCGCACGCCTGGCTCTTTATTTCGTCGCTGATT<br>AACCACCGTTTAACCGGCGAATTCACTACTGATATCACGATGGCCGGAACCAGCC<br>AGATGCTGGATATCCAGCAACGCGATTTCAGTCCGCAAATTTTACAAGCCACCGG<br>TATTCCACGCCGACTCTTCCCTCGTCTGGTGGAAGCGGGTGAACAGATTGGTACG<br>CTACAGAACAGCGCCGCAGCAATGCTCGGCTTACCCGTTGGCATACCGGTGATTT<br>CCGCAGGTCACGATACCCAGTTCGCCCTTTTTGGCGCTGGTGCTGAACAAAATGA<br>ACCCGTGCTCTCTTCCGGTACATGGGAAATTTTAATGGTTCGCAGCGCCCAGGTT<br>GATACTTCGCTGTTAAGTCAGTACGCCGGTTCCACCTGCGAACTGGATAGCCAGG<br>CAGGGTTGTATAACCCAGGTATGCAATGGCTGGCATCCGGCGTGCTGGAATGGGT<br>GAGAAAACTGTTCTGGACGGCTGAAACACCCTGGCAAATGTTGATTGAAGAAGCT<br>CGTCTGATCGCGCCTGGCGCGGATGGCGTAAAAATGCAGTGTGATTTATTGTCGT<br>GTCAGAACGCTGGCTGGCAAGGAGTGACGCTTAATACCACGCGGGGGCATTTCTA<br>TCGCGCGGCGCTGGAAGGGTTAACTGCGCAATTACAGCGCAATCTACAGATGCTG<br>GAAAAAATCGGGCACTTTAAGGCCTCTGAATTATTGTTAGTCGGTGGAGGAAGTC<br>GCAACACATTGTGGAATCAGATTAAAGCCAATATGCTTGATATTCCGGTAAAAGT<br>TCTCGACGACGCCGAAACGACCGTCGCAGGAGCTGCGCTGTTCGGTTGGTATGGC<br>GTAGGGGAATTTAACAGCCCGGAAGAAGCCCGCGCACAGATTCATTATCAGTACC<br>GTTATTTCTACCCGCAAACTGAACCTGAATTTATAGAGGAAGTGTGA |
| SEQ ID NO: 7 | *Escherichia coli* L-fuculokinase FucK codon optimized NT<br>sequence<br>ATGATGAAACAAGAAGTTATCCTGGTACTCGACTGTGGCGCGACCAATGTCAGGG<br>CCATCGCGGTTAATCGGCAGGGCAAAATTGTTGCCCGCGCCTCAACGCCTAATGC<br>CAGCGATATCGCGATGGAAAACAACACCTGGCACCAGTGGTCTTTAGACGCCATT<br>TTGCAACGCTTTGCTGATTGCTGTCGGCAAATCAATAGTGAACTGACTGAATGCC<br>ACATCCGCGGTATCGCCGTCACCACCTTTGGTGTGGATGGCGCTCTGGTAGATAA<br>GCAAGGCAATCTGCTCTATCCGATTATTAGCTGGAAATGTCCGCGAACAGCAGCG<br>GTTATGGACAATATTGAACGGTTAATCTCCGCACAGCGGTTGCAGGCTATTTCTG<br>GCGTCGGAGCCTTTAGTTTCAATACGTTATATAAGTTGGTGTGGTTGAAAGAAAA<br>TCATCCACAACTGCTGGAACGCGCGCACGCCTGGCTCTTTATTTCGTCGCTGATT<br>AACCACCGTTTAACCGGCGAATTCACTACTGATATCACGATGGCCGGAACCAGCC<br>AGATGCTGGATATCCAGCAACGCGATTTCAGTCCGCAAATTTTACAAGCCACCGG<br>TATTCCACGCCGACTCTTCCCTCGTCTGGTGGAAGCGGGTGAACAGATTGGTACG<br>CTACAGAACAGCGCCGCAGCAATGCTCGGCTTACCCGTTGGCATACCGGTGATTT<br>CCGCAGGTCACGATACCCAGTTCGCCCTTTTTGGCGCTGGTGCTGAACAAAATGA<br>ACCCGTGCTCTCTTCCGGTACATGGGAAATTTTAATGGTTCGCAGCGCCCAGGTT<br>GATACTTCGCTGTTAAGTCAGTACGCCGGTTCCACCTGCGAACTGGATAGCCAGG<br>CAGGGTTGTATAACCCAGGTATGCAATGGCTGGCATCCGGCGTGCTGGAATGGGT<br>GAGAAAACTGTTCTGGACGGCTGAAACACCCTGGCAAATGTTGATTGAAGAAGCT<br>CGTCTGATCGCGCCTGGCGCGGATGGCGTAAAAATGCAGTGTGATTTATTGTCGT<br>GTCAGAACGCTGGCTGGCAAGGAGTGACGCTTAATACCACGCGGGGGCATTTCTA<br>TCGCGCGGCGCTGGAAGGGTTAACTGCGCAATTACAGCGCAATCTACAGATGCTG<br>GAAAAAATCGGGCACTTTAAGGCCTCTGAATTATTGTTAGTCGGTGGAGGAAGTC<br>GCAACACATTGTGGAATCAGATTAAAGCCAATATGCTTGATATTCCGGTAAAAGT<br>TCTCGACGACGCCGAAACGACCGTCGCAGGAGCTGCGCTGTTCGGTTGGTATGGC<br>GTAGGGGAATTTAACAGCCCGGAAGAAGCCCGCGCACAGATTCATTATCAGTACC<br>GTTATTTCTACCCGCAAACTGAACCTGAATTTATAGAGGAAGTGTGA |
| SEQ ID NO: 8 | *Escherichia coli* L-fuculokinase fucK AA sequence<br>MMKQEVILVLDCGATKVRAIAVNRQGKIVARASTPNASDIAMENNTWHQWSLDAI<br>LQRFADCCRQINSELTECHIRGIAVTTFGVDGALVDKQGMLLYPIISWKCPRTAA<br>VMDNIERLISAQRLQAISGVGAFSFNTLYKLVWLKENHPQLLERAHAWLFISSLI<br>NHRLTGEFTTDITMAGTSQMLDIQQRDFSPQILQATGIPRRLFPRLVEAGEQIGT<br>LQNSAAAMLGLPVGIPVISAGHDTQFALFGAGAEQNEPVLSSGTWEILMVRSAQV<br>DTSLLSQYAGSTCELDSQAGLYNPGMQWLASGVLEWVRKLFWTAETPWQMLIEEA<br>RLIAPGADGVKMQCDLLSCQNAGWQGVTLNTTRGHFYRAALEGLTAQLQRNLQML<br>EKIGHFKASELLLVGGGSRNTLWNQIKANMLDIPVKVLDDAETTVAGAALFGWYG<br>VGEFNSPEEARAQIHYQYRYFYPQTEPEFIEEV |

SEQUENCE LISTING

| | |
|---|---|
| SEQ ID NO: 9 | *Escherichia coli* L-fuculose phosphate aldolase fucA NT sequence<br>ATGGAACGAAATAAACTTGCTCGTCAGATTATTGACACTTGCCTGGAAATGACCC<br>GCCTGGGACTGAACCAGGGGACAGCGGGGAACGTCAGTGTACGTTATCAGGATGG<br>GATGCTGATTACGCCTACAGGCATTCCATATGAAAAACTGACGGAGTCGCATATT<br>GTCTTTATTGATGGCAACGGTAAACATGAGGAAGGAAAGCTCCCCTCAAGCGAAT<br>GGCGTTTCCATATGGCAGCCTATCAAAGCAGACCGGATGCCAACGCGGTTGTTCA<br>CAATCATGCCGTTCATTGCACGGCAGTTTCCATTCTTAACCGATCGATCCCCGCT<br>ATTCACTACATGATTGCGGCGGCTGGCGGTAATTCTATTCCTTGCGCGCCTTATG<br>CGACCTTTGGAACACGCGAACTTTCTGAACATGTTGCGCTGGCTCTCAAAAATCG<br>TAAGGCAACTTTGTTACAACATCATGGGCTTATCGCTTGTGAGGTGAATCTGGAA<br>AAAGCGTTATGGCTGGCGCATGAAGTTGAAGTGCTGGCGCAACTTTACCTGACGA<br>CCCTGGCGATTACGGACCCGGTGCCAGTGCTGAGCGATGAAGAGATTGCCGTAGT<br>GCTGGAGAAATTCAAAACCTATGGGTTACGAATTGAAGAGTAA |
| SEQ ID NO: 10 | *Escherichia coli* L-fuculose phosphate aldolase fucA codon optimized NT sequence<br>ATGGAACGAAATAAACTTGCTCGTCAGATTATTGACACTTGCCTGGAAATGACCC<br>GCCTGGGACTGAACCAGGGGACAGCGGGGAACGTCAGTGTACGTTATCAGGATGG<br>GATGCTGATTACGCCTACAGGCATTCCATATGAAAAACTGACGGAGTCGCATATT<br>GTCTTTATTGATGGCAACGGTAAACATGAGGAAGGAAAGCTCCCCTCAAGCGAAT<br>GGCGTTTCCATATGGCAGCCTATCAAAGCAGACCGGATGCCAACGCGGTTGTTCA<br>CAATCATGCCGTTCATTGCACGGCAGTTTCCATTCTTAACCGATCGATCCCCGCT<br>ATTCACTACATGATTGCGGCGGCTGGCGGTAATTCTATTCCTTGCGCGCCTTATG<br>CGACCTTTGGAACACGCGAACTTTCTGAACATGTTGCGCTGGCTCTCAAAAATCG<br>TAAGGCAACTTTGTTACAACATCATGGGCTTATCGCTTGTGAGGTGAATCTGGAA<br>AAAGCGTTATGGCTGGCGCATGAAGTTGAAGTGCTGGCGCAACTTTACCTGACGA<br>CCCTGGCGATTACGGACCCGGTGCCAGTGCTGAGCGATGAAGAGATTGCCGTAGT<br>GCTGGAGAAATTCAAAACCTATGGGTTACGAATTGAAGAGTAA |
| SEQ ID NO: 11 | *Escherichia coli* L-fuculose phosphate aldolase fucA AA sequence<br>MERNKIARQIIDTCLEMTRLGLNQGTAGNVSVRYQDGMLITPTGIPYEKLTESHI<br>VFIDGNGKKEEGKLPSSEWRFHMAAYQSRPDANAVVHNHAVHCTAVSILNRSIPA<br>IHYMIAAAGGNSIPCAPYATFGTRELSEHVALALKNRKATLLQHHGLIACEVNLE<br>KALWLAHEVEVLAQLYLTTLAITDPVPVLSDEEIAVVLEKFKTYGLRIEE |
| SEQ ID NO: 12 | *Escherichia coli* glycerol dehydrogenase gldA NT sequence<br>ATGGACCGCATTATTCAATCACCGGGTAAATACATCCAGGGCGCTGATGTGATTA<br>ATCGTCTGGGCGAATACCTGAAGCCGCTGGCAGAACGCTGGTTAGTGGTGGGTGA<br>CAAATTTGTTTTAGGTTTTGCTCAATCCACTGTCGAGAAAAGCTTTAAAGATGCT<br>GGACTGGTAGTAGAAATTGCGCCGTTTGGCGGTGAATGTTCGCAAAATGAGATCG<br>ACCGTCTGCGTGGCATCGCGGAGACTGCGCAGTGTGGCGCAATTCTCGGTATCGG<br>TGGCGGAAAAACCCTCGATACTGCCAAAGCACTGGCACATTTCATGGGTGTTCCG<br>GTAGCGATCGCACCGACTATCGCCTCTACCGATGCACCGTGCAGCGCATTGTCTG<br>TTATCTACACCGATGAGGGTGAGTTTGACCGCTATCTGCTGTTGCCAAATAACCC<br>GAATATGGTCATTGTCGACACCAAAATCGTCGCTGGCGCACCTGCACGTCTGTTA<br>GCGGCGGGTATCGGCGATGCGCTGGCAACCTGGTTTGAAGCGCGTGCCTGCTCTC<br>GTAGCGGCGCGACCACCATGGCGGGCGGCAAGTGCACCCAGGCTGCGCTGGCACT<br>GGCTGAACTGTGCTACAACACCCTGCTGGAAGAAGGCGAAAAAGCGATGCTTGCT<br>GCCGAACAGCATGTAGTGACTCCGGCGCTGGAGCGCGTGATTGAAGCGAACACCT<br>ATTTGAGCGGTGTTGGTTTTGAAAGTGGTGGTCTGGCTGCGGCGCACGCAGTGCA<br>TAACGGCCTGACCGCTATCCCGGACGCGCATCACTATTATCACGGTGAAAAAGTG<br>GCATTCGGTACGCTGACGCAGCTGGTTCTGGAAAATGCGCCGGTGGAGGAAATCG<br>AAACCGTAGCTGCCCTTAGCCATGCGGTAGGTTTGCCAATAACTCTCGCTCAACT<br>GGATATTAAAGAAGATGTCCCGGCGAAAATGCGAATTGTGGCAGAAGCGGCATGT<br>GCAGAAGGTGAAACCATTCACAACATGCCTGGCGGCGCGACGCCAGATCAGGTTT<br>ACGCCGCTCTGCTGGTAGCCGACCAGTACGGTCAGCGTTTCCTGCAAGAGTGGGA<br>ATAA |
| SEQ ID NO: 13 | *Escherichia coli* glycerol dehydrogenase gldA AA sequence<br>MDRIIQSPGKYIQGADVINRLGEYLKPLAERWLVVGDKFVLGFAQSTVEKSFKDA<br>GLVVEIAPFGGECSQNEIDRLRGIAETAQCGAILGIGGGKTLDTAKALAHFMGVP<br>VAIAPTIASTDAPCSALSVIYTDEGEFDRYLLLPNNPNMVIVDTKIVAGAPARLL<br>AAGIGDALATWFEARACSRSGATTMAGGKCTQAALALAELCYNTLLEEGEKAMLA<br>AEQHVVTPALERVIEANTYLSGVGFESGGLAAAHAVHNGLTAIPDAHHYYHGEKV<br>AFGTLTQLVLENAPVEEIETVAALSHAVGLPITLAQLDIKEDVPAKMRIVAEAAC<br>AEGETIHNMPGGATPDQVYAALLVADQYGQRFLQEWE |
| SEQ ID NO: 14 | *Saccharomyces cerevisiae* methylglyoxal reductase GRE2 NT sequence<br>ATGTCAGTTTTCGTTTCAGGTGCTAACGGGTTCATTGCCCAACACATTGTCGATC<br>TCCTGTTGAAGGAAGACTATAAGGTCATCGGTTCTGCCAGAAGTCAAGAAAGGC<br>CGAGAATTTAACGAGGCCTTTGGTAACAACCCAAAATTCTCCATGGAAGTTGTC<br>CCAGACATATCTAAGCTGGACGCATTTGACCATGTTTTCCAAAAGCACGGCAAGG |

| SEQUENCE LISTING | |
|---|---|
| | ATATCAAGATAGTTCTACATACGGCCTCTCCATTCTGCTTTGATATCACTGACAG<br>TGAACGCGATTTATTAATTCCTGCTGTGAACGGTGTTAAGGGAATTCTCCACTCA<br>ATTAAAAAATACGCCGCTGATTCTGTAGAACGTGTAGTTCTCACCTCTTCTTATG<br>CAGCTGTGTTCGATATGGCAAAAGAAAACGATAAGTCTTTAACATTTAACGAAGA<br>ATCCTGGAACCCAGCTACCTGGGAGAGTTGCCAAAGTGACCCAGTTAACGCCTAC<br>TGTGGTTCAAGAAGTTTGCTGAAAAAGCAGCTTGGGAATTTCTAGAGGAGAATA<br>GAGACTCTGTAAAATTCGAATTAACTGCCGTTAACCCAGTTTACGTTTTTGGTCC<br>GCAAATGTTTGACAAAGATGTGAAAAAACACTTGAACACATCTTGCGAACTCGTC<br>AACAGCTTGATGCATTTATCACCAGAGGACAAGATACCGGAACTATTTGGTGGAT<br>ACATTGATGTTCGTGATGTTGCAAAGGCTCATTTAGTTGCCTTCCAAAAGAGGGA<br>AACAATTGGTCAAAGACTAATCGTATCGGAGGCCAGATTTACTATGCAGGATGTT<br>CTCGATATCCTTAACGAAGACTTCCCTGTTCTAAAAGGCAATATTCCAGTGGGGA<br>AACCAGGTTCTGGTGCTACCCATAACACCCTTGGTGCTACTCTTGATAATAAAA<br>GAGTAAGAAATTGTTAGGTTTCAAGTTCAGGAACTTGAAAGAGACCATTGACGAC<br>ACTGCCTCCCAAATTTTAAAATTTGAGGGCAGAATATAA |
| SEQ ID NO: 15 | *Saccharomyces cerevisiae* methylglyoxal reductase GRE2<br>AA sequence<br>MSVPISGANGFTAQHTVDLLLKEDYKVIGSARSQENAENLTEAFGNNPKFSMEVV<br>PDISRIDAFDHVFQKHGKDIKIVIHTASPECEDITDSERDLLIPAVNGVKGILHS<br>IKKYAADSVERVVLTSSYAAVFDMAKENDKSLTENEESWNPATWESCQSDPVNAY<br>CGSKKFAEKAAWEFLEENRDSVKFELTAVNPVYVFGPQMFDKDVKKHLNTSCELV<br>NSLMHLSPEDKTPELFGGYTDVRIWAKAHLVAFQKRETIGQRLIVSEARFTMQDV<br>LDILNEDFPVLKGNIPVGKPSGATHNTLGATLDNKKSKKLLGFKFRNLKETIDD<br>TASQILKFEGRI |
| SEQ ID NO: 16 | *Saccharomyces cerevisiae* aldose reductase GRE3 NT<br>sequence<br>ATGTCTTCACTGGTTACTCTTAATAACGGTCTGAAAATGCCCCTAGTCGGCTTAG<br>GGTGCTGGAAAATTGACAAAAAGTCTGTGCGAATCAAATTTATGAAGCTATCAA<br>ATTAGGCTACCGTTTATTCGATGGTGCTTGCGACTACGGCAACGAAAAGGAAGTT<br>GGTGAAGGTATCAGGAAAGCCATCTCCGAAGGTCTTGTTTCTAGAAAGGATATAT<br>TTGTTGTTTCAAAGTTATGGAACAATTTTCACCATCCTGATCATGTAAAATTAGC<br>TTTAAAGAAGACCTTAAGCGATATGGGACTTGATTATTTAGACCTGTATTATATT<br>CACTTCCCAATCGCCTTCAAATATGTTCCATTTGAAGAGAAATACCCTCCAGGAT<br>TCTATACGGGCGCAGATGACGAGAAGAAAGGTCACATCACCGAAGCACATGTACC<br>AATCATAGATACGTACCCGGGCTCTGGAAGAATGTGTTGATGAAGGCTTGATTAAG<br>TCTATTGGTGTTTCCAACTTTCAGGGAAGCTTGATTCAAGATTATTACGTGGTT<br>GTAGAATCAAGCCCGTGGCTTTGCAAATTGAACACCATCCTTATTTGACTCAAGA<br>ACACCTAGTTGAGTTTTGTAAATTAGACGATATCCAAGTAGTTGCTTACTCCTCC<br>TTCGGTCCTCAATCATTCATTGAGATGGACTTACAGTTGGCAAAAACCACGCCAA<br>CTCTGTTCGAGAATGATGTAATCAAGAAGGTCTCACAAAACCATCCAGGCAGTAC<br>CACTTCCCAAGTATTGCTTAGATGGGCAACTCAGAGAGGCATTGCCGTCATTCCA<br>AAATCTTCCAAGAAGGAAAGGTTACTTGGCAACCTAGAAATCGAAAAAAAGTTCA<br>CTTTAACGGAGCAAGAATTGAAGGATATTTCTGCACTAAATGCCAACATCAGATT<br>TAATGATCCATGGACCTGGTTGGATGGTAAATTCCCCACTTTTGCCTGA |
| SEQ ID NO: 17 | *Saccharomyces cerevisiae* aldose reductase GRE3 AA<br>sequence<br>MSSLVTLNNGLKMPLVGLGCWKIDKKVCANQIYEAIKLGYRLFDGACDYGNEKEV<br>GEGIRKAISEGLVSRKDIFVVSKLWNMFHHPDHVKLALKKTLSDMGLDYLDLYYI<br>HFPIAFKYVPFEEKYPPGFYTGADDEKKGHITEAHVPIIDTYPALEECVDEGLIK<br>SIGVSNFQGSLIQDLLRGCRIKPVALQIEHHPYLTQEHLVEFCKLHDIQVVAYSS<br>FGPQSFIEMDLQLAKTTPTLFENDVIKKVSQNKPGSTTSQVLLRWATQRGIAVIP<br>KSSKKERLLGNLEIEKKFTLTECELKDISALNANIRFNDPWTWLDGKFPTFA |
| SEQ ID NO: 18 | *Escherichia coli* alcohol dehydrogenase yqhD* NT<br>sequence<br>ATGAACAACTTTAATCTGCACACCCCAACCCGCATTCTGTTTGGTAAAGGCGCAA<br>TCGCTGGTTTACGCGAACAAATTCCTCACGATGCTCGCGTATTGATTACCTACGG<br>CGGCGGCAGCGTGAAAAAAACCGGCGTTCTCGATCAAGTTCTGGATGCCCTGAAA<br>GGCATGGACGTGCTGGAATTTGGCGGTATTGAGCCAAACCCGGCTTATGAAACGC<br>TGATGAACGCCGTGAAACTGGTTCGCGAACAGAAAGTGACTTTCCTGCTGGCGGT<br>TGGCGGCGGTTCTGTACTGGACGGCACCAAATTTATCGCCGCAGCGGTAACTAT<br>CCGGAAAATATCGATCCGTGGCACATTCTGCAAACGGGCGGTAAAGAGATTAAA<br>GCGCCATCCCGATGGGCTGTGTGCTGACGCTGCCAGCAACCGGTTCAGAATCCAA<br>CGCAGAAGCGGTGATCTCCCGTAAAACCACAGGCGACAAGCAGGCGTTCCATTCT<br>GCCCATGTTCAGCCGGTATTTGCCGTGCTCGATCCGGTTTATACCTACACCCTGC<br>CGCCGCGTCAGGTGGCTAACGGCGTAGTGGACGCCTTTGTACACACCGTGGAACA<br>GTATGTTACCAAACCGGTTGATGCCAAATTCAGGACCGTTTCGCAGAAGGCATT<br>TTGCTGACGCTAATCGAAGATGGTCCGAAAGCCCTGAAAGAGCCAGAAAACTACG<br>ATGTGCGCGCCAACGTCATGTGGGCGGCGACTCAGGCGCTGAACGGTTTGATTGG<br>CGCTGGCGTACCGCAGGACTGGGCAACGCATATGCTGGGCCACGAACTGACTGCG<br>ATGCACGGTCTGGATCACGCGCAAACACTGGCTATCGTCCTGCCTGCACTGTGGA<br>ATGAAAAACGCGATACCAAGCGCGCTAAGCTGCTGCAATATGCTGAACGCGTCTG<br>GAACATCACTGAAGGTTCCGATGATGAGCGTATTGACGCCGCGATTGCCGCAACC<br>CGCAATTTCTTTGAGCAATTAGGCGTGCCGACCCACCTCTCCGACTACGGTCTGG |

| SEQUENCE LISTING | |
|---|---|
| | ACGGCAGCTCCATCCCGGCTTTGCTGAAAAAACTGGAAGAGCACGGCATGACCCA<br>ACTGGGCGAAAATCATGACATTACGTTGGATGTCAGCCGCCGTATATACGAAGCC<br>GCCCGCTAA |
| SEQ ID NO: 19 | *Escherichia coli* alcohol dehydrogenase yqhD* codon<br>optimized NT sequence<br>ATGAACAATTTTAATTTGCATACTCCAACTAGAATATTATTTGGAAAAGGTGCAA<br>TTGCAGGTTTAAGGGAACAAATACCACATGATGCAAGGGTATTAATCACATACGG<br>TGGTGGTTCTGTCAAGAAAACTGGTGTATTGGATCAAGTATTGGATGCTTTAAAG<br>GGTATGGATGTCTTGGAATTTGGAGGAATCGAACCAAACCCTGCTTACGAGACTT<br>TAATGAATGCTGTCAAATTGGTCAGAGAACAAAAGGTAACATTCTTATTGGCTGT<br>TGGAGGTGGATCAGTATTAGATGGTACAAAGTTCATTGCTGCTGCAGCAAATTAT<br>CCAGAAAACATTGATCCATGGCATATATTGCAAACTGGTGGTAAGGAAATAAAGT<br>CAGCTATCCCAATGGGATGTGTTTTGACATTGCCTGCAACAGGATCAGAATCAAA<br>CGCTGAAGCAGTCATCTCAAGAAAGACTACAGGTGACAAACAGGCATTCCATTCT<br>GCCCATGTCCAACCTGTATTTGCTGTTTTAGACCCTGTATACACTTACACATTAC<br>CACCAAGGCAAGTCGCAAATGGAGTTGTCGATGCCTTTGTTCACACTGTAGAACA<br>GTACGTCACCAAACCAGTCGATGCAAAGATCCAGGACAGGTTTGCAGAAGGTATT<br>TTATTGACATTAATCGAAGATGGACCAAAAGCATTGAAAGAGCCAGAGAACTATG<br>ACGTTAGGGCAAATGTTATGTGGGCTGCTACCCAGGCATTGAACGGTTTAATTGG<br>TGCAGGAGTTCCACAAGATTGGGCTACACACATGTTGGGTCACGAGTTGACCGCC<br>ATGCACGGTTTGGACCATGCACAGACTTTAGCCATTGTTTTGCCTGCCTTATGGA<br>ACGAGAAAAGAGATACTAAGAGGGCTAAGTTATTACAATACGCTGAAAGGGTTTG<br>GAATATCACCGAGGGATCTGATGATGAAAGGATTGATGCCGTATTGCAGCCACT<br>AGAAACTTCTTTGAACAATTAGGTGTTCCAACTCACTTGTCTGACTATGGTTTAG<br>ATGGATCATCTATTCCAGCTTTGTTGAAGAAATTGGAAGAGCACGGTATGACCCA<br>GTTGGGTGAGAATCATGATATAACCTTAGATGTATCTAGGAGAATCTACGAGGCT<br>GCTAGATAATGA |
| SEQ ID NO: 20 | *Escherichia coli* alcohol dehydrogenase yqhD* AA<br>sequence<br>MNNFNLHTPTRILFGKGAIAGLREQIPHDARVLITYGGGSVKKTGVLDQVLDALK<br>GMDVLEFGGIEPNPAYETLMNAVKLVREQKVTFLLAVGGGSVLDGTKFIAAAANY<br>PENIDPWHILQTGGKEIKSAIPMGCVLTLPATGSESNAEAVISRKTTGDKQAFHS<br>AHVQPVFAVLDPVYTYTLPPRQVANGVVDAFVHTVEQYVTKPVDAKIQDRFAEGI<br>LLTLIEDGPKALKEPENYDVRANVMWAATQALNGLIGAGVPQDWATHMLGHELTA<br>MHGLDHAQTLAIVLPALWNEKRDTKRAKLLQYAERVWNITEGSDDERIDAAIAAT<br>RNFFEQLGVPTHLSDYGLDGSSIPALLKKLEEHGMTQLGENHDITLDVSRRIYEA<br>AR |
| SEQ ID NO: 21 | *Escherichia coli* alcohol dehydrogenase yqhD NT sequence<br>ATGAACAACTTTAATCTGCACACCCCAACCCGCATTCTGTTTGGTAAAGGCGCAA<br>TCGCTGGTTTACGCGAACAAATTCCTCACGATGCTCGCGTATTGATTACCTACGG<br>CGGCGGCAGCGTGAAAAAAACCGGCGTTCTCGATCAAGTTCTGGATGCCCTGAAA<br>GGCATGGACGTGCTGGAATTTGGCGGTATTGAGCCAAACCCGGCTTATGAAACGC<br>TGATGAACGCCGTGAAACTGGTTCGCGAACAGAAAGTGACTTTCCTGCTGGCGGT<br>TGGCGGCGGTTCTGTACTGGACGGCACCAAATTTATCGCCGCAGCGGCTAACTAT<br>CCGGAAAATATCGATCCGTGGCACATTCTGCAAACGGGCGGTAAAGAGATTAAAA<br>GCGCCATCCCGATGGGCTGTGTGCTGACGCTGCCAGCAACCGGTTCAGAATCCAA<br>CGCAGGCGCGGTGATCTCCCGTAAAACCACAGGCGACAAGCAGGCGTTCCATTCT<br>GCCCATGTTCAGCCGGTATTTGCCGTGCTCGATCCGGTTTATACCTACACCCTGC<br>CGCCGCGTCAGGTGGCTAACGGCGTAGTGGACGCCTTTGTACACACCGTGGAACA<br>GTATGTTACCAAACCGGTTGATGCCAAAATTCAGGACCGTTTCGCAGAAGGCATT<br>TTGCTGACGCTAATCGAAGATGGTCCGAAAGCCCTGAAAGAGCCAGAAAACTACG<br>ATGTGCGCGCCAACGTCATGTGGGCGGCGACTCAGGCGCTGAACGGTTTGATTGG<br>CGCTGGCGTACCGCAGGACTGGGCAACGCATATGCTGGGCCACGAACTGACTGCG<br>ATGCACGGTCTGGATCACGCGCAAACACTGGCTATCGTCCTGCCTGCACTGTGGA<br>ATGAAAAACGCGATACCAAGCGCGCTAAGCTGCTGCAATATGCTGAACGCGTCTG<br>GAACATCACTGAAGGTTCCGATGATGAGCGTATTGACGCCGCGATTGCCGCAACC<br>CGCAATTTCTTTGAGCAATTAGGCGTGCCGACCCACCTCTCCGACTACGGTCTGG<br>ACGGCAGCTCCATCCCGGCTTTGCTGAAAAAACTGGAAGAGCACGGCATGACCCA<br>ACTGGGCGAAAATCATGACATTACGTTGGATGTCAGCCGCCGTATATACGAAGCC<br>GCCCGCTAA |
| SEQ ID NO: 22 | *Escherichia coli* alcohol dehydrogenase yqhD codon<br>optimized NT sequence<br>ATGAACAACTTTAATCTGCACACCCCAACCCGCATTCTGTTTGGTAAAGGCGCAA<br>TCGCTGGTTTACGCGAACAAATTCCTCACGATGCTCGCGTATTGATTACCTACGG<br>CGGCGGCAGCGTGAAAAAAACCGGCGTTCTCGATCAAGTTCTGGATGCCCTGAAA<br>GGCATGGACGTGCTGGAATTTGGCGGTATTGAGCCAAACCCGGCTTATGAAACGC<br>TGATGAACGCCGTGAAACTGGTTCGCGAACAGAAAGTGACTTTCCTGCTGGCGGT<br>TGGCGGCGGTTCTGTACTGGACGGCACCAAATTTATCGCCGCAGCGGCTAACTAT<br>CCGGAAAATATCGATCCGTGGCACATTCTGCAAACGGGCGGTAAAGAGATTAAAA<br>GCGCCATCCCGATGGGCTGTGTGCTGACGCTGCCAGCAACCGGTTCAGAATCCAA<br>CGCAGGCGCGGTGATCTCCCGTAAAACCACAGGCGACAAGCAGGCGTTCCATTCT<br>GCCCATGTTCAGCCGGTATTTGCCGTGCTCGATCCGGTTTATACCTACACCCTGC<br>CGCCGCGTCAGGTGGCTAACGGCGTAGTGGACGCCTTTGTACACACCGTGGAACA |

| | SEQUENCE LISTING |
|---|---|
| | GTATGTTACCAAACCGGTTGATGCCAAAATTCAGGACCGTTTCGCAGAAGGCATT<br>TTGCTGACGCTAATCGAAGATGGTCCGAAAGCCCTGAAAGAGCCAGAAAACTACG<br>ATGTGCGCGCCAACGTCATGTGGGCGGCGACTCAGGCGCTGAACGGTTTGATTGG<br>CGCTGGCGTACCGCAGGACTGGGCAACGCATATGCTGGGCCACGAACTGACTGCG<br>ATGCACGGTCTGGATCACGCGCAAACACTGGCTATCGTCCTGCCTGCACTGTGGA<br>ATGAAAAACGCGATACCAAGCGCGCTAAGCTGCTGCAATATGCTGAACGCGTCTG<br>GAACATCACTGAAGGTTCCGATGATGAGCGTATTGACGCCGCGATTGCCGCAACC<br>CGCAATTTCTTTGAGCAATTAGGCGTGCCGACCCACCTCTCCGACTACGGTCTGG<br>ACGGCAGCTCCATCCCGGCTTTGCTGAAAAAACTGGAAGAGCACGGCATGACCCA<br>ACTGGGCGAAAATCATGACATTACGTTGGATGTCAGCCGCCGTATATACGAAGCC<br>GCCCGCTAA |
| SEQ ID NO: 23 | *Escherichia coli* alcohol dehydrogenase yqhD AA sequence<br>MNNFNLHTPTRILFGKGAIAGLREQIPHDARVLITYGGGSVKKTGVLDQVLDALK<br>GMDVLEFGGIEPNPAYETLMNAVKLVREQKVTFLLAVGGGSVLDGTKFIAAAANY<br>PENIDPWHILQTGGKEIKSAIPMGCVLTLPATGSESNAGAVISRKTTGDKQAFHS<br>AHVQPVFAVLDPVYTYTLPPRQVANGVVDAFVHTVEQYVTKPVDAKIQDRFAEGI<br>LLTLIEDGPKALKEPENYDVRANVMWAATQALNGLIGAGVPQDWATHMLGHELTA<br>MHGLDHAQTLAIVLPALWNEKRDTKRAKLLQYAERVWNITEGSDDERIDAAIAAT<br>RNFFEQLGVPTHLSDYGLDGSSIPALLKKLEEHGMTQLGENHDITLDVSRRIYEA<br>AR |
| SEQ ID NO: 24 | *Escherichia coli* methylglyoxal reductase ydjG NT<br>sequence<br>ATGAAAAAGATACCTTTAGGCACAACGGATATTACGCTTTCGCGAATGGGGTTGG<br>GGACATGGGCCATTGGCGGCGGTCCTGCATGGAATGGCGATCTCGATCGGCAAAT<br>ATGTATTGATACGATTCTTGAAGCCCATCGTTGTGGCATTAATCTGATTGATACT<br>GCGCCAGGATATAACTTTGGCAATAGTGAAGTTATCGTCGGTCAGGCGTTAAAAA<br>AACTGCCCCGTGAACAGGTTGTAGTAGAAACCAAATGCGGCATTGTCTGGGAACG<br>AAAAGGAAGTTTATTCAACAAAGTTGGCGATCGGCAGTTGTATAAAAACCTTTCC<br>CCGGAATCTATCCGCGAAGAGGTAGCAGCGAGCTTGCAACGTCTGGGTATTGATT<br>ACATCGATATCTACATGACGCACTGGCAGTCGGTGCCGCCATTTTTTACGCCGAT<br>CGCTGAAACTGTCGCAGTGCTTAATGAGTTAAAGTCTGAAGGGAAAATTCGCGCT<br>ATAGGCGCTGCTAACGTCGATGCTGACCATATCCGCGAGTATCTGCAATATGGTG<br>AACTGGATATTATTCAGGCGAAATACAGTATCCTCGACCGGGCAATGGAAAACGA<br>ACTGCTGCCACTATGTCGTGATAATGGCATTGTGGTTCAGGTTTATTCCCCGCTA<br>GAGCAGGGATTGTTGACCGGCACCATCACTCGTGATTACGTTCCGGGCGGCGCTC<br>GGGCAAATAAAGTCTGGTTCCAGCGTGAAAACATGCTGAAAGTGATTGATATGCT<br>TGAACAGTGGCAGCCACTTTGTGCTCGTTATCAGTGCACAATTCCCACTCTGGCA<br>CTGGCGTGGATATTAAAACAGAGTGATTTAATCTCCATTCTTAGTGGGGCTACTG<br>CACCGGAACAGGTACGCGAAAATGTCGCGGCACTGAATATCAACTTATCGGATGC<br>AGACGCAACATTGATGAGGGAAATGGCAGAGGCCCTGGAGCGTTAA |
| SEQ ID NO: 25 | *Escherichia coli* methylglyoxal reductase ydjG AA<br>sequence<br>MKKIPLGTTDITLSRMGLGTWAIGGGPAWNGDLDRQICIDTILEAHRCGINLIDT<br>APGYNFGNSEVIVGQALKKLPREQVVVETKCGIVWERKGSLFNKVGDRQLYKNLS<br>PESIREEVAASLQRLGIDYIDIYMTHWQSVPPFFTPIAETVAVLNELKSEGKIRA<br>IGAANVDADHIREYLQYGELDIIQAKYSILDRAMENELLPLCRDNGIVVQVYSPL<br>EQGLLTGTITRDYVPGGARANKVWFQRENMLKVIDMLEQWQPLCARYQCTIPTLA<br>LAWILKQSDLISILSGATAPEQVRENVAALNINLSDADATLMREMAEALER |
| SEQ ID NO: 26 | *Escherichia coli* lactaldehyde reductase fucO NT<br>sequence<br>ATGGCTAACAGAATGATTCTGAACGAAACGGCATGGTTTGGTCGGGGTGCTGTTG<br>GGGCTTTAACCGATGAGGTGAAACGCCGTGGTTATCAGAAGGCGCTGATCGTCAC<br>CGATAAAACGCTGGTGCAATGCGGCGTGGTGGCGAAAGTGACCGATAAGATGGAT<br>GCTGCAGGGCTGGCATGGGCGATTTACGACGGCGTAGTGCCCAACCCAACAATTA<br>CTGTCGTCAAAGAAGGGCTCGGTGTATTCCAGAATAGCGGCGCGGATTACCTGAT<br>CGCTATTGGTGGTGGTTCTCCACAGGATACTTGTAAAGCGATTGGCATTATCAGC<br>AACAACCCGGAGTTTGCCGATGTGCGTAGCCTGGAAGGGCTTTCCCCGACCAATA<br>AACCCAGTGTACCGATTCTGGCAATTCCTACCACAGCAGGTACTGCGGCAGAAGT<br>GACCATTAACTACGTGATCACTGACGAAGAGAAACGGCGCAAGTTTGTTTGCGTT<br>GATCCGCATGATATCCCGCAGGTGGCGTTTATTGACGCTGACATGATGGATGGTA<br>TGCCTCCAGCGCTGAAAGCTGCGACGGGTGTCGATGCGCTCACTCATGCTATTGA<br>GGGGTATATTACCCGTGGCGCGTGGGCGCTAACGATGCACTGCACATTAAAGCG<br>ATTGAAATCATTGCTGGGCGCTGCGAGGATCGGTTGCTGGTGATAAGGATGCCG<br>GAGAAGAAATGGCGCTCGGGCAGTATGTTGCGGGTATGGGCTTCTCGAATGTTGG<br>GTTAGGGTTGGTGCATGGTATGGCGCATCCACTGGGCGCGTTTTATAACACTCCA<br>CACGGTGTTGCGAACGCCATCCTGTTACCGCATGTCATGCGTTATAACGCTGACT<br>TTACCGGTGAGAAGTACCGCGATATCGCGCGCGTTATGGGCGTGAAAGTGGAAGG<br>TATGAGCCTGGAAGAGGCGCGTAATGCCGCTGTTGAAGCGGTGTTTGCTCTCAAC<br>CGTGATGTCGGTATTCCGCCACATTTGCGTGATGTTGGTGTACGCAAGGAAGACA<br>TTCCGGCACTGGCGCAGGCGGCACTGGATGATGTTTGTACCGGTGGCAACCCGCG<br>TGAAGCAACGCTTGAGGATATTGTAGAGCTTTACCATACCGCCTGGTAA |

| SEQUENCE LISTING | |
|---|---|
| SEQ ID NO: 27 | *Escherichia coli* lactaldehyde reductase fucO codon optimized NT sequence<br>ATGGCTAACAGAATGATTCTGAACGAAACGGCATGGTTTGGTCGGGGTGCTGTTG<br>GGGCTTTAACCGATGAGGTGAAACGCCGTGGTTATCAGAAGGCGCTGATCGTCAC<br>CGATAAAACGCTGGTGCAATGCGGCGTGGTGGCGAAAGTGACCGATAAGATGGAT<br>GCTGCAGGGCTGGCATGGGCGATTTACGACGGCGTAGTGCCCAACCCAACAATTA<br>CTGTCGTCAAAGAAGGGCTCGGTGTATTCCAGAATAGCGGCGCGGATTACCTGAT<br>CGCTATTGGTGGTGGTTCTCCACAGGATACTTGTAAAGCGATTGGCATTATCAGC<br>AACAACCCGGAGTTTGCCGATGTGCGTAGCCTGGAAGGGCTTTCCCCGACCAATA<br>AACCCAGTGTACCGATTCTGGCAATTCCTACCACAGCAGGTACTGCGGCAGAAGT<br>GACCATTAACTACGTGATCACTGACGAAGAGAAACGGCGCAAGTTTGTTTGCGTT<br>GATCCGCATGATATCCCGCAGGTGGCGTTTATTGACGCTGACATGATGGATGGTA<br>TGCCTCCAGCGCTGAAAGCTGCGACGGGTGTCGATGCGCTCACTCATGCTATTGA<br>GGGGTATATTACCCGTGGCGCGTGGGCGCTAACCGATGCACTGCACATTAAAGCG<br>ATTGAAATCATTGCTGGGGCGCTGCGAGGATCGGTTGCTGGTGATAAGGATGCCG<br>GAGAAGAAATGGCGCTCGGGCAGTATGTTGCGGGTATGGGCTTCTCGAATGTTGG<br>GTTAGGGTTGGTGCATGGTATGGCGCATCCACTGGGCGCGTTTTATAACACTCCA<br>CACGGTGTTGCGAACGCCATCCTGTTACCGCATGTCATGCGTTATAACGCTGACT<br>TTACCGGTGAGAAGTACCGCGATATCGCGCGCGTTATGGGCGTGAAAGTGGAAGG<br>TATGAGCCTGGAAGAGGCGCGTAATGCCGCTGTTGAAGCGGTGTTTGCTCTCAAC<br>CGTGATGTCGGTATTCCGCCACATTTGCGTGATGTTGGTGTACGCAAGGAAGACA<br>TTCCGGCACTGGCGCAGGCGGCACTGGATGATGTTTGTACCGGTGGCAACCCGCG<br>TGAAGCAACGCTTGAGGATATTGTAGAGCTTTACCATACCGCCTGGTAA |
| SEQ ID NO: 28 | *Escherichia coli* lactaldehyde reductase fucO AA sequence<br>MANRMILNETAWFGRGAVGALTDEVKRRGYQKALIVTDKTLVQCGVVAKVTDKMD<br>AAGLAWAIYDGVVPNPTITVVKEGLGVFQNSGADYLIAIGGGSPQDTCKAIGIIS<br>NNPEFADVRSLEGLSPTNKPSVPILAIPTTAGTAAEVTINYVITDEEKRRKFVCV<br>DPHDIPQVAFIDADMMDGMPPALKAATGVDALTHAIEGYITRGAWALTDALHIKA<br>IEIIAGALRGSVAGDKDAGEEMALGQYVAGMGFSNVGLGLVHGMAHPLGAFYNTP<br>HGVANAILLPHVMRYNADFTGEKYRDIARVMGVKVEGMSLEEARNAAVEAVFALN<br>RDVGIPPHLRDVGVRKEDIPALAQAALDDVCTGGNPREATLEDIVELYHTAW |
| SEQ ID NO: 29 | *Escherichia coli* methylglyoxal reductase yafB (dkgB) [multifunctional] NT sequence<br>ATGGCTATCCCTGCATTTGGTTTAGGTACTTTCCGTCTGAAAGACGACGTTGTTA<br>TTTCATCTGTGATAACGGCGCTTGAACTTGGTTATCGCGCAATTGATACCGCACA<br>AATCTATGATAACGAAGCCGCAGTAGGTCAGGCGATTGCAGAAAGTGGCGTGCCA<br>CGTCATGAACTCTACATCACCACTAAAATCTGGATTGAAAATCTCAGCAAAGACA<br>AATTGATCCCAAGTCTGAAAGAGAGCCTGCAAAAATTGCGTACCGATTATGTTGA<br>TCTGACGCTAATCCACTGGCCGTCACCAAACGATGAAGTCTCTGTTGAAGAGTTT<br>ATGCAGGCGCTGCTGGAAGCCAAAAAACAAGGGCTGACGCGTGAGATCGGTATTT<br>CCAACTTCACGATCCCGTTGATGGAAAAAGCGATTGCTGCTGTTGGTGCTGAAAA<br>CATCGCTACTAACCAGATTGAACTCTCTCCTTATCTGCAAAACCGTAAAGTGGTT<br>GCCTGGGCTAAACAGCACGGCATCCATATTACTTCCTATATGACGCTGGCGTATG<br>GTAAGGCCCTGAAAGATGAGGTTATTGCTCGTATCGCAGCTAAACACAATGCGAC<br>TCCGGCACAAGTGATTCTGGCGTGGGCTATGGGGGAAGGTTACTCAGTAATTCCT<br>TCTTCTACTAAACGTAAAAACCTGGAAAGTAATCTTAAGGCACAAAATTTACAGC<br>TTGATGCCGAAGATAAAAAAGCGATCGCCGCACTGGATTGCAACGACCGCCTGGT<br>TAGCCCGGAAGGTCTGGCTCCTGAATGGGATTAA |
| SEQ ID NO: 30 | *Escherichia coli* methylglyoxal reductase yafB (dkgB) [multifunctional] AA sequence<br>MAIPAFGLGTFRLKDDVVISSVITALELGYRAIDTAQIYDNEAAVGQAIAESGVP<br>RHELYITTKIWIENLSKDKLIPSLKESLQKLRTDYVDLTLIHWPSPNDEVSVEEF<br>MQALLEAKKQGLTREIGISNFTIPLMEKAIAAVGAENIATNQIELSPYLQNRKVV<br>AWAKQHGIHITSYMTLAYGKALKDEVIARIAAKHNATPAQVILAWAMGEGYSVIP<br>SSTKRKNLESNLKAQNLQLDAEDKKAIAALDCNDRLVSPEGLAPEWD |
| SEQ ID NO: 31 | *Escherichia coli* 2,5-diketo-D-gluconic acid reductase A yqhE (dkgA) NT sequence<br>ATGGCTAATCCAACCGTTATTAAGCTACAGGATGGCAATGTCATGCCCCAGCTGG<br>GACTGGGCGTCTGGCAAGCAAGTAATGAGGAAGTAATCACCGCCATTCAAAAAGC<br>GTTAGAAGTGGGTTATCGCTCGATTGATACCGCCGCGGCCTACAAGAACGAAGAA<br>GGTGTCGGCAAAGCCCTGAAAAATGCCTCAGTCAACAGAGAAGAACTGTTCATCA<br>CCACTAAGCTGTGGAACGACGACCACAAGCGCCCCCGCGAAGCCCTGCTCGACAG<br>CCTGAAAAAACTCCAGCTTGATTATATCGACCTCTACTTAATGCACTGGCCCGTT<br>CCCGCTATCGACCATTATGTCGAAGCATGGAAAGGCATGATCGAATTGCAAAAAG<br>AGGGATTAATCAAAAGCATCGGCGTGTGCAACTTCCAGATCCATCACCTGCAACG<br>CCTGATTGATGAAACTGGCGTGACGCCTGTGATAAACCAGATCGAACTTCATCCG<br>CTGATGCAACAACGCCAGCTACACGCCTGGAACGCGACACACAAATCCAGACCG<br>AATCCTGGAGCCCATTAGCGCAAGGAGGGAAAGGCGTTTTCGATCAGAAAGTCAT<br>TCGCGATCTGGCAGATAAATACGGCAAAACCCCGGCGCAGATTGTTATCCGCTGG<br>CATCTGGATAGCGGCCTGGTGGTGATCCCGAAATCGGTCACACCTTCACGTATTG<br>CCGAAAACTTTGATGTCTGGGATTTCCGTCTCGACAAAGACGAACTCGGCGAAAT |

| | |
|---|---|
| | TGCAAAACTCGATCAGGGCAAGCGTCTCGGTCCCGATCCTGACCAGTTCGGCGGC<br>TAA |
| SEQ ID NO: 32 | *Escherichia coli* 2,5-diketo-D-gluconic acid reductase A<br>yqhE (dkgA) AA sequence<br>MANPTVIKLQDGNVMPQLGLGVWQASNEEVITAIQKALEVGYRSIDTAAAYKNEE<br>GVGKALKNASVNREELFITTKLWNDDHKRPREALLDSLKKLQLDYIDLYLMHWPV<br>PAIDHYVEAWKGMIELQKEGLIKSIGVCNFQIHHLQRLIDETGVTPVINQIELHP<br>LMQQRQLHAWNATHKIQTESWSPLAQGGKGVFDQKVIRDLADKYGKTPAQIVIRW<br>HLDSGLVVIPKSVTPSRIAENFDVWDFRLDKDELGEIAKLDQGKRLGPDPDQFGG |
| SEQ ID NO: 33 | *Clostridium acetobutylicum* acetyl coenzyme A<br>acetyltransferase thlA NT sequence<br>ATGAAAGAAGTTGTAATAGCTAGTGCAGTAAGAACAGCGATTGGATCTTATGGAA<br>AGTCTCTTAAGGATGTACCAGCAGTAGATTAGGAGCTACAGCTATAAAGGAAGC<br>AGTTAAAAAAGCAGGAATAAAACCAGAGGATGTTAATGAAGTCATTTTAGGAAAT<br>GTTCTTCAAGCAGGTTTAGGACAGAATCCAGCAAGACAGGCATCTTTTAAAGCAG<br>GATTACCAGTTGAAATTCCAGCTATGACTATTAATAAGGTTTGTGGTTCAGGACT<br>TAGAACAGTTAGCTTAGCAGCACAAATTATAAAAGCAGGAGATGCTGACGTAATA<br>ATAGCAGGTGGTATGGAAAATATGTCTAGAGCTCCTTACTTAGCGAATAACGCTA<br>GATGGGGATATAGAATGGGAAACGCTAAATTTGTTGATGAAATGATCACTGACGG<br>ATTGTGGGATGCATTTAATGATTACCACATGGGAATAACAGCAGAAAACATAGCT<br>GAGAGATGGAACATTTCAAGAGAAGAACAAGATGAGTTTGCTCTTGCATCACAAA<br>AAAAAGCTGAAGAAGCTATAAAATCAGGTCAATTTAAAGATGAAATAGTTCCTGT<br>AGTAATTAAAGGCAGAAAGGGAGAAACTGTAGTTGATACAGATGAGCACCCTAGA<br>TTTGGATCAACTATAGAAGGACTTGCAAAATTAAAACCTGCCTTCAAAAAAGATG<br>GAACAGTTACAGCTGGTAATGCATCAGGATTAAATGACTGTGCAGCAGTACTTGT<br>AATCATGAGTGCAGAAAAAGCTAAAGAGCTTGGAGTAAAACCACTTGCTAAGATA<br>GTTTCTTATGGTTCAGCAGGAGTTGACCCAGCAATAATGGGATATGGACCTTTCT<br>ATGCAACAAAAGCAGCTATTGAAAAGCAGGTTGGACAGTTGATGAATTAGATTT<br>AATAGAATCAAATGAAGCTTTTGCAGCTCAAAGTTTAGCAGTAGCAAAAGATTTA<br>AAATTTGATATGAATAAAGTAAATGTAAATGGAGGAGCTATTGCCCTTGGTCATC<br>CAATTGGAGCATCAGGTGCAAGAATACTCGTTACTCTTGTACACGCAATGCAAAA<br>AAGAGATGCAAAAAAAGGCTTAGCAACTTTATGTATAGGTGGCGGACAAGGAACA<br>GCAATATTGCTAGAAAAGTGCTAG |
| SEQ ID NO: 34 | *Clostridium acetobutylicum* acetyl coenzyme A<br>acetyltransferase thlA codon optimized NT sequence<br>ATGAAAGAAGTTGTTATTGCGAGCGCGGTTCGTACCGCGATTGGCAGCTATGGCA<br>AGAGCCTGAAGGATGTTCCGGCGGTGGACCTGGGTGCGACCGCGATCAAGGAGGC<br>GGTTAAGAAAGCGGGCATTAAACCGGAGGATGTGAACGAAGTTATCCTGGGTAAC<br>GTGCTGCAAGCGGGTCTGGGCCAAAACCCGGCGCGTCAGGCGAGCTTCAAGGCGG<br>GCCTGCCGGTTGAAATCCCGGCGATGACCATTAACAAAGTTTGCGGTAGCGGCCT<br>GCGTACCGTGAGCCTGGCGGCGCAAATCATTAAGGCGGGTGACGCGGATGTTATC<br>ATTGCGGGTGGCATGGAGAACATGAGCCGTGCGCCGTACCTGGCGAACAACGCGC<br>GTTGGGGTTATCGTATGGGCAACGCGAAATTCGTGGACGAAATGATTACCGACGG<br>TCTGTGGGATGCGTTTAACGACTACCACATGGGCATCACCGCGGAGAACATTGCG<br>GAACGTTGGAACATTAGCCGTGAGGAACAAGATGAGTTCGCGCTGGCGAGCCAGA<br>AGAAAGCGGAGGAAGCGATCAAGAGCGGCCAGTTTAAAGACGAAATCGTTCCGGT<br>GGTTATTAAGGGTCGTAAGGGTGAAACCGTGGTGGACACCGATGAACACCCGCGT<br>TTCGGTAGCACCATTGAGGGCCTGGCGAAGCTGAAACCGGCGTTTAAGAAAGATG<br>GCACCGTGACCGCGGGTAACGCGAGCGGCCTGAACGACTGCGCGGCGGTGCTGGT<br>TATCATGAGCGCGGAGAAGGCGAAAGAACTGGGTGTGAAGCCGCTGGCGAAATT<br>GTTAGCTACGGTAGCGCGGGTGTGGACCCGGCGATCATGGGTTACGGCCCGTTTT<br>ATGCGACCAAGGCGGCGATTGAGAAAGCGGGTTGGACCGTGGACGAACTGGATCT<br>GATCGAGAGCAACGAAGCGTTCGCGGCGCAAAGCCTGGCGGTGGCGAAGGATCTG<br>AAATTTGACATGAACAAGGTGAACGTGAACGGTGGTGCGATTGCGCTGGGTCACC<br>CGATTGGTGCAGCGGCGCGCGTATCCTGGTGACCCTGGTTCACGCGATGCAGAA<br>ACGTGACGCGAAGAAAGGTCTGGCGACCCTGTGCATTGGTGGTGGTCAAGGCACC<br>GCGATTCTGCTGGAAAAGTGCTAA |
| SEQ ID NO: 35 | *Clostridium acetobutylicum* acetyl coenzyme A<br>acetyltransferase thlA AA sequence<br>MKEVVIASAVRTAIGSYGKSLKDVPAVDLGATAIKEAVKKAGIKPEDVNEVILGN<br>VLQAGLGQNPARQASFKAGLPVEIPAMTINKVCGSGLRTVSLAAQIIKAGDADVI<br>IAGGMENMSRAPYLANNARWGYRMGNAKFVDEMITDGLWDAFNDYHMGITAENIA<br>ERWNISREEQDEFALASQKKAEEAIKSGQFKDEIVPVVIKGRKGETVVDTDEHPR<br>FGSTIEGLAKLKPAFKKDGTVTAGNASGLNDCAAVLVIMSAEKAKELGVKPLAKI<br>VSYGSAGVDPAIMGYGPFYATKAAIEKAGWTVDELDLIESNEAFAAQSLAVAKDL<br>KFDMNKVNVNGGAIALGHPIGASGARILVTLVHAMQKRDAKKGLATLCIGGGQGT<br>AILLEKC |
| SEQ ID NO: 36 | *Escherichia coli* acetyl coenzyme A acetyltransferase<br>atoB NT sequence<br>ATGAAAAATTGTGTCATCGTCAGTGCGGTACGTACTGCTATCGGTAGTTTTAACG<br>GTTCACTCGCTTCCACCAGCGCCATCGACCTGGGGGCGACAGTAATTAAAGCCGC<br>CATTGAACGTGCAAAAATCGATTCACAACACGTTGATGAAGTGATTATGGGTAAC |

```
                    GTGTTACAAGCCGGGCTGGGGCAAAATCCGGCGCGTCAGGCACTGTTAAAAAGCG
                    GGCTGGCAGAAACGGTGTGCGGATTCACGGTCAATAAAGTATGTGGTTCGGGTCT
                    TAAAAGTGTGGCGCTTGCCGCCCAGGCCATTCAGGCAGGTCAGGCGCAGAGCATT
                    GTGGCGGGGGGTATGGAAAATATGAGTTTAGCCCCCTACTTACTCGATGCAAAAG
                    CACGCTCTGGTTATCGTCTTGGAGACGGACAGGTTTATGACGTAATCCTGCGCGA
                    TGGCCTGATGTGCGCCACCCATGGTTATCATATGGGGATTACCGCCGAAAACGTG
                    GCTAAAGAGTACGAATTACCCGTGAAATGCAGGATGAACTGGCGCTACATTCAC
                    AGCGTAAAGCGGCAGCCGCAATTGAGTCCGGTGCTTTTACAGCCGAAATCGTCCC
                    GGTAAATGTTGTCACTCGAAAGAAAACCTTCGTCTTCAGTCAAGACGAATTCCCG
                    AAAGCGAATTCAACGGCTGAAGCGTTAGGTGCATTGCGCCCGGCCTTCGATAAAG
                    CAGGAACAGTCACCGCTGGGAACGCGTCGGTATTAACGACGGTGCTGCCGCTCT
                    GGTGATTATGGAAGAATCTGCGGCGCTGGCAGCAGGCCTTACCCCCCTGGCTCGC
                    ATTAAAAGTTATGCCAGCGGTGGCGTGCCCCCCGCATTGATGGGTATGGGGCCAG
                    TACCTGCCACGCAAAAAGCGTTACAACTGGCGGGGCTGCAACTGGCGGATATTGA
                    TCTCATTGAGGCTAATGAAGCATTTGCTGCACAGTTCCTTGCCGTTGGGAAAAAC
                    CTGGGCTTTGATTCTGAGAAAGTGAATGTCAACGGCGGGGCCATCGCGCTCGGGC
                    ATCCTATCGGTGCCAGTGGTGCTCGTATTCTGGTCACACTATTACATGCCATGCA
                    GGCACGCGATAAAACGCTGGGGCTGGCAACACTGTGCATTGGCGGCGGTCAGGGA
                    ATTGCGATGGTGATTGAACGGTTGAATTAA

SEQ ID NO: 37      Escherichia coli acetyl coenzyme A acetyltransferase
                   atoB AA sequence
                   MKNCVIVSAVRTAIGSFNGSLASTSAIDLGATVIKAAIERAKIDSQHVDEVIMGN
                   VLQAGLGQNPARQALLKSGLAETVCGFTVNKVCGSGLKSVALAAQAIQAGQAQSI
                   VAGGMENMSLAPYLLDAKARSGYRLGDGQVYDVILRDGLMCATHGYHMGITAENV
                   AKEYGITREMQDELALHSQRKAAAAIESGAFTAEIVPVNVVTRKKTFVFSQDEFP
                   KANSTAEALGLRPAFDKAGTVTAGNASGINDGAAALVIMEESAALAAGLTPLAR
                   IKSYASGGVPPALMGMGPVPATQKALQLAGLQLADIDLIEANEAFAAQFLAVGKN
                   LGFDSEKVNVNGGAIALGHPIGASGARILVTLLHAMQARDKTLGLATLCIGGGQG
                   IAMVIERLN SEQ ID NO: 38      Saccharomyces cerevisiae acetyl coenzyme A
                   acetyltransferase ERG10 NT sequence
                   ATGTCTCAGAACGTTTACATTGTATCGACTGCCAGAACCCCAATTGGTTCATTCC
                   AGGGTTCTCTATCCTCCAAGACAGCAGTGGAATTGGGTGCTGTTGCTTTAAAAGG
                   CGCCTTGGCTAAGGTTCCAGAATTGGATGCATCCAAGGATTTTGACGAAATTATT
                   TTTGGTAACGTTCTTTCTGCCAATTTGGGCCAAGCTCCGGCCAGACAAGTTGCTT
                   TGGCTGCCGGTTTGAGTAATCATATCGTTGCAAGCACAGTTAACAAGGTCTGTGC
                   ATCCGCTATGAAGGCAATCATTTTGGGTGCTCAATCCATCAAATGTGGTAATGCT
                   GATGTTGTCGTAGCTGGTGGTTGTGAATCTATGACTAACGCACCATACTACATGC
                   CAGCAGCCCGTGCGGGTGCCAAATTTGGCCAAACTGTTCTTGTTGATGGTGTCGA
                   AAGAGATGGGTTGAACGATGCGTACGATGGTCTAGCCATGGGTGTACACGCAGAA
                   AAGTGTGCCCGTGATTGGGATATTACTAGAGAACAACAAGACAATTTTGCCATCG
                   AATCCTACCAAAAATCTCAAAAATCTCAAAAGGAAGGTAAATTCGACAATGAAAT
                   TGTACCTGTTACCATTAAGGGATTTAGAGGGTAAGCCTGATACTCAAGTCACGAAG
                   GACGAGGAACCTGCTAGATTACACGTTGAAAAATTGAGATCTGCAAGGACTGTTT
                   TCCAAAAAGAAAACGGTACTGTTACTGCCGCTAACGCTTCTCCAATCAACGATGG
                   TGCTGCAGCCGTCATCTTGGTTTCCGAAAAAGTTTTGAAGGAAAAGAATTTGAAG
                   CCTTTGGCTATTATCAAAGGTTGGGGTGAGGCCGCTCATCAACCAGCTGATTTTA
                   CATGGGCTCCATCTCTTGCAGTTCCAAAGGCTTTGAAACATGCTGGCATCGAAGA
                   CATCAATTCTGTTGATTACTTTGAATTCAATGAAGCCTTTTCGGTTGTCGGTTTG
                   GTGAACACTAAGATTTTGAAGCTAGACCCATCTAAGGTTAATGTATATGGTGGTG
                   CTGTTGCTCTAGGTCACCCATTGGGTTGTTCTGGTGCTAGAGTGGTTGTTACACT
                   GCTATCCATCTTACAGCAAGAAGGAGGTAAGATCGGTGTTGCCGCCATTTGTAAT
                   GGTGGTGGTGGTGCTTCCTCTATTGTCATTGAAAAGATATGA SEQ ID NO: 39      Saccharomyces cerevisiae acetyl coenzyme A
                   acetyltransferase ERG10 codon optimized NT sequence
                   ATGTCTCAGAACGTTTACATTGTATCGACTGCCAGAACCCCAATTGGTTCATTCC
                   AGGGTTCTCTATCCTCCAAGACAGCAGTGGAATTGGGTGCTGTTGCTTTAAAAGG
                   CGCCTTGGCTAAGGTTCCAGAATTGGATGCATCCAAGGATTTTGACGAAATTATT
                   TTTGGTAACGTTCTTTCTGCCAATTTGGGCCAAGCTCCGGCCAGACAAGTTGCTT
                   TGGCTGCCGGTTTGAGTAATCATATCGTTGCAAGCACAGTTAACAAGGTCTGTGC
                   ATCCGCTATGAAGGCAATCATTTTGGGTGCTCAATCCATCAAATGTGGTAATGCT
                   GATGTTGTCGTAGCTGGTGGTTGTGAATCTATGACTAACGCACCATACTACATGC
                   CAGCAGCCCGTGCGGGTGCCAAATTTGGCCAAACTGTTCTTGTTGATGGTGTCGA
                   AAGAGATGGGTTGAACGATGCGTACGATGGTCTAGCCATGGGTGTACACGCAGAA
                   AAGTGTGCCCGTGATTGGGATATTACTAGAGAACAACAAGACAATTTTGCCATCG
                   AATCCTACCAAAAATCTCAAAAATCTCAAAAGGAAGGTAAATTCGACAATGAAAT
                   TGTACCTGTTACCATTAAGGGATTTAGAGGGTAAGCCTGATACTCAAGTCACGAAG
                   GACGAGGAACCTGCTAGATTACACGTTGAAAAATTGAGATCTGCAAGGACTGTTT
                   TCCAAAAAGAAAACGGTACTGTTACTGCCGCTAACGCTTCTCCAATCAACGATGG
                   TGCTGCAGCCGTCATCTTGGTTTCCGAAAAAGTTTTGAAGGAAAAGAATTTGAAG
                   CCTTTGGCTATTATCAAAGGTTGGGGTGAGGCCGCTCATCAACCAGCTGATTTTA
                   CATGGGCTCCATCTCTTGCAGTTCCAAAGGCTTTGAAACATGCTGGCATCGAAGA
                   CATCAATTCTGTTGATTACTTTGAATTCAATGAAGCCTTTTCGGTTGTCGGTTTG
                   GTGAACACTAAGATTTTGAAGCTAGACCCATCTAAGGTTAATGTATATGGTGGTG
```

| SEQUENCE LISTING |
| --- |
| CTGTTGCTCTAGGTCACCCATTGGGTTGTTCTGGTGCTAGAGTGGTTGTTACACT<br>GCTATCCATCTTACAGCAAGAAGGAGGTAAGATCGGTGTTGCCGCCATTTGTAAT<br>GGTGGTGGTGGTGCTTCCTCTATTGTCATTGAAAAGATATGA |

SEQ ID NO: 40    *Saccharomyces cerevisiae* acetyl coenzyme A
                 acetyltransferase ERG10 AA sequence
                 MSQNVYIVSTARTPIGSFQGSLSSKTAVELGAVALKGALAKVPELDASKDFDEII
                 FGNVLSANLGQAPARQVALAAGLSNHIVASTVNKVCASAMKAIILGAQSIKCGNA
                 DVVVAGGCESMTNAPYYMPAARAGAKFGQTVLVDGVERDGLNDAYDGLAMGVHAE
                 KCARDWDITREQQDNFAIESYQKSQKSQKEGKFDNEIVPVTIKGFRGKPDTQVTK
                 DEEPARLHVEKLRSARTVFQKENGTVTAANASPINDGAAAVILVSEKVLKEKNLK
                 PLAIIKGWGEAAHQPADFTWAPSLAVPKALKHAGIEDINSVDYFEFNEAFSVVGL
                 VNTKILKLDPSKVNVYGGAVALGHPLGCSGARVVVTLLSILQQEGGKIGVAAICN
                 GGGGASSIVIEKI SEQ ID NO: 41    *Escherichia coli* Acetyl-CoA:acetoacetate-CoA
                 transferase subunit atoA NT sequence
                 ATGGATGCGAAACAACGTATTGCGCGCCGTGTGGCGCAAGAGCTTCGTGATGGTG
                 ACATCGTTAACTTAGGGATCGGTTTACCCACAATGGTCGCCAATTATTTACCGGA
                 GGGTATTCATATCACTCTGCAATCGGAAAACGGCTTCCTCGGTTTAGGCCCGGTC
                 ACGACAGCGCATCCAGATCTGGTGAACGCTGGCGGGCAACCGTGCGGTGTTTTAC
                 CCGGTGCAGCCATGTTTGATAGCGCCATGTCATTTGCGCTAATCCGTGGCGGTCA
                 TATTGATGCCTGCGTGCTCGGCGGTTTGCAAGTAGACGAAGAAGCAAACCTCGCG
                 AACTGGGTAGTGCCTGGGAAAATGGTGCCCGGTATGGGTGGCGCGATGGATCTGG
                 TGACCGGGTCGCGCAAAGTGATCATCGCCATGGAACATTGCGCCAAAGATGGTTC
                 AGCAAAAATTTTGCGCCGCTGCACCATGCCACTCACTGCGCAACATGCGGTGCAT
                 ATGCTGGTTACTGAACTGGCTGTCTTTCGTTTTATTGACGGCAAAATGTGGCTCA
                 CCGAAATTGCCGACGGGTGTGATTTAGCCACCGTGCGTGCCAAAACAGAAGCTCG
                 GTTTGAAGTCGCCGCCGATCTGAATACGCAACGGGGTGATTTATGA SEQ ID NO: 42    *Escherichia coli* Acetyl-CoA:acetoacetate-CoA
                 transferase subunit atoA codon optimized NT sequence
                 ATGGATGCGAAACAACGTATTGCGCGCCGTGTGGCGCAAGAGCTTCGTGATGGTG
                 ACATCGTTAACTTAGGGATCGGTTTACCCACAATGGTCGCCAATTATTTACCGGA
                 GGGTATTCATATCACTCTGCAATCGGAAAACGGCTTCCTCGGTTTAGGCCCGGTC
                 ACGACAGCGCATCCAGATCTGGTGAACGCTGGCGGGCAACCGTGCGGTGTTTTAC
                 CCGGTGCAGCCATGTTTGATAGCGCCATGTCATTTGCGCTAATCCGTGGCGGTCA
                 TATTGATGCCTGCGTGCTCGGCGGTTTGCAAGTAGACGAAGAAGCAAACCTCGCG
                 AACTGGGTAGTGCCTGGGAAAATGGTGCCCGGTATGGGTGGCGCGATGGATCTGG
                 TGACCGGGTCGCGCAAAGTGATCATCGCCATGGAACATTGCGCCAAAGATGGTTC
                 AGCAAAAATTTTGCGCCGCTGCACCATGCCACTCACTGCGCAACATGCGGTGCAT
                 ATGCTGGTTACTGAACTGGCTGTCTTTCGTTTTATTGACGGCAAAATGTGGCTCA
                 CCGAAATTGCCGACGGGTGTGATTTAGCCACCGTGCGTGCCAAAACAGAAGCTCG
                 GTTTGAAGTCGCCGCCGATCTGAATACGCAACGGGGTGATTTATGA SEQ ID NO: 43    *Escherichia coli* Acetyl-CoA:acetoacetate-CoA
                 transferase subunit atoA AA sequence
                 MDAKQRIARRVAQELRDGDIVNLGIGLPTMVANYLPEGIHITLQSENGFLGLGPV
                 TTAHPDLVNAGGQPCGVLPGAAMFDSAMSFALIRGGHIDACVLGGLQVDEEANLA
                 NWVVPGKMVPGMGGAMDLVTGSRKVIIAMEHCAKDGSAKILRRCTMPLTAQHAVH
                 MLVTELAVFRFIDGKMWLTEIADGCDLATVRAKTEARFEVAADLNTQRGDL SEQ ID NO: 44    *Escherichia coli* Acetyl-CoA:acetoacetate-CoA
                 transferase subunit atoD NT sequence
                 ATGAAAACAAAATTGATGACATTACAAGACGCCACCGGCTTCTTTCGTGACGGCA
                 TGACCATCATGGTGGGCGGATTTATGGGGATTGGCACTCCATCCCGCCTGGTTGA
                 AGCATTACTGGAATCTGGTGTTCGCGACCTGACATTGATAGCCAATGATACCGCG
                 TTTGTTGATACCGGCATCGGTCCGCTCATCGTCAATGGTCGAGTCCGCAAAGTGA
                 TTGCTTCACATATCGGCACCAACCCGGAAACAGGTCGGCGCATGATATCTGGTGA
                 GATGGACGTCGTTCTGGTGCCGCAAGGTACGCTAATCGAGCAAATTCGCTGTGGT
                 GGAGCTGGACTTGGTGGTTTTCTCACCCCAACGGGTGTCGGCACCGTCGTAGAGG
                 AAGGCAAACAGACACTGACACTCGACGGTAAAACCTGGCTGCTCGAACGCCCACT
                 GCGCGCCGACCTGGCGCTAATTCGCGCTCATCGTTGCGACACACTTGGCAACCTG
                 ACCTATCAACTTAGCGCCCGCAACTTTAACCCCCTGATAGCCCTTGCGGCTGATA
                 TCACGCTGGTAGAGCCAGATGAACTGGTCGAAACCGGCGAGCTGCAACCTGACCA
                 TATTGTCACCCCTGGTGCCGTTATCGACCACATCATCGTTTCACAGGAGAGCAAA
                 TAA SEQ ID NO: 45    *Escherichia coli* Acetyl-CoA:acetoacetate-CoA
                 transferase subunit atoD codon optimized NT sequence
                 ATGAAAACAAAATTGATGACATTACAAGACGCCACCGGCTTCTTTCGTGACGGCA
                 TGACCATCATGGTGGGCGGATTTATGGGGATTGGCACTCCATCCCGCCTGGTTGA
                 AGCATTACTGGAATCTGGTGTTCGCGACCTGACATTGATAGCCAATGATACCGCG
                 TTTGTTGATACCGGCATCGGTCCGCTCATCGTCAATGGTCGAGTCCGCAAAGTGA
                 TTGCTTCACATATCGGCACCAACCCGGAAACAGGTCGGCGCATGATATCTGGTGA
                 GATGGACGTCGTTCTGGTGCCGCAAGGTACGCTAATCGAGCAAATTCGCTGTGGT
                 GGAGCTGGACTTGGTGGTTTTCTCACCCCAACGGGTGTCGGCACCGTCGTAGAGG

| | SEQUENCE LISTING |
|---|---|
| | AAGGCAAACAGACACTGACACTCGACGGTAAAACCTGGCTGCTCGAACGCCCACT<br>GCGCGCCGACCTGGCGCTAATTCGCGCTCATCGTTGCGACACACTTGGCAACCTG<br>ACCTATCAACTTAGCGCCCGCAACTTTAACCCCCTGATAGCCCTTGCGGCTGATA<br>TCACGCTGGTAGAGCCAGATGAACTGGTCGAAACCGGCGAGCTGCAACCTGACCA<br>TATTGTCACCCCTGGTGCCGTTATCGACCACATCATCGTTTCACAGGAGAGCAAA<br>TAA |
| SEQ ID NO: 46 | *Escherichia coli* Acetyl-CoA:acetoacetate-CoA<br>transferase subunit atoD AA sequence<br>MKTKLMTLQDATGFFRDGMTIMVGGFMGIGTPSRLVEALLESGVRDLTLIANDTA<br>FVDTGIGPLIVNGRVRKVIASHIGTNPETGRRMISGEMDVVLVPQGTLIEQIRCG<br>GAGLGGFLTPTGVGTVVEEGKQTLTLDGKTWLLERPLRADLALIRAHRCDTLGNL<br>TYQLSARNFNPLIALAADITLVEPDELVETGELQPDHIVTPGAVIDHIIVSQESK |
| SEQ ID NO: 47 | *Clostridium acetobutylicum* acetoacetate decarboxylase<br>adc NT sequence<br>ATGTTAAAGGATGAAGTAATTAAACAAATTAGCACGCCATTAACTTCGCCTGCAT<br>TTCCTAGAGGACCCTATAAATTTCATAATCGTGAGTATTTTAACATTGTATATCG<br>TACAGATATGGATGCACTTCGTAAAGTTGTGCCAGAGCCTTTAGAAATTGATGAG<br>CCCTTAGTCAGGTTTGAAATTATGGCAATGCATGATACGAGTGGACTTGGTTGTT<br>ATACAGAAAGCGGACAGGCTATTCCCGTAAGCTTTAATGGAGTTAAGGGAGATTA<br>TCTTCATATGATGTATTTAGATAATGAGCCTGCAATTGCAGTAGGAAGGGAATTA<br>AGTGCATATCCTAAAAAGCTCGGGTATCCAAAGCTTTTTGTGGATTCAGATACTT<br>TAGTAGGAACTTTAGACTATGGAAAACTTAGAGTTGCGACAGCTACAATGGGGTA<br>CAAACATAAAGCCTTAGATGCTAATGAAGCAAAGGATCAAATTTGTCGCCCTAAT<br>TATATGTTGAAAATAATACCCAATTATGATGGAAGCCCTAGAATATGTGAGCTTA<br>TAAATGCGAAAATCACAGATGTTACCGTACATGAAGCTTGGACAGGACCAACTCG<br>ACTGCAGTTATTTGATCACGCTATGGCGCCACTTAATGATTTGCCAGTAAAAGAG<br>ATTGTTTCTAGCTCTCACATTCTTGCAGATATAATATTGCCTAGAGCTGAAGTTA<br>TATATGATTATCTTAAGTAA |
| SEQ ID NO: 48 | *Clostridium acetobutylicum* acetoacetate decarboxylase<br>adc codon optimized NT sequence<br>ATGCTGAAGGACGAGGTTATTAAGCAGATTAGCACCCCGCTGACCAGCCCGGCGT<br>TCCCGCGTGGTCCGTACAAGTTCCATAATCGCGAATACTTCAACATTGTGTATCG<br>TACCGACATGGATGCGCTGCGTAAGGTGGTTCCGGAGCCGCTGGAAATTGACGAG<br>CCGCTGGTTCGTTTCGAAATCATGGCGATGCACGATACCAGCGGTCTGGGCTGCT<br>ACACCGAGAGCGGTCAGGCGATTCCGGTGAGCTTTAACGGTGTTAAAGGCGACTA<br>CCTGCACATGATGTATCTGGATAACGAACCGGCGATTGCGGTGGGTCGTGAGCTG<br>AGCGCGTACCCGAAGAAACTGGGCTATCCGAAGCTGTTCGTGGACAGCGATACCC<br>TGGTGGGCACCCTGGACTACGGCAAACTGCGTGTTGCGACCGCGACCATGGGCTA<br>TAAGCACAAAGCGCTGGACGCGAACGAAGCGAAGGATCAGATTTGCCGTCCGAAC<br>TACATGCTGAAAATCATTCCGAACTATGACGGTAGCCCGCGTATCTGCGAACTGA<br>TTAACGCGAAGATCACCGATGTTACCGTTCATGAGGCGTGGACCGGCCCGACCCG<br>TCTGCAACTGTTTGACCACGCGATGGCGCCGCTGAACGATCTGCCGGTGAAAGAG<br>ATCGTTAGCAGCAGCCACATCCTGGCGGACATCATCCTGCCGCGTGCGGAAGTTA<br>TCTACGATTACCTGAAGTAA |
| SEQ ID NO: 49 | *Clostridium acetobutylicum* acetoacetate decarboxylase<br>adc AA sequence<br>MLKDEVIKQISTPLTSPAFPRGPYKFHNREYFNIVYRTDMDALRKVVPEPLEIDE<br>PLVRFEIMAMHDTSGLGCYTESGQAIPVSFNGVKGDYLHMMYLDNEPAIAVGREL<br>SAYPKKLGYPKLFVDSDTLVGTLDYGKLRVATATMGYKHKALDANEAKDQICRPN<br>YMLKIIPNYDGSPRICELINAKITDVTVHEAWTGPTRLQLFDHAMAPLNDLPVKE<br>IVSSSHILADIILPRAEVIYDYLK |
| SEQ ID NO: 50 | *Clostridium beijerinckii* acetoacetate decarboxylase adc<br>NT sequence<br>ATGTTAGAAAGTGAAGTATCTAAACAAATTACAACTCCACTTGCTGCTCCAGCGT<br>TTCCTAGAGGACCCATATAGGTTTCACAATAGAGAATATCTAAACATTATTTATCG<br>AACTGATTTAGATGCTCTTCGAAAAATAGTACCAGAGCCACTTGAATTAGATAGA<br>GCATATGTTAGATTTGAAATGATGGCTATGCCTGATACAACCGGACTAGGCTCAT<br>ATACAGAATGTGGTCAAGCTATTCCAGTAAAATATAATGGTGTTAAGGGTGACTA<br>CTTGCATATGATGTATCTAGATAATGAACCTGCTATTGCTGTTGGAAGAGAAAGT<br>AGCGCTTATCCAAAAAAGCTTGGCTATCCAAAGCTATTTGTTGATTCAGATACTT<br>TAGTTGGGACACTTAAATATGGTACATTACCAGTAGCTACTGCAACAATGGGATA<br>TAAGCACGAGCCTCTAGATCTTAAAGAAGCCTATGCTCAAATTGCAAGACCCAAT<br>TTTATGCTAAAAATCATTCAAGGTTACGATGGTAAGCCAAGAATTTGTGAACTAA<br>TATGTGCAGAAAATACTGATATAACTATTCACGGTGCTTGGACTGGAAGTGCACG<br>TCTACAATTATTTAGCCATGCACTAGCTCCTCTTGCTGATTTACCTGTATTAGAG<br>ATTGTATCAGCATCTCATATCCTCACAGATTTAACTCTTGGAACACCTAAGGTTG<br>TACATGATTATCTTTCAGTAAAATAA |
| SEQ ID NO: 51 | *Clostridium beijerinckii* acetoacetate decarboxylase adc<br>codon optimized NT sequence<br>ATGCTGGAGAGCGAAGTTAGCAAACAAATCACCACCCCGCTGGCGGCGCCGGCGT<br>TCCCGCGTGGCCCCGTACCGTTTTCATAACCGTGAGTACCTGAACATCATTTATCG |

| SEQUENCE LISTING |
| --- |
| TACCGACCTGGATGCGCTGCGTAAGATTGTGCCGGAGCCGCTGGAACTGGACCGT<br>GCGTACGTTCGTTTCGAGATGATGGCGATGCCGGATACCACCGGTCTGGGCAGCT<br>ACACCGAATGCGGTCAGGCGATCCCGGTGAAGTATAACGGTGTTAAAGGCGACTA<br>CCTGCACATGATGTATCTGGATAACGAGCCGGCGATTGCGGTGGGTCGTGAAAGC<br>AGCGCGTACCCGAAGAAACTGGGCTATCCGAAGCTGTTTGTGGACAGCGATACCC<br>TGGTGGGCACCCTGAAATATGGCACCCTGCCGGTTGCGACCGCGACCATGGGCTA<br>CAAGCACGAGCCGCTGGACCTGAAAGAAGCGTATGCGCAGATTGCGCGTCCGAAC<br>TTCATGCTGAAGATCATTCAAGGTTATGACGGCAAACCGCGTATCTGCGAGCTGA<br>TTTGCGCGGAAAACACCGATATCACCATCCATGGTGCGTGGACCGGCAGCGCGCG<br>TCTGCAACTGTTTAGCCATGCGCTGGCGCCGCTGGCGGATCTGCCGGTGCTGGAA<br>ATCGTTAGCGCGAGCCACATTCTGACCGATCTGACCCTGGGCACCCCGAAGGTTG<br>TGCATGACTATCTGAGCGTGAAGTAA |

SEQ ID NO: 52      *Clostridium beijerinckii* acetoacetate decarboxylase adc
AA sequence
MLESEVSKQITTPLAAPAFPRGPYRFHNREYLNIIYRTDLDALRKIVPEPLELDR
AYVRFEMMAMPDTTGLGSYTECGQAIPVKYNGVKGDYLHMMYLDNEPAIAVGRES
SAYPKKLGYPKLFVDSDTLVGTLKYGTLPVATATMGYKHEPLDLKEAYAQIARPN
FMLKIIQGYDGKPRICELICAENTDITIHGAWTGSARLQLFSHALAPLADLPVLE
IVSASHILTDLTLGTPKVVHDYLSVK SEQ ID NO: 53      *Homo sapiens* ketohexokinase C khk-C cDNA sequence
ATGGAAGAGAAGCAGATCCTGTGCGTGGGGCTAGTGGTGCTGGACGTCATCAGCC
TGGTGGACAAGTACCCTAAGGAGGACTCGGAGATAAGGTGTTTGTCCCAGAGATG
GCAGCGCGGAGGCAACGCGTCCAACTCCTGCACCGTTCTCTCCCTGCTCGGAGCC
CCTGTGCCTTCATGGGCTCAATGGCTCCTGGCCATGTTGCTGATTTTGTCCTGG
ATGACCTCCGCCGCTATTCTGTGGACCTACGCTACACAGTCTTTCAGACCACAGG
CTCCGTCCCCATCGCCACGGTCATCATCAACGAGGCCAGTGGTAGCCGCACCATC
CTATACTATGACAGGAGCCTGCCAGATGTGTCTGCTACAGACTTTGAGAAGGTTG
ATCTGACCCAGTTCAAGTGGATCCACATTGAGGGCCGGAACGCATCGGAGCAGGT
GAAGATGCTGCAGCGGATAGACGCACACAACACCAGGCAGCCTCCAGAGCAGAAG
ATCCGGGTGTCCGTGGAGGTGGAGAAGCCACGAGAGGAGCTCTTCCAGCTGTTTG
GCTACGAGACGTGGTGTTTGTCAGCAAAGATGTGGCCAAGCACTTGGGGTTCCA
GTCAGCAGAGGAAGCCTTGAGGGGCTTGTATGGTCGTGTGAGGAAAGGGGCTGTG
CTTGTCTGTGCCTGGGCTGAGGAGGGCGCCGACGCCCTGGGCCCTGATGGCAAAT
TGCTCCACTCGGATGCTTTCCCGCCACCCCGCGTGGTGGATACACTGGGAGCTGG
AGACACCTTCAATGCCTCCGTCATCTTCAGCCTCTCCCAGGGGAGGAGCGTGCAG
GAAGCACTGAGATTCGGGTGCCAGGTGGCCGGCAAGAAGTGTGGCCTGCAGGGCT
TTGATGGCATCGTTTAA SEQ ID NO: 54      *Homo sapiens* ketohexokinase C khk-C codon optimized
cDNA sequence
ATGGAGGAAAAGCAAATTCTGTGCGTTGGTCTGGTGGTTCTGGACGTGATTAGCC
TGGTTGATAAGTACCCGAAAGAGGATAGCGAAATCCGTTGCCTGAGCCAGCGTTG
GCAACGTGGTGGCAACGCGAGCAATAGCTGCACCGTTCTGAGCCTGCTGGGTGCG
CCGTGCGCGTTCATGGGTAGCATGGCGCCGGGTCATGTTGCGGACTTCCTGGTGG
CGGATTTTCGTCGTCGTGGTGGACGTTAGCCAGGTTGCGTGGCAAAGCAAGGG
CGATACCCCGAGCTCCTGCTGCATCATTAACAACAGCAACGGTAACCGTACCATT
GTGCTGCACGACACCAGCCTGCCGGATGTTAGCGCGACCGACTTCGAGAAGGTGG
ATCTGACCCAGTTTAAATGGATTCACATTGAGGGCCGTAACGCGAGCGAACAGGT
TAAAATGCTGCAACGTATTGATGCGCACAACACCCGTCAGCCGCCGGAACAAAAG
ATTCGTGTGAGCGTTGAGGTGGAAAAACCGCGTGAGGAACTGTTCCAACTGTTTG
GTTACGGCGACGTGGTTTTCGTTAGCAAGGATGTGGCGAAACACCTGGGTTTTCA
AAGCGCGGAGGAAGCGCTGCGTGGTCTGTATGGCCGTGTGCGTAAAGGCGCGGTT
CTGGTGTGCGCGTGGGCGGAGGAAGGCGCGGATGCGCTGGGTCCGGATGGCAAAC
TGCTGCACAGCGATGCGTTCCCGCCGCCGCGTGTGGTTGACACCCTGGGTGCGGG
CGATACCTTCAACGCGAGCGTTATCTTTAGCCTGAGCCAGGGCCGTAGCGTGCAA
GAGGCGCTGCGTTTCGGCTGCCAAGTTGCGGGTAAAAAATGCGGTCTGCAAGGCT
TTGACGGTATCGTGTAA SEQ ID NO: 55      *Homo sapiens* ketohexokinase C khk-C AA sequence
MEEKQILCVGLVVLDVISLVDKYPKEDSEIRCLSQRWQRGGNASNSCTVLSLLGA
PCAFMGSMAPGHVADFLVADFRRRGVDVSQVAWQSKGDTPSSCCIINNSNGNRTI
VLHDTSLPDVSATDFEKVDLTQFKWIHIEGRNASEQVKMLQRIDAHNTRQPPEQK
IRVSVEVEKPREELFQLFGYGDVVFVSKDVAKHLGFQSAEEALRGLYGRVRKGAV
LVCAWAEEGADALGPDGKLLHSDAFPPPRVVDTLGAGDTFNASVIFSLSQGRSVQ
EALRFGCQVAGKKCGLQGFDGIV SEQ ID NO: 56      *Homo sapiens* Fructose-bisphosphate aldolase B aldoB
cDNA sequence
ATGGCCCACCGATTTCCAGCCCTCACCCAGGAGCAGAAGAAGGAGCTCTCAGAAA
TTGCCCAGAGCATTGTTGCCAATGGAAAGGGGATCCTGGCTGCAGATGAATCTGT
AGGTACCATGGGGAACCGCCTGCAGAGGATCAAGGTGGAAAACACTGAAGAGAAC
CGCCGGCAGTTCCGAGAAATCCTCTTCTCTGTGGACAGTTCCATCAACCAGAGCA
TCGGGGGTGTGATCCTTTTCCACGAGACCCTCTACCAGAAGGACAGCCAGGGAAA
GCTGTTCAGAAACATCCTCAAGGAAAGGGGATCGTGGTGGGAATCAAGTTAGAC
CAAGGAGGTGCTCCTCTTGCAGGAACAAACAAAGAAACCACCATTCAAGGGCTTG

| SEQUENCE LISTING |
| --- |
| ATGGCCTCTCAGAGCGCTGTGCTCAGTACAAGAAAGATGGTGTTGACTTTGGGAA<br>GTGGCGTGCTGTGCTGAGGATTGCCGACCAGTGTCCATCCAGCCTCGCTATCCAG<br>GAAAACGCCAACGCCCTGGCTCGCTACGCCAGCATCTGTCAGCAGAATGGACTGG<br>TACCTATTGTTGAACCAGAGGTAATTCCTGATGGAGACCATGACCTGGAACACTG<br>CCAGTATGTTACTGAGAAGGTCCTGGCTGCTGTCTACAAGGCCCTGAATGACCAT<br>CATGTTTACCTGGAGGGCACCCTGCTAAAGCCCAACATGGTGACTGCTGGACATG<br>CCTGCACCAAGAAGTATACTCCAGAACAAGTAGCTATGGCCACCGTAACAGCTCT<br>CCACCGTACTGTTCCTGCAGCTGTTCCTGGCATCTGCTTTTTGTCTGGTGGCATG<br>AGTGAAGAGGATGCCACTCTCAACCTCAATGCTATCAACCTTTGCCCTCTACCAA<br>AGCCCTGGAAACTAAGTTTCTCTTATGGACGGGCCCTGCAGGCCAGTGCACTGGC<br>TGCCTGGGGTGGCAAGGCTGCAAACAAGGAGGCAACCCAGGAGGCTTTTATGAAG<br>CGGGCCATGGCTAACTGCCAGGCGGCCAAAGGACAGTATGTTCACACGGGTTCTT<br>CTGGGGCTGCTTCCACCCAGTCGCTCTTCACAGCCTGCTATACCTACTAG |

SEQ ID NO: 57    *Homo sapiens* Fructose-bisphosphate aldolase B aldoB
                 codon optimized cDNA sequence
                 ATGGCGCACCGTTTTCCGGCGCTGACCCAAGAGCAGAAGAAGGAGCTGAGCGAGA
                 TTGCGCAGAGCATCGTGGCGAATGGTAAAGGTATTCTGGCGGCGGATGAGAGCGT
                 TGGTACCATGGGCAACCGTCTGCAGCGTATTAAGGTGGAGAACACCGAGGAAAAC
                 CGTCGTCAATTCCGTGAAATCCTGTTTAGCGTTGATAGCAGCATCAACCAGAGCA
                 TTGGTGGCGTGATCCTGTTCCACGAAACCCTGTACCAGAAGGACAGCCAAGGTAA
                 ACTGTTTCGTAACATTCTGAAGGAAAAAGGTATTGTGGTTGGCATCAAGCTGGAT
                 CAAGGTGGCGCGCCGCTGGCGGGCACCAACAAGGAAACCACCATCCAGGGTCTGG
                 ACGGCCTGAGCGAACGTTGCGCGCAATATAAGAAAGATGGTGTTGACTTCGGCAA
                 GTGGCGTGCGGTGCTGCGTATTGCGGACCAGTGCCCGAGCAGCCTGGCGATCCAA
                 GAAAACGCGAACGCGCTGGCGCGTTACGCGAGCATCTGCCAGCAAAACGGTCTGG
                 TGCCGATTGTTGAGCCGGAAGTTATCCCGGACGGCGATCACGACCTGGAGCACTG
                 CCAGTATGTGACCGAAAAGGTTCTGGCGGCGGTGTACAAAGCGCTGAACGATCAC
                 CACGTTTATCTGGAGGGTACCCTGCTGAAACCGAACATGGTGACCGCGGGCCATG
                 CGTGCACCAAGAAATACACCCCGGAACAGGTGGCGATGGCGACCGTGACCGCGCT
                 GCACCGTACCGTTCCGGCGGCGGTGCCGGGTATTTGCTTTCTGAGCGGTGGCATG
                 AGCGAAGAGGACGCGACCCTGAACCTGAACGCGATCAACCTGTGCCCGCTGCCGA
                 AGCCGTGGAAACTGAGCTTCAGCTACGGCCGTGCGCTGCAGGCGAGCGCGCTGGC
                 GGCGTGGGGTGGCAAGGCGGCGAACAAAGAGGCGACCCAAGAAGCGTTTATGAAG
                 CGTGCGATGGCGAACTGCCAGGCGGCGAAAGGTCAATATGTGCATACCGGCAGCA
                 GCGGTGCGGCGAGCACCCAGAGCCTGTTTACCGCGTGCTATACCTATTAA SEQ ID NO: 58    *Homo sapiens* Fructose-bisphosphate aldolase B aldoB AA
                 sequence
                 MAHRFPALTQEQKKELSEIAQSIVANGKGILAADESVGTMGNRLQRIKVENTEEN
                 RRQFREILFSVDSSINQSIGGVILFHETLYQKDSQGKLFRNILKEKGIVVGIKLD
                 QGGAPLAGTNKETTIQGLDGLSERCAQYKKDGVDFGKWRAVLRIADQCPSSLAIQ
                 ENANALARYASICQQNGLVPIVEPEVIPDGDHDLEHCQYVTEKVLAAVYKALNDH
                 HVYLEGTLLKPNMVTAGHACTKKYTPEQVAMATVTALHRTVPAAVPGICFLSGGM
                 SEEDATLNLNAINLCPLPKPWKLSFSYGRALQASALAAWGGKAANKEATQEAFMK
                 RAMANCQAAKGQYVHTGSSGAASTQSLFTACYTY SEQ ID NO: 59    *Caulobacter crescentus* D-xylose 1-dehydrogenase xylB NT
                 sequence
                 ATGTCCTCAGCCATCTATCCCAGCCTGAAGGGCAAGCGCGTCGTCATCACCGGCG
                 GCGGCTCGGGCATCGGGGCCGGCCTCACCGCCGGCTTCGCCCGTCAGGGCGCGGA
                 GGTGATCTTCCTCGACATCGCCGACGAGGACTCCAGGGCTCTTGAGGCCGAGCTG
                 GCCGGCTCGCCGATCCCGCCGGTCTACAAGGCTGCGACCTGATGAACCTCGAGG
                 CGATCAAGGCGGTCTTCGCCGAGATCGGCGACGTCGACGTGCTGGTCAACAACGC
                 CGGCAATGACGACCGCCACAAGCTGGCCGACGTGACCGGCGCCTATTGGGACGAG
                 CGGATCAACGTCAACCTGCGCCACATGCTGTTCTGCACCCAGGCCGTCGCGCCGG
                 GCATGAAGAAGCGTGGCGGCGGGGCGGTGATCAACTTCGGTTCGATCAGCTGGCA
                 CCTGGGGCTTGAGGACCTCGTCCTCTACGAAACCGCCAAGGCCGGCATCGAAGGC
                 ATGACCCGCGCGCTGGCCCGGGAGCTGGGTCCCGACGACATCCGCGTCACCTGCG
                 TGGTGCCGGGCAACGTCAAGACCAAGCGCCAGGAGAAGTGGTACACGCCCGAAGG
                 CGAGGCCCAGATCGTGGCGGCCCAATGCCTGAAGGGCCGCATCGTCCCGGAGAAC
                 GTCGCCGCGCTGGTCGTGTTCCTGGCCTCGGATGACGCGTCGCTCTGCACCGGCC
                 ACGAATACTGGATCGACGCCGGCTGGCGTTGA SEQ ID NO: 60    *Caulobacter crescentus* D-xylose 1-dehydrogenase xylB
                 codon optimized NT sequence
                 ATGAGCAGCGCGATCTACCCGAGCCTGAAAGGTAAACGTGTGGTGATTACCGGCG
                 GCGGCAGCGGCATTGGTGCGGGCCTGACCGCGGGCTTCGCGCGTCAGGGTGCGGA
                 AGTGATCTTTCTGGACATTGCGGACGAAGATAGCCGTGCGCTGGAGGCGGAACTG
                 GCGGGCAGCCCGATCCCGCCGGTGTACAAGCGTTGCGATCTGATGAACCTGGAGG
                 CGATCAAAGCGGTTTTCGCGGAAATTGGCGACGTGGATGTTCTGGTGAACAACGC
                 GGGTAACGACGACCGTCACAAGCTGGCGGATGTGACCGGTGCGTATTGGGATGAG
                 CGTATTAACGTTAACCTGCGTCACATGCTGTTCTGCACCCAGGCGGTGGCGCCGG
                 GTATGAAGAAACGTGGTGGCGGTGCGGTTATCAACTTTGGCAGCATTAGCTGGCA
                 CCTGGGTCTGGAGGACCTGGTGCTGTACGAAACCGCGAAGCGGGCATCGAGGGT
                 ATGACCCGTGCGCTGGCGCGTGAACTGGGTCCGGACGATATTCGTGTGACCTGCG
                 TGGTTCCGGGTAACGTTAAGACCAAACGTCAAGAGAAGTGGTATACCCCGGAGGG

| | SEQUENCE LISTING |
|---|---|
| | TGAAGCGCAGATTGTTGCGGCGCAATGCCTGAAAGGTCGTATTGTTCCGGAAAAC<br>GTGGCGGCGCTGGTTCTGTTTCTGGCGAGCGATGATGCGAGCCTGTGCACCGGCC<br>ATGAGTATTGGATTGATGCGGGCTGGCGTTAA |
| SEQ ID NO: 61 | *Caulobacter crescentus* D-xylose 1-dehydrogenase xylB AA<br>sequence<br>MSSAIYPSLKGKRVVITGGGSGIGAGLTAGFARQGAEVIFLDIADEDSRALEAEL<br>AGSPIPPVYKRCDLMNLEAIKAVFAEIGDVDVLVNNAGNDDRHKLADVTGAYWDE<br>RINVNLRHMLFCTQAVAPGMKKRGGGAVINFGSISWHLGLEDLVLYETAKAGIEG<br>MTRALARELGPDDIRVTCVVPGNVKTKRQEKWYTPEGEAQIVAAQCLKGRIVPEN<br>VAALVLFLASDDASLCTGHEYWIDAGWR |
| SEQ ID NO: 62 | *Haloferax volcanii* D-xylose 1-dehydrogenase xdh1,<br>HVO_B0028 NT sequence<br>ATGAGCCCCGCCCCCACCGACATCGTCGAGGAGTTCACGCGCCGCGACTGGCAGG<br>GAGACGACGTGACGGGCACCGTGCGGGTCGCCATGATCGGCCTCGGCTGGTGGAC<br>CCGCGACGAGGCGATTCCCGCGGTCGAGGCGTCCGAGTTCTGCGAGACGACGGTC<br>GTCGTCAGCAGTTCGAAGGAGAAAGCCGAGGGCGCGACGGCGTTGACCGAGTCGA<br>TAACCCACGGCCTCACCTACGACGAGTTCCACGAGGGGGTCGCCGCCGACGCCTA<br>CGACGCGGTGTACGTCGTCACGCCGAACGGTCTGCATCTCCCGTACGTCGAGACC<br>GCCGCCGAGTTGGGGAAGGCGGTCCTCTGCGAGAAACCGCTGGAAGCGTCGGTCG<br>AGCGGGCCGAAAAGCTCGTCGCCGCCTGCGACCGCGCCGACGTGCCCCTGATGGT<br>CGCCTATCGGATGCAGACCGAGCCGGCCGTCCGGCGCGCCCGCGAACTCGTCGAG<br>GCCGGCGTCATCGGCGAGCCGGTGTTCGTCCACGGCCACATGTCCCAGCGCCTGC<br>TCGACGAGGTCGTCCCCGACCCCGACCAGTGGCGGCTCGACCCCGAACTCTCCGG<br>CGGCGCGACCGTCATGGACATCGGGCTCTACCCGCTGAACACCGCCCGGTTCGTC<br>CTCGACGCCGACCCCGTCCGCGTCAGGGCGACCGCCCGCGTCGACGACGAGGCGT<br>TCGAGGCCGTCGGCGACGAGCACGTCAGTTTCGGCGTCGACTTCGACGACGGCAC<br>GCTCGCGGTCTGCACCGCCAGCCAGTCGGCTTACCAGTTGAGCCACCTCCGGGTG<br>ACCGGCACCGAGGGCGAACTCGAAATCGAGCCCGCGTTCTACAACCGCAAAAGC<br>GGGGATTCCGACTGTCGTGGGGGGACCAGTCCGCCGACTACGACTTCGAGCAGGT<br>AAACCAGATGACGGAGGAGTTCGACTACTTCGCGTCCCGGCTCCTGTCGGATTCC<br>GACCCCGCGCCCGACGGCGACCACGCGCTCGTGGACATGCGCGCGATGGACGCGA<br>TTTACGCCGCGGCGGAGCGCGGGACCGATGTCGCCGTCGACGCCGCCGACTCCGA<br>TTCCGCCGACTCCGATTCCGCCGACGCTGCCGCCGCCAACCACGACGCCGACCCC<br>GATTCCGACGGGACGTAG |
| SEQ ID NO: 63 | *Haloferax volcanii* D-xylose 1-dehydrogenase xdh1,<br>HVO_B0028 AA sequence<br>MSPAPTDIVEEFTRRDWQGDDVTGTVRVAMIGLGWWTRDEAIPAVEASEFCETTV<br>VVSSSKEKAEGATALTESITHGLTYDEFHEGVAADAYDAVYVVTPNGLHLPYVET<br>AAELGKAVLCEKPLEASVERAEKLVAACDRADVPLMVAYRMQTEPAVRRARELVE<br>AGVIGEPVFVHGHMSQRLLDEVVPDPDQWRLDPELSGGATVMDIGLYPLNTARFV<br>LDADPVRVRATARVDDEAFEAVGDEHVSFGVDFDDGTLAVCTASQSAYQLSHLRV<br>TGTEGELEIEPAFYNRQKRGFRLSWGDQSADYDFEQVNQMTEEFDYFASRLLSDS<br>DPAPDGDHALVDMRAMDAIYAAAERGTDVAVDAADSDSADSDSADAAAANHDADP<br>DSDGT |
| SEQ ID NO: 64 | *Trichoderma reesei* D-xylose 1-dehydrogenase xyd1 NT<br>sequence<br>ATGGCGTCTGGAAACCCTTACACCCTGAAATGGGGCATCATGGCCACCGGCGGAA<br>TCGCAGAGACCTTCTGCAAGGATCTCCTGTGCAACCCCGCGATTCGAGGCGCCGA<br>TGATGTGCGCCACGAGATTGGCCGTGGCCTCTTCCAGCAGCAGCAAGAGAGCA<br>GAGGAGTTCCTCCAGAGAATCGACGGTGCCTTTGACGCCAAGACGTACGGATCAT<br>ACCCGGAACTTGTGGCAGACCCCAACGTCGACATCGTCTATGTGGCAACTCCCCA<br>CAGCCACCACTTCCAGAACACCATGCTGGCGCTGGAAGCCGGCAAGAACGTCTTG<br>TGCGAAAAGGCTTTCACCGTGACGGCCGCGCAGGCCCGAAAGCTGGTTGAGACGG<br>CCAAGGCCAAGAAGCTCTTCCTGATGGAAGCTGTGTGGACACGGTACTTTCCGCT<br>GAGTATCAAGATTCGAGAGCTCATTGCCGCCGGCGAGATTGGCACTGTCTTTCGA<br>ACAATCGCCGACTTGTCCATCAACGCAAACTCAGAGCAGGGTCAAGCCCTGAAAT<br>TCGCAGACTCACATCGAATGGTCAACCCGGACCTCGCAGGCGGTGCCACCTTGGA<br>TCTCGGAGTCTATCCCTTGACCTGGGTGTTCCAGACCCTGTATCATTTGCAACCG<br>GAGGAAGACAAGGAGGCTCCCACCGTGGTTGCTTCCAGCAACAAGTACACCACTG<br>GCGCAGACGAGAATACCGCCATCATCTGCAGCTTCCCTCGCCACAACAGCATTGG<br>AATTGCTTCGACGACGATGAGGGCGGACACCGACCCCGAGAAGGACACCATTCCG<br>GCGGTCCGAATTCAAGGATCCAAGGGAGAAATCCAAGTCTTCTTCCCGACCTACC<br>GACCGCTCAAGTACAAGGTGGTGAAGACGAACGGCGAGGCGCAGAGGTTGACTG<br>CCCCATCCCCGGAGACCCCGCGCGCAAGGGCTCGGGCCACGGAATGTTCTGGGAG<br>GCGGACGAGTGTGCTCGATGCCTTCGCGATGGCAAGTTGGAGAGTGCCACGTTGC<br>CATGGAAGGAGAGCATTGTCATTATGGAAACGATGGAGGAGGCGCTGAGGCAGGG<br>TGGCGTCACGTATCCGGAGCTGATTACCACGGATGTCTATGATCCCAAGAGCCCT<br>CTCAACACGGGGAATCAGTAG |
| SEQ ID NO: 65 | *Trichoderma reesei* D-xylose 1-dehydrogenase xyd1 AA<br>sequence<br>MASGNPYTLKWGIMATGGIAETFCKDLLCNPAIRGADDVRHEIVAVASSSSSKRA<br>EEFLQRIDGAFDAKTYGSYPELVADPNVDIVYVATPHSHHFQNTMLALEAGKNVL |

| | SEQUENCE LISTING |
|---|---|
| | CEKAFTVTAAQARKLVETAKAKKLFLMEAVWTRYFPLSIKIRELIAAGEIGTVFR<br>TIADLSINANSEQGQALKFADSHRMVNPDLAGGATLDLGVYPLTWVFQTLYHLQP<br>EEDKEAPTVVASSNKYTTGADENTAIICSFPRHNSIGIASTTMRADTDPEKDTIP<br>AVRIQGSKGEIQVFFPTYRPLKYKVVKTNGEAQTVDCPIPGDPARKGSHGMFWE<br>ADECARCLRDGKLESATLPWKESIVIMETMEEALRQGGVTYPELITTDVYDPKSP<br>LNTGNQ |
| SEQ ID NO: 66 | *Caulobacter crescentus* Xylonolactonase xylC NT sequence<br>ATGACCGCTCAAGTCACTTGCGTATGGGATCTGAAGGCCACGTTGGGCGAAGGCC<br>CGATCTGGCATGGCGACACCCTGTGGTTCGTCGACATCAAGCAGCGTAAAATCCA<br>CAACTACCACCCCGCCACCGGCGAGCGCTTCAGCTTCGACGCGCCGGATCAGGTG<br>ACCTTCCTCGCGCCGATCGTCGGCGCGACCGGCTTTGTCGTCGGTCTGAAGACCG<br>GGATTCACCGCTTCCACCCGGCCACGGGCTTCAGCCTGCTGCTCGAGGTCGAGGA<br>CGCGGCGCTGAACAACCGCCCCAACGACGCCACGGTCGACGCGCAAGGCCGTCTG<br>TGGTTCGGCACCATGCACGACGGGGAAGAGAACAATAGCGGCTCGCTCTATCGGA<br>TGGACCTCACCGGCGTCGCCCGGATGGACCGCGACATCTGCATCACCAACGGCCC<br>GTGCGTCTCGCCCGACGGCAAGACCTTCTACCACACCGACACCCTGGAAAAGACG<br>ATCTACGCCTTCGACCTGGCCGAGGACGGCCTGCTGTCGAACAAGCGCGTCTTCG<br>TGCAGTTCGCCCTGGGCGACGATGTCTATCCGGACGGTTCGGTCGTCGATTCCGA<br>AGGCTATCTGTGGACCGCCCTGTGGGGCGGTTTCGGCGCGGTCCGCTTCTCGCCG<br>CAAGGCGACGCCGTGACGCGCATCGAACTGCCCGCCCCCAACGTCACCAAGCCCT<br>GCTTCGGCGGGCCTGACCTGAAGACCCTCTATTTCACCACCGCCCGCAAGGGCCT<br>GAGCGACGAGACCCTGGCCCAGTACCCGCTGGCCGGCGGTGTGTTCGCCGTTCCG<br>GTCGATGTGGCCGGCCAACCCCAGCATGAGGTCCGCCTTGTCTAA |
| SEQ ID NO: 67 | *Caulobacter crescentus* Xylonolactonase xylC AA sequence<br>MTAQVTCVWDLKATLGEGPIWHGDTLWFVDIKQRKIHNYHPATGERFSFDAPDQV<br>TFLAPIVGATGFVVGLKTGIHRFHPATGFSLLLEVEDAALNNRPNDATVDAQGRL<br>WFGTMHDGEENNSGSLYRMDLTGVARMDRDICITNGPCVSPDGKTFYHTDTLEKT<br>IYAFDLAEDGLLSNKRVFVQFALGDDVYPDGSVVDSEGYLWTALWGGFGAVRFSP<br>QGDAVTRIELPAPNVTKPCFGGPDLKTLYFTTARKGLSDETLAQYPLAGGVFAVP<br>VDVAGQPQHEVRLV |
| SEQ ID NO: 68 | *Caulobacter crescentus* xylonate dehydratase xylD NT<br>sequence<br>TTGTCTAACCGCACGCCCCGCCGGTTCCGGTCCCGCGATTGGTTCGATAACCCCG<br>ACCATATCGACATGACCGCGCTCTATCTGGAGCGCTTCATGAACTACGGGATCAC<br>GCCGGAGGAGCTGCGCAGCGGCAAGCCGATCATCGGCATCGCCCAGACCGGCAGC<br>GACATCTCGCCCTGCAACCGCATCCACCTGGACCTGGTCCAGCGGGTGCGGGACG<br>GGATCCGCGACGCCGGGGGCATCCCCATGGAGTTCCCGGTCCATCCGATCTTCGA<br>GAACTGCCGTCGCCCGACGGCGGCGCTGGACCGGAACCTCTCGTACCTGGGTCTC<br>GTCGAGACCCTGCACGGCTATCCGATCGACGCCGTGGTTCTGACCACCGGCTGCG<br>ACAAGACCACCCCGGCCGGGATCATGGCCGCCACCACGGTCAATATCCCGGCCAT<br>CGTGCTGTCGGGCGGCCCGATGCTGGACGGCTGGCACGAGAACGAGCTCGTGGGC<br>TCGGGCACCGTGATCTGGCGCTCGCGCCGCAAGCTGGCGGCCGGCGAGATCACCG<br>AGGAAGAGTTCATCGACCGCGCCGCCAGCTCGGCGCCGTCGGCGGGCCACTGCAA<br>CACCATGGGCACGGCCTCGACCATGAACGCCGTGGCCGAGGCGCTGGGCCTGTCG<br>CTGACCGGCTGCGCGGCCATCCCCGCCCCTACCGCGAGCGCGGCCAGATGGCCT<br>ACAAGACCGGCCAGCGCATCGTCGATCTGGCCTATGACGACGTCAAACCGCTCGA<br>CATCCTGACCAAGCAAGCCTTCGAGAACGCCATCGCCCTGGTGGCCGGCGGCCGGC<br>GGCTCGACCAACGCCCAGCCGCACATCGTGGCCATGGCCCGTCACGCCGGCGTCG<br>AGATCACCGCCGACGACTGGCGCGCGGCCTATGACATCCCGCTGATCGTCAACAT<br>GCAGCCGGCCGGCAAGTATCTGGGCGAGCGCTTCCACCGAGCCGGCGGCGCGCCG<br>GCGGTGCTGTGGGAGCTGTTGCAGCAAGGCCGCCTGCACGGCGACGTGCTGACCG<br>TCACCGGCAAGACGATGAGCGAGAACCTGCAAGGCCGCGAAACCAGCGACCGCGA<br>GGTGATCTTCCCGTACCACGAGCGCTGGCCGAGAAGGCCGGGTTCCTGGTTCTC<br>AAGGGCAACCTCTTCGACTTCGCGATCATGAAGTCCAGCGTGATCGGCGAGGAGT<br>TCCGCAAGCGCTACCTGTCGCAGCCCGGCCAGGAAGGCGTGTTCGAAGCCCGCGC<br>CATCGTGTTCGACGGCTCGGACGACTATCACAAGCGGATCAACGATCCGGCCCTG<br>GAGATCGACGAGCGCTGCATCCTGGTGATCCGCGGCGCGGGTCCGATCGGCTGGC<br>CCGGCTCGGCCGAGGTCGTCAACATGCAGCCGCCGGATCACCTTCTGAAGAAGGG<br>GATCATGAGCCTGCCCACCCTGGGCGATGGCCGTCAGTCGGGCACCGCCGACAGC<br>CCCTCGATCCTGAACGCCTCGCCCGAAAGCGCGATCGGCGGCGGCCTGTCGTGGC<br>TGCGCACCGGCGACACCATCCGCATCGACCTCAACACCGGCCGCTGCGACGCCCT<br>GGTCGACGAGGCGACGATCGCCGCGCAAGCAGGACGGCATCCCGGCGGTTCCC<br>GCCACCATGACGCCCTGGCAGGAAATCTACCGCGCCCACGCCAGTCAGCTCGACA<br>CCGGCGGCGTGCTGGAGTTCGCGGTCAAGTACCAGGACCTGGCGGCCAAGCTGCC<br>CCGCCACAACCACTGA |
| SEQ ID NO: 69 | *Caulobacter crescentus* xylonate dehydratase xylD AA<br>sequence<br>MSNRTPRRFRSRDWFDNPDHIDMTALYLERFMNYGITPEELRSGKPIIGIAQTGS<br>DISPCNRIHLDLVQRVRDGIRDAGGIPMEFPVHPIFENCRRPTAALDRNLSYLGL<br>VETLHGYPIDAVVLTTGCDKTTPAGIMAATTVNIPAIVLSGGPMLDGWHENELVG<br>SGTVIWRSRRKLAAGEITEEEFIDRAASSAPSAGHCNTMGTASTMNAVAEALGLS<br>LTGCAAIPAPYRERGQMAYKTGQRIVDLAYDDVKPLDILTKQAFENAIALVAAAG<br>GSTNAQPHIVAMARHAGVEITADDWRAAYDIPLIVNMQPAGKYLGERFHRAGGAP |

|  |  |
|---|---|
|  | AVLWELLQQGRLHGDVLTVTGKTMSENLQGRETSDREVIFPYHEPLAEKAGFLVL<br>KGNLFDFAIMKSSVIGEEFRKRYLSQPGQEGVFEARAIVFDGSDDYHKRINDPAL<br>EIDERCILVIRGAGPIGWPGSAEVVNMQPPDHLLKKGIMSLPTLGDGRQSGTADS<br>PSILNASPESAIGGGLSWLRTGDTIRIDLNTGRCDALVDEATIAARKQDGIPAVP<br>ATMTPWQEIYRAHASQLDTGGVLEFAVKYQDLAAKLPRHNH |
| SEQ ID NO: 70 | *Escherichia coli* xylonate dehydratase yjhG NT sequence<br>ATGTCTGTTCGCAATATTTTTGCTGACGAGAGCCACGATATTTACACCGTCAGAA<br>CGCACGCCGATGGCCCGGACGGCGAACTCCCATTAACCGCAGAGATGCTTATCAA<br>CCGCCCGAGCGGGGATCTGTTCGGTATGACCATGAATGCCGGAATGGGTTGGTCT<br>CCGGACGAGCTGGATCGGGACGGTATTTTACTGCTCAGTACACTCGGTGGCTTAC<br>GCGGCGCAGACGGTAAACCCGTGGCGCTGGCGTTGCACCAGGGGCATTACGAACT<br>GGACATCCAGATGAAAGCGGCGGCCGAGGTTATTAAAGCCAACCATGCCCTGCCC<br>TATGCCGTGTACGTCTCCGATCCTTGTGACGGGCGTACTCAGGGTACAACGGGGA<br>TGTTTGATTCGCTACCATACCGAAATGACGCATCGATGGTAATGCGCCGCCTTAT<br>TCGCTCTCTGCCCGACGCGAAAGCAGTTATTGGTGTGGCGAGTTGCGATAAGGGG<br>CTTCCGGCCACCATGATGGCACTCGCCGCGCAGCACAACATCGCAACCGTGCTGG<br>TCCCCGGCGGCGCGACGCTGCCCGCAAAGGATGGAGAAGACAACGGCAAGGTGCA<br>AACCATTGGCGCACGCTTCGCCAATGGCGAATTATCTCTACAGGACGCACGCCGT<br>GCGGGCTGTAAAGCCTGTGCCTCTTCCGGCGGCGGCTGTCAATTTTTGGGCACTG<br>CCGGGACATCTCAGGTGGTGGCCGAAGGATTGGGACTGGCAATCCCACATTCAGC<br>CCTGGCCCCTTCCGGTGAGCCTGTGTGGCGGGAGATCGCCAGAGCTTCCGCGCGA<br>GCTGCGCTGAACCTGAGTCAAAAAGGCATCACCACCCGGGAAATTCTCACCGATA<br>AAGCGATAGAGAATGCGATGACGGTCCATGCCGCGTTCGGTGGTTCAACAAACCT<br>GCTGTTACACATCCCGGCAATTGCTCACCAGGCAGGTTGCCATATCCCGACCGTT<br>GATGACTGGATCCGCATCAACAAGCGCGTGCCCCGACTGGTGAGCGTACTGCCTA<br>ATGGCCCGGTTTATCATCCAACGGTCAATGCCTTTATGGCAGGTGGTGTGCCGGA<br>AGTCATGTTGCATCTGCGCAGCCTCGGATTGTTGCATGAAGACGTTATGACGGTT<br>ACCGGCAGCACGCTGAAAGAAAACCTCGACTGGTGGGAGCACTCCGAACGGCGTC<br>AGCGGTTCAAGCAACTCCTGCTCGATCAGGAACAAATCAACGCTGACGAAGTGAT<br>CATGTCTCCGCAGCAAGCAAAAGCGCGCGGATTAACCTCAACTATCACCTTCCCG<br>GTGGGCAATATTGCGCCAGAAGGTTCGGTGATCAAATCCACCGCCATTGACCCCT<br>CGATGATTGATGAGCAAGGTATCTATTACCATAAAGGTGTGGCGAAGGTTTATCT<br>GTCCGAGAAAAGTGCGATTTACGATATCAAACATGACAAGATCAAGGCGGGCGAT<br>ATTCTGGTCATTATTGGCGTTGGACCTTCAGGTACAGGGATGGAAGAAACCTACC<br>AGGTTACCAGTGCCCTGAAGCATCTGTCATACGGTAAGCATGTTTCGTTAATCAC<br>CGATGCACGTTTCTCGGGCGTTTCTACTGGCGCGTGCATCGGCCATGTGGGGCCA<br>GAAGCGCTGGCCGAGGCCCCATCGGTAAATTACGCACCGGGGATTTAATTGAAA<br>TTAAAATTGATTGTCGCGAGCTTCACGGCGAAGTCAATTTCCTCGGAACCCGTAG<br>CGATGAACAATTACCTTCACAGGAGGAGGCAACTGCAATATTAAATGCCAGACCC<br>AGCCATCAGGATTTACTTCCCGATCCTGAATTGCCAGATGATACCCGGCTATGGG<br>CAATGCTTCAGGCCGTGAGTGGTGGGACATGGACCGGTTGTATTTATGATGTAAA<br>CAAAATTGGCGCGGCTTTGCGCGATTTTATGAATAAAAACTGA |
| SEQ ID NO: 71 | *Escherichia coli* xylonate dehydratase yjhG codon<br>optimized NT sequence<br>ATGTCTGTTCGCAATATTTTTGCTGACGAGAGCCACGATATTTACACCGTCAGAA<br>CGCACGCCGATGGCCCGGACGGCGAACTCCCATTAACCGCAGAGATGCTTATCAA<br>CCGCCCGAGCGGGGATCTGTTCGGTATGACCATGAATGCCGGAATGGGTTGGTCT<br>CCGGACGAGCTGGATCGGGACGGTATTTTACTGCTCAGTACACTCGGTGGCTTAC<br>GCGGCGCAGACGGTAAACCCGTGGCGCTGGCGTTGCACCAGGGGCATTACGAACT<br>GGACATCCAGATGAAAGCGGCGGCCGAGGTTATTAAAGCCAACCATGCCCTGCCC<br>TATGCCGTGTACGTCTCCGATCCTTGTGACGGGCGTACTCAGGGTACAACGGGGA<br>TGTTTGATTCGCTACCATACCGAAATGACGCATCGATGGTAATGCGCCGCCTTAT<br>TCGCTCTCTGCCCGACGCGAAAGCAGTTATTGGTGTGGCGAGTTGCGATAAGGGG<br>CTTCCGGCCACCATGATGGCACTCGCCGCGCAGCACAACATCGCAACCGTGCTGG<br>TCCCCGGCGGCGCGACGCTGCCCGCAAAGGATGGAGAAGACAACGGCAAGGTGCA<br>AACCATTGGCGCACGCTTCGCCAATGGCGAATTATCTCTACAGGACGCACGCCGT<br>GCGGGCTGTAAAGCCTGTGCCTCTTCCGGCGGCGGCTGTCAATTTTTGGGCACTG<br>CCGGGACATCTCAGGTGGTGGCCGAAGGATTGGGACTGGCAATCCCACATTCAGC<br>CCTGGCCCCTTCCGGTGAGCCTGTGTGGCGGGAGATCGCCAGAGCTTCCGCGCGA<br>GCTGCGCTGAACCTGAGTCAAAAAGGCATCACCACCCGGGAAATTCTCACCGATA<br>AAGCGATAGAGAATGCGATGACGGTCCATGCCGCGTTCGGTGGTTCAACAAACCT<br>GCTGTTACACATCCCGGCAATTGCTCACCAGGCAGGTTGCCATATCCCGACCGTT<br>GATGACTGGATCCGCATCAACAAGCGCGTGCCCCGACTGGTGAGCGTACTGCCTA<br>ATGGCCCGGTTTATCATCCAACGGTCAATGCCTTTATGGCAGGTGGTGTGCCGGA<br>AGTCATGTTGCATCTGCGCAGCCTCGGATTGTTGCATGAAGACGTTATGACGGTT<br>ACCGGCAGCACGCTGAAAGAAAACCTCGACTGGTGGGAGCACTCCGAACGGCGTC<br>AGCGGTTCAAGCAACTCCTGCTCGATCAGGAACAAATCAACGCTGACGAAGTGAT<br>CATGTCTCCGCAGCAAGCAAAAGCGCGCGGATTAACCTCAACTATCACCTTCCCG<br>GTGGGCAATATTGCGCCAGAAGGTTCGGTGATCAAATCCACCGCCATTGACCCCT<br>CGATGATTGATGAGCAAGGTATCTATTACCATAAAGGTGTGGCGAAGGTTTATCT<br>GTCCGAGAAAAGTGCGATTTACGATATCAAACATGACAAGATCAAGGCGGGCGAT<br>ATTCTGGTCATTATTGGCGTTGGACCTTCAGGTACAGGGATGGAAGAAACCTACC<br>AGGTTACCAGTGCCCTGAAGCATCTGTCATACGGTAAGCATGTTTCGTTAATCAC<br>CGATGCACGTTTCTCGGGCGTTTCTACTGGCGCGTGCATCGGCCATGTGGGGCCA<br>GAAGCGCTGGCCGAGGCCCCATCGGTAAATTACGCACCGGGGATTTAATTGAAA |

| | SEQUENCE LISTING |
|---|---|
| | TTAAAATTGATTGTCGCGAGCTTCACGGCGAAGTCAATTTCCTCGGAACCCGTAG<br>CGATGAACAATTACCTTCACAGGAGGAGGCAACTGCAATATTAAATGCCAGACCC<br>AGCCATCAGGATTTACTTCCCGATCCTGAATTGCCAGATGATACCCGGCTATGGG<br>CAATGCTTCAGGCCGTGAGTGGTGGGACATGGACCGGTTGTATTTATGATGTAAA<br>CAAAATTGGCGCGGCTTTGCGCGATTTTATGAATAAAAACTGA |
| SEQ ID NO: 72 | *Escherichia coli* xylonate dehydratase yjhG AA sequence<br>MSVRNIFADESHDIYTVRTHADGPDGELPLTAEMLINRPSGDLFGMTMNAGMGWS<br>PDELDRDGILLLSTLGGLRGADGKPVALALHQGHYELDIQMKAAAEVIKANHALP<br>YAVYVSDPCDGRTQGTTGMFDSLPYRNDASMVMRRLIRSLPDAKAVIGVASCDKG<br>LPATMMALAAQHNIATVLVPGGATLPAKDGEDNGKVQTIGARFANGELSLQDARR<br>AGCKACASSGGGCQFLGTAGTSQVVAEGLGLAIPHSALAPSGEPVWREIARASAR<br>AALNLSQKGITTREILTDKAIENAMTVHAAFGGSTNLLLHIPAIAHQAGCHIPTV<br>DDWIRINKRVPRLVSVLPNGPVYHPTVNAFMAGGVPEVMLHRSLGLLHEDVMTV<br>TGSTLKENLDWWEHSERRQRFKQLLLDQEQINADEVIMSPQQAKARGLTSTITFP<br>VGNIAPEGSVIKSTAIDPSMIDEQGIYYHKGVAKVYLSEKSAIYDIKHDKIKAGD<br>ILVIIGVGPSGTGMEETYQVTSALKHLSYGKHVSLITDARFSGVSTGACIGHVGP<br>EALAGGPIGKLRTGDLIEIKIDCRELHGEVNFLGTRSDEQLPSQEEATAILNARP<br>SHQDLLPDPELPDDTRLWAMLQAVSGGTWTGCIYDVNKIGAALRDFMNKN |
| SEQ ID NO: 73 | *Escherichia coli* xylonate dehydratase yagF NT sequence<br>ATGACCATTGAGAAAATTTTCACCCCGCAGGACGACGCGTTTTATGCGGTGATCA<br>CCCACGCGGCGGGGCCGCAGGGCGCTCTGCCGCTGACCCCGCAGATGCTGATGGA<br>ATCTCCCAGCGGCAACCTGTTCGGCATGACGCAGAACGCCGGGATGGGCTGGGAC<br>GCCAACAAGCTCACCGGCAAAGAGGTGCTGATTATCGGCACTCAGGGCGGCATCC<br>GCGCCGGAGACGGACGCCCAATCGCGCTGGGCTACCACACCGGGCATTGGGAGAT<br>CGGCATGCAGATGCAGGCGGCGGCGAAGGAGATCACCCGCAATGGCGGGATCCCG<br>TTCGCGGCCTTCGTCAGCGATCCGTGCGACGGGCGCTCGCAGGGCACGCACGGTA<br>TGTTCGATTCCCTGCCGTACCGCAACGACGCGGCGATCGTGTTTCGCCGCCTGAT<br>CCGCTCCCTGCCGACGCGGCGGGCGGTGATCGGCGTAGCGACCTGCGATAAAGGG<br>CTGCCCGCCACCATGATTGCGCTGGCCGCGATGCACGACCTGCCGACTATTCTGG<br>TGCCGGGCGGGGCGACGCTGCCGCCGACCGTCGGGGAAGACGCGGGCAAGGTGCA<br>GACCATCGGCGCGTTTCGCCAACCACGAACTCTCCCTGCAGGAGGCCGCCGAA<br>CTGGGCTGTCGCGCCTGCGCCTCGCGGGCGGCGGGTGTCAGTTCCTCGGCACGG<br>CGGGCACCTCGCAGGTGGTCGCGGAGGCGCTGGGTCTGGCGCTGCCGCACTCCGC<br>GCTGGCGCCGTCCGGGCAGGCGGTGTGGCTGGAGATCGCCCGCCAGTCGGCGCGC<br>GCGGTCAGCGAGCTGGATAGCCGCGGCATCACCACGCGGGATATCCTCTCCGATA<br>AAGCCATCGAAAACGCGATGGTGATCCACGCGGCGTTCGGCGGCTCCACCAATTT<br>ACTGCTGCACATTCCGGCCATCGCCCACGCGGCGGGCTGCACGATCCCGGACGTT<br>GAGCACTGGACGCGCATCAACCGTAAAGTGCCGCGTCTGGTGAGCGTGCTGCCCA<br>ACGGCCCGGACTATCACCCGACCGTCGCGCGCCTTCCTCGCGGGCGGCGTGCCGGA<br>GGTGATGCTCCACCTGCGCGACCTCGGCCTGCTGCATCTGGACGCCATGACCGTG<br>ACCGGCCAGACGGTGGGCGAGAACCTTGAATGGTGGCAGGCGTCCGAGCGCCGGG<br>CGCGCTTCCGCCAGTGCCTGCGCGAGCAGGACGGCGTAGAGCCGGATGACGTGAT<br>CCTGCCGCCGGAGAAGGCAAAAGCGAAAGGGCTGACCTCGACGGTCTGCTTCCCG<br>ACGGGCAACATCGCTCCGGAAGGTTCGGTGATCAAGGCCACGGCGATCGACCCGT<br>CGGTGGTGGGCGAAGATGGCGTATACCACCACACCGGCCGGGTGCGGGTGTTTGT<br>CTCGGAAGCGCAGGCGATCAAGGCGATCAAGCGGGAAGAGATTGTGCAGGGCGAT<br>ATCATGGTGGTGATCGGCGGCGGGCCGTCCGGCACCGGCATGGAAGAGACCTACC<br>AGCTCACCTCCGCGCTAAAGCATATCTCGTGGGGCAAGACGGTGTCGCTCATCAC<br>CGATGCGCGCTTCTCGGGCGTGTCGACGGGCGCCTGCTTCGGCCACGTGTCGCCG<br>GAGGCGCTGGCGGGCGGGCCGATTGGCAAGCTGCGCGATAACGACATCATCGAGA<br>TTGCCGTGGATCGTCTGACGTTAACTGGCAGCGTGAACTTCATCGGCACCGCGGA<br>CAACCCGCTGACGCCGGAAGAGGGCGCGCGCGAGCTGGCGCGGCGGCAGACGCAC<br>CCGGACCTGCACGCCCACGACTTTTTGCCGGACGACACCCGGCTGTGGCGGCAC<br>TGCAGTCGGTGAGCGGCGGCACCTGGAAAGGCTGTATTTATGACACCGATAAAAT<br>TATCGAGGTAATTAACGCCGGTAAAAAAGCGCTCGGAATTTAA |
| SEQ ID NO: 74 | *Escherichia coli* xylonate dehydratase yagF codon<br>optimized NT sequence<br>ATGACCATTGAGAAAATTTTCACCCCGCAGGACGACGCGTTTTATGCGGTGATCA<br>CCCACGCGGCGGGGCCGCAGGGCGCTCTGCCGCTGACCCCGCAGATGCTGATGGA<br>ATCTCCCAGCGGCAACCTGTTCGGCATGACGCAGAACGCCGGGATGGGCTGGGAC<br>GCCAACAAGCTCACCGGCAAAGAGGTGCTGATTATCGGCACTCAGGGCGGCATCC<br>GCGCCGGAGACGGACGCCCAATCGCGCTGGGCTACCACACCGGGCATTGGGAGAT<br>CGGCATGCAGATGCAGGCGGCGGCGAAGGAGATCACCCGCAATGGCGGGATCCCG<br>TTCGCGGCCTTCGTCAGCGATCCGTGCGACGGGCGCTCGCAGGGCACGCACGGTA<br>TGTTCGATTCCCTGCCGTACCGCAACGACGCGGCGATCGTGTTTCGCCGCCTGAT<br>CCGCTCCCTGCCGACGCGGCGGGCGGTGATCGGCGTAGCGACCTGCGATAAAGGG<br>CTGCCCGCCACCATGATTGCGCTGGCCGCGATGCACGACCTGCCGACTATTCTGG<br>TGCCGGGCGGGGCGACGCTGCCGCCGACCGTCGGGGAAGACGCGGGCAAGGTGCA<br>GACCATCGGCGCGTTTCGCCAACCACGAACTCTCCCTGCAGGAGGCCGCCGAA<br>CTGGGCTGTCGCGCCTGCGCCTCGCGGGCGGCGGGTGTCAGTTCCTCGGCACGG<br>CGGGCACCTCGCAGGTGGTCGCGGAGGCGCTGGGTCTGGCGCTGCCGCACTCCGC<br>GCTGGCGCCGTCCGGGCAGGCGGTGTGGCTGGAGATCGCCCGCCAGTCGGCGCGC<br>GCGGTCAGCGAGCTGGATAGCCGCGGCATCACCACGCGGGATATCCTCTCCGATA<br>AAGCCATCGAAAACGCGATGGTGATCCACGCGGCGTTCGGCGGCTCCACCAATTT |

SEQUENCE LISTING

```
                      ACTGCTGCACATTCCGGCCATCGCCCACGCGGCGGGCTGCACGATCCCGGACGTT
                      GAGCACTGGACGCGCATCAACCGTAAAGTGCCGCGTCTGGTGAGCGTGCTGCCCA
                      ACGGCCCGGACTATCACCCGACCGTGCGCGCCTTCCTCGCGGGCGGCGTGCCGGA
                      GGTGATGCTCCACCTGCGCGACCTCGGCCTGCTGCATCTGGACGCCATGACCGTG
                      ACCGGCCAGACGGTGGGCGAGAACCTTGAATGGTGGCAGGCGTCCGAGCGCCGGG
                      CGCGCTTCCGCCAGTGCCTGCGCGAGCAGGACGGCGTAGAGCCGGATGACGTGAT
                      CCTGCCGCCGGAGAAGGCAAAAGCGAAAGGGCTGACCTCGACGGTCTGCTTCCCG
                      ACGGGCAACATCGCTCCGGAAGGTTCGGTGATCAAGGCCACGGCGATCGACCCGT
                      CGGTGGTGGGCGAAGATGGCGTATACCACCACACCGGCCGGGTGCGGGTGTTTGT
                      CTCGGAAGCGCAGGCGATCAAGGCGATCAAGCGGGAAGAGATTGTGCAGGGCGAT
                      ATCATGGTGGTGATCGGCGGCGGGCCGTCCGGCACCGGCATGGAAGAGACCTACC
                      AGCTCACCTCCGCGCTAAAGCATATCTCGTGGGGCAAGACGGTGTCGCTCATCAC
                      CGATGCGCGCTTCTCGGGCGTGTCGACGGGCGCCTGCTTCGGCCACGTGTCGCCG
                      GAGGCGCTGGCGGGCGGGCCGATTGGCAAGCTGCGCGATAACGACATCATCGAGA
                      TTGCCGTGGATCGTCTGACGTTAACTGGCAGCGTGAACTTCATCGGCACCGCGGA
                      CAACCCGCTGACGCCGGAAGAGGGCGCGCGAGCTGGCGCGGCGGCAGACGCAC
                      CCGGACCTGCACGCCCACGACTTTTTGCCGGACGACACCCGGCTGTGGGCGGCAC
                      TGCAGTCGGTGAGCGGCGGCACCTGGAAAGGCTGTATTTATGACACCGATAAAAT
                      TATCGAGGTAATTAACGCCGGTAAAAAAGCGCTCGGAATTTAA

SEQ ID NO: 75         Escherichia coli xylonate dehydratase yagF AA sequence
                      MTIEKIFTPQDDAFYAVITHAAGPQGALPLTPQMLMESPSGNLFGMTQNAGMGWD
                      ANKLTGKEVLIIGTQGGIRAGDGRPIALGYHTGHWEIGMQMQAAAKEITRNGGIP
                      FAAFVSDPCDGRSQGTHGMFDSLPYRNDAAIVFRRLIRSLPTRRAVIGVATCDKG
                      LPATMIALAAMHDLPTILVPGGATLPPTVGEDAGKVQTIGARFANHELSLQEAAE
                      LGCRACASPGGGCQFLGTAGTSQVVAEALGLALPHSALAPSGQAVWLEIARQSAR
                      AVSELDSRGITTRDILSDKAIENAMVIHAAFGGSTNLLLHIPAIAHAAGCTIPDV
                      EHWTRINRKVPRLVSVLPNGPDYHPTVRAFLAGGVPEVMLHLRDLGLLHLDAMTV
                      TGQTVGENLEWWQASERRARFRQCLREQDGVEPDDVILPPEKAKAKGLTSTVCFP
                      TGNIAPEGSVIKATAIDPSVVGEDGVYHHTGRVRVFVSEAQAIKAIKREEIVQGD
                      IMVVIGGGPSGTGMEETYQLTSALKHISWGKTVSLITDARFSGVSTGACFGHVSP
                      EALAGGPIGKLRDNDIIEIAVDRLTLTGSVNFIGTADNPLTPEEGARELARRQTH
                      PDLHAHDFLPDDTRLWAALQSVSGGTWKGCIYDTDKIIEVINAGKKALGI SEQ ID NO: 76         Escherichia coli Uncharacterized lyase yjhH NT sequence
                      ATGAAAAAATTCAGCGGCATTATTCCACCGGTATCCAGCACGTTTCATCGTGACG
                      GAACCCTTGATAAAAAGGCAATGCGCGAAGTTGCCGACTTCCTGATTAATAAAGG
                      GGTCGACGGGCTGTTTTATCTGGGTACCGGTGGTGAATTTAGCCAAATGAATACA
                      GCCCAGCGCATGGCACTCGCCGAAGAAGCTGTAACCATTGTCGACGGGCGAGTGC
                      CGGTATTGATTGGCGTCGGTTCCCCTTCCACTGACGAAGCGGTCAAACTGGCGCA
                      GCATGCGCAAGCCTACGGCGCTGATGGTATCGTCGCCATCAACCCCTACTACTGG
                      AAAGTCGCACCACGAAATCTTGACGACTATTACCAGCAGATCGCCCGTAGCGTCA
                      CCCTACCGGTGATCCTGTACAACTTTCCGGATCTGACGGGTCAGGACTTAACCCC
                      GGAAACCGTGACGCGTCTGGCTCTGCAAAACGAGAATATCGTTGGCATCAAAGAC
                      ACCATCGACAGCGTTGGTCACTTGCGTACGATGATCAACACAGTTAAGTCGGTAC
                      GCCCGTCGTTTTCGGTATTCTGCGGTTACGATGATCATTTGCTGAATACGATGCT
                      GCTGGGCGGCGACGGTGCGATAACCGCCAGCGCTAACTTTGCTCCGGAACTCTCC
                      GTCGGCATCTACCGCGCCTGGCGTGAAGGCGATCTGGCGACCGCTGCGACGCTGA
                      ATAAAAAACTACTACAACTGCCCGCTATTTACGCCCTCGAAACACCGTTTGTCTC
                      ACTGATCAAATACAGCATGCAGTGTGTCGGGCTGCCTGTAGAGACATATTGCTTA
                      CCACCGATTCTTGAAGCATCTGAAGAAGCAAAAGATAAAGTCCACGTGCTGCTTA
                      CCGCGCAGGGCATTTTACCAGTCTGA SEQ ID NO: 77         Escherichia coli Uncharacterized lyase yjhH codon
                      optimized NT sequence
                      ATGAAAAAATTCAGCGGCATTATTCCACCGGTATCCAGCACGTTTCATCGTGACG
                      GAACCCTTGATAAAAAGGCAATGCGCGAAGTTGCCGACTTCCTGATTAATAAAGG
                      GGTCGACGGGCTGTTTTATCTGGGTACCGGTGGTGAATTTAGCCAAATGAATACA
                      GCCCAGCGCATGGCACTCGCCGAAGAAGCTGTAACCATTGTCGACGGGCGAGTGC
                      CGGTATTGATTGGCGTCGGTTCCCCTTCCACTGACGAAGCGGTCAAACTGGCGCA
                      GCATGCGCAAGCCTACGGCGCTGATGGTATCGTCGCCATCAACCCCTACTACTGG
                      AAAGTCGCACCACGAAATCTTGACGACTATTACCAGCAGATCGCCCGTAGCGTCA
                      CCCTACCGGTGATCCTGTACAACTTTCCGGATCTGACGGGTCAGGACTTAACCCC
                      GGAAACCGTGACGCGTCTGGCTCTGCAAAACGAGAATATCGTTGGCATCAAAGAC
                      ACCATCGACAGCGTTGGTCACTTGCGTACGATGATCAACACAGTTAAGTCGGTAC
                      GCCCGTCGTTTTCGGTATTCTGCGGTTACGATGATCATTTGCTGAATACGATGCT
                      GCTGGGCGGCGACGGTGCGATAACCGCCAGCGCTAACTTTGCTCCGGAACTCTCC
                      GTCGGCATCTACCGCGCCTGGCGTGAAGGCGATCTGGCGACCGCTGCGACGCTGA
                      ATAAAAAACTACTACAACTGCCCGCTATTTACGCCCTCGAAACACCGTTTGTCTC
                      ACTGATCAAATACAGCATGCAGTGTGTCGGGCTGCCTGTAGAGACATATTGCTTA
                      CCACCGATTCTTGAAGCATCTGAAGAAGCAAAAGATAAAGTCCACGTGCTGCTTA
                      CCGCGCAGGGCATTTTACCAGTCTGA SEQ ID NO: 78         Escherichia coli Uncharacterized lyase yjhH AA sequence
                      MKKFSGIIPPVSSTFHRDGTLDKKAMREVADFLINKGVDGLFYLGTGGEFSQMNT
                      AQRMALAEEEAVTIVDGRVPVLIGVGSPSTDEAVKLAQHAQAYGADGIVAINPYYW
                      KVAPRNLDDYYQQIARSVTLPVILYNFPDLTGQDLTPETVTRLALQNENIVGIKD
```

| | SEQUENCE LISTING |
|---|---|
| | TIDSVGHLRTMINTVKSVRPSFSVFCGYDDHLLNTMLLGGDGAITASANFAPELS<br>VGIYRAWREGDLATAATLNKKLLQLPAIYALETPFVSLIKYSMQCVGLPVETYCL<br>PPILEASEEAKDKVHVLLTAQGILPV |
| SEQ ID NO: 79 | *Escherichia coli* Probable 2-keto-3-deoxy-galactonate<br>aldolase yagE NT sequence<br>ATGCCGCAGTCCGCGTTGTTCACGGGAATCATTCCCCCTGTCTCCACCATTTTTA<br>CCGCCGACGGCCAGCTCGATAAGCCGGGCACCGCCGCGCTGATCGACGATCTGAT<br>CAAAGCAGGCGTTGACGGCCTGTTCTTCCTGGGCAGCGGTGGCGAGTTCTCCCAG<br>CTCGGCGCCGAAGAGCGTAAAGCCATTGCCCGCTTTGCTATCGATCATGTCGATC<br>GTCGCGTGCCGGTGCTGATCGGCACCGGCGGCACCAACGCCCGGGAAACCATCGA<br>ACTCAGCCAGCACGCGCAGCAGGCGGGCGCGGACGGCATCGTGGTGATCAACCCC<br>TACTACTGGAAAGTGTCGGAAGCGAACCTGATCCGCTATTTCGAGCAGGTGGCCG<br>ACAGCGTCACGCTGCCGGTGATGCTCTATAACTTCCCGGCGCTGACCGGGCAGGA<br>TCTGACTCCGGCGCTGGTGAAAACCCTCGCCGACTCGCGCAGCAATATTATCGGC<br>ATCAAAGACACCATCGACTCCGTCGCCCACCTGCGCAGCATGATCCATACCGTCA<br>AGGGTGCCCATCCGCACTTCACCGTGCTCTGCGGCTACGACGATCATCTGTTCAA<br>TACCCTGCTGCTCGGCGGCGACGGGGCGATATCGGCGAGCGGCAACTTTGCCCCG<br>CAGGTGTCGGTGAATCTTCTGAAAGCCTGGCGCGACGGGGACGTGGCGAAAGCGG<br>CCGGGTATCATCAGACCTTGCTGCAAATTCCGCAGATGTATCAGCTGGATACGCC<br>GTTTGTGAACGTGATTAAAGAGGCGATCGTGCTCTGCGGTCGTCCTGTCTCCACG<br>CACGTGCTGCCGCCCGCCTCGCCGCTGGACGAGCCGCGCAAGGCGCAGCTGAAAA<br>CCCTGCTGCAACAGCTCAAGCTTTGCTGA |
| SEQ ID NO: 80 | *Escherichia coli* Probable 2-keto-3-deoxy-galactonate<br>aldolase yagE codon optimized NT sequence<br>ATGCCGCAGTCCGCGTTGTTCACGGGAATCATTCCCCCTGTCTCCACCATTTTTA<br>CCGCCGACGGCCAGCTCGATAAGCCGGGCACCGCCGCGCTGATCGACGATCTGAT<br>CAAAGCAGGCGTTGACGGCCTGTTCTTCCTGGGCAGCGGTGGCGAGTTCTCCCAG<br>CTCGGCGCCGAAGAGCGTAAAGCCATTGCCCGCTTTGCTATCGATCATGTCGATC<br>GTCGCGTGCCGGTGCTGATCGGCACCGGCGGCACCAACGCCCGGGAAACCATCGA<br>ACTCAGCCAGCACGCGCAGCAGGCGGGCGCGGACGGCATCGTGGTGATCAACCCC<br>TACTACTGGAAAGTGTCGGAAGCGAACCTGATCCGCTATTTCGAGCAGGTGGCCG<br>ACAGCGTCACGCTGCCGGTGATGCTCTATAACTTCCCGGCGCTGACCGGGCAGGA<br>TCTGACTCCGGCGCTGGTGAAAACCCTCGCCGACTCGCGCAGCAATATTATCGGC<br>ATCAAAGACACCATCGACTCCGTCGCCCACCTGCGCAGCATGATCCATACCGTCA<br>AGGGTGCCCATCCGCACTTCACCGTGCTCTGCGGCTACGACGATCATCTGTTCAA<br>TACCCTGCTGCTCGGCGGCGACGGGGCGATATCGGCGAGCGGCAACTTTGCCCCG<br>CAGGTGTCGGTGAATCTTCTGAAAGCCTGGCGCGACGGGGACGTGGCGAAAGCGG<br>CCGGGTATCATCAGACCTTGCTGCAAATTCCGCAGATGTATCAGCTGGATACGCC<br>GTTTGTGAACGTGATTAAAGAGGCGATCGTGCTCTGCGGTCGTCCTGTCTCCACG<br>CACGTGCTGCCGCCCGCCTCGCCGCTGGACGAGCCGCGCAAGGCGCAGCTGAAAA<br>CCCTGCTGCAACAGCTCAAGCTTTGCTGA |
| SEQ ID NO: 81 | *Escherichia coli* Probable 2-keto-3-deoxy-galactonate<br>aldolase yagE AA sequence<br>MPQSALFTGIIPPVSTIFTADGQLDKPGTAALIDDLIKAGVDGLFFLGSGGEFSQ<br>LGAEERKAIARFAIDHVDRRVPVLIGTGGTNARETIELSQHAQQAGADGIVVINP<br>YYWKVSEANLIRYFEQVADSVTLPVMLYNFPALTGQDLTPALVKTLADSRSNIIG<br>IKDTIDSVAHLRSMIHTVKGAHPHFTVLCGYDDHLFNTLLLGGDGAISASGNFAP<br>QVSVNLLKAWRDGDVAKAAGYHQTLLQIPQMYQLDTPFVNVIKEAIVLCGRPVST<br>HVLPPASPLDEPRKAQLKTLLQQLKLC |
| SEQ ID NO: 82 | *Scheffersomyces stipitis* D-xylose reductase xyl1 NT<br>sequence<br>ATGCCTTCTATTAAGTTGAACTCTGGTTACGACATGCCAGCCGTCGGTTTCGGCT<br>GTTGGAAAGTCGACGTCGACACCTGTTCTGAACAGATCTACCGTGCTATCAAGAC<br>CGGTTACAGATTGTTCGACGGTGCCGAAGATTACGCCAACGAAAAGTTAGTTGGT<br>GCCGGTGTCAAGAAGGCCATTGACGAAGGTATCGTCAAGCGTGAAGATTTGTTCC<br>TTACCTCCAAGTTGTGGAACAACTACCACCACCCAGACAACGTCGAAAAGGCCTT<br>GAACAGAACCCTTTCTGACTTGCAAGTTGACTACGTTGACTTGTTCTTGATCCAC<br>TTCCCAGTCACCTTCAAGTTCGTTCCATTAGAAGAAAAGTACCCACCAGGATTCT<br>ACTGTGGTAAGGGTGACAACTTCGACTACGAAGATGTTCCAATTTTAGAGACTTG<br>GAAGGCTCTTGAAAAGTTGGTCAAGGCCGGTAAGATCAGATCTATCGGTGTTTCT<br>AACTTCCCAGGTGCTTTGCTCTTGGACTTGTTGAGAGGTGCTACCATCAAGCCAT<br>CTGTCTTGCAAGTTGAACACCACCCATACTTGCAACAACCAAGATTGATCGAATT<br>CGCTCAATCCCGTGGTATTGTCGTCACCGCTTACTCTTCGTTCGGTCCTCAATCT<br>TTCGTTGAATTGAACCAAGGTAGAGCTTTGAACACTTCTCCATTGTTCGAGAACG<br>AAACTATCAAGGCTATCGCTGCTAAGCACGGTAAGTCTCCAGCTCAAGTCTTGTT<br>GAGATGGTCATCCCAAAGAGGCATTGCCATCATTCCAAAGTCCAACACTGTCCCA<br>AGATTGTTGGAAAACAAGGACGTCAACAGCTTCGACTTGGACGAACAAGATTTCG<br>CTGACATTGCCAAGTTGGACATCAACTTGAGATTCAACGACCCATGGGACTGGGA<br>CAAGATTCCTATCTTCGTCTAA |

| SEQUENCE LISTING | |
|---|---|
| SEQ ID NO: 83 | *Scheffersomyces stipitis* D-xylose reductase xyl1 codon optimized NT sequence<br>ATGCCATCTATCAAGTTAAATTCCGGTTACGACATGCCTGCTGTTGGTTTCGGTT<br>GCTGGAAGGTTGATGTCGATACTTGTTCCGAGCAAATTTACCGTGCTATCAAGAC<br>TGGTTACAGATTGTTCGATGGTGCTGAAGACTACGCCAACGAAAAGTTAGTCGGT<br>GCTGGTGTTAAAAAGGCTATCGACGAAGGTATTGTTAAAAGAGAAGACTTGTTCT<br>TGACTTCTAAGTTGTGGAACAACTACCACCATCCTGATAACGTCGAAAAAGCTTT<br>GAACCGTACCTTGTCCGATTTGCAAGTCGATTACGTTGATTTGTTCTTGATTCAT<br>TTCCCAGTTACCTTCAAGTTCGTTCCATTGGAAGAGAAGTATCCACCAGGTTTCT<br>ACTGTGGTAAGGGTGATAACTTCGATTACGAAGATGTCCCAATCTTAGAAACCTG<br>GAAGGCTTTAGAAAAGTTGGTTAAGGCTGGTAAGATCAGATCCATCGGTGTTTCT<br>AACTTCCCAGGTGCCTTATTGTTAGACTTATTGAGAGGTGCTACCATTAAGCCTT<br>CCGTTTTGCAAGTTGAACATCATCCTTACTTGCAACAACCAAGATTGATCGAATT<br>CGCTCAATCTAGAGGTATCGCTGTTACTGCCTACTCTTCCTTCGGTCCACAATCT<br>TTCGTTGAGTTGAACCAAGGTAGAGCTTTGAACACCTCTCCATTGTTCGAAAACG<br>AAACTATTAAGGCCATTGCTGCTAAGCATGGTAAGTCTCCAGCCCAAGTTTTGTT<br>GAGATGGTCTTCTCAAAGAGGTATCGCTATTATCCCAAAGTCTAATACTGTCCCA<br>AGATTGTTGGAAAACAAGGACGTTAACTCCTTTGATTTGGATGAACAAGACTTTG<br>CTGACATCGCTAAATTGGACATCAACTTGAGATTCAACGACCCATGGGACTGGGA<br>CAAGATTCCAATTTTTGTTTAA |
| SEQ ID NO: 84 | *Scheffersomyces stipitis* D-xylose reductase xyl1 AA sequence<br>MPSIKLNSGYDMPAVGFGCWKVDVDTCSEQIYRAIKTGYRLFDGAEDYANEKLVG<br>AGVKKAIDEGIVKREDLFLTSKLWNNYHHPDNVEKALNRTLSDLQVDYVDLFLIH<br>FPVTFKFVPLEEKYPPGFYCGKGDNFDYEDVPILETWKALEKLVKAGKIRSIGVS<br>NFPGALLLDLLRGATIKPSVLQVEHHPYLQQPRLIEFAQSRGIAVTAYSSFGPQS<br>FVELNQGRALNTSPLFENETIKAIAAKHGKSPAQVLLRWSSQRGIAIIPKSNTVP<br>RLLENKDVNSFDLDEQDFADIAKLDINLRFNDPWDWDKIPIFV |
| SEQ ID NO: 85 | *Saccharomyces cerevisiae* aldose reductase GRE3 NT sequence<br>ATGTCTTCACTGGTTACTCTTAATAACGGTCTGAAAATGCCCCTAGTCGGCTTAG<br>GGTGCTGGAAAATTGACAAAAAGTCTGTGCGAATCAAATTTATGAAGCTATCAA<br>ATTAGGCTACCGTTTATTCGATGGTGCTTGCGACTACGGCAACGAAAAGGAAGTT<br>GGTGAAGGTATCAGGAAAGCCATCTCCGAAGGTCTTGTTTCTAGAAAGGATATAT<br>TTGTTGTTTCAAAGTTATGGAACAATTTTCACCATCCTGATCATGTAAAATTAGC<br>TTTAAAGAAGACCTTAAGCGATATGGGACTTGATTATTTAGACCTGTATTATATT<br>CACTTCCCAATCGCCTTCAAATATGTTCCATTTGAAGAGAAATACCCTCCAGGAT<br>TCTATACGGGCGCAGATGACGAGAAGAAAGGTCACATCACCGAAGCACATGTACC<br>AATCATAGATACGTACCGGGCTCTGGAAGAATGTGTTGATGAAGGCTTGATTAAG<br>TCTATTGGTGTTTCCAACTTTCAGGGAAGCTTGATTCAAGATTATTACGTGGTT<br>GTAGAATCAAGCCCGTGGCTTTGCAAATTGAACACCATCCTTATTTGACTCAAGA<br>ACACCTAGTTGAGTTTTGTAAATTACACGATATCCAAGTAGTTGCTTACTCCTCC<br>TTCGGTCCTCAATCATTCATTGAGATGGACTTACAGTTGGCAAAAACCACGCCAA<br>CTCTGTTCGAGAATGATGTAATCAAGAAGGTCTCACAAAACCATCCAGGCAGTAC<br>CACTTCCCAAGTATTGCTTAGATGGGCAACTCAGAGAGGCATTGCCGTCATTCCA<br>AAATCTTCCAAGAAGGAAAGGTTACTTGGCAACCTAGAAATCGAAAAAAAGTTCA<br>CTTTAACGGAGCAAGAATTGAAGGATATTTCTGCACTAAATGCCAACATCAGATT<br>TAATGATCCATGGACCTGGTTGGATGGTAAATTCCCCACTTTTGCCTGA |
| SEQ ID NO: 86 | *Saccharomyces cerevisiae* aldose reductase GRE3 codon optimized NT sequence<br>ATGTCTTCACTGGTTACTCTTAATAACGGTCTGAAAATGCCCCTAGTCGGCTTAG<br>GGTGCTGGAAAATTGACAAAAAGTCTGTGCGAATCAAATTTATGAAGCTATCAA<br>ATTAGGCTACCGTTTATTCGATGGTGCTTGCGACTACGGCAACGAAAAGGAAGTT<br>GGTGAAGGTATCAGGAAAGCCATCTCCGAAGGTCTTGTTTCTAGAAAGGATATAT<br>TTGTTGTTTCAAAGTTATGGAACAATTTTCACCATCCTGATCATGTAAAATTAGC<br>TTTAAAGAAGACCTTAAGCGATATGGGACTTGATTATTTAGACCTGTATTATATT<br>CACTTCCCAATCGCCTTCAAATATGTTCCATTTGAAGAGAAATACCCTCCAGGAT<br>TCTATACGGGCGCAGATGACGAGAAGAAAGGTCACATCACCGAAGCACATGTACC<br>AATCATAGATACGTACCGGGCTCTGGAAGAATGTGTTGATGAAGGCTTGATTAAG<br>TCTATTGGTGTTTCCAACTTTCAGGGAAGCTTGATTCAAGATTATTACGTGGTT<br>GTAGAATCAAGCCCGTGGCTTTGCAAATTGAACACCATCCTTATTTGACTCAAGA<br>ACACCTAGTTGAGTTTTGTAAATTACACGATATCCAAGTAGTTGCTTACTCCTCC<br>TTCGGTCCTCAATCATTCATTGAGATGGACTTACAGTTGGCAAAAACCACGCCAA<br>CTCTGTTCGAGAATGATGTAATCAAGAAGGTCTCACAAAACCATCCAGGCAGTAC<br>CACTTCCCAAGTATTGCTTAGATGGGCAACTCAGAGAGGCATTGCCGTCATTCCA<br>AAATCTTCCAAGAAGGAAAGGTTACTTGGCAACCTAGAAATCGAAAAAAAGTTCA<br>CTTTAACGGAGCAAGAATTGAAGGATATTTCTGCACTAAATGCCAACATCAGATT<br>TAATGATCCATGGACCTGGTTGGATGGTAAATTCCCCACTTTTGCCTGA |
| SEQ ID NO: 87 | *Saccharomyces cerevisiae* aldose reductase GRE3 AA sequence<br>MSSLVTLNNGLKMPLVGLGCWKIDKKVCANQIYEAIKLGYRLFDGACDYGNEKEV<br>GEGIRKAISEGLVSRKDIFVVSKLWNNFHHPDHVKLALKKTLSDMGLDYLDLYYI<br>HFPIAFKYVPFEEKYPPGFYTGADDEKKGHITEAHVPIIDTYRALEECVDEGLIK |

| | SEQUENCE LISTING |
|---|---|
| | SIGVSNFQGSLIQDLLRGCRIKPVALQIEHHPYLTQEHLVEFCKLHDIQVVAYSS<br>FGPQSFIEMDLQLAKTTPTLFENDVIKKVSQNHPGSTTSQVLLRWATQRGIAVIP<br>KSSKKERLLGNLEIEKKFTLTEQELKDISALNANIRFNDPWTWLDGKFPTFA |
| SEQ ID NO: 88 | *Scheffersomyces stipitis* D-xylulose reductase xyl2 NT sequence<br>ATGACTGCTAACCCTTCCTTGGTGTTGAACAAGATCGACGACATTTCGTTCGAAA<br>CTTACGATGCCCCAGAAATCTCTGAACCTACCGATGTCCTCGTCCAGGTCAAGAA<br>AACCGGTATCTGTGGTTCCGACATCCACTTCTACGCCCATGGTAGAATCGGTAAC<br>TTCGTTTTGACCAAGCCAATGGTCTTGGGTCACGAATCCGCCGGTACTGTTGTCC<br>AGGTTGGTAAGGGTGTCACCTCTCTTAAGGTTGGTGACAACGTCGCTATCGAACC<br>AGGTATTCCATCCAGATTCTCCGACGAATACAAGAGCGGTCACTACAACTTGTGT<br>CCTCACATGGCCTTCGCCGCTACTCCTAACTCCAAGGAAGGCGAACCAAACCCAC<br>CAGGTACCTTATGTAAGTACTTCAAGTCGCCAGAAGACTTCTTGGTCAAGTTGCC<br>AGACCACGTCAGCTTGGAACTCGGTGCTCTTGTTGAGCCATTGTCTGTTGGTGTC<br>CACGCCTCTAAGTTGGGTTCCGTTGCTTTCGGCGACTACGTTGCCGTCTTTGGTG<br>CTGGTCCTGTTGGTCTTTTGGCTGCTGCTGTCGCCAAGACCTTCGGTGCTAAGGG<br>TGTCATCGTCGTTGACATTTTCGACAACAAGTTGAAGATGGCCAAGGACATTGGT<br>GCTGCTACTCACACCTTCAACTCCAAGACCGGTGGTTCTGAAGAATTGATCAAGG<br>CTTTCGGTGGTAACGTGCCAAACGTCGTTTTGGAATGTACTGGTGCTGAACCTTG<br>TATCAAGTTGGGTGTTGACGCCATTGCCCCAGGTGGTCGTTTCGTTCAAGTCGGT<br>AACGCTGCTGGTCCAGTCAGCTTCCCAATCACCGTTTTCGCCATGAAGGAATTGA<br>CTTTGTTCGGTTCTTTCAGATACGGATTCAACGACTACAAGACTGCTGTTGGAAT<br>CTTTGACACTAACTACCAAAACGGTAGAGAAAATGCTCCAATTGACTTTGAACAA<br>TTGATCACCCACAGATACAAGTTCAAGGACGCTATTGAAGCCTACGACTTGGTCA<br>GAGCCGGTAAGGGTGCTGTCAAGTGTCTCATTGACGGCCCTGAGTAA |
| SEQ ID NO: 89 | *Scheffersomyces stipitis* D-xylulose reductase xyl2 codon optimized NT sequence<br>ATGACTGCTAACCCTTCCTTGGTGTTGAACAAGATCGACGACATTTCGTTCGAAA<br>CTTACGATGCCCCAGAAATCTCTGAACCTACCGATGTCCTCGTCCAGGTCAAGAA<br>AACCGGTATCTGTGGTTCCGACATCCACTTCTACGCCCATGGTAGAATCGGTAAC<br>TTCGTTTTGACCAAGCCAATGGTCTTGGGTCACGAATCCGCCGGTACTGTTGTCC<br>AGGTTGGTAAGGGTGTCACCTCTCTTAAGGTTGGTGACAACGTCGCTATCGAACC<br>AGGTATTCCATCCAGATTCTCCGACGAATACAAGAGCGGTCACTACAACTTGTGT<br>CCTCACATGGCCTTCGCCGCTACTCCTAACTCCAAGGAAGGCGAACCAAACCCAC<br>CAGGTACCTTATGTAAGTACTTCAAGTCGCCAGAAGATTTCTTGGTCAAGTTGCC<br>AGACCACGTCAGCTTGGAACTCGGTGCTCTTGTTGAGCCATTGTCTGTTGGTGTC<br>CACGCCTCTAAGTTGGGTTCCGTTGCTTTCGGCGACTACGTTGCCGTCTTTGGAG<br>CAGGTCCTGTTGGTCTTTTGGCTGCTGCTGTCGCCAAGACCTTCGGTGCTAAGGG<br>TGTCATCGTCGTTGACATTTTCGACAACAAGTTGAAGATGGCCAAGGACATTGGA<br>GCTGCTACTCACACCTTCAACTCCAAGACCGGTGGTTCTGAAGAATTGATCAAGG<br>CTTTCGGTGGTAACGTGCCAAACGTCGTTTTGGAATGTACAGGTGCAGAACCTTG<br>TATCAAGTTGGGTGTTGACGCCATTGCCCCAGGTGGTCGTTTCGTTCAAGTCGGT<br>AACGCTGCTGGTCCAGTCAGCTTCCCAATCACCGTTTTCGCCATGAAGGAATTGA<br>CTTTGTTCGGTTCTTTCAGATACGGATTCAACGACTACAAGACTGCTGTTGGAAT<br>CTTTGACACTAACTACCAAAACGGTAGAGAAAATGCTCCAATTGACTTTGAACAA<br>TTGATCACCCACAGATACAAGTTCAAGGACGCTATTGAAGCCTACGACTTGGTCA<br>GAGCCGGTAAGGGTGCTGTCAAGTGTCTCATTGACGGCCCTGAGTAA |
| SEQ ID NO: 90 | *Scheffersomyces stipitis* D-xylulose reductase xyl2 AA sequence<br>MTANPSLVLNKIDDISFETYDAPEISEPTDVLVQVKKTGICGSDIHFYAHGRIGN<br>FVLTKPMVLGHESAGTVVQVGKGVTSLKVGDNVAIEPGIPSRFSDEYKSGHYNLC<br>PHMAFAATPNSKEGEPNPPGTLCKYFKSPEDFLVKLPDHVSLELGALVEPLSVGV<br>HASKLGSVAFGDYVAVFGAGPVGLLAAAVAKTFGAKGVIVVDIFDNKLKMAKDIG<br>AATHTFNSKTGGSEELIKAFGGNVPNVVLECTGAEPCIKLGVDAIAPGGRFVQVG<br>NAAGPVSFPITVFAMKELTLFGSFRYGFNDYKTAVGIFDTNYQNGRENAPIDFEQ<br>LITHRYKFKDAIEAYDLVRAGKGAVKCLIDGPE |
| SEQ ID NO: 91 | *Trichoderma reesei* Xylitol dehydrogenase xdh1 NT sequence<br>ATGGCGACTCAAACGATCAACAAGGATGCGATCAGCAACCTCTCCTTCGTCCTCA<br>ACAAGCCCGGCGACGTGACCTTTGAGGAGCGGCCGAAGCCGACCATCACGGACCC<br>CAACGACGTCCTCGTCGCCGTCAACTACACGGGCATCTGCGGCTCCGACGTGCAC<br>TACTGGGTGCACGGCGCCATCGGGCACTTCGTCGTCAAGGACCCGATGGTGCTGG<br>GCCACGAGTCGGCCGGCACCGTCGTCGAGGTCGGCCGGCCGTCAAGAGCCTCAA<br>GCCCGGCGACCGCGTCGCCCTCGAGCCCGGCTACCCGTGCCGGCGGTGCTCCTTC<br>TGCCGCGCCGGCAAATACAACCTGTGCCCGGACATGGTCTTCGCCGCCACGCCGC<br>CGTACCACGGCACCCTGACGGGCTGTGGGCGGCGCCCGCCGACTTCTGCTACAA<br>GCTGCCGGACGGCGTGTCGCTGCAGGAGGGCGCGCTGATCGAGCCGCTGGCCGTG<br>GCCGTCCACATTGTCAAGCAGGCCCGCGTCAGCCGGGCCAGTCCGTCGTCGTCA<br>TGGGCGCCGGCCCCGTCGGCCTGCTGTGCGCCGCCGTGGCCAAGGCGTACGGCGC<br>CTCCACCATTGTCAGCGTCGACATCGTGCAGTCCAAGCTCGACTTTGCGCGCGGC<br>TTCTGCTCGACGCACACGTACGTCTCGCAGCGCATCTCGGCTGAGGACAACGCAA<br>AGGCCATCAAGGAGCTGGCGGGCCTGCCCGGCGGCGCCGACGTCGTCGATTGACGC<br>CAGCGGCGCGGAGCCGTCGATCCAGACGAGCATTCACGTCGTCCGCATGGGCGGC |

| SEQUENCE LISTING |
| --- |
| ACGTACGTCCAGGGCGGCATGGGCAAGAGCGACATCACGTTCCCCATCATGGCCA<br>TGTGCCTCAAGGAGGTGACGGTCCGGGGCTCGTTCCGCTACGGCGCCGGCGACTA<br>CGAGCTGGCGGTCGAGCTGGTCCGGACGGGGCGGGTGGACGTCAAGAAGCTGATT<br>ACGGGCACCGTCAGCTTCAAGCAGGCGGAGGAGGCGTTCCAAAAGGTCAAGTCTG<br>GGGAGGCCATCAAGATTCTGATTGCCGGGCCCAACGAGAAGGTGTAA |
| SEQ ID NO: 92    *Trichoderma reesei* Xylitol dehydrogenase xdh1 AA sequence<br>MATQTINKDAISNLSFVLNKPGDVTFEERPKPTITDPNDVLVAVNYTGICGSDVH<br>YWVHGAIGHFVVKDPMVLGHESAGTVVEVGPAVKSLKPGDRVALEPGYPCRRCSF<br>CRAGKYNLCPDMVFAATPPYHGTLTGLWAAPADFCYKLPDGVSLQEGALIEPLAV<br>AVHIVKQARVQPGQSVVVMGAGPVGLLCAAVAKAYGASTIVSVDIVQSKLDFARG<br>FCSTHTYVSQRISAEDNAKAIKELAGLPGGADVVIDASGAEPSIQTSIHVVRMGG<br>TYVQGGMGKSDITFPIMAMCLKEVTVRGSFRYGAGDYELAVELVRTGRVDVKKLI<br>TGTVSFKQAEEAFQKVKSGEAIKILIAGPNEKV |
| SEQ ID NO: 93    *Pyromyces* sp. *xylose* isomerase xylA NT sequence<br>ATGGCTAAGGAATATTTCCCACAAATTCAAAAGATTAAGTTCGAAGGTAAGGATT<br>CTAAGAATCCATTAGCCTTCCACTACTACGATGCTGAAAAGGAAGTCATGGGTAA<br>GAAAATGAAGGATTGGTTACGTTTCGCCATGGCCTGGTGGCACACTCTTTGCGCC<br>GAAGGTGCTGACCAATTCGGTGGAGGTACAAAGTCTTTCCCATGGAACGAAGGTA<br>CTGATGCTATTGAAATTGCCAAGCAAAAGGTTGATGCTGGTTTCGAAATCATGCA<br>AAAGCTTGGTATTCCATACTACTGTTTCCACGATGTTGATCTTGTTTCCGAAGGT<br>AACTCTATTGAAGAATACGAATCCAACCTTAAGGCTGTCGTTGCTTACCTCAAGG<br>AAAAGCAAAAGGAAACCGGTATTAAGCTTCTCTGGAGTACTGCTAACGTCTTCGG<br>TCACAAGCGTTACATGAACGGTGCCTCCACTAACCCAGACTTTGATGTTGTCGCC<br>CGTGCTATTGTTCAAATTAAGAACGCCATAGACGCCGGTATTGAACTTGGTGCTG<br>AAAACTACGTCTTCTGGGGTGGTCGTGAAGGTTACATGAGTCTCCTTAACACTGA<br>CCAAAAGCGTGAAAAGGAACACATGGCCACTATGCTTACCATGGCTCGTGACTAC<br>GCTCGTTCCAAGGGATTCAAGGGTACTTTCCTCATTGAACCAAAGCCAATGGAAC<br>CAACCAAGCACCAATACGATGTTGACACTGAAACCGCTATTGGTTTCCTTAAGGC<br>CCACAACTTAGACAAGGACTTCAAGGTCAACATTGAAGTTAACCACGCTACTCTT<br>GCTGGTCACACTTTCGAACACGAACTTGCCTGTGCTGTTGATGCTGGTATGCTCG<br>GTTCCATTGATGCTAACCGTGGTGACTACCAAAACGGTTGGGATACTGATCAATT<br>CCCAATTGATCAATACGAACTCGTCCAAGCTTGGATGGAAATCATCCGTGGTGGT<br>GGTTTCGTTACTGGTGGTACCAACTTCGATGCCAAGACTCGTCGTAACTCTACTG<br>ACCTCGAAGACATCATCATTGCCCACGTTTCTGGTATGGATGCTATGGCTCGTGC<br>TCTTGAAAACGCTGCCAAGCTCCTCCAAGAATCTCCATACACCAAGATGAAGAAG<br>GAACGTTACGCTTCCTTCGACAGTGGTATTGGTAAGGACTTTGAAGATGGTAAGC<br>TCACCCTCGAACAAGTTTACGAATACGGTAAGAAGAACGGTGAACCAAAGCAAAC<br>TTCTGGTAAGCAAGAACTCTACGAAGCTATTGTTGCCATGTACCAATAA |
| SEQ ID NO: 94    *Pyromyces* sp. *xylose* isomerase xylA codon optimized NT sequence<br>ATGGCCAAGGAATACTTCCCACAAATCCAAAAGATTAAATTCGAAGGTAAAGATT<br>CCAAGAACCCATTGGCTTTTCACTACTACGATGCTGAGAAGGAAGTTATGGGTAA<br>GAAGATGAAGGATTGGTTGAGATTCGCTATGGCTTGGTGGCACACTTTGTGCGCT<br>GAAGGTGCTGACCAATTCGGTGGTGGTACTAAGTCTTTCCCATGGAACGAAGGTA<br>CTGATGCTATTGAAATCGCTAAGCAAAAAGTCGATGCTGGTTTTGAGATTATGCA<br>AAAATTGGGTATCCCATACTACTGTTTCCACGACGTCGACTTGGTTTCTGAAGGT<br>AATTCTATCGAAGAATACGAATCTAATTTGAAGGCTGTTGTCGCTTACTTAAAAG<br>AAAAGCAAAAGGAGACTGGTATTAAGTTGTTGTGGTCCACCGCTAACGTCTTTGG<br>TCATAAAAGATACATGAACGGTGCTTCCACCAACCCAGACTTCGATGTCGTCGCC<br>AGAGCTATCGTTCAAATTAAAAACGCCATCGACGCTGGTATTGAATTGGGTGCTG<br>AAAATTACGTCTTTTGGGGTGGTCGTGAAGGTTACATGTCTTTGTTGAACACTGA<br>CCAAAAGAGAGAAAAAGAACACATGGCCACTATGTTGACCATGGCCAGAGATTAC<br>GCCAGATCTAAGGGTTTCAAGGGTACCTTCTTAATTGAACCAAAACCTATGGAAC<br>CAACTAAGCACCAATACGACGTTGACACTGAAACTGCTATCGGTTTTTTGAAGGC<br>TCACAACTTGGATAAGGATTTTAAAGTCAACATTGAAGTTAACCATGCTACTTTG<br>GCTGGTCACACTTTTGAACATGAATTGGCCTGTGCTGTTGATGCTGGTATGTTGG<br>GTTCTATCGATGCTAATAGAGGTGACTATCAAAACGGTTGGGACACTGATCAATT<br>CCCAATCGATCAATATGAATTAGTTCAAGCTTGGATGGAAATTATCAGAGGTGGT<br>GGTTTCGTTACTGGTGGTACTAACTTCGATGCTAAGACCAGAAGAAACTCTACTG<br>ATTTGGAAGATATTATCATTGCCCACGTTTCCGGTATGGATGCCATGGCCAGAGC<br>TTTGGAAAACGCCGCCAAGTTATTGCAAGAGTCCCCATACACCAAGATGAAAAAG<br>GAACGTTACGCTTCTTTCGACTCTGGTATCGGTAAAGACTTCGAAGATGGTAAGT<br>TGACCTTGGAACAAGTTTACGAATACGGTAAGAAGAACGGTGAACCTAAACAAAC<br>CTCTGGTAAACAAGAATTGTATGAAGCTATTGTTGCCATGTACCAATAA |
| SEQ ID NO: 95    *Pyromyces* sp. *xylose* isomerase xylA AA sequence<br>MAKEYFPQIQKIKFEGKDSKNPLAFHYYDAEKEVMGKKMKDWLRFAMAWWHTLCA<br>EGADQFGGGTKSFPWNEGTDAIEIAKQKVDAGFEIMQKLGIPYYCFHDVDLVSEG<br>NSIEEYESNLKAVVAYLKEKQKETGIKLLWSTANVFGHKRYMNGASTNPDFDVVA<br>RAIVQIKNAIDAGIELGAENYVFWGGREGYMSLLNTDQKREKEHMATMLTMARDY<br>ARSKGFKGTFLIEPKPMEPTKHQYDVDTETAIGFLKAHNLDKDFKVNIEVNHATL<br>AGHTFEHELACAVDAGMLGSIDANRGDYQNGWDTDQFPIDQYELVQAWMEIIRGG |

| | |
|---|---|
| | GFVTGGTNFDAKTRRNSTDLEDIIIAHVSGMDAMARALENAAKLLQESPYTKMKK<br>ERYASFDSGIGKDFEDGKLTLEQVYEYGKKNGEPKQTSGKQELYEAIVAMYQ |
| SEQ ID NO: 96 | *Clostridium acetobutylicum* butyrate-acetoacetate CoA-<br>transferase, complex A ctfA NT sequence<br>ATGAACTCTAAAATAATTAGATTTGAAAATTTAAGGTCATTCTTTAAAGATGGGA<br>TGACAATTATGATTGGAGGTTTTTTAAACTGTGGCACTCCAACCAAATTAATTGA<br>TTTTTTAGTTAATTTAAATATAAAGAATTTAACGATTATAAGTAATGATACATGT<br>TATCCTAATACAGGTATTGGTAAGTTAATATCAAATAATCAAGTAAAAAAGCTTA<br>TTGCTTCATATATAGGCAGCAACCCAGATACTGGCAAAAAACTTTTTAATAATGA<br>ACTTGAAGTAGAGCTCTCTCCCCAAGGAACTCTAGTGGAAAGAATACGTGCAGGC<br>GGATCTGGCTTAGGTGGTGTACTAACTAAAACAGGTTTAGGAACTTTGATTGAAA<br>AAGGAAAGAAAAAAATATCTATAAATGGAACGGAATATTTGTTAGAGCTACCTCT<br>TACAGCCGATGTAGCATTAATTAAAGGTAGTATTGTAGATGAGGCCGGAAACACC<br>TTCTATAAAGGTACTACTAAAAACTTTAATCCCTATATGGCAATGGCAGCTAAAA<br>CCGTAATAGTTGAAGCTGAAAATTTAGTTAGCTGTGAAAAACTAGAAAAGGAAAA<br>AGCAATGACCCCCGGAGTTCTTATAAATTATATAGTAAAGGAGCCTGCATAA |
| SEQ ID NO: 97 | *Clostridium acetobutylicum* butyrate-acetoacetate CoA-<br>transferase, complex A ctfA AA sequence<br>MNSKIIRFENLRSFFKDGMTIMIGGFLNCGTPTKLIDFLVNLNIKNLTIISNDTC<br>YPNTGIGKLISNNQVKKLIASYIGSNPDTGKKLFNNELEVELSPQGTLVERIRAG<br>GSGLGGVLTKTGLGTLIEKGKKKISINGTEYLLELPLTADVALIKGSIVDEAGNT<br>FYKGTTKNFNPYMAMAAKTVIVEAENLVSCEKLEKEKAMTPGVLINYIVKEPA |
| SEQ ID NO: 98 | *Clostridium acetobutylicum* butyrate-acetoacetate CoA-<br>transferase, subunit B ctfB NT sequence<br>ATGATTAATGATAAAAACCTAGCGAAAGAAATAATAGCCAAAAGAGTTGCAAGAG<br>AATTAAAAAATGGTCAACTTGTAAACTTAGGTGTAGGTCTTCCTACCATGGTTGC<br>AGATTATATACCAAAAAATTTCAAAATTACTTTCCAATCAGAAAACGGAATAGTT<br>GGAATGGGCGCTAGTCCTAAAATAAATGAGGCAGATAAAGATGTAGTAAATGCAG<br>GAGGAGACTATACAACAGTACTTCCTGACGGCACATTTTTCGATAGCTCAGTTTC<br>GTTTTCACTAATCCGTGGTGGTCACGTAGATGTTACTGTTTTAGGGGCTCTCCAG<br>GTAGATGAAAAGGGTAATATAGCCAATTGGATTGTTCCTGGAAAAATGCTCTCTG<br>GTATGGGTGGAGCTATGGATTTAGTAAATGGAGCTAAGAAAGTAATAATTGCAAT<br>GAGACATACAAATAAAGGTCAACCTAAAATTTTAAAAAAATGTACACTTCCCCTC<br>ACGGCAAAGTCTCAAGCAAATCTAATTGTAACAGAACTTGGAGTAATTGAGGTTA<br>TTAATGATGGTTTACTTCTCACTGAAATTAATAAAAACACAACCATTGATGAAAT<br>AAGGTCTTTAACTGCTGCAGATTTACTCATATCCAATGAACTTAGACCCATGGCT<br>GTTTAG |
| SEQ ID NO: 99 | *Clostridium acetobutylicum* butyrate-acetoacetate CoA-<br>transferase, subunit B ctfB AA sequence<br>MINDKNLAKEIIAKRVARELKNGQLVNLGVGLPTMVADYIPKNFKITFQSENGIV<br>GMGASPKINEADKDVVNAGGDYTTVLPDGTFFDSSVSFSLIRGGHVDVTVLGALQ<br>VDEKGNIANWIVPGKMLSGMGGAMDLVNGAKKVIIAMRHTNKGQPKILKKCTLPL<br>TAKSQANLIVTELGVIEVINDGLLLTEINKNTTIDEIRSLTAADLLISNELRPMA<br>V |
| SEQ ID NO: 100 | *Escherichia coli* (strain K12) Acetyl-CoA:acetoacetate-<br>CoA transferase subunit atoA NT sequence<br>ATGGATGCGAAACAACGTATTGCGCGCCGTGTGGCGCAAGAGCTTCGTGATGGTG<br>ACATCGTTAACTTAGGGATCGGTTTACCCACAATGGTCGCCAATTATTTACCGGA<br>GGGTATTCATATCACTCTGCAATCGGAAAACGGCTTCCTCGGTTTAGGCCCGGTC<br>ACGACAGCGCATCCAGATCTGGTGAACGCTGGCGGGCAACCGTGCGGTGTTTTAC<br>CCGGTGCAGCCATGTTTGATAGCGCCATGTCATTTGCGCTAATCCGTGGCGGTCA<br>TATTGATGCCTGCGTGCTCGGCGGTTTGCAAGTAGACGAAGAAGCAAACCTCGCG<br>AACTGGGTAGTGCCTGGGAAAATGGTGCCCGGTATGGGTGGCGCGATGGATCTGG<br>TGACCGGGTCGCGCAAAGTGATCATCGCCATGGAACATTGCGCCAAAGATGGTTC<br>AGCAAAAATTTTGCGCCGCTGCACCATGCCACTCACTGCGCAACATGCGGTGCAT<br>ATGCTGGTTACTGAACTGGCTGTCTTTCGTTTTATTGACGGCAAAATGTGGCTCA<br>CCGAAATTGCCGACGGGTGTGATTTAGCCACCGTGCGTGCCAAAACAGAAGCTCG<br>GTTTGAAGTCGCCGCCGATCTGAATACGCAACGGGGTGATTTATGA |
| SEQ ID NO: 101 | *Escherichia coli* (strain K12) Acetyl-CoA:acetoacetate-<br>CoA transferase subunit atoA AA sequence<br>MDAKQRIARRVAQELRDGDIVNLGIGLPTMVANYLPEGIHITLQSENGFLGLPV<br>TTAHPDLVNAGGQPCGVLPGAAMFDSAMSFALIRGGHIDACVLGGLQVDEEANLA<br>NWVVPGKMVPGMGGAMDLVTGSRKVIIAMEHCAKDGSAKILRRCTMPLTAQHAVH<br>MLVTELAVFRFIDGKMWLTEIADGCDLATVRAKTEARFEVAADLNTQRGDL |
| SEQ ID NO: 102 | *Escherichia coli* (strain K12) Acetyl-CoA:acetoacetate-<br>CoA transferase subunit atoD NT sequence<br>ATGAAAACAAAATTGATGACATTACAAGACGCCACCGGCTTCTTTCGTGACGGCA<br>TGACCATCATGGTGGGCGGATTTATGGGGATTGGCACTCCATCCCGCCTGGTTGA<br>AGCATTACTGGAATCTGGTGTTCGCGACCTGACATTGATAGCCAATGATACCGCG<br>TTTGTTGATACCGGCATCGGTCCGCTCATCGTCAATGGTCGAGTCCGCAAAGTGA |

| | |
|---|---|
| | TTGCTTCACATATCGGCACCAACCCGGAAACAGGTCGGCGCATGATATCTGGTGA<br>GATGGACGTCGTTCTGGTGCCGCAAGGTACGCTAATCGAGCAAATTCGCTGTGGT<br>GGAGCTGGACTTGGTGGTTTTCTCACCCCAACGGGTGTCGGCACCGTCGTAGAGG<br>AAGGCAAACAGACACTGACACTCGACGGTAAAACCTGGCTGCTCGAACGCCCACT<br>GCGCGCCGACCTGGCGCTAATTCGCGCTCATCGTTGCGACACACTTGGCAACCTG<br>ACCTATCAACTTAGCGCCCGCAACTTTAACCCCCTGATAGCCCTTGCGGCTGATA<br>TCACGCTGGTAGAGCCAGATGAACTGGTCGAAACCGGCGAGCTGCAACCTGACCA<br>TATTGTCACCCCTGGTGCCGTTATCGACCACATCATCGTTTCACAGGAGAGCAAA<br>TAA |
| SEQ ID NO: 103 | *Escherichia coli* (strain K12) Acetyl-CoA:acetoacetate-<br>CoA transferase subunit atoD AA sequence<br>MKTKLMTLQDATGFFRDGMTIMVGGFMGIGTPSRLVEALLESGVRDLTLIANDTA<br>FVDTGIGPLIVNGRVRKVIASHIGTNPETGRRMISGEMDVVLVPQGTLIEQIRCG<br>GAGLGGFLTPTGVGTVVEEGKQTLTLDGKTWLLERPLRADLALIRAHRCDTLGNL<br>TYQLSARNFNPLIALAADITLVEPDELVETGELQPDHIVTPGAVIDHIIVSQESK |
| SEQ ID NO: 104 | *Clostridium beijerinckii* secondary alcohol<br>dehydrogenase adh NT sequence<br>ATGAAAGGTTTTGCAATGCTAGGTATTAATAAGTTAGGATGGATCGAAAAAGAAA<br>GGCCAGTTGCGGGTTCATATGATGCTATTGTACGCCCATTAGCAGTATCTCCGTG<br>TACATCAGATATACATACTGTTTTTGAGGGAGCTCTTGGAGATAGGAAGAATATG<br>ATTTTAGGGCATGAAGCTGTAGGTGAAGTTGTTGAAGTAGGAAGTGAAGTGAAGG<br>ATTTTAAACCTGGTGACAGAGTTATAGTTCCTTGTACAACTCCAGATTGGAGATC<br>TTTGGAAGTTCAAGCTGGTTTTCAACAGCACTCAAACGGTATGCTCGCAGGATGG<br>AAATTTTCAAATTTCAAGGATGGAGTTTTTGGTGAATATTTTCATGTAAATGATG<br>CGGATATGAATCTTGCGATTCTACCTAAAGACATGCCATTAGAAAATGCTGTTAT<br>GATAACAGATATGATGACTACTGGATTTCATGGAGCAGAACTTGCAGATATTCAA<br>ATGGGTTCAAGTGTTGTGGTAATTGGCATTGGAGCTGTTGGCTTAATGGGAATAG<br>CAGGTGCTAAATTACGTGGAGCAGGTAGAATAATTGGAGTGGGGAGCAGGCCGAT<br>TTGTGTTGAGGCTGCAAAATTTTATGGAGCAACAGATATTCTAAATTATAAAAAT<br>GGTCATATAGTTGATCAAGTTATGAAATTAACGAATGGAAAAGGCGTTGACCGCG<br>TAATTATGGCAGGCGGTGGTTCTGAAACATTATCCCAAGCAGTATCTATGGTTAA<br>ACCAGGAGGAATAATTTCTAATATAAATTATCATGGAAGTGGAGATGCTTTACTA<br>ATACCACGTGTAGAATGGGGATGTGGAATGGCTCACAAGACTATAAAGGAGGTC<br>TTTGTCCTGGGGGACGTTTGAGAGCAGAAATGTTAAGAGATATGGTAGTATATAA<br>TCGTGTTGATCTAAGTAAATTAGTTACACATGTATATCATGGATTTGATCACATA<br>GAAGAAGCACTGTTATTAATGAAAGACAAGCCAAAAGACTTAATTAAAGCAGTAG<br>TTATATTATAA |
| SEQ ID NO: 105 | *Clostridium beijerinckii* secondary alcohol<br>dehydrogenase adh codon optimized NT sequence<br>ATGAAAGGGTTTGCCATGTTAGGTATCAATAAACTGGGCTGGATTGAAAAAGAGC<br>GCCCGGTGGCGGGTTCATACGATGCAATTGTTCGTCCGCTGGCCGTCAGTCCGTG<br>CACCAGCGACATCCATACAGTCTTTGAAGGTGCCCTGGGTGATCGGAAAAACATG<br>ATTCTGGGCCATGAAGCCGTAGGCGAAGTAGTGGAAGTGGGCAGCGAGGTAAAGG<br>ATTTCAAACCGGGTGATCGCGTAATTGTTCCTTGCACGACCCCAGATTGGCGCTC<br>ACTGGAAGTTCAGGCTGGTTTTCAGCAGCATAGTAACGGTATGTTAGCAGGCTGG<br>AAGTTTAGCAATTTTAAAGACGGGGTGTTCGGGGAGTATTTTCATGTCAACGATG<br>CGGACATGAATCTGGCTATTTTACCTAAAGATATGCCGCTGGAGAACGCAGTGAT<br>GATTACCGACATGATGACGACAGGCTTTCACGGTGCAGAACTGGCTGACATCCAA<br>ATGGGCTCCAGTGTGGTGGTTATCGGTATTGGTGCGGTCGGGCTGATGGGTATCG<br>CGGGCGCGAAATTACGGGGCGCTGGTCGCATCATCGGTGTCGGCAGCCGTCCAAT<br>TTGCGTTGAAGCAGCTAAATTCTATGGTGCCACGGACATTCTGAACTATAAAAAT<br>GGTCACATCGTCGATCAGGTGATGAAACTGACCAATGGCAAAGGTGTGGACCGCG<br>TGATCATGGCGGGCGGCGGCTCAGAGACTTTATCTCAAGCGGTGTCTATGGTTAA<br>ACCTGGGGGCATCATTTCTAATATTAACTATCATGGCTCCGGCGACGCATTACTG<br>ATCCCGCGTGTTGAATGGGGCTGTGGGATGGCCCACAAAACCATTAAAGGGGGGT<br>TATGTCCGGGTGGTCGCCTGCGTGCCGAAATGCTGCGTGACATGGTGGTTTACAA<br>CCGTGTGGATCTGTCCAAACTGGTAACTCACGTATACCACGGTTTCGATCACATT<br>GAAGAGGCGCTGCTGCTGATGAAGGATAAGCCAAAGGATCTGATTAAGGCGGTTG<br>TTATCCTGTAA |
| SEQ ID NO: 106 | *Clostridium beijerinckii* secondary alcohol<br>dehydrogenase adh AA sequence<br>MKGFAMLGINKLGWIEKERPVAGSYDAIVRPLAVSPCTSDIHTVFEGALGDRKNM<br>ILGHEAVGEVVEVGSEVKDFKPGDRVIVPCTTPDWRSLEVQAGFQQHSNGMLAGW<br>KFSNFKDGVFGEYFHVNDADMNLAILPKDMPLENAVMITDMMTTGFHGAELADIQ<br>MGSSVVVIGIGAVGLMGIAGAKLRGAGRIIGVGSRPICVEAAKFYGATDILNYKN<br>GHIVDQVMKLTNGKGVDRVIMAGGGSETLSQAVSMVKPGGIISNINYHGSGDALL<br>IPRVEWGCGMAHKTIKGGLCPGGRLRAEMLRDMVVYNRVDLSKLVTHVYHGFDHI<br>EEALLLMKDKPKDLIKAVVIL |
| SEQ ID NO: 107 | *Clostridium carboxidivorans* alcohol dehydrogenase adh<br>NT sequence<br>ATGAAGGTAACTAATGTTGAAGAACTGATGAAAAAAATGCAGGAAGTGCAAAATG<br>CTCAAAAAAAATTTGGGAGTTTTACTCAGGAACAAGTAGATGAAATTTTCAGGCA |

SEQUENCE LISTING

```
                AGCAGCACTAGCAGCTAACAGTGCCAGAATAGATCTAGCTAAAATGGCAGTGGAA
                GAAACTAAAATGGGAATTGTAGAGGATAAGGTTATAAAAAATCATTTTGTTGCAG
                AATACATATATAATAAGTATAAAAATGAAAAAACTTGTGGGATTTTGGAAGAAGA
                TGAAGGCTTTGGAATGGTTAAAATTGCAGAACCTGTAGGTGTGATTGCAGCAGTA
                ATTCCAACAACAAATCCAACATCTACAGCAATATTTAAAGCATTATTAGCTTTGA
                AAACAAGAAATGGTATAATTTTTTCACCACATCCAAGAGCAAAAAAGTGTACTAT
                TGCAGCAGCTAAGTTAGTTCTTGATGCTGCAGTTAAAGCAGGTGCTCCTAAAGGA
                ATTATAGGTTGGATAGATGAACCTTCTATTGAACTTTCACAGATAGTAATGAAAG
                AAGCTGATATAATCCTTGCAACAGGTGGTCCAGGTATGGTTAAAGCAGCTTATTC
                TTCAGGTAAACCTGCTATAGGGGTTGGTCCTGGTAACACACCTGCTTTAATTGAT
                GAAAGTGCTGATATTAAAATGGCAGTAAATTCAATACTTCTTTCCAAAACTTTTG
                ATAATGGTATGATTTGTGCTTCAGAGCAGTCGGTAGTAGTTGTAGATTCAATATA
                TGAAGAAGTTAAGAAAGAATTTGCTCATAGAGGAGCTTATATTTTAAGTAAGGAT
                GAAACAACTAAAGTTGGAAAAATACTCTTAGTTAATGGTACATTAAATGCTGGTA
                TCGTTGGTCAGAGTGCTTATAAAATAGCAGAAATGGCAGGAGTTAAAGTTCCAGA
                AGATGCTAAAGTTCTTATAGGAGAAGTAAAATCAGTGGAGCATTCAGAAGAGCCA
                TTTTCACATGAAAAGTTATCTCCAGTTTTAGCTATGTATAGAGCTAAAAATTTTG
                ATGAAGCTCTTTTAAAAGCTGGAAGATTAGTTGAACTCGGTGGAATGGGTCATAC
                ATCTGTATTATATGTAAATGCAATAACTGAAAAAGTAAAAGTAGAAAAATTTAGA
                GAAACTATGAAGACTGGTAGAACATTAATAAATATGCCTTCAGCACAAGGTGCTA
                TAGGAGACATATATAACTTTAAACTAGCTCCTTCATTAACATTAGGTTGTGGTTC
                ATGGGGAGGAAACTCCGTATCAGAAAATGTTGGACCTAAACACTTATTAAATATA
                AAAAGTGTTGCTGAGAGGAGAGAAAATATGCTTTGGTTTAGAGTTCCTGAAAAGG
                TTTATTTTAAATATGGTAGTCTTGGAGTTGCATTAAAAGAATTAGATATTTTGGA
                TAAGAAAAAAGTATTTATAGTAACAGATAAAGTTCTTTATCAATTAGGTTATATA
                GATAGAGTTACAAAGATTCTTGAAGAATTGAAAATTTCATATAAAATATTTACAG
                ATGTAGAACCAGATCCAACCCTAGCTACAGCTAAAAAAGGTGCAGAAGAATTGTT
                ATCATTTAATCCAGATACTATTATAGCAGTTGGTGGTGGTTCAGCAATGGATGCT
                GCTAAGATTATGTGGGTAATGTATGAACATCCGGAAGTAAGATTTGAAGATTTAG
                CTATGAGATTTATGGATATAAGAAAGAGAGTATATACTTTTCCTAAGATGGGTGA
                AAAAGCAATGATGATTTCTGTTGCAACATCAGCAGGAACAGGATCAGAAGTAACA
                CCTTTTGCAGTAATTACTGATGAAAAAACAGGAGCTAAATATCCATTAGCTGATT
                ATGAATTAACTCCAAATATGGCTATAATTGATGCTGAACTTATGATGGGTATGCC
                AAAAGGATTAACAGCAGCTTCAGGAATAGATGCACTAACTCATGCAATAGAAGCT
                TATGTATCAATAATGGCTTCAGAATATACTAATGGATTAGCGTTAGAAGCAATAA
                GATTGATATTTAAGTATTTACCAATAGCTTACAGTGAAGGAACAACAAGTATAAA
                GGCAAGAGAAAAAATGGCGCATGCTTCAACAATAGCTGGTATGGCATTTGCTAAT
                GCATTTTTAGGAGTATGTCATTCAATGGCACATAAATTAGGATCAACTCATCACG
                TACCACATGGCATTGCCAATGCACTACTTATAAATGAAGTTATAAAATTTAATGC
                AGTAGAAAATCCAAGAAAACAAGCTGCATTTCCACAATATAAGTATCCAAATATA
                AAAAAGAGATATGCTAGAATAGCAGATTACCTTAACTTAGGTGGGTCAACAGACG
                ATGAAAAGTACAATTATTAATAAATGCTATAGATGAATTAAAAGCTAAGATAAA
                TATTCCAGAAAGTATTAAAGAAGCAGGAGTAACAGAAGAAAATTTTATGCTACT
                TTAGATAAAATGTCAGAATTAGCTTTTGATGATCAATGTACAGGTGCAAACCCTA
                GATATCCATTAATAAGTGAAATAAAACAAATGTATGTAAATGCATTTTAA
```

SEQ ID NO: 108     *Clostridium carboxidivorans* alcohol dehydrogenase adh
                 AA sequence

```
                MKVTNVEELMKKMQEVQNAQKKFGSFTQEQVDEIFRQAALAANSARIDLAKMAVE
                ETKMGIVEDKVIKNHFVAEYIYNKYKNEKTCGILEEDEGFGMVKIAEPVGVIAAV
                IPTTNPTSTAIFKALLALKTRNGIIFSPHPRAKKCTIAAAKLVLDAAVKAGAPKG
                IIGWIDEPSIELSQIVMKEADIILATGGPGMVKAAYSSGKPAIGVGPGNTPALID
                ESADIKMAVNSILLSKTFDNGMICASEQSVVVVDSIYEEVKKEFAHRGAYILSKD
                ETTKVGKILLVNGTLNAGIVGQSAYKIAEMAGVKVPEDAKVLIGEVKSVEHSEEP
                FSHEKLSPVLAMYRAKNFDEALLKAGRLVELGGMGHTSVLYVNAITEKVKVEKFR
                ETMKTGRTLINMPSAQGAIGDIYNFKLAPSLTLGCGSWGGNSVSENVGPKHLLNI
                KSVAERRENMLWFRVPEKVYFKYGSLGVALKELDILDKKKVFIVTDKVLYQLGYI
                DRVTKILEELKISYKIFTDVEPDPTLATAKKGAEELLSFNPDTIIAVGGGSAMDA
                AKIMWVMYEHPEVRFEDLAMRFMDIRKRVYTFPKMGEKAMMISVATSAGTGSEVT
                PFAVITDEKTGAKYPLADYELTPNMAIIDAELMMGMPKGLTAASGIDALTHAIEA
                YVSIMASEYTNGLALEAIRLIFKYLPIAYSEGTTSIKAREKMAHASTIAGMAFAN
                AFLGVCHSMAHKLGSTHHVPHGIANALLINEVIKFNAVENPRKQAAFPQYKYPNI
                KKRYARIADYLNLGGSTDDEKVQLLINAIDELKAKINIPESIKEAGVTEEKFYAT
                LDKMSELAFDDQCTGANPRYPLISEIKQMYVNAF
```

SEQ ID NO: 109     *Escherichia coli* soluble pyridine nucleotide
                 transhydrogenase NT sequence

```
                ATGCCACATTCCTACGATTACGATGCCATAGTAATAGGTTCCGGCCCCGGCGGCGAAGGC
                GCTGCAATGGGCCTGGTTAAGCAAGGTGCGCGCGTCGCAGTTATCGAGCGTTATCAAAAT
                GTTGGCGGCGGTTGCACCCACTGGGGCACCATCCCGTCGAAAGCTCTCCGTCACGCCGTC
                AGCCGCATTATAGAATTCAATCAAAACCCACTTTACAGCGACCATTCCCGACTGCTCCGC
                TCTTCTTTTGCCGATATCCTTAACCATGCCGATAACGTGATTAATCAACAAACGCGCATG
                CGTCAGGGATTTTACGAACGTAATCACTGTGAAATATTGCAGGGAAACGCTCGCTTTGTT
                GACGAGCATACCGTTGGCGCTGGATTGCCCGGACGGCAGCGTTGAAACACTAACCGCTGAA
                AAATTTGTTATTGCCTGCGGCTCTCGTCCATATCATCCAACAGATGTTGATTTCACCCAT
                CCACGCATTTACGACAGCGACTCAATTCTCAGCATGCACCACGAACCGCGCCATGTACTT
                ATCTATGGTGCTGGAGTGATCGGCTGTGAATATGCGTCGATCTTCCGCGGTATGGATGTA
```

SEQUENCE LISTING

|  |  |
|---|---|
|  | AAAGTGGATCTGATCAACACCCGCGATCGCCTGCTGGCATTTCTCGATCAAGAGATGTCA<br>GATTCTCTCTCCTATCACTTCTGGAACAGTGGCGTAGTGATTCGTCACAACGAAGAGTAC<br>GAGAAGATCGAAGGCTGTGACGATGGTGTGATCATGCATCTGAAGTCGGGTAAAAAACTG<br>AAAGCTGACTGCCTGCTCTATGCCAACGGTCGCACCGGTAATACCGATTCGCTGGCGTTA<br>CAGAACATTGGGCTAGAAACTGACAGCCGCGGACAGCTGAAGGTCAACAGCATGTATCAG<br>ACCGCACAGCCACACGTTTACGCGGTGGGCGACGTGATTGGTTATCCGAGCCTGGCGTCG<br>GCGGCCTATGACCAGGGGCGCATTGCCGCGCAGGCGCTGGTAAAAGGCGAAGCCACCGCA<br>CATCTGATTGAAGATATCCCTACCGGTATTTACACCATCCCGGAAATCAGCTCTGTGGGC<br>AAAACCGAACAGCAGCTGACCGCAATGAAAGTGCCATATGAAGTGGGCCGCGCCCAGTTT<br>AAACATCTGGCACGCGCACAAATCGTCGGCATGAACGTGGGCACGCTGAAAATTTTGTTC<br>CATCGGGAAACAAAAGAGATTCTGGGTATTCACTGCTTTGGCGAGCGCGCTGCCGAAATT<br>ATTCATATCGGTCAGGCGATTATGGAACAGAAAGGTGGCGGCAACACTATTGAGTACTTC<br>GTCAACACCACCTTTAACTACCCGACGATGGCGGAAGCCTATCGGGTAGCTGCGTTAAAC<br>GGTTTAAACCGCCTGTTTTAA |
| SEQ ID NO: 110 | *Escherichia coli* soluble pyridine nucleotide<br>transhydrogenase AA sequence<br>MPHSYDYDAIVIGSGPGGEGAAMGLVKQGARVAVIERYQNVGGGCTHWGTIPSKA<br>LRHAVSRIIEFNQNPLYSDHSRLLRSSFADILNHADNVINQQTRMRQGFYERNHC<br>EILQGNARFVDEHTLALDCPDGSVETLTAEKFVIACGSRPYHPTDVDFTHPRIYD<br>SDSILSMHHEPRHVLIYGAGVIGCEYASIFRGMDVKVDLINTRDRLLAFLDQEMS<br>DSLSYHFWNSGVVIRHNEEYEKIEGCDDGVIMHLKSGKKLKADCLLYANGRTGNT<br>DSLALQNIGLETDSRGQLKVNSMYQTAQPHVYAVGDVIGYPSLASAAYDQGRIAA<br>QALVKGEATAHLIEDIPTGIYTIPEISSVGKTEQQLTAMKVPYEVGRAQFKHLAR<br>AQIVGMNVGTLKILFHRETKEILGIHCFGERAAEIIHIGQAIMEQKGGGNTIEYF<br>VNTTFNYPTMAEAYRVAALNGLNRLF |
| SEQ ID NO: 111 | Forward primer to amplify fucA and fucO<br>CCTTTAATAAGGAGATATACCATGGAACGAAATAAACTTGC |
| SEQ ID NO: 112 | Reverse primer to amplify fucA and fucO<br>GGTTATTCCTCCTTATTTAGAGCTCTAAACGAATTCTTACCAGGCG GTATGGTAAA |
| SEQ ID NO: 113 | Forward primer to amplify fucK<br>GAATTCGTTTAGAGCTCTAAATAAGGAGGAATAACCATGATGAAACAAGAAGTTA<br>T |
| SEQ ID NO: 114 | Reverse primer to amplify fucK<br>GAGCT CGGTACCCGGGGATCCAAAAAACCCCTCAAGACCC |
| SEQ ID NO: 115 | Forward primer to amplify thl<br>CTGTTGTTATATTGTAATGATGTATGCAAGAGGGATAAA |
| SEQ ID NO: 116 | Reverse primer to amplify thl<br>TATATCTCCTTCTTAAAGTTCATAAATCACCCCGTTGC |
| SEQ ID NO: 117 | Forward primer to amplify fucO<br>ATGGCTAACAGAATGATTCTG |
| SEQ ID NO: 118 | Reverse primer to amplify fucO<br>TTACCAGGCGGTATGGTAAAGCT |
| SEQ ID NO: 119 | Forward primer to amplify atoA/D<br>CTGTTGTTATATTGTAATGATGTATGCAAGAGGGATAAA |
| SEQ ID NO: 120 | Reverse primer to amplify atoA/D<br>TATATCTCCTTCTTAAAGTTCATAAATCACCCCGTTGC |

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

NUMBERED EMBODIMENTS OF THE DISCLOSURE

Particular subject matter contemplated by the present disclosure is set out in the below numbered embodiments.

1. A recombinant microorganism capable of co-producing monoethylene glycol (MEG) and acetone from exogenous D-xylose, wherein the recombinant microorganism expresses one or more of the following:

(a) at least one endogenous or exogenous nucleic acid molecule encoding a D-tagatose 3-epimerase that catalyzes the conversion of D-xylulose to D-ribulose;
(b) at least one endogenous or exogenous nucleic acid molecule encoding a D-ribulokinase that catalyzes the conversion of D-ribulose from (a) to D-ribulose-1-phosphate;
(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);
(d) at least one endogenous or exogenous nucleic acid molecule encoding a glycolaldehyde reductase that catalyzes the conversion of glycolaldehyde from (c) to MEG;
(e) at least one exogenous nucleic acid molecule encoding a thiolase that catalyzes the conversion of acetyl-CoA to acetoacetyl-CoA;
(f) at least one endogenous or exogenous nucleic acid molecule encoding an acetate:acetoacetyl-CoA transferase or hydrolase that catalyzes the conversion of acetoacetyl-CoA from (e) to acetoacetate; and/or
(g) at least one endogenous or exogenous nucleic acid molecule encoding an acetoacetate decarboxylase that catalyzes the conversion of acetoacetate from (f) to acetone;
wherein the produced intermediate DHAP is converted to acetyl-CoA through the endogenous glycolysis pathway in the microorganism, and wherein MEG and acetone are co-produced.

2. The recombinant microorganism of claim 1, wherein the recombinant microorganism further comprises at least one endogenous or exogenous nucleic acid molecule encoding a secondary alcohol dehydrogenase that catalyzes the conversion of acetone from (g) to isopropanol.

3. The recombinant microorganism of claim 2, wherein the recombinant microorganism further comprises at least one endogenous or exogenous nucleic acid molecule encoding a dehydratase that catalyzes the conversion of isopropanol to propene.

4. The recombinant microorganism of any one of claims 1-3, wherein the recombinant microorganism further comprises one or more modifications selected from the group consisting of:
(a) a deletion, insertion, or loss of function mutation in a gene encoding a D-xylulose-5-kinase that catalyzes the conversion of D-xylulose to D-xylulose-5-phosphate;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

5. The recombinant microorganism of any one of claims 1-4, wherein an endogenous D-xylose isomerase catalyzes the conversion of D-xylose to D-xylulose.

6. A recombinant microorganism capable of co-producing monoethylene glycol (MEG) and acetone from exogenous D-xylose, wherein the recombinant microorganism expresses one or more of the following:

(a) at least one endogenous or exogenous nucleic acid molecule encoding a D-xylulose 1-kinase that catalyzes the conversion of D-xylulose to D-xylulose-1-phosphate;
(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);
(c) at least one endogenous or exogenous nucleic acid molecule encoding a glycolaldehyde reductase that catalyzes the conversion of glycolaldehyde from (b) to MEG;
(d) at least one endogenous or exogenous nucleic acid molecule encoding a thiolase that catalyzes the conversion of acetyl-CoA to acetoacetyl-CoA;
(e) at least one endogenous or exogenous nucleic acid molecule encoding an acetate:acetoacetyl-CoA transferase or hydrolase that catalyzes the conversion of acetoacetyl-CoA from (d) to acetoacetate; and/or
(f) at least one endogenous or exogenous nucleic acid molecule encoding an acetoacetate decarboxylase that catalyzes the conversion of acetoacetate from (e) to acetone;
wherein the produced intermediate DHAP is converted to acetyl-CoA through the endogenous glycolysis pathway in the microorganism, and wherein MEG and acetone are co-produced.

7. The recombinant microorganism of claim 6, wherein the recombinant microorganism further comprises at least one exogenous nucleic acid molecule encoding a secondary alcohol dehydrogenase that catalyzes the conversion of acetone from (f) to isopropanol.

8. The recombinant microorganism of claim 7, wherein the recombinant microorganism further comprises at least one exogenous nucleic acid molecule encoding a dehydratase that catalyzes the conversion of isopropanol to propene.

9. The recombinant microorganism of any one of claims 6-8, wherein the recombinant microorganism further comprises one or more modifications selected from the group consisting of:
(a) a deletion, insertion, or loss of function mutation in a gene encoding a D-xylulose-5-kinase that catalyzes the conversion of D-xylulose to D-xylulose-5-phosphate;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

10. The recombinant microorganism of any one of claims 6-9, wherein an endogenous D-xylose isomerase catalyzes the conversion of D-xylose to D-xylulose.

11. A recombinant microorganism capable of co-producing monoethylene glycol (MEG) and acetone from exogenous D-xylose and glucose, wherein the recombinant microorganism expresses one or more of the following:
(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;
(b) at least one exogenous nucleic acid molecule encoding a D-xylose isomerase that catalyzes the conversion of D-xylose to D-xylulose, and
wherein the microorganism further expresses one or more of the following:
(c) at least one endogenous or exogenous nucleic acid molecule encoding a D-tagatose 3-epimerase that catalyzes the conversion of D-xylulose from (a) or (b) to D-ribulose;
(d) at least one endogenous or exogenous nucleic acid molecule encoding a D-ribulokinase that catalyzes the conversion of D-ribulose from (c) to D-ribulose-1-phosphate;
(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);
(f) at least one endogenous or exogenous nucleic acid molecule encoding a glycolaldehyde reductase or methylglyoxal reductase that catalyzes the conversion of glycolaldehyde from (e) to MEG;
(g) at least one endogenous or exogenous nucleic acid molecule encoding a thiolase that catalyzes the conversion of acetyl-CoA to acetoacetyl-CoA;
(h) at least one endogenous or exogenous nucleic acid molecule encoding an acetate:acetoacetyl-CoA transferase or hydrolase that catalyzes the conversion of acetoacetyl-CoA from (g) to acetoacetate; and/or
(i) at least one endogenous or exogenous nucleic acid molecule encoding an acetoacetate decarboxylase that catalyzes the conversion of acetoacetate from (h) to acetone;
wherein the produced intermediate DHAP is converted to acetyl-CoA through the endogenous glycolysis pathway in the microorganism, and wherein MEG and acetone are co-produced.

12. The recombinant microorganism of claim 11, wherein the recombinant microorganism further comprises at least one exogenous nucleic acid molecule encoding a secondary alcohol dehydrogenase that catalyzes the conversion of acetone from (i) to isopropanol.

13. The recombinant microorganism of claim 12, wherein the recombinant microorganism further comprises at least one exogenous nucleic acid molecule encoding a dehydratase that catalyzes the conversion of isopropanol to propene.

14. The recombinant microorganism of any one of claims 11-13, wherein the recombinant microorganism further comprises one or more modifications selected from the group consisting of:
(a) a deletion, insertion, or loss of function mutation in a gene encoding a D-xylulose-5-kinase that catalyzes the conversion of D-xylulose to D-xylulose-5-phosphate; and
(b) a deletion, insertion, or loss of function mutation in a gene encoding an alkaline phosphatase that catalyzes the conversion of D-xylulose-5-phosphate to D-xylulose.

15. The recombinant microorganism of any one of claims 11-14, wherein the microorganism is a fungus.

16. A recombinant microorganism capable of co-producing monoethylene glycol (MEG) and acetone from exogenous D-xylose, wherein the recombinant microorganism expresses one or more of the following:
(a) at least one endogenous or exogenous nucleic acid molecule encoding a xylose dehydrogenase that catalyzes the conversion of D-xylose to D-xylonolactone;
(b) at least one endogenous or exogenous nucleic acid molecule encoding a xylonolactonase that catalyzes the conversion of D-xylonolactone from (a) to D-xylonate;
(c) at least one endogenous or exogenous nucleic acid molecule encoding a xylonate dehydratase that catalyzes the conversion of D-xylonate from (b) to 2-keto-3-deoxy-xylonate;
(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;
(e) at least one endogenous or exogenous nucleic acid molecule encoding a glycolaldehyde reductase that catalyzes the conversion of glycolaldehyde from (d) to MEG;
(f) at least one exogenous nucleic acid molecule encoding a thiolase that catalyzes the conversion of acetyl-CoA to acetoacetyl-CoA;
(g) at least one endogenous or exogenous nucleic acid molecule encoding an acetate:acetoacetyl-CoA transferase or hydrolase that catalyzes the conversion of acetoacetyl-CoA from (f) to acetoacetate; and/or
(h) at least one exogenous nucleic acid molecule encoding an acetoacetate decarboxylase that catalyzes the conversion of acetoacetate from (g) to acetone;
wherein the produced intermediate pyruvate is converted to acetyl-CoA through the endogenous glycolysis pathway in the microorganism, and wherein MEG and acetone are co-produced.

17. The recombinant microorganism of claim 16, wherein the recombinant microorganism further comprises at least one exogenous nucleic acid molecule encoding a secondary alcohol dehydrogenase that catalyzes the conversion of acetone from (h) to isopropanol.

18. The recombinant microorganism of claim 17, wherein the recombinant microorganism further comprises at least one exogenous nucleic acid molecule encoding a dehydratase that catalyzes the conversion of isopropanol to propene.

19. The recombinant microorganism of any one of claims 16-18, wherein the recombinant microorganism further comprises one or more modifications selected from the group consisting of:
(a) a deletion, insertion, or loss of function mutation in a gene encoding a D-xylose isomerase that catalyzes the conversion of D-xylose to D-xylulose;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

20. A recombinant microorganism capable of co-producing monoethylene glycol (MEG) and acetone from exogenous D-xylose, wherein the recombinant microorganism expresses one or more of the following:

(a) at least one endogenous or exogenous nucleic acid molecule encoding a xylose dehydrogenase that catalyzes the conversion of D-xylose to D-xylonate;
(b) at least one endogenous or exogenous nucleic acid molecule encoding a xylonate dehydratase that catalyzes the conversion of D-xylonate from (a) to 2-keto-3-deoxy-xylonate;
(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;
(d) at least one exogenous nucleic acid molecule encoding a glycolaldehyde reductase that catalyzes the conversion of glycolaldehyde from (c) to MEG;
(e) at least one exogenous nucleic acid molecule encoding a thiolase that catalyzes the conversion of acetyl-CoA to acetoacetyl-CoA;
(f) at least one endogenous or exogenous nucleic acid molecule encoding an acetate:acetoacetyl-CoA transferase or hydrolase that catalyzes the conversion of acetoacetyl-CoA from (e) to acetoacetate; and/or
(g) at least one exogenous nucleic acid molecule encoding an acetoacetate decarboxylase that catalyzes the conversion of acetoacetate from (f) to acetone;
wherein the produced intermediate pyruvate is converted to acetyl-CoA through the endogenous glycolysis pathway in the microorganism, and wherein MEG and acetone are co-produced.

21. The recombinant microorganism of claim 20, wherein the recombinant microorganism further comprises at least one exogenous nucleic acid molecule encoding a secondary alcohol dehydrogenase that catalyzes the conversion of acetone from (g) to isopropanol.

22. The recombinant microorganism of claim 21, wherein the recombinant microorganism further comprises at least one exogenous nucleic acid molecule encoding a dehydratase that catalyzes the conversion of isopropanol to propene.

23. The recombinant microorganism of any one of claims 20-22, wherein the recombinant microorganism further comprises one or more modifications selected from the group consisting of:
(a) a deletion, insertion, or loss of function mutation in a gene encoding a D-xylose isomerase that catalyzes the conversion of D-xylose to D-xylulose;
(b) a deletion, insertion, or loss of function mutation in a gene encoding a glycolaldehyde dehydrogenase that catalyzes the conversion of glycolaldehyde to glycolic acid; and
(c) a deletion, insertion, or loss of function mutation in a gene encoding a lactate dehydrogenase that catalyzes the conversion of pyruvate to lactate.

24. The recombinant microorganism of claim 1 or claim 11, wherein the D-tagatose 3-epimerase is encoded by one or more nucleic acid molecules obtained from a microorganism selected from *Pseudomonas* sp., *Mesorhizobium* sp. or *Rhodobacter* sp.

25. The recombinant microorganism of claim 24, wherein the microorganism is selected from *Pseudomonas cichorii*, *Pseudomonas* sp. ST-24, *Mesorhizobium loti* or *Rhodobacter sphaeroides*.

26. The recombinant microorganism of claim 24, wherein the one or more nucleic acid molecules is dte and/or C1 KKR1.

27. The recombinant microorganism of claim 1 or claim 11, wherein the D-ribulokinase is encoded by one or more nucleic acid molecules obtained from *E. coli*.

28. The recombinant microorganism of claim 27, wherein the one or more nucleic acid molecules is fucK.

29. The recombinant microorganism of claim 1 or claim 11, wherein the D-ribulose-1-phosphate aldolase is encoded by one or more nucleic acid molecules obtained from *E. coli*.

30. The recombinant microorganism of claim 29, wherein the one or more nucleic acid molecules is fucA.

31. The recombinant microorganism of any one of claim 1, 6, 11, 16 or 20, wherein the glycolaldehyde reductase is encoded by one or more nucleic acid molecules obtained from a microorganism selected from *E. coli* or *S. cerevisiae*.

32. The recombinant microorganism of claim 31, wherein the one or more nucleic acid molecules is selected from fucO, yqhD, dkgA (yqhE), dkgB (yafB), yeaE, yghZ, gldA and/or GRE2.

33. The recombinant microorganism of any one of claim 1, 6, 11, 16 or 20, wherein the thiolase is encoded by one or more nucleic acid molecules obtained from a microorganism selected from *Clostridium* sp., *Bacillus* sp., *E. coli* and *Marinobacter* sp.

34. The recombinant microorganism of claim 33, wherein the microorganism is selected from *Clostridium acetobutylicum*, *Clostridium thermosaccharolyticum*, *Bacillus cereus*, *E. coli* and *Marinobacter hydrocarbonoclasticus*.

35. The recombinant microorganism of claim 33, wherein the one or more nucleic acid molecules is thlA and/or atoB.

36. The recombinant microorganism of any one of claim 1, 6, 11, 16 or 20, wherein the acetate:acetoacetyl-CoA transferase or hydrolase is encoded by one or more nucleic acid molecules obtained from a microorganism selected from *Clostridium* sp. or *E. coli*.

37. The recombinant microorganism of claim 36, wherein the microorganism is *Clostridium acetobutylicum*.

38. The recombinant microorganism of claim 36, wherein the one or more nucleic acid molecules encoding the acetate:acetoacetyl-CoA transferase is atoA and/or atoD.

39. The recombinant microorganism of claim 36, wherein the one or more nucleic acid molecules encoding the acetate:acetoacetyl-CoA hydrolase is ctfA and/or ctfB.

40. The recombinant microorganism of any one of claim 1, 6, 11, 16 or 20, wherein the acetoacetate decarboxylase is encoded by one or more nucleic acid molecules obtained from a microorganism selected from *Clostridium* sp., *Bacillus* sp., *Chromobacterium* sp. and *Pseudomonas* sp.

41. The recombinant microorganism of claim 40, wherein the microorganism is selected from *Clostridium acetobutylicum*, *Clostridium beijerinckii*, *Clostridium cellulolyticum*, *Bacillus polymyxa*, *Chromobacterium violaceum* and *Pseudomonas putida*.

42. The recombinant microorganism of claim 40, wherein the one or more nucleic acid molecules encoding the acetoacetate decarboxylase is adc.

43. The recombinant microorganism of any one of claim 2, 7, 12, 17 or 21, wherein the secondary alcohol dehydrogenase is encoded by one or more nucleic acid molecules obtained from a microorganism selected from *Burkholderia* sp, *Alcaligenes* sp., *Clostridium* sp., *Thermoanaerobacter* sp., *Phytomonas* sp., *Rhodococ-*

*cus* sp., *Methanobacterium* sp., *Methanogenium* sp., *Entamoeba* sp., *Trichomonas* sp., and *Tritrichomonas* sp.

44. The recombinant microorganism of claim 43, wherein the microorganism is selected from *Burkholderia* sp. AIU 652, *Alcaligenes eutrophus*, *Clostridium ragsdalei*, *Clostridium beijerinckii*, *Thermoanaerobacter brockii*, *Thermoanaerobacter ethanolicus* (*Clostridium thermohydrosulfuricum*), *Rhodococcus ruber*, *Methanobacterium palustre*, methanogenic archaea *Methanogenium liminatans*, parasitic protist *Entamoeba histolytica*, parasitic protozoan *Tritrichomonas foetus* and human parasite *Trichomonas vaginalis*.

45. The recombinant microorganism of claim 43, wherein the one or more nucleic acid molecules encoding the secondary alcohol dehydrogenase is adhB or EhAdh1.

46. The recombinant microorganism of claim 6, wherein the D-xylulose 1-kinase is encoded by one or more nucleic acid molecules obtained from *Homo sapiens*.

47. The recombinant microorganism of claim 46, wherein the one or more nucleic acid molecules encoding the D-xylulose 1-kinase is ketohexokinase C (khk-C).

48. The recombinant microorganism of claim 6, wherein the D-xylulose-1-phosphate aldolase is encoded by one or more nucleic acid molecules obtained from *Homo sapiens*.

49. The recombinant microorganism of claim 48, wherein the one or more nucleic acid molecules encoding the D-xylulose-1-phosphate aldolase is aldolase B (ALDOB).

50. The recombinant microorganism of claim 11, wherein the xylose reductase or aldose reductase is encoded by one or more nucleic acid molecules obtained from a microorganism selected from *Hypocrea* sp., *Saccharomyces* sp., *Pachysolen* sp., *Pichia* sp., *Candida* sp., *Aspergillus* sp., *Neurospora* sp., and *Cryptococcus* sp.

51. The recombinant microorganism of claim 50, wherein the microorganism is selected from *Hypocrea jecorina*, *S. cerevisiae*, *Pachysolen tannophilus*, *Pichia stipitis*, *Pichia quercuum*, *Candida shehatae*, *Candida tenuis*, *Candida tropicalis*, *Aspergillus niger*, *Neurospora crassa* and *Cryptococcus lactativorus*.

52. The recombinant microorganism of claim 50, wherein the one or more nucleic acid molecules encoding the xylose reductase or aldose reductase is xyl1 or GRE3.

53. The recombinant microorganism of claim 11, wherein the xylitol dehydrogenase is encoded by one or more nucleic acid molecules obtained from a microorganism selected from *Pichia* sp., *Saccharomyces* sp., *Gluconobacter* sp., *Galactocandida* sp., *Neurospora* sp., and *Serratia* sp.

54. The recombinant microorganism of claim 53, wherein the microorganism is selected from *Pichia stipitis*, *S. cerevisiae*, *Gluconobacter oxydans*, *Galactocandida mastotermitis*, *Neurospora crassa* and *Serratia marcescens*.

55. The recombinant microorganism of claim 53, wherein the one or more nucleic acid molecules encoding the xylitol dehydrogenase is xyl2 or xdh1.

56. The recombinant microorganism of claim 11, wherein the xylose isomerase is encoded by one or more nucleic acid molecules obtained from *E. coli*.

57. The recombinant microorganism of claim 56, wherein the one or more nucleic acid molecules encoding the xylose isomerase is xylA.

58. The recombinant microorganism of claim 16 or claim 20, wherein the xylose dehydrogenase is encoded by one or more nucleic acid molecules obtained from a microorganism selected from *Caulobacter* sp., *Haloarcula* sp., *Haloferax* sp., *Halorubrum* sp. and *Trichoderma* sp.

59. The recombinant microorganism of claim 58, wherein the microorganism is selected from *Caulobacter crescentus*, *Haloarcula marismortui*, *Haloferax volcanii*, *Halorubrum lacusprofundi* and *Trichoderma reesei*.

60. The recombinant microorganism of claim 58, wherein the one or more nucleic acid molecules encoding the xylose dehydrogenase is selected from xylB, xdh or xyd1.

61. The recombinant microorganism of claim 16, wherein the xylonolactonase is encoded by one or more nucleic acid molecules obtained from a microorganism selected from *Caulobacter* sp. and *Haloferax* sp.

62. The recombinant microorganism of claim 61, wherein the microorganism is selected from *Caulobacter crescentus*, *Haloferax volcanii* and *Haloferax gibbonsii*.

63. The recombinant microorganism of claim 61, wherein the one or more nucleic acid molecules encoding the xylonolactonase is xylC.

64. The recombinant microorganism of claim 16 or claim 20, wherein the xylonate dehydratase is encoded by one or more nucleic acid molecules obtained from a microorganism selected from *Caulobacter* sp., *Haloferax* sp., *Sulfolobus* sp. and *E. coli*.

65. The recombinant microorganism of claim 64, wherein the microorganism is selected from *Caulobacter crescentus*, *Haloferax volcanii*, *E. coli* and *Sulfolobus solfataricus*.

66. The recombinant microorganism of claim 64, wherein the one or more nucleic acid molecules encoding the xylonate dehydratase is selected from xylD, yjhG, yagF and xad.

67. The recombinant microorganism of claim 16 or claim 20, wherein the 2-keto-3-deoxy-D-pentonate aldolase is encoded by one or more nucleic acid molecules obtained from a microorganism selected from *Pseudomonas* sp. and *E. coli*.

68. The recombinant microorganism of claim 67, wherein the microorganism is *E. coli*.

69. The recombinant microorganism of claim 67, wherein the one or more nucleic acid molecules encoding the 2-keto-3-deoxy-D-pentonate aldolase is selected from yjhH and yagE.

70. The recombinant microorganism of any one of claim 1, 6, 11, 16 or 20, wherein MEG is produced through the conversion of glycolaldehyde in a C-2 branch pathway and acetone is produced through the conversion of DHAP or pyruvate in a C-3 branch pathway.

71. The recombinant microorganism of any one of claim 2, 7, 12, 17 or 21, wherein MEG is produced through the conversion of glycolaldehyde in a C-2 branch pathway and IPA is produced through the conversion of DHAP or pyruvate in a C-3 branch pathway.

72. The recombinant microorganism of any one of claim 3, 8, 13, 18 or 22, wherein MEG is produced through the conversion of glycolaldehyde in a C-2 branch pathway and propene is produced through the conversion of DHAP or pyruvate in a C-3 branch pathway.

73. The recombinant microorganism of any one of claims 70-72, wherein at least a portion of the excess NADH produced in the C-3 branch is used as a source of reducing equivalents in the C-2 branch.

74. The recombinant microorganism of any one of claims 70-72, wherein at least a portion of the excess NADH produced in the C-3 branch is used to produce ATP.

75. The recombinant microorganism of any one of claim 1, 6, 11, 16 or 20, wherein the co-produced MEG and acetone comprise a yield potential greater than 90% of the thermodynamic maximum yield potential without carbon fixation.

76. The recombinant microorganism of any one of claim 2, 7, 12, 17 or 21, wherein the co-produced MEG and IPA comprise a yield potential greater than 90% of the thermodynamic maximum yield potential without carbon fixation.

77. The recombinant microorganism of any one of claim 3, 8, 13, 18 or 22, wherein the co-produced MEG and propene comprise a yield potential greater than 90% of the thermodynamic maximum yield potential without carbon fixation.

78. The recombinant microorganism of any one of claim 1, 6, 11, 16 or 20, wherein excess biomass formation is minimized and production of MEG and acetone is maximized.

79. The recombinant microorganism of any one of claim 2, 7, 12, 17 or 21, wherein excess biomass formation is minimized and production of MEG and IPA is maximized.

80. The recombinant microorganism of any one of claim 3, 8, 13, 18 or 22, wherein excess biomass formation is minimized and production of MEG and propene is maximized.

81. A method of producing MEG and a three carbon compound using a recombinant microorganism of any of the preceding claims, wherein the method comprises cultivating the recombinant microorganism in a culture medium containing a feedstock providing a carbon source until the MEG and the three carbon compound is produced.

82. A method of producing a recombinant microorganism that produces or accumulates MEG and acetone from exogenous D-xylose, comprising introducing into the recombinant microorganism and/or overexpressing one or more of the following:
    (a) at least one endogenous or exogenous nucleic acid molecule encoding a D-tagatose 3-epimerase that catalyzes the conversion of D-xylose to D-ribulose;
    (b) at least one endogenous or exogenous nucleic acid molecule encoding a D-ribulokinase that catalyzes the conversion of D-ribulose from (a) to D-ribulose-1-phosphate;
    (c) at least one endogenous or exogenous nucleic acid molecule encoding a D-ribulose-1P aldolase that catalyzes the conversion of D-ribulose-1-phosphate from (b) to glycolaldehyde and dihydroxyacetonephosphate (DHAP);
    (d) at least one endogenous or exogenous nucleic acid molecule encoding a glycolaldehyde reductase that catalyzes the conversion of glycolaldehyde from (c) to MEG;
    (e) at least one exogenous nucleic acid molecule encoding a thiolase that catalyzes the conversion of acetyl-CoA to acetoacetyl-CoA;
    (f) at least one endogenous or exogenous nucleic acid molecule encoding an acetate:acetoacetyl-CoA transferase or hydrolase that catalyzes the conversion of acetoacetyl-CoA from (e) to acetoacetate; and/or
    (g) at least one exogenous nucleic acid molecule encoding an acetoacetate decarboxylase that catalyzes the conversion of acetoacetate from (f) to acetone;

wherein the produced intermediate DHAP is converted to acetyl-CoA through the endogenous glycolysis pathway in the microorganism, and wherein MEG and acetone are co-produced.

83. The method of claim 82, wherein the method further comprises introducing into the recombinant microorganism at least one exogenous nucleic acid molecule encoding a secondary alcohol dehydrogenase that catalyzes the conversion of acetone from (g) to isopropanol.

84. The method of claim 83, wherein the method further comprises introducing into the recombinant microorganism at least one exogenous nucleic acid molecule encoding a dehydratase that catalyzes the conversion of isopropanol to propene.

85. The method of any one of claims 82-84, wherein the method further comprises introducing into the recombinant microorganism one or more modifications selected from the group consisting of:
    (a) a deletion, insertion, or loss of function mutation in a gene encoding a D-xylulose-5-kinase that catalyzes the conversion of D-xylulose to D-xylulose-5-phosphate;
    (b) a deletion, insertion, or loss of function mutation in a gene encoding a glycolaldehyde dehydrogenase that catalyzes the conversion of glycolaldehyde to glycolic acid; and
    (c) a deletion, insertion, or loss of function mutation in a gene encoding a lactate dehydrogenase that catalyzes the conversion of pyruvate to lactate.

86. The method of any one of claims 82-85, wherein an endogenous D-xylose isomerase catalyzes the conversion of D-xylose to D-xylulose.

87. A method of producing a recombinant microorganism that produces or accumulates MEG and acetone from exogenous D-xylose, comprising introducing into the recombinant microorganism and/or overexpressing one or more of the following:
    (a) at least one exogenous nucleic acid molecule encoding a D-xylulose 1-kinase that catalyzes the conversion of D-xylulose to D-xylulose-1-phosphate;
    (b) at least one exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);
    (c) at least one endogenous or exogenous nucleic acid molecule encoding a glycolaldehyde reductase that catalyzes the conversion of glycolaldehyde from (b) to MEG;
    (d) at least one exogenous nucleic acid molecule encoding a thiolase that catalyzes the conversion of acetyl-CoA to acetoacetyl-CoA;
    (e) at least one endogenous or exogenous nucleic acid molecule encoding an acetate:acetoacetyl-CoA transferase or hydrolase that catalyzes the conversion of acetoacetyl-CoA from (d) to acetoacetate; and/or
    (f) at least one exogenous nucleic acid molecule encoding an acetoacetate decarboxylase that catalyzes the conversion of acetoacetate from (e) to acetone;

wherein the produced intermediate DHAP is converted to acetyl-CoA through the endogenous glycolysis pathway in the microorganism, and wherein MEG and acetone are co-produced.

88. The method of claim 87, wherein the method further comprises introducing into the recombinant microorganism at least one exogenous nucleic acid molecule encoding a secondary alcohol dehydrogenase that catalyzes the conversion of acetone from (f) to isopropanol.

89. The method of claim 88, wherein the method further comprises introducing into the recombinant microorganism at least one exogenous nucleic acid molecule encoding a dehydratase that catalyzes the conversion of isopropanol to propene.

90. The method of any one of claims 87-89, wherein the method further comprises introducing into the recombinant microorganism one or more modifications selected from the group consisting of:
   (a) a deletion, insertion, or loss of function mutation in a gene encoding a D-xylulose-5-kinase that catalyzes the conversion of D-xylulose to D-xylulose-5-phosphate;
   (b) a deletion, insertion, or loss of function mutation in a gene encoding a glycolaldehyde dehydrogenase that catalyzes the conversion of glycolaldehyde to glycolic acid; and
   (c) a deletion, insertion, or loss of function mutation in a gene encoding a lactate dehydrogenase that catalyzes the conversion of pyruvate to lactate.

91. The method of any one of claims 87-89, wherein an endogenous D-xylose isomerase catalyzes the conversion of D-xylose to D-xylulose.

92. A method of producing a recombinant microorganism that produces or accumulates MEG and acetone from exogenous D-xylose and glucose, comprising introducing into the recombinant microorganism and/or overexpressing one or more of the following:
   (a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;
   (b) at least one exogenous nucleic acid molecule encoding a D-xylose isomerase that catalyzes the conversion of D-xylose to D-xylulose, and
wherein the method further comprises introducing into the recombinant microorganism and/or overexpressing one or more of the following:
   (c) at least one exogenous nucleic acid molecule encoding a D-tagatose 3-epimerase that catalyzes the conversion of D-xylulose from (a) or (b) to D-ribulose;
   (d) at least one exogenous nucleic acid molecule encoding a D-ribulokinase that catalyzes the conversion of D-ribulose from (c) to D-ribulose-1-phosphate;
   (e) at least one exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);
   (f) at least one exogenous nucleic acid molecule encoding a glycolaldehyde reductase or methylglyoxal reductase that catalyzes the conversion of glycolaldehyde from (e) to MEG;
   (g) at least one exogenous nucleic acid molecule encoding a thiolase that catalyzes the conversion of acetyl-CoA to acetoacetyl-CoA;
   (h) at least one endogenous or exogenous nucleic acid molecule encoding an acetate:acetoacetyl-CoA transferase or hydrolase that catalyzes the conversion of acetoacetyl-CoA from (g) to acetoacetate; and/or
   (i) at least one exogenous nucleic acid molecule encoding an acetoacetate decarboxylase that catalyzes the conversion of acetoacetate from (h) to acetone;
wherein the produced intermediate DHAP is converted to acetyl-CoA through the endogenous glycolysis pathway in the microorganism, and wherein MEG and acetone are co-produced.

93. The method of claim 92, wherein the method further comprises introducing into the recombinant microorganism at least one exogenous nucleic acid molecule encoding a secondary alcohol dehydrogenase that catalyzes the conversion of acetone from (i) to isopropanol.

94. The method of claim 93, wherein the method further comprises introducing into the recombinant microorganism at least one exogenous nucleic acid molecule encoding a dehydratase that catalyzes the conversion of isopropanol to propene.

95. The method of any one of claims 92-94, wherein the method further comprises introducing into the recombinant microorganism one or more modifications selected from the group consisting of:
   (a) a deletion, insertion, or loss of function mutation in a gene encoding a D-xylulose-5-kinase that catalyzes the conversion of D-xylulose to D-xylulose-5-phosphate; and
   (b) a deletion, insertion, or loss of function mutation in a gene encoding an alkaline phosphatase that catalyzes the conversion of D-xylulose-5-phosphate to D-xylulose.

96. The method of any one of claims 92-95, wherein the microorganism is a fungus.

97. A method of producing a recombinant microorganism that produces or accumulates MEG and acetone from exogenous D-xylose, comprising introducing into the recombinant microorganism and/or overexpressing one or more of the following:
   (a) at least one endogenous or exogenous nucleic acid molecule encoding a xylose dehydrogenase that catalyzes the conversion of D-xylose to D-xylonolactone;
   (b) at least one endogenous or exogenous nucleic acid molecule encoding a xylonolactonase that catalyzes the conversion of D-xylonolactone from (a) to D-xylonate;
   (c) at least one endogenous or exogenous nucleic acid molecule encoding a xylonate dehydratase that catalyzes the conversion of D-xylonate from (b) to 2-keto-3-deoxy-xylonate;
   (d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;
   (e) at least one exogenous nucleic acid molecule encoding a glycolaldehyde reductase that catalyzes the conversion of glycolaldehyde from (d) to MEG;
   (f) at least one exogenous nucleic acid molecule encoding a thiolase that catalyzes the conversion of acetyl-CoA to acetoacetyl-CoA;
   (g) at least one endogenous or exogenous nucleic acid molecule encoding an acetate:acetoacetyl-CoA transferase or hydrolase that catalyzes the conversion of acetoacetyl-CoA from (f) to acetoacetate; and/or
   (h) at least one exogenous nucleic acid molecule encoding an acetoacetate decarboxylase that catalyzes the conversion of acetoacetate from (g) to acetone;

wherein the produced intermediate pyruvate is converted to acetyl-CoA through the endogenous glycolysis pathway in the microorganism, and wherein MEG and acetone are co-produced.

98. The method of claim 97, wherein the method further comprises introducing into the recombinant microorganism at least one exogenous nucleic acid molecule encoding a secondary alcohol dehydrogenase that catalyzes the conversion of acetone from (h) to isopropanol.

99. The method of claim 98, wherein the method further comprises introducing into the recombinant microorganism at least one exogenous nucleic acid molecule encoding a dehydratase that catalyzes the conversion of isopropanol to propene.

100. The method of any one of claims 97-99, wherein the method further comprises introducing into the recombinant microorganism one or more modifications selected from the group consisting of:
    (a) a deletion, insertion, or loss of function mutation in a gene encoding a D-xylose isomerase that catalyzes the conversion of D-xylose to D-xylulose;
    (b) a deletion, insertion, or loss of function mutation in a gene encoding a glycolaldehyde dehydrogenase that catalyzes the conversion of glycolaldehyde to glycolic acid; and
    (c) a deletion, insertion, or loss of function mutation in a gene encoding a lactate dehydrogenase that catalyzes the conversion of pyruvate to lactate.

101. A method of producing a recombinant microorganism that produces or accumulates MEG and acetone from exogenous D-xylose, comprising introducing into the recombinant microorganism and/or overexpressing one or more of the following:
    (a) at least one endogenous or exogenous nucleic acid molecule encoding a xylose dehydrogenase that catalyzes the conversion of D-xylose to D-xylonate;
    (b) at least one endogenous or exogenous nucleic acid molecule encoding a xylonate dehydratase that catalyzes the conversion of D-xylonate from (a) to 2-keto-3-deoxy-xylonate;
    (c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;
    (d) at least one exogenous nucleic acid molecule encoding a glycolaldehyde reductase that catalyzes the conversion of glycolaldehyde from (c) to MEG;
    (e) at least one exogenous nucleic acid molecule encoding a thiolase that catalyzes the conversion of acetyl-CoA to acetoacetyl-CoA;
    (f) at least one endogenous or exogenous nucleic acid molecule encoding an acetate:acetoacetyl-CoA transferase or hydrolase that catalyzes the conversion of acetoacetyl-CoA from (e) to acetoacetate; and/or
    (g) at least one exogenous nucleic acid molecule encoding an acetoacetate decarboxylase that catalyzes the conversion of acetoacetate from (f) to acetone;
wherein the produced intermediate pyruvate is converted to acetyl-CoA through the endogenous glycolysis pathway in the microorganism, and wherein MEG and acetone are co-produced.

102. The method of claim 101, wherein the method further comprises introducing into the recombinant microorganism at least one exogenous nucleic acid molecule encoding a secondary alcohol dehydrogenase that catalyzes the conversion of acetone from (g) to isopropanol.

103. The method of claim 102, wherein the method further comprises introducing into the recombinant microorganism at least one exogenous nucleic acid molecule encoding a dehydratase that catalyzes the conversion of isopropanol to propene.

104. The method of any one of claims 101-103, wherein the method further comprises introducing into the recombinant microorganism one or more modifications selected from the group consisting of:
    (a) a deletion, insertion, or loss of function mutation in a gene encoding a D-xylose isomerase that catalyzes the conversion of D-xylose to D-xylulose;
    (b) a deletion, insertion, or loss of function mutation in a gene encoding a glycolaldehyde dehydrogenase A that catalyzes the conversion of glycolaldehyde to glycolic acid; and
    (c) a deletion, insertion, or loss of function mutation in a gene encoding a lactate dehydrogenase A that catalyzes the conversion of pyruvate to lactate.

105. The method of claim 82 or claim 92, wherein the D-tagatose 3-epimerase is encoded by one or more nucleic acid molecules obtained from a microorganism selected from *Pseudomonas* sp., *Mesorhizobium* sp. or *Rhodobacter* sp.

106. The method of claim 105, wherein the microorganism is selected from *Pseudomonas cichorii, Pseudomonas* sp. ST-24, *Mesorhizobium loti* or *Rhodobacter sphaeroides*.

107. The method of claim 105, wherein the one or more nucleic acid molecules is dte and/or C1 KKR1.

108. The method of claim 82 or claim 92, wherein the D-ribulokinase is encoded by one or more nucleic acid molecules obtained from *E. coli*.

109. The method of claim 108, wherein the one or more nucleic acid molecules is fucK.

110. The method of claim 82 or claim 92, wherein the D-ribulose-1-phosphate aldolase is encoded by one or more nucleic acid molecules obtained from *E. coli*.

111. The method of claim 110, wherein the one or more nucleic acid molecules is fucA.

112. The method of any one of claim 82, 87, 92, 97 or 101, wherein the glycolaldehyde reductase is encoded by one or more nucleic acid molecules obtained from a microorganism selected from *E. coli* or *S. cerevisiae*.

113. The method of claim 112, wherein the one or more nucleic acid molecules is selected from fucO, yqhD, dkgA (yqhE), dkgB (yafB), yeaE, yghZ, gldA and/or GRE2.

114. The method of any one of claim 82, 87, 92, 97 or 101, wherein the thiolase is encoded by one or more nucleic acid molecules obtained from a microorganism selected from *Clostridium* sp., *Bacillus* sp. or *Marinobacter* sp.

115. The method of claim 114, wherein the microorganism is selected from *Clostridium acetobutylicum, Clostridium thermosaccharolyticum, Bacillus cereus, E. coli* and *Marinobacter hydrocarbonoclasticus*.

116. The method of claim 114, wherein the one or more nucleic acid molecules is thlA and/or atoB.

117. The method of any one of claim 82, 87, 92, 97 or 101, wherein the acetate:acetoacetyl-CoA transferase or hydrolase is encoded by one or more nucleic acid molecules obtained from a microorganism selected from *Clostridium* sp. or *E. coli*.

118. The method of claim 117, wherein the microorganism is *Clostridium acetobutylicum*.

119. The method of claim 117, wherein the one or more nucleic acid molecules encoding the acetate:acetoacetyl-CoA transferase is atoA and/or atoD.

120. The method of claim 117, wherein the one or more nucleic acid molecule encoding the acetate:acetoacetyl-CoA hydrolase is ctfA and/or ctfB.

121. The method of any one of claim 82, 87, 92, 97 or 101, wherein the acetoacetate decarboxylase is encoded by one or more nucleic acid molecules obtained from a microorganism selected from *Clostridium* sp., *Bacillus* sp., *Chromobacterium* sp. and *Pseudomonas* sp.

122. The method of claim 121, wherein the microorganism is selected from *Clostridium acetobutylicum, Clostridium beijerinckii, Clostridium cellulolyticum, Bacillus polymyxa, Chromobacterium violaceum* and *Pseudomonas putida*.

123. The method of claim 121, wherein the one or more nucleic acid molecules encoding the acetoacetate decarboxylase is adc.

124. The method of any one of claim 83, 88, 93, 98 or 102, wherein the secondary alcohol dehydrogenase is encoded by one or more nucleic acid molecules obtained from a microorganism selected from *Burkholderia* sp, *Alcaligenes* sp., *Clostridium* sp., *Thermoanaerobacter* sp., *Phytomonas* sp., *Rhodococcus* sp., *Methanobacterium* sp., *Methanogenium* sp., *Entamoeba* sp., *Trichomonas* sp., and *Tritrichomonas* sp.

125. The method of claim 124, wherein the microorganism is selected from *Burkholderia* sp. AIU 652, *Alcaligenes eutrophus, Clostridium ragsdalei, Clostridium beijerinckii, Thermoanaerobacter brockii, Thermoanaerobacter ethanolicus* (*Clostridium thermohydrosulfuricum*), *Rhodococcus ruber, Methanobacterium palustre*, methanogenic archaea *Methanogenium liminatans*, parasitic protist *Entamoeba histolytica*, parasitic protozoan *Tritrichomonas foetus* and human parasite *Trichomonas vaginalis*.

126. The method of claim 124, wherein the one or more nucleic acid molecules encoding the secondary alcohol dehydrogenase is adhB or EhAdh1.

127. The method of claim 87, wherein the D-xylulose 1-kinase is encoded by one or more nucleic acid molecules obtained from *Homo sapiens*.

128. The method of claim 127, wherein the one or more nucleic acid molecules encoding the D-xylulose 1-kinase is ketohexokinase C (khk-C).

129. The method of claim 87, wherein the D-xylulose-1-phosphate aldolase is encoded by one or more nucleic acid molecules obtained from *Homo sapiens*.

130. The method of claim 129, wherein the one or more nucleic acid molecules encoding the D-xylulose-1-phosphate aldolase is aldolase B (ALDOB).

131. The method of claim 92, wherein the xylose reductase or aldose reductase is encoded by one or more nucleic acid molecules obtained from a microorganism selected from *Hypocrea* sp, *Saccharomyces* sp., *Pachysolen* sp., *Pichia* sp., *Candida* sp., *Aspergillus* sp., *Neurospora* sp., and *Cryptococcus* sp.

132. The method of claim 131, wherein the microorganism is selected from *Hypocrea jecorina, S. cerevisiae, Pachysolen tannophilus, Pichia stipitis, Pichia quercuum, Candida shehatae, Candida tenuis, Candida tropicalis, Aspergillus niger, Neurospora crassa* and *Cryptococcus lactativorus*.

133. The method of claim 131, wherein the one or more nucleic acid molecules encoding the xylose reductase or aldose reductase is xyl1 or GRE3.

134. The method of claim 92, wherein the xylitol dehydrogenase is encoded by one or more nucleic acid molecules obtained from a microorganism selected from *Pichia* sp., *Saccharomyces* sp., *Gluconobacter* sp., *Galactocandida* sp., *Neurospora* sp., and *Serratia* sp.

135. The method of claim 134, wherein the microorganism is selected from *Pichia stipitis, S. cerevisiae, Gluconobacter oxydans, Galactocandida mastotermitis, Neurospora crassa* and *Serratia marcescens*.

136. The method of claim 134, wherein the one or more nucleic acid molecules encoding the xylitol dehydrogenase is xyl2 or xdh1.

137. The method of claim 92, wherein the xylose isomerase is encoded by one or more nucleic acid molecules obtained from *E. coli*.

138. The method of claim 137, wherein the one or more nucleic acid molecules encoding the xylose isomerase is xylA.

139. The method of claim 97 or claim 101, wherein the xylose dehydrogenase is encoded by one or more nucleic acid molecules obtained from a microorganism selected from *Caulobacter* sp., *Haloarcula* sp., *Haloferax* sp., *Halorubrum* sp. and *Trichoderma* sp.

140. The method of claim 139, wherein the microorganism is selected from *Caulobacter crescentus, Haloarcula marismortui, Haloferax volcanii, Halorubrum lacusprodundi* and *Trichoderma reesei*.

141. The method of claim 139, wherein the one or more nucleic acid molecules encoding the xylose dehydrogenase is selected from xylB, xdh or xyd1.

142. The method of claim 97, wherein the xylonolactonase is encoded by one or more nucleic acid molecules obtained from a microorganism selected from *Caulobacter* sp. and *Haloferax* sp.

143. The method of claim 142, wherein the microorganism is selected from *Caulobacter crescentus, Haloferax volcanii* and *Haloferax gibbonsii*.

144. The method of claim 142, wherein the one or more nucleic acid molecules encoding the xylonolactonase is xylC.

145. The method of claim 97 or claim 101, wherein the xylonate dehydratase is encoded by one or more nucleic acid molecules obtained from a microorganism selected from *Caulobacter* sp., *Haloferax* sp., *Sulfolobus* sp. and *E. coli*.

146. The method of claim 145, wherein the microorganism is selected from *Caulobacter crescentus, Haloferax volcanii, E. coli* and *Sulfolobus solfataricus*.

147. The method of claim 145, wherein the one or more nucleic acid molecules encoding the xylonate dehydratase is selected from xylD, yjhG, yagF and xad.

148. The method of claim 97 or 101, wherein the 2-keto-3-deoxy-D-pentonate aldolase is encoded by one or more nucleic acid molecules obtained from a microorganism selected from *Pseudomonas* sp. and *E. coli*.

149. The method of claim 148, wherein the microorganism is *E. coli*.

150. The method of claim 148, wherein the one or more nucleic acid molecules encoding the 2-keto-3-deoxy-D-pentonate aldolase is selected from yjhH and yagE.

151. A recombinant microorganism co-producing mono-ethylene glycol (MEG) and a three carbon compound.

152. The recombinant microorganism of claim 151, wherein the three carbon compound is acetone.

153. The recombinant microorganism of claim 151, wherein the three carbon compound is isopropanol.

154. The recombinant microorganism of claim 151, wherein the three carbon compound is propene.

---

What is claimed is:

1. A recombinant microorganism capable of co-producing monoethylene glycol (MEG) and acetone from a feedstock comprising exogenous D-xylose, wherein the recombinant microorganism expresses one or more of the following:

(a) at least one endogenous or exogenous nucleic acid molecule encoding a D-xylulose 1-kinase that catalyzes the conversion of D-xylulose to D-xylulose-1-phosphate;

(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP); and/or (c) at least one endogenous or exogenous nucleic acid molecule encoding a glycolaldehyde reductase that catalyzes the conversion of glycolaldehyde from (b) to MEG;

wherein the recombinant microorganism further expresses one or more of the following from (d) to (f):

(d) at least one endogenous or exogenous nucleic acid molecule encoding a thiolase that catalyzes the conversion of acetyl-CoA to acetoacetyl-CoA;

(e) at least one endogenous or exogenous nucleic acid molecule encoding an acetate:acetoacetyl-CoA transferase or hydrolase that catalyzes the conversion of acetoacetyl-CoA from (d) to acetoacetate; and/or (f) at least one endogenous or exogenous nucleic acid molecule encoding an acetoacetate decarboxylase that catalyzes the conversion of acetoacetate from (e) to acetone;

wherein the produced intermediate DHAP is converted to acetyl-CoA through the endogenous glycolysis pathway in the microorganism, wherein MEG and acetone are co-produced, and wherein at least a portion of excess NADH produced in the production of acetone is used as a source of reducing equivalents in the production of MEG.

2. The recombinant microorganism of claim 1, wherein the feedstock comprises exogenous glucose.

3. The recombinant microorganism of claim 1, wherein an endogenous or exogenous D-xylose isomerase catalyzes the conversion of D-xylose to D-xylulose.

4. The recombinant microorganism of claim 1, wherein the recombinant microorganism further comprises at least one endogenous or exogenous nucleic acid molecule encoding a secondary alcohol dehydrogenase that catalyzes the conversion of acetone to isopropanol.

5. The recombinant microorganism of claim 1, wherein the recombinant microorganism further comprises one or more modifications selected from the group consisting of:
   (a) a deletion, insertion, or loss of function mutation in a gene encoding a D-xylulose-5-kinase that catalyzes the conversion of D-xylulose to D-xylulose-5-phosphate;
   (b) a deletion, insertion, or loss of function mutation in a gene encoding a glycolaldehyde dehydrogenase that catalyzes the conversion of glycolaldehyde to glycolic acid; and
   (c) a deletion, insertion, or loss of function mutation in a gene encoding a lactate dehydrogenase that catalyzes the conversion of pyruvate to lactate.

6. A method of producing MEG and acetone using the recombinant microorganism of claim 1, wherein the method comprises cultivating the recombinant microorganism in a culture medium containing a feedstock providing a carbon source until the MEG and acetone are produced.

7. A method of producing MEG and isopropanol using the recombinant microorganism of claim 1, wherein the method further comprises:
   introducing into and/or overexpressing in the recombinant microorganism at least one endogenous or exogenous nucleic acid molecule encoding a secondary alcohol dehydrogenase that catalyzes the conversion of acetone to isopropanol; and
   cultivating the recombinant microorganism in a culture medium containing a feedstock providing a carbon source until the MEG and isopropanol are produced.

* * * * *